US007517648B2

(12) United States Patent
Hildebrandt et al.

(10) Patent No.: US 7,517,648 B2
(45) Date of Patent: Apr. 14, 2009

(54) NPHP NUCLEIC ACIDS AND PROTEINS

(75) Inventors: Friedhelm Hildebrandt, Ann Arbor, MI (US); Edgar A. Otto, Ann Arbor, MI (US); Hemant Khanna, Ann Arbor, MI (US); Anand Swaroop, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 391 days.

(21) Appl. No.: 11/061,626

(22) Filed: Feb. 18, 2005

(65) Prior Publication Data

US 2005/0214864 A1 Sep. 29, 2005

Related U.S. Application Data

(63) Continuation-in-part of application No. 10/648,512, filed on Aug. 26, 2003, now abandoned.

(60) Provisional application No. 60/406,001, filed on Aug. 26, 2002.

(51) Int. Cl.
*C12Q 1/68* (2006.01)
*C07H 21/04* (2006.01)

(52) U.S. Cl. .................. 435/6; 435/40.52; 436/503; 436/811; 536/23.5

(58) Field of Classification Search .................. 435/6, 435/7.1, 40.52; 436/503, 518, 811; 536/23.5
See application file for complete search history.

(56) References Cited

U.S. PATENT DOCUMENTS 7,171,311 B2 * 1/2007 Dai et al. ................. 702/19
2005/0042624 A1 * 2/2005 Itoh et al. ................. 435/6

OTHER PUBLICATIONS

Nomura et al., 1994. Prediction of the coding sequences of unidentified human genes. I. The coding sequences of 40 new genes (KIAA0001-KIAA0040) deduced by analysis of randomly sampled cDNA clones from human immature myeloid cell line KG-1. DNA Research 1: 27-35.*
Otto et al., 2005, Nephrocystin-5, a ciliary IQ domain protein, is mutated in Senior-Loken syndrome and interacts with RPGR and calmodulin. Nature Genetics 37: 282-288, Suppl. Table 1, Suppl. Figs. 1-5.*
Gattone et al., Inhibition of renal cystic disease development and progression by a vasopressin V2 receptor antagonist, Nat Med 9:1323 2003.
Otto et al. "Nephrocystin: Gene Expression and Sequence Conservation between Human, Mouse, and Caenorhabditis Elegans", J. Am. Soc. Nephrol. 11:270 2000.
Ansley et al., Basal body dysfunction is a likely cause of pleiotropic Bardet-Biedl syndrome Nature 425:628, [2003].
Hong et al., Invest Opthalmol Vis Sci 43:3373 [2002].

Gagnadoux et al., Infantile chronic tubulo-interstitial nephritis with cortical microcysts: variant of nephronophthisis or new disease entity? Pediatr. Nephrol. 3, 50 [1989].
Dehal et al., The Draft Genome of Ciona intestinalis: Insights into Chordate and Vertebrate Origins, Science 298:2157 [2002].
Otto et al., J Am Soc Nephrol., Nephrocystin: Gene Expression and Sequence Conservation between Human,Mouse, and Caenorhabditis Elegans, 11:270 [2000].
Otto et al., Nat Genet. Mutations in INVS encoding inversin cause nephronophthisis type 2, linking renal cystic disease to the function of primary cilia and left-right axis, 34:413 [2003].
Olbrich et al., Nat Genet, Mutations in a novel gene, NPHP3, cause adolescent nephronophthisis, tapeto-retinal degeneration and hepatic fibrosis, 34:455 [2003].
Fillastre et al., Senior-Loken syndrome (nephronophthisis and tapeto-retinal degeneration): a study of 8 cases from 5 familes, Clin Nephrol 5:14-19 [1976].
Vervoort et al., Nat Genet, Mutational hot spot within a new RPGR exon in X-linked retinitis pigmentosa, 25:462 [2000].
Watnick et al., Nat Genet, From cilia to cyst, 34:355 [2003].
Hong et al., Invest Opthalmol Vis Sci 44:2413 [2003].
Roepman et al., Hum Mol Genet, The Retinitis pigmentosa GTPase regulator (RPGR) interacts with novel transport-like proteins in the outer segments of rod photoreceptors, 9:2095 [2000].
Cuenca et al., J. Neurocytol 31:649 [2002].
Chen et al., PNAS, Subunit 2 (or β) of Retinal rod cGMP-Gated Cation Channel is a Component of the 240-kDa Channel-Associated Protein and Mediates Ca2+-Calmodulin Modulation, 91:11757 [1994].
Zeisberg et al., Renal fibrosis: an update, Hypertens. 10:315 [2001].
Smith et al., Am. J. Dis. Child. 69:369 [1945].
Fanconi et al., Helv. Paediatr. Acta. 6:1 [1951].
Hildebrandt et al., Nature Genet. 17:149 [1997].
Mochizuki et al., Nature 395, 177 [1998].
Antignac et al., Nature Genet. 3:342 [1993].
Hildebrandt et al., Am J Hum Genet 53:1256-1261 [1993].
Haider et al."A Bedouin Kindred with Infantile Nephronopthisis Demonstrates Linkage to Chromosome 9 by Homozygosity Mapping", Am J Hum Genet 63:1404-1410 [1998].
Omran et al."Identification of a New Gene Locus for Adolescent Nephronophthisis on Chromosome 3q22 in a Large Venezuelan Pedigree", Am J Hum Genet 66:118-127 [2000].
Waldherr et al., Virchows Arch A Pathol Anat Histol 394:235-254 [1982].
Schuemann et al."Mapping of Gene Loci for Nephronophthisis Type 4 and Senior-Løken Syndrome, to Chromosome 1p36", Am. J. Hum. Genet. 70:1240 [2002].
Dib et al., Nature 380:152 [1996].

(Continued)

*Primary Examiner*—Ann Y. Lam
*Assistant Examiner*—James L Grun
(74) *Attorney, Agent, or Firm*—Casimir Jones, S.C.

(57) ABSTRACT

The present invention relates to Nephronophthisis, in particular to the NPHP5 protein (nephrocystin-5) and nucleic acids encoding the NPHP5 protein. The present invention also provides assays for the detection of NPHP5 polymorphisms and mutations associated with disease states.

6 Claims, 81 Drawing Sheets

OTHER PUBLICATIONS

Hildebrandt and Otto, "Molecular Genetics of Nephronophthisis and Medullary Cystic Kidney Disease" J Am Soc Nephrol 11:1753-1761 [2000].

Donaldson et al., Exp Cell Res 256:168-178 [2000].

Benzing et al. "Nephrocystin interacts with Pyk2, p130(Cas), and tensin and triggers phoshphorylation of Pyk2", Proc Natl Acad Sci USA 98:9784-9789 [2001].

Donaldson et al. "Nephrocystin-conserved Domains Involved in Targeting to Epithelial Cell-Cell Junctions, Interaction with Filamins, and Est" J Biol Chem 277:29028-29035 [2002].

Senior et al., Am J Ophthalmol 52:625-633 [1961].

Løken et al., Acta Paediatr 50:177-184 [1961].

Caridi et al., Am J Kidney Dis 32:1059-1062 [1998].

Polak et al., Am J Ophthalmol 95:487-494 [1983].

Nurnberger et al. ARPKD and Inversin (inv): Isoforms and Cellular Distributions. Journal of the American Society of Nephrology. Sep. 2001, vol. 12, p. 542A, see Abstract # A2810.

Nurnberger et al. Inversion Forms a Complex with Catenins and N-Cadherin in Polarized Epithelial Cells, Molecular Biology of the Cell. Sep. 2002, vol. 13, No. 9, pp. 3096-3106, see entire document.

Morgan et al., Nat. Genet. 20, 149 [1998].

\* cited by examiner

Figure 1

| p-ter | F30 II-2 | | F30 II-3 | | F32 II-1 | | F60 II-1 | |
|---|---|---|---|---|---|---|---|---|
| D1S2845 | 201 | 207 | 201 | 207 | 215 | 201 | 219 | 219 |
| D1S2660 | 257 | 259 | 257 | 259 | 261 | 261 | 261 | 261 |
| D1S2660_e | 166 | 166 | 166 | 166 | 174 | 153 | 166 | 166 |
| D1S2660_l | 224 | 224 | 224 | 224 | nd | nd | 232 | 232 |
| D1S2660_k | 149 | 149 | 149 | 149 | 145 | 145 | 149 | 149 |
| D1S2660_h | 263 | 259 | 263 | 259 | 255 | 255 | 261 | 261 |
| D1S2660_d | 128 | 136 | 128 | 136 | 134 | 136 | 128 | 128 |
| D1S2660_c | 155 | 159 | nd | nd | 155 | 169 | 155 | 155 |
| D1S2660_b | 156 | 154 | 156 | 154 | 158 | 154 | 156 | 156 |
| *D1E23 | 175 | 171 | 175 | 171 | 175 | 175 | 175 | 175 |
| D1E22 | 123 | 123 | 123 | 123 | 121 | 121 | 123 | 123 |
| D1S2660_q | 149 | 149 | 149 | 149 | 149 | 149 | 149 | 149 |
| **D1E19 | 266 | 266 | 266 | 266 | 266 | 272 | nd | nd |
| D1S2795 | 219 | 219 | 219 | 219 | 217 | 217 | 217 | 217 |
| D1S2660_t | 170 | 170 | 170 | 170 | 170 | 170 | 173 | 173 |
| D1E18 | 212 | 212 | 212 | 212 | 212 | 212 | 208 | 208 |
| D1S2660_p | 197 | 197 | 197 | 197 | 199 | 199 | 191 | 191 |
| D1S2660_u | 180 | 180 | 180 | 180 | 180 | 180 | 180 | 180 |
| D1E17 | 243 | 243 | 243 | 243 | 235 | 235 | 242 | 242 |
| D1S2660_a | nd | nd | 117 | 117 | 127 | 127 | 115 | 115 |
| D1S2660_r | 191 | 191 | 191 | 191 | 183 | 183 | 191 | 191 |
| D1E16 | 189 | 189 | 189 | 189 | 198 | 198 | 189 | 189 |
| D1E15 | 126 | 126 | 126 | 126 | 138 | 138 | 126 | 126 |
| D1E14 | 127 | 127 | 127 | 127 | 123 | 123 | 127 | 127 |
| D1S2660_m | 205 | 205 | 205 | 205 | 209 | 209 | 205 | 205 |
| D1E13 | 166 | 166 | 166 | 166 | 174 | 174 | 174 | 174 |
| D1S2633_g | 236 | 236 | 236 | 236 | 263 | 263 | 246 | 246 |
| D1S2633_e | 206 | 206 | 206 | 206 | 206 | 206 | 206 | 206 |
| D1E12 | 128 | 128 | 128 | 128 | 128 | 128 | 128 | 128 |
| D1S2633_f | 165 | 165 | 165 | 165 | 173 | 173 | 165 | 165 |
| D1S2633_c | 161 | 161 | 161 | 161 | 157 | 157 | 161 | 161 |
| D1E11 | 142 | 142 | nd | nd | 142 | 142 | 140 | 140 |
| D1S2633_a | 140 | 140 | 140 | 140 | 140 | 140 | 140 | 140 |
| D1E9 | 184 | 184 | 184 | 184 | 184 | 184 | 184 | 184 |
| D1E8 | 180 | 180 | 180 | 180 | 180 | 180 | 180 | 180 |
| D1E4 | 148 | 148 | nd | nd | 148 | 148 | 148 | 148 |
| **D1S2870 | 208 | 208 | 208 | 208 | 200 | 200 | 207 | 190 |
| D1S253 | 2 | 2 | 2 | 2 | nd | nd | nd | nd |
| D1S2870_c | 171 | 171 | 171 | 171 | 187 | 187 | 187 | 187 |
| D1E3 | 127 | 127 | 127 | 127 | 131 | 131 | 131 | 131 |
| *SNP-KIAA0720-Ex19 | A | A | A | T | nd | nd | nd | nd |
| D1S2642_f | 138 | 138 | 138 | 144 | 138 | 138 | 144 | 148 |
| D1S2642_b | 151 | 151 | 151 | 149 | 151 | 151 | 161 | 166 |
| D1S2642 | 181 | 181 | 181 | 223 | 183 | 183 | 181 | 179 |
| D1S214 | 122 | 122 | 122 | 118 | 138 | 138 | 142 | 142 |
| D1S2663 | 201 | 199 | 201 | 193 | 189 | 189 | 197 | 195 |
| cen | | | | | | | | |

FIGURE 4

```
   GACGCGAGGCGGGTTCTTGGACTGAGTGTGCGGCGCGGTGCGCCGCCTTCCGAGGCTCCTCCCGCGG
   GTGGCAGCGGACGGGGCGCGCCCCTCGGCCAGTCCTCGCTCCTCAGGCTTGTGGCTCCGTTGAGCAC     Exon 1
   CGGCCGCCGGGCCTCTGGGTCCGTCGAGTGGAGACTCTCTGAAAAGCGTGGGCTCCGTGGCCTCCGG
   CGCGGCCGCGGCGGGTCGGTCTCCTAG................................

1  ATGAACGATTGGCACCGTATTTTCACTCAAAATGTGTTGGTGCCTCCTCATCCACAGAGA   60
    1  M  N  D  W  H  R  I  F  T  Q  N  V  L  V  P  P  H  P  Q  R    20     Exon 2

61  .........................................................  120
   21  A  R  Q  P  W  K  E  S  T  A  F  Q  C  V  L  K  W  L  D  G    40

121  ......................GGCGTGCTGGAGGTACTGTCAGAGGTTGAATGCCATCTGCGAGTG  180
   41  P  V  I  R  Q  G  V  L  E  V  L  S  E  V  E  C  H  L  R  V    60     Exon 3

181  TCTTTCTTTGATGTCACCTACCGGCACTTCTTTGGGAGGACGTGGAAAACCACAGTGAAG  240
   61  S  F  F  D  V  T  Y  R  H  F  F  G  R  T  W  K  T  T  V  K    80

241  CCGACGAAGAGACCGCCGTCCAGGATCGTCTTTAATGAG.....................  300
   81  P  T  K  R  P  P  S  R  I  V  F  N  E  P  L  Y  F  H  T  S   100

301  .........................................................  360
  101  L  N  H  P  H  I  V  A  V  V  E  V  V  A  E  G  K  K  R  D   120     Exon 4

361  .........................................................  420
  121  G  S  L  Q  T  L  S  C  G  F  G  I  L  R  I  F  S  N  Q  P   140

421  ..................CCAGGACAAAACGTTGCGGCTGTACCATGGCACCCCCAGA  480     Exon 5
  141  D  S  P  I  S  A  S  Q  D  K  R  L  R  L  Y  H  G  T  P  R   160

481  CCCCTCCTCCACCCCCTTCTCCAGGACCCCCCACACC.....................  540
  161  A  L  L  H  P  L  L  Q  D  P  A  E  Q  N  R  H  M  T  L  I   180

541  .........................................................  600     Exon 6
  181  E  N  C  S  L  Q  Y  T  L  K  P  H  P  A  L  E  P  A  F  H   200

601  .........................................................  660
  201  L  L  P  E  N  L  L  V  S  G  L  Q  Q  I  P  G  L  I  P  A   220

661  ......CCCCGACCCTCTCCCAAAGCCTCCCCTCCAGAAGCCCATCACCGGCCAC  720
  221  H  G  E  S  G  D  A  L  R  K  P  R  L  Q  K  P  I  T  G  H   240     Exon 7

721  TTGGATGACTTATTCTTCACCCTGTACCCCTCCCTGGAGAAGTTTGAGGAAGAGCTGCTG  780
  241  L  D  D  L  F  F  T  L  Y  P  S  L  E  K  F  E  E  E  L  L   260

781  GAGCTCCACGTCCAGGACCACTTCCAGGAG.............................  840
  261  E  L  H  V  Q  D  H  F  Q  E  C  C  C  P  L  D  C  G  A  L   280

Exon 8
```

FIGURE 4 (cont.)

```
 841 CAGATCTGCAGCGGCTGCGCGTCGGCGTGCACAATGGCTCTGGCTTCGTGCAGAGG  900
 281 E  I  L  E  R  R  L  R  V  G  V  H  N  G  L  G  F  V  Q  R   300

901 CCGCAGGTGGTGTTGGTGCCTGAGATGGATGTGGCTCTGACGCGTTCAGCTTCTTC  960
 301 P  Q  V  V  V  L  V  P  E  M  D  V  A  L  T  R  S  A  S  F   320

961 AGCAAGGAAGTGGTGTCCTCTTCCAAGACCAGCTCCGGGAGCCAAGCTCTGGTTTTGAGA 1020
 321 S  R  K  V  V  S  S  S  K  T  S  S  G  S  Q  A  L  V  L  R   340
```
Exon 9
```
1021 AGCCGCCTCCGCCTCCCAGAGATGGTCGGCCACCCTGCATTTGCGGTCATCTTCCAGCTG 1080
 341 S  R  L  R  L  P  E  M  V  G  H  P  A  F  A  V  I  F  Q  L   360

1081 GAGTACGTGTTCAGCAGCCCTGCAGGAGTGGACGGCAATGCAGCTTCGGTCACCTCTCTG 1140
 361 E  Y  V  F  S  S  P  A  G  V  D  G  N  A  A  S  V  T  S  L   380
```
Exon 10
```
1141 TCTAACCTGGCGTGCATGCACATGGTGCGCTGGGCTGTTTGGAACCCTCTGCTGGAAGCT 1200
 381 S  N  L  A  C  M  H  M  V  R  W  A  V  W  N  P  L  L  E  A   400

1201 GATTCTGGACGGGTGACTCTGCCTCAGGGTGGAATCCAGCCCAACCCTAGCCATTGT    1260
 401 D  S  G  R  V  T  L  P  L  Q  G  G  I  Q  P  N  P  S  H  C   420

1261 CTGGTTTACAAGGTACCTTCAGCAAGCATGAGCTCTGAAGAGGTGAAGCAGGTGGAGTCG 1320
 421 L  V  Y  K  V  P  S  A  S  M  S  S  E  E  V  K  Q  V  E  S   440
```
Exon 11
```
1321 GGTACACTCCGGTTCCAGTTCTCGCTGGGCTCAGAAGAACACCTGGATGCACCCACGGAG 1380
 441 G  T  L  R  F  Q  F  S  L  G  S  E  E  H  L  D  A  P  T  E   460

1381 CCTGTCAGTGGCCCCAAAGTGGAGCGGCGGCCTTCCAGGAAACCACCCACGTCCCCTTCG 1440
 461 P  V  S  G  P  K  V  E  R  R  P  S  R  K  P  P  T  S  P  S   480
```
Exon 12
```
1441 AGCCCGGCAGCGCCAGTACTCGAGTTCGGCTGCCCCGCAGAACTCACCTGTGGGACCA    1500
 481 S  P  P  A  P  V  P  R  V  L  A  A  P  Q  N  S  P  V  G  P   500
```
Exon 13
```
1501 GGGTTGTCAATTTCCCAGCTGGCGGCCTCCCCGCGGTCCCCGACTCAGCACTGCTTGGCC 1560
 501 G  L  S  I  S  Q  L  A  A  S  P  R  S  P  T  Q  H  C  L  A   520

1561 AGGCCTACTTCACAGCTACCCCATGGCTCTCAGGCCTCCCCGGCCCAGGCACAGGAGTTC 1620
 521 R  P  T  S  Q  L  P  H  G  S  Q  A  S  P  A  Q  A  Q  E  F   540
```
Exon 14
```
1621 CCGTTGGAAGCCGGTATCTCACATCTGGAAGACCTGAGCCAGACCTCTCTGGTCCTC    1680
 541 P  L  E  A  G  I  S  H  L  E  A  D  L  S  Q  T  S  L  V  L   560

1681 GAAACATCCATTGCCGAACAGTTACAGGAGTTGCCTTCACCCTTCACACGCCATATT    1740
 561 E  T  S  I  A  E  Q  L  Q  E  L  P  F  T  P  L  H  A  P  I   580

1741 GTTGTGGAAACCCAGACTAGGAGCTCTGCAGGGCAGCCCTCGAGAGCCTCCATGGTGCTC 1800
 581 V  V  G  T  Q  T  R  S  S  A  G  Q  P  S  R  A  S  M  V  L   600
```
Exon 15
```
1801 CTGCAGTCCTCCGGCTTTCCCGAGATTCTGGATGCCAATAAACAGCCAGCCGAGGCTGTC 1860
 601 L  Q  S  S  G  F  P  E  I  L  D  A  N  K  Q  P  A  E  A  V   620

1861 AGCGCTACAGAACCTGTGACGTTTAACCCTCAGAAGGAAGAATCAGATTGTCTACAAAGC 1920
```

---------|---------|---------|---------|---------|---------|
1921 AACGAGATGGTGCTACAGTTTCTTGCCTTTAGCAGAGTGGCTCAGGACTGCCGAGGAACA 1980
 641 N  E  M  V  L  Q  F  L  A  F  S  R  V  A  Q  D  C  R  G  T   660    Exon 16

---------|---------|---------|---------|---------|---------|
1981 TCATTCACAAAGACTGTGTATTTCACCTTCCAGTTCTACCGTTTCCCGCCAGCAACCACG 2040
 661 S  W  P  K  T  V  Y  F  T  F  Q  F  Y  R  F  P  P  A  T  T   680

---------|---------|---------|---------|---------|---------|
2041 CCACGGCTGCAGCTGGTGCAGCTGGATGAGGCCGGCCAGCCAAGCTCGGGCGCCCTGACC 2100
 681 P  R  L  Q  L  V  Q  L  D  E  A  G  Q  P  S  S  G  A  L  T   700

---------|---------|---------|---------|---------|---------|
2101 CACATTCTCGTCCCTGTAAGCAGAGATGGTACCTTTGATGCTGGGTCTCCTGGCTTCCAG 2160
 701 H  I  L  V  P  V  S  R  D  G  T  F  D  A  G  S  P  G  F  Q   720

---------|---------|---------|---------|---------|---------|
2161 CTGAGGTACATGGTGGGCCCTGGGTTCCTGAAGCCAGGTGAGCGGCGCTGCTTTGCCCGC 2220
 721 L  R  Y  M  V  G  P  G  F  L  K  P  G  E  R  R  C  F  A  R   740    Exon 17

---------|---------|---------|---------|---------|---------|
2221 TACCTGGCCGTGCAGACCCTGCAGATTGACGTCTGGGACGGAGACTCCCTGCTGCTCATC 2280
 741 Y  L  A  V  Q  T  L  Q  I  D  V  W  D  G  D  S  L  L  L  I   760

---------|---------|---------|---------|---------|---------|
2281 GGATCTGCTGCCGTCCAGATGAAGCACCTCCTGCGCCAAGGCCGGCCGGCTGTGCAGGCC 2340
 761 G  S  A  A  V  Q  M  K  H  L  L  R  Q  G  R  P  A  V  Q  A   780

---------|---------|---------|---------|---------|---------|
2341 TCTCACGAGCTTGTAGTGGCTACGGAGTACGAGCAAGATAACATGGTCGTCAGCTGTGA  2400    Exon 18
 781 S  H  E  L  V  V  A  T  E  Y  E  Q  D  N  M  V  V  S  C     800

---------|---------|---------|---------|---------|---------|
2401 GACATGCTGGGTTTTGGCCGTGTCAAGCCTATCGGGGTCCACTCTGTGGTAAAGGGTCGG 2460
 801 D  M  L  G  F  G  R  V  K  P  I  G  V  E  S  V  V  K  G  R   820

---------|---------|---------|---------|---------|---------|
2461 CTCCACCTGACTTTGGCCAATGTGGGTCACCCCGTCTGAACAGAAAGTCAGAGGTTCTACC 2520
 821 L  H  L  T  L  A  N  V  G  H  P  C  E  Q  K  V  R  G  C  S   840

---------|---------|---------|---------|---------|---------|
2521 ACATTGCCACCGTCCAGATCTCGGGTCATCTCAAACGATGGAGCCAGCCGCTTCTCTGGA 2580    Exon 19
 841 T  I  P  P  S  R  S  R  V  I  S  N  D  G  A  S  R  F  S  G   860

---------|---------|---------|---------|---------|---------|
2581 GGCAGCCTCCTCACGACTGGAAGCTCAAGGCGAAAACACGTTGTGCAAGCAGAAGCTG   2640
 861 G  S  L  L  T  T  G  S  S  R  R  K  H  V  V  Q  A  Q  K  L   880

---------|---------|---------|---------|---------|---------|
2641 GCGGATGTCGAGAGTGAGCTGGCTGCCATGCTGATCACGCATGCCCGACAGGGAAAGGG  2700    Exon 20
 881 A  D  V  D  S  E  L  A  A  M  L  I  T  H  A  R  Q  G  K  G   900

---------|---------|---------|---------|---------|---------|
2701 CCCCCAGGACGTCAGCCGTGAGTCGGATGCCACTCGGCGTAAGTTGAGCGGATGAGG   2760
 901 P  Q  D  V  S  R  E  S  D  A  T  R  R  R  K  L  E  R  M  R   920

---------|---------|---------|---------|---------|---------|
2761 TCTGTGCGCCTCCAGGAGGCCGGGGGAGACTTGGCCGGCGCGGGACATCTGTTGCG    2820
 921 S  V  R  L  Q  E  A  G  G  D  L  G  R  R  G  T  S  V  L  A   940

---------|---------|---------|---------|---------|---------|
2821 CAGCAGAGCGTCCGCACACAGCACTTGCGGGACCTACAGGTCATCGCCGCCTACCGGGAA 2880    Exon 21
 941 Q  Q  S  V  R  T  Q  H  L  R  D  L  Q  V  I  A  A  Y  R  E   960

---------|---------|---------|---------|---------|---------|
2881 CGCACGAAGGCCGAGAGCATCGCCAGCCTGCTGAGCCTGGCCATCACCACGGAGCACACG 2940
 961 R  T  K  A  E  S  I  A  S  L  L  S  L  A  I  T  T  E  H  T   980
```

FIGURE 4 (cont.)

```
         ----------|----------|----------|----------|----------|----------|
    2941 CTCCACGCCACGCTGGGGGTCGCCGAGTTCTTTGAGTTTGTGCTTAAGAACCCCCACAAC 3000
     981 L  H  A  T  L  G  V  A  E  F  F  E  F  V  L  K  N  P  H  N  1000

----------|----------|----------|----------|----------|----------|
    3001 ACACAGCACACGGTGACTGTGGAGATCGACAACCCCGAGCTCAGCGTATCCGTGGACAGT 3060
    1001 T  Q  H  T  V  T  V  E  I  D  N  P  E  L  S  V  I  V  D  S  1020

----------|----------|----------|----------|----------|----------|
    3061 CAGGAGTGGAGGGACTTCAAGGGTGCTGCTGGCCTGCACACACCGTGGAGGAGGACATG 3120    Exon 22
    1021 Q  E  W  R  D  F  K  G  A  A  G  L  H  T  ?  V  E  E  D  M  1040

----------|----------|----------|----------|----------|----------|
    3121 TTTCACCTGCGTGGAAGCTTGGCCCCCAGTTGACTTGCGCCTCACGAGATCGCTCAC 3180
    1041 F  H  L  R  G  S  L  A  P  Q  L  Y  L  R  ?  H  E  T  A  H  1060

----------|----------|----------|----------|----------|----------|
    3181 GTGCCCTTGAAGTTCCAGAGTTTCTCTGCAGGCCAGCTTGCCATGCTGCAGCCTCTCCT 3240
    1061 V  P  F  K  F  Q  S  F  S  A  G  Q  L  A  M  V  Q  A  S  P  1080    Exon 23

----------|----------|----------|----------|----------|----------|
    3241 GGGTTGAGCAACGAGAAGGGCATGGACGCCGTGTCACCTTGGAAGTCCAGCGCAGTGCCC 3300
    1081 G  L  S  N  E  K  G  M  D  A  V  S  P  W  K  S  S  A  V  P  1100

----------|----------|----------|----------|----------|----------|
    3301 ACTAAACACGCCAAGGTCTTGTTCCGAGCGAGTGGTGGCAAGCCCATCGCCGTGCTCTGC 3360    Exon 24
    1101 T  K  H  A  K  V  L  F  R  A  S  G  G  K  ?  I  A  V  L  C  1120

----------|----------|----------|----------|----------|----------|
    3361 CTGACTGTGAAGCTGTATCTATCTGGTGACAAGGTCTTCGCTTTATACTGGAG 3420
    1121 L  T  V  E  L  Q  P  H  V  V  D  Q  V  F  R  F  Y  H  P  E  1140

----------|----------|----------|----------|----------|----------|
    3421 CTCTCCTTCCTGAAGAAAGCCATTCGCCTGCCGCCGTGGCACACATTCCAGGTGCTCCG 3480
    1141 L  S  F  L  K  K  A  I  R  L  P  P  W  H  T  F  P  G  A  P  1160    Exon 25

----------|----------|----------|----------|----------|----------|
    3481 GTCCGAATCCTTGCTGACGACCCCCACTCCATGTTCGCTCCACCGACCCCAACGTCATC 3540
    1161 V  G  M  L  G  E  D  P  P  V  H  V  R  C  S  D  P  N  V  I  1180

----------|----------|----------|----------|----------|----------|
    3541 TGTGAGACCCAGAATGTGGGCCCGGGGGAACCACGGGACAGATTCTCGAAGCTGGCCAGT 3600
    1181 C  E  T  Q  N  V  G  P  G  E  P  R  D  I  F  L  K  V  A  S  1200    Exon 26

----------|----------|----------|----------|----------|----------|
    3601 GGTCCAAGCCCGGAAATCAAAGACTTTTTTGTTATCATTTACTCGGATCGCTGGCTGGCG 3660
    1201 G  P  S  P  E  I  K  D  F  F  V  I  I  Y  S  D  R  W  L  A  1220

----------|----------|----------|----------|----------|----------|
    3661 ACACCCACACAGACGTGGCAGGTCTACCTCCACTCCCTGCAGCGCGTGGATGTCTCCTGC 3720
    1221 T  P  T  Q  T  W  Q  V  Y  L  H  S  L  Q  R  V  D  V  S  C  1240    Exon 27

----------|----------|----------|----------|----------|----------|
    3721 GTCGCAGGCCAGCTGACCCGCCTGTCCCTTGTCCTTCGGGGACACAGACAGTGAGGAAA 3780
    1241 V  A  G  Q  L  T  R  L  S  L  V  L  R  G  T  Q  T  V  R  K  1260

----------|----------|----------|----------|----------|----------|
    3781 GTGAGAGCTTTCACCTCTCATCCCCAGGAGCTGAAGACAGACCCCAAGGGTGTGTTCGTG 3840
    1261 V  R  A  F  T  S  H  P  Q  E  L  K  T  D  P  K  G  V  F  V  1280    Exon 28

----------|----------|----------|----------|----------|----------|
    3841 CTGCCGCCTCGTGGTGTTCAGGATCTGCATGTTGGTGTGAGGCCTTTAGGCGGCAGT 3900
    1281 L  P  P  R  G  V  Q  D  L  H  V  G  V  R  P  L  R  A  G  S  1300

----------|----------|----------|----------|----------|----------|
    3901 CGCTTTGTGCATCTCAACATCGTTGACGTCGATTGCCACCAGCTGGTCGCTCCTGCTG 3960
    1301 R  F  V  H  L  N  I  V  D  V  D  C  H  Q  L  V  A  S  W  L  1320

----------|----------|----------|----------|----------|----------|
    3961 GTGTGCGTGTCGGAGCGCAGCGCGCTCATTGCAAGGCCTTTGAGATCATGTTGGCTGCG 4020
```

---------|---------|---------|---------|---------|---------|
4021 GGCGAAGGGAAGGGTGTCAACAAGAGGATCACCTACACCAACCCCTACCCCTCCCGGAGG 4080     Exon 29
1341 G  E  G  K  G  V  N  K  R  I  T  Y  T  N  P  Y  P  S  R  R  1360

---------|---------|---------|---------|---------|---------|
4081 ACATTCCACCTGCACAGCGACCACCCGGAGCTGCTGCGGTTCAGAGAGGACTCCTTCCAG 4140
1361 T  F  H  L  H  S  D  H  P  E  L  L  R  F  R  E  D  S  F  Q  1380

---------|---------|---------|---------|---------|---------|
4141 GTGGGGGGTGGCGAGACCTACACGATCGGTTGCAGTTTGCGCCTTGTCAGCAGCGGGT    4200
1381 V  G  G  G  E  T  Y  T  I  G  L  Q  F  A  P  S  Q  R  V  G  1400     Exon 30

---------|---------|---------|---------|---------|---------|
4201 GAGGAGGAGATCCTCATCTACATCAATGACCATGAAGACAAAAACGAAGAGGCATTTTGC 4260
1401 E  E  E  I  L  I  Y  I  N  D  H  E  D  K  N  E  E  A  F  C  1420

---------|---------|-
4261 GTGAAGGTCATCTACCAGTAA  4281
1421 V  K  V  I  Y  Q  *  1426
```

FIGURE 5

```
human   MNDWHRIFTQ  NVLVPPHPQR  ARQFWKESTA  FQCVLKWLDG  PVIRQ       45
mouse   MSDWHRAFTQ  NTLVPPHPQR  ARQLGKESTA  FQCILKWLDG  PLIKQ       45
CEleg   . . . . . . . . . .  . . . . . . . . . .  . . . . . . . . . .  . . . . . . . . . .  . . . . .   0 human   GVLEVLSEVE  CHLRVSFDV   TYRHFFGRTW  KTTVKPTKP   . . .FS    87
mouse   GILDMLSELE  CHLRVTLFDV  TYKHFFGRTW  KTTVKPTNQP  SKQEP       90
CEleg   . . . . . . . . . .  . . . .MSVNDW  YSLFLANRPV  EMKRNVSRGT  KALCY      31 human   RIVFNEP. .  . .LYFHTSLN  HPHIVAVVEV  VAEGKKR...  . . . . .D  120
mouse   RITFNEP. .  . .LYFHTTLS  HPSIVAVVEV  VTSGRKR...  . . . . .D  123
CEleg   SMFISNLTSP  QTLYFXSIKN  SRDVLLXLEF  VESGSDEING  RTFEN       76 human   GSLQTLSCGF  GILRIFSN..  QPDSPISASQ  DKRLRLYHGT  PRALL      163
mouse   GTLQLLSCGF  GILRIFGN..  KPESPTSAAQ  DKRLRLYHGT  PRALL      166
CEleg   PKSTKITAPA  TSVGWFSTHI  EKKTPVEISN  TKIFDIFGGT  PKLLI      121 human   HPLLQDPAEQ  NRHMTLIENC  SLQYTLKPHP  ALEPAFHLLP  ENLLV      208
mouse   HPLLQDPIEQ  NKFMRLMENC  SLQYTLKPHP  PLEPAFHLLP  ENLLV      211
CEleg   F. . . . . .DK  ETVDKPVGNV  ECTYNIFEMP  P. .FFQCLF  EFCIV      157

[NLS]                    [ ]
human   SGLQQIPGLL  PAHGESGDAL  RKFRLQKPIT  GHLDDLFFTL  YPSLE      253
mouse   SGFQQIPGLL  PPHGDTGDAL  RKFRFQKPTT  WHLDDLFFTL  YPSLE      256
CEleg   CDKDIIPGII  KDSSD.EWWL  STPKEMPTIP  AAIDAIVIQF  KNNVP      201

[E-rich]
human   KFEERLLELH  VQDHFQEGCG  FLDGGALEIL  ERRLRVGVHN  GLGFV      298
mouse   KFEELVQLL   ISD..REGVG  LLDSGTLEEL  ERRLHVCVHN  GLGFV      299
CEleg   ELEKITHDI   EKEWALKEGG  TLKPKAI.IN  DRKLRIGVHN  GYTYV      245

[S-rich]
human   QRPQVVVLVP  EMDVALTRSA  SFSRKVVSSS  KTSSGSQALV  LRS. .     341
mouse   QRPQVVVLVP  EMDVALTRSA  SFSRKISASS  KNSSGNQALV  LRS. .     342
CEleg   TEPFTVDLEI  ISSNAGDTLR  SRKKPIDFGK  SSNWEEQLLF  QAAGN      290 human   .RLRLPEMVG  HPAFAIIFQL  EYVFSSPAGV  DGNAASVTSL  SNLAC      385
mouse   .HLRLPEMVS  HPAFAIFQL   EYVFNSPSGA  DGGASSPTSI  SSVAC      386
CEleg   PRLALRNIYA  DPRMAIIFLL  RYTFHREDNQ  SLNQTILIGW  AAWTF      335 human   MHMVRWAVWN  FLLEADSGRV  TLFLQGGIQP  NPSHCLVYKV  PSASM      430
mouse   MHMVRWAVWN  PDLEVGPGKV  TLPLQGGVQQ  NPSRCLVYKV  PSASM      431
CEleg   FS. . . . . .D  GAFSGKEVET  RVSFVGGPRP  NPEGVLCYKN  VLNQP      373

[P-rich]
human   SSEEVKQVES  GTLRFQFSLG  SEEHLDAPTE  PVSGPKVERR  PSRKP      475
mouse   SSEEVKQVRS  GTIQFQPSLS  S. . .DGPTE  HANGPRVGRR  SSRKM      472
CEleg   DSLKPLNEKL  EIFVDFKFYE  NGRSVHNTPT  SRRAADSARV  QTGRS      418

[P-rich]
human   PTSPSSPPAP  VPRVLAAPQN  SPVGPGLSIS  QLAASPESPT  QHCLA      520
mouse   PASPS. . . .  . . . . . . . . . .  . . . . . . . . . .  . . . . . . . . . .  . . . . .  477
CEleg   GDNGQSARSM  RKSVKIETFR  SPENSN..RF  PALVDTGRSV  SSVDE      461 human   RPTSQLPHGS  QASPAQAQEF  PLEAGISHLE  ADLSQTSLVL  ETSIA      565
mouse   . . . . . . . . . .  . . . .QES   VLESEVSHLE  ADLSQPASLQ  GTPAV      505
CEleg   LRSINEDLNR  FIEEPMEIPV  QDVVVAKKPV  EKPLPITSVY  KIPFD      506 human   EQLQELPFTP  LHAPIVVGTQ  TRSSAGQPSR  ASMVLLQSSG  FPEIL      610
mouse   SHLQELPFTP  LHAPIVVGAQ  TRSSRSQLSR  AAMVLLQSSG  FPEIL      550
CEleg   ELKPINFP..  . . . . . . . . . .  . . . . . . . .R  SAHSMFARQN  FTQLK      530
```

```
human  VSCVAGQLTR  LSLVLRGTQT  VRKVRAFTSH  PQELKTDPKG  VFVLP  1282
mouse  VSCVAGQLTR  LSLVLRGTQT  VRKVRAFTSH  PQELKTDPAG  VFVLP  1222
CEleg  VRSIVGQTTR  LHLLVHRRSE  HDGVPDDLLK  VYTASGCMEV  VDSVL  1129 human  PRGVQDLHVG  VRPLEAGSRF  VHLNLVDVDC  HQLVASWLVC  LCCRQ  1327
mouse  PHGVQDLHVG  VRPRAGSRF   VHLNLVDIDY  HQLVASWLVC  LSCRQ  1267
CEleg  TERTPTATID  FTPNFIGTKE  LVVSVVNTNT  LKLERGFLVY  GKSEA  1174 human  PLISKAFEIM  LAAGEGKGVH  KRITYTNPYP  SRRTFHLHSD  HPELL  1372
mouse  PLISKAFEIT  MAAGDEKGTH  KRITYTNPYP  SRRTYRLHSD  RPELL  1312
CEleg  PRITQKFVIQ  IPSSDEAIRK  VC........  ..........  ..... 1186 human  RFFEDSFQVG  GGETYTIGLQ  FAPSQRVGEE  EILIYINDHE  DKNEE  1417
mouse  RFFEDSFQVA  GGETYTIGLP  FLPSGSAGQE  EILIYINDHE  DKNEE  1357
CEleg  ..........  ..........  ..........  ..........  ..... 1186

ER
human  AFCVKVIYQ 1426
mouse  TFCVKVLYQ 1366
CEleg  .........1186
```

FIGURE 6

```
      GACGCGAGGCGGGTTCTTGGACTGAGTGTGCGGCGCGGTGCGCCGCCTTCCGAGGCTCCTCCCGCGG      Exon 1
      CTCCCAGCCGACCGCGCCCCCCCTCCCCACTCCTCCGTCCTCACCCTTCTGCCTCCCTTCAGCAC
      CGGCCGCCGGGCCTCTGGGTCCGTCGAGTGGAGACTCTCTGAAAAGCGTGGGCTCCGTGGCCTCCGG
      CGCGGCCGCGGCGGGTCGGTCTCCTAGATCATCCGGGAGCCCACGGGACCCTCAGGCGGGCAGG
     ---------|---------|---------|---------|---------|---------|
   1 ATGAACGACTGGCACAGATTCTTCACCCAAAACGTGCTGCCGCCGCACCCACAGACA           60
   1  M  N  D  W  H  R  I  F  T  Q  N  V  L  V  P  P  H  P  Q  R        20     Exon 2

---------|---------|---------|---------|---------|---------|
  61 GCGCGCCAGCCTTGGAAGGAATCCACGGCATTCCAGTGCGTCCTCAAGTGGCTGGACGGA         120
  21  A  R  Q  P  W  K  E  S  T  A  F  Q  C  V  L  K  W  L  D  G        40

---------|---------|---------|---------|---------|---------|
 121 CCGGTAATTAGGCAGGGCGTGCTGGAGGTACTGTCAGAGGTTGAATGCCATCTGCGAGTG         180
  41  P  V  I  R  Q  G  V  L  E  V  L  S  E  V  E  C  H  L  R  V        60     Exon 3

---------|---------|---------|---------|---------|---------|
 181 TCTTTCTTTGATGTCACCTACCGGCACTTCTTTGGGAGGACGTGGAAAACCACAGTCAAG         240
  61  S  F  F  D  V  T  Y  R  H  F  F  G  R  T  W  K  T  T  V  K        80

---------|---------|---------|---------|---------|---------|
 241 CCGACGAAGAGACCGCCGTCCAGGATCGTCTTTAATGAGCCGCTCTATTTTCACACATCC         300
  81  P  T  K  R  P  P  S  R  I  V  F  N  E  P  L  Y  F  H  T  S       100

---------|---------|---------|---------|---------|---------|
 301 CTAAACCACCCTCATATCGTGGCTGTGGTGGAAGTGGTGGCAGAGTGCAAGAAAGGTGAT         360
 101  L  N  H  P  H  I  V  A  V  V  E  V  V  A  E  C  K  K  R  D       120

---------|---------|---------|---------|---------|---------|        Exon 4
 361 GGCAGCCTCCAGACATTGTCTGCGAGTTTGGAATTCTTCGGATCTTCAGCAACCAGCCG          420
 121  G  S  L  Q  T  L  S  C  G  F  G  I  L  R  I  F  S  N  Q  P       140

---------|---------|---------|---------|---------|---------|
 421 GACTCTCCTATTTCAGCTTCACAGGACAAAAAGTTGCGGCTGTACCATGGCACCCCCAGA        480
 141  D  S  P  I  S  A  S  Q  D  K  R  L  R  L  Y  H  G  T  P  R       160     Exon 5

---------|---------|---------|---------|---------|---------|
 481 GCCCTCCTGCACCCGCTTCTCCAGGACCCCGCAGAGCAAAACCGACATATGACCCTCATT        540
 161  A  L  L  H  P  L  L  Q  D  P  A  E  Q  N  R  H  M  T  L  I       180

---------|---------|---------|---------|---------|---------|
 541 GAGAACTGCAGCCTGCAGTACACGCTGAAGCCACACCCGGCCCTGGAGCCTGCTTTCCAC        600     Exon 6
 181  E  N  C  S  L  Q  Y  T  L  K  P  H  P  A  L  E  P  A  F  H       200

---------|---------|---------|---------|---------|---------|
 601 CTTCTTCCAGAGAACCTTCTGGTGAGCGGTTTGCAGCAGATACCCGGCTGCTTCAGCT          660
 201  L  L  P  E  N  L  L  V  S  G  L  Q  Q  I  P  G  L  L  P  A       220

---------|---------|---------|---------|---------|---------|
 661 CATGGAGAATCCGGCGACGCTCTCCGAAAGCCTCGCCTCAGAAGCCCATCACGGGGCAC        720
 221  H  G  E  S  G  D  A  L  R  K  P  R  L  Q  K  P  I  T  G  H       240     Exon 7

---------|---------|---------|---------|---------|---------|
 721 TTGGATGACTTATTCTTCACCCTGTACCCCTCCTGGAGAAGTTTGAGGAAGAGCTGCTG         780
 241  L  D  D  L  F  F  T  L  Y  P  S  L  E  K  F  E  E  E  I  L       260

---------|---------|---------|---------|---------|---------|
 781 CACCTCCACCTCCACCACCACTTCCACCACGAGGATGCCGAGTGCACGCTGTTCGTCTG        840
 261  E  L  H  V  Q  D  H  F  Q  E  G  C  G  P  L  D  G  G  A  L       280

---------|---------|---------|---------|---------|---------|
 841 GAGATCCTGGAGCGGCGCCTCCGCGTCGGGGTCCACAATGGTCTGGGCTTCGTGCAAAGG        900     Exon 8
 281  E  I  L  E  R  R  L  R  V  G  V  H  N  G  L  G  F  V  Q  R       300
```

FIGURE 6 (cont.)

```
       ---------|---------|---------|---------|---------|---------|
 901   CTCCACTCCTTCTACTGCTCCTCACATTCATTGTCCTTACCTCTTACCTACCTTC  960
 301   P  Q  V  V  V  L  V  P  E  M  D  V  A  L  T  R  S  A  S  F   320

---------|---------|---------|---------|---------|---------|
 961   AGCAGAAAGTGGTCTCCTCTCAGACCAGCTCCGGGAGCCAAGCTCTGGTTTTGAGA 1020
 321   S  R  K  V  V  S  S  S  K  T  S  S  G  S  Q  A  L  V  L  R   340

---------|---------|---------|---------|---------|---------|
1021   AGCCGCCTCCGCCTCCCAGAGATGGTCGGCCACCCTGCATTTGCGGTCATCTTCCAGCTG 1080
 341   S  R  L  R  L  P  E  M  V  G  H  P  A  F  A  V  I  F  Q  L   360

---------|---------|---------|---------|---------|---------|
1081   GAGTACGTGTTCAGCAGCCCTGCAGGAGTGGACGGCAATGCAGCTTCAGTGACTTCTCTG 1140
 361   E  Y  V  F  S  S  P  A  G  V  D  G  N  A  A  S  V  T  S  L   380

---------|---------|---------|---------|---------|---------|
1141   TCTAACTTGCCATGCATGGAGATGGTCCGCTGGGCTGTTTGGAATCCTTGCTGAAGCT 1200
 381   S  N  L  A  C  M  E  M  V  R  W  A  V  W  N  P  L  L  E  A   400

---------|---------|---------|---------|---------|---------|
1201   GATTCTGGAGGTGTCACTCTGCCTCAGGGTGGGATCCAGCCTAACCCTTCCCATTGT 1260
 401   D  S  G  R  V  T  L  P  L  Q  G  G  I  Q  P  N  P  S  H  C   420

---------|---------|---------|---------|---------|---------|
1261   CTGGTGTACAAGGTACCCTCAGCCAGCATGAGCTCTGAAGAGGTGAAGCAGGTGGAGTCG 1320
 421   L  V  Y  K  V  P  S  A  S  M  S  S  E  E  V  K  Q  V  E  S   440

---------|---------|---------|---------|---------|---------|
1321   GGTACACTCCGGTTCCAGTTCTCGCTGGGCTCAGAAGAACACCTGGATGCACCCACGGAG 1380
 441   G  T  L  R  F  Q  F  S  L  G  S  E  E  H  L  D  A  P  T  E   460

---------|---------|---------|---------|---------|---------|
1381   CCTGTCAGTGGCCCCAAAGTGGAGCGGCGGCCTTCCAGGAAACCACCCACGTCCCCTTCG 1440
 461   P  V  S  G  P  K  V  E  R  R  P  S  R  K  P  P  T  S  P  S   480

---------|---------|---------|---------|---------|---------|
1441   AGCCCGCTGCGCCAGTACCCGAGTGCTCCGCCGCCGGAACTACTGTGCGACCA 1500
 481   S  P  P  A  P  V  P  R  V  L  A  A  P  Q  N  S  P  V  G  P   500

---------|---------|---------|---------|---------|---------|
1501   GCGTTGTCAATTTCCCAGCTGGCGGCCTCCCCGCGGTCCCCGACTCAGCACTGCTTGGCC 1560
 501   C  L  S  I  S  Q  L  A  A  S  P  R  S  P  T  Q  H  C  L  A   520

---------|---------|---------|---------|---------|---------|
1561   AGGCCTACTTCACAGCTACCCCATGGCTCTCAGGCCTCCCCGGCCCAGGCACAGGAGTTC 1620
 521   R  P  T  S  Q  L  P  H  G  S  Q  A  S  P  A  Q  A  Q  E  F   540

---------|---------|---------|---------|---------|---------|
1621   CCTTTCAGGGCTATCTCCACTGCAGTGCACTGAAGCAAACTCTCTGGTTCTC 1680
 541   P  L  F  A  G  T  S  H  L  E  A  D  L  S  Q  T  S  L  V  L   560

---------|---------|---------|---------|---------|---------|
1681   GAAACTCGTTCGCAGAGCAGTTGGAGTTGCCTTTCACTCCTCTGCATGCTCTATT 1740
 561   E  T  S  I  A  E  Q  L  Q  E  L  P  F  T  P  L  H  A  P  I   580

---------|---------|---------|---------|---------|---------|
1741   GGTGTGGGAACCCACACCAGCAGCTCTGCAGGGCAGCCCTCGAGAGCCTCCATGGTGCTC 1800
 581   V  V  G  T  Q  T  R  S  S  A  G  Q  P  S  R  A  S  M  V  L   600

---------|---------|---------|---------|---------|---------|
1801   CTCCACTCCTCCCGCTTTCCCGACATTCTGCCATCCCAATAAACAGCCACCCCAGCCTCTC 1860
 601   L  Q  S  S  G  F  P  E  I  L  D  A  N  K  Q  P  A  E  A  V   620

---------|---------|---------|---------|---------|---------|
1861   AGCGCTACAGAACCTGTGACGTTTAACCCTCAGAAGGAAGAATCAGATTGTCTACAAAGC 1920
 621   S  A  T  E  P  V  T  F  N  P  Q  K  E  E  S  D  C  L  Q  S   640
```

| Exon 9 |
| Exon 10 |
| Exon 11 |
| Exon 12 |
| Exon 13 |
| Exon 14 |
| Exon 15 |

FIGURE 6 (cont.)

```
         ---------|---------|---------|---------|---------|---------|
1921 AACGAGATGGTGCTACAGTTTCTTGCCTTTAGCAGAGTGGCTCAGCGCTGCTGAGGAACA 1980
 641  N  E  M  V  L  Q  F  L  A  F  S  R  V  A  Q  D  C  R  G  T   660

---------|---------|---------|---------|---------|---------|
1981 TCGTGGCCAAGACTGTGTATTTCACCTTCCAGTTCTACCGGTTCCACCTGCCAGCGACC 2040
 661  S  W  P  K  T  V  Y  F  T  F  Q  F  Y  R  F  P  P  A  T  T   680

---------|---------|---------|---------|---------|---------|
2041 CCACGACTGCAGCTGGTCCAGCTGGATGAGGCCGGCCAGCCCAGCTCTGGGGCCCTGACC 2100
 681  P  R  L  Q  L  V  Q  L  D  E  A  G  Q  P  S  S  G  A  L  T   700

---------|---------|---------|---------|---------|---------|
2101 CATATCCTCGTGCCTGTCAGCAGAGATGGCACCTTTGATGCTGGGTCTCCTGGCTTCCAG 2160
 701  H  I  L  V  P  V  S  R  D  G  T  F  D  A  G  S  P  G  F  Q   720

---------|---------|---------|---------|---------|---------|
2161 CTGAGGTACATGGTGGGCCCTGGGTTCCTGAAGCCAGGTGAGCGGCGCTGCTTTGCCCGC 2220
 721  L  R  Y  M  V  G  P  G  F  L  K  P  G  E  R  R  C  F  A  R   740

---------|---------|---------|---------|---------|---------|
2221 TACCTGGCCGTGCAGACCCTGCAGATTGACGTCTGGGACGGAGACTCCCTGCTGCTCATC 2280
 741  Y  L  A  V  Q  T  L  Q  I  D  V  W  D  G  D  S  L  L  L  I   760

---------|---------|---------|---------|----------|--F3|C2335T
2281 GGATCTGCTGCCGTCCAGATGAAGCATCTCCTCCGGCAGGGCCGGGCCGTGTGAG---- 2340
 761  G  S  A  A  V  Q  M  K  H  L  L  R  Q  G  R  P  A  V  X  -   780
```

Exon 16

Exon 17

Exon 18

Figure 7

```
      GACGCGAGCCGGGTTCTTGGACTGAGTGTGCGGCGCGGTGCGCCGCCTTCCGAGGCTCCTCCCGCGGGTGGCAG
      CGGACGGGGCGCGCCCCTCGGCCAGTCCTCGGTCCTCAGGCTTGTGGCTCCGTTGAGCACCGGCCGCCGGGCCT      Exon 1
      CTGGGTCCCTCGAGTGGAGACTCTCTGAAAAGCGTGGGCTCCGTGGCCTCCGGCGCCGCCGCGGCGGGTCGTC
      TCCTAG.TCATTCTC.AGTCT.CGGACTCTCAGTGTGGCAGT
      ---------|---------|---------|---------|---------|---------|
    1 ATGAATGACTGGCACAGATTCTTTACTCAAAACGTGCTTGTCCTTCCACTCACACAGA 60
    1 M  N  D  W  H  R  I  F  T  Q  N  V  L  V  P  ?  H  P  Q  R  20        Exon 2

---------|---------|---------|---------|---------|---------|
   61 GCGCCCAGCCTTGGAAGGAATCTACGGCATTCAGTGTGTCCTCAAGTGGTTGGACTCA 120
   21 A  R  Q  P  W  K  E  S  T  A  F  Q  C  V  L  K  W  L  D  G  40

---------|---------|---------|---------|---------|---------|
  121 CCGGTAATTAGGCAGGGCGTGCTGGAGGTACTGTCAGAGGTTGAATGCCATCTGCGAGTG 180
   41 P  V  I  R  Q  G  V  L  E  V  L  S  E  V  E  C  H  L  R  V  60        Exon 3

---------|---------|---------|---------|---------|---------|
  181 TCTTTCTTTGATGTCACCTACCGGCACTTCTTTGGGAGGACGTGGAAAACCACAGTGAAG 240
   61 S  F  F  D  V  T  Y  R  H  F  F  G  R  T  W  K  T  T  V  K  80

---------|---------|---------|---------|---------|---------|
  241 CCGACGAAGAGACCGCCGTCCAGGATCGTCTTTAATGAGCCTCTGTATTTCACACATC 300
   81 P  T  K  R  P  P  S  R  I  V  F  N  E  P  L  Y  F  H  S  100

---------|---------|---------|---------|---------|---------|
  301 CTAAACCACCCTCATATCGTGGCTGTGGTGGAAGTGGTGGCTGAAGGCAAGAAGCGAT 360
  101 L  N  H  P  H  I  V  A  V  V  E  V  V  A  E  G  K  K  R  D  120       Exon 4

---------|---------|---------|---------|---------|---------|
  361 GGATCCCTGCAGACACTGTCCTGTGGCTTCGGAATTCTCAGATTCAGTAACCAGCCG 420
  121 G  S  L  Q  T  L  S  C  G  F  G  I  L  R  I  F  S  N  Q  P  140

---------|---------|---------|---------|---------|---------|
  421 GACTCCCCTATCTCTGCTTCCCAGGACAAAAGGTTGCGGCTGTACCATGGCACCCCCAGA 480
  141 D  S  P  I  S  A  S  Q  D  K  R  L  R  L  Y  H  G  T  P  R  160       Exon 5

---------|---------|---------|---------|---------|---------|
  481 GCCCTCCTCCACCCCTTCTCCAGGACCCCCACAGCCAAAATAATAATCACCCTCATT 540
  161 A  L  L  H  P  L  L  Q  D  P  A  E  N  R  H  M  T  L  I  180

---------|---------|---------|---------|---------|---------|
  541 GAGAATTGCAGTCTGCAGTACACCCTGAAGCCACATGCCCTCGAACCTGCTTTCCAC 600
  181 E  N  C  S  L  Q  Y  T  L  K  P  H  ?  A  L  E  P  A  F  H  200       Exon 6

---------|---------|---------|---------|---------|---------|
  601 CTGCTGCCAGAGAACCTGCTGGTGTCTGGGCTGCAGCAGATACCTGGTCTGCTTCCAGCT 660
  201 L  L  P  E  N  L  L  V  S  G  L  Q  Q  I  P  G  L  L  P  A  220

---------|---------|---------|---------|---------|---------|
  661 CATGGAGAATCTGCGACGCTCTCCGAAAGCCTCGCCTCCAGAAGCCCATCACGGGGCAC 720
  221 H  G  E  S  C  D  A  L  R  K  P  R  L  Q  K  P  I  T  G  H  240       Exon 7

---------|---------|---------|---------|---------|---------|
  721 TTGGATGACTTATTCTTCACCCTGTACCCCTCCCTGGAGAAGTTTGAGGAAGAGCTGCTG 780
  241 L  D  D  L  F  F  T  L  Y  P  S  L  E  K  F  E  E  E  L  L  260

---------|---------|---------|---------|---------|---------|
  781 GAGCTCCACGTCCAGGACCACTTCCAGGAGGCATGTGGCCCATTGGACGGTGCTGCCCTC 840
  261 E  L  H  V  Q  D  H  F  Q  E  G  C  G  P  L  D  G  G  A  L  280

---------|---------|---------|---------|---------|---------|
  841 GAGATCCTGGAGCGGCGGCTGCGTGTGGGAGTGCACAATGGTCTGGGCTTTGTGCAGAGG 900
  281 E  I  L  E  R  R  L  R  V  G  V  H  N  G  L  G  F  V  Q  R  300       Exon 8

---------|---------|---------|---------|---------|---------|
  901 CCGCAGGTGGTGCTGGTGCCTGAGATGGATGTAGCTCTGACCCGAAGTGCCAGTTTC 960
  301 P  Q  V  V  V  L  V  ?  E  M  D  V  A  L  T  R  S  A  S  F  320

---------|---------|---------|---------|---------|---------|
  961 AGCAGGAAAGTGGTCTCCTCCTCCAAGACCAGCTCCGGGAGCCAAGCTCTGGTTTTGAGA 1020
  321 S  R  K  V  V  S  S  S  K  T  S  S  G  S  Q  A  L  V  L  R  340       Exon 9
```

FIGURE 7 (cont.)

```
          ---------|---------|---------|---------|---------|---------|
     1021 ACCCCCCTCCCCCTCCCAGACATCCTCCCCCACCCTCCATTTGCCGTCATCTTCCACCTG 1080
      341  S  R  L  R  L  P  E  M  V  G  H  P  A  F  A  V  I  F  Q  L  360

---------|---------|---------|---------|---------|---------|
     1081 GAGTACGTGTTCAGCAGCCCTGCAGGAGTGGACGGCAATGCAGCTTCGGTAACCTCTCTG 1140
      361  E  Y  V  F  S  S  P  A  G  V  D  G  N  A  A  S  V  T  S  L  380

---------|---------|---------|---------|---------|---------|      ┌─────────┐
     1141 TCTAACCTGGCATGCATGCATGTGCTCTGCGCTGTTCAACCCCTTGCTCTCAAGGC      1200    │ Exon 10 │
      381  S  N  L  A  C  M  H  M  V  R  W  A  V  W  N  P  L  L  E  A  400 └─────────┘

---------|---------|---------|---------|---------|---------|
     1201 GATTCTGGAGGGTGACCCTGCTGCAGGCGTGGGATCAGCCGAACCCTGCACTGT      1260
      401  D  S  C  R  V  T  L  P  L  Q  C  C  I  Q  P  N  P  S  H  C  420

---------|---------|---------|---------|---------|---------|
     1261 CTGGTGTACAAGGTACCCTCAGCCAGCATGAGCTCGAAGAGGTGAAGCAGGTGGAGTCG 1320   ┌─────────┐
      421  L  V  Y  K  V  P  S  A  S  M  S  S  E  E  V  K  Q  V  E  S  440   │ Exon 11 │
                                                                              └─────────┘
          ---------|---------|---------|---------|---------|---------|
     1321 GGTACACTCCGGTTCCAGTTCTCGCTGGGCTCAGAAGAACACCTGGATGCACCCACGGAG 1380
      441  G  T  L  R  F  Q  F  S  L  G  S  E  E  H  L  D  A  P  T  E  460

---------|---------|---------|---------|---------|---------|
     1381 CCTGTCAGTGGCCCCAAAGTGGAGCGGCGGCCTTCCAGGAAACCACCCACGTCCCCTTCG 1440
      461  P  V  S  G  P  K  V  E  R  R  P  S  R  K  P  P  T  S  P  S  480

---------|---------|---------|---------|---------|---------|      ┌─────────┐
     1441 AGCCCAGCACCTGTGCCTACGTGAGTTCCGTGTGCGGCAACTCACTGTCGGACA      1500    │ Exon 12 │
      481  S  P  P  A  P  V  P  R  V  L  A  A  P  Q  N  S  P  V  G  P  500 └─────────┘

---------|---------|---------|---------|---------|---------|      ┌─────────┐
     1501 GGGTTGTCAATTTCCCAGCTGGCGGCCTCCCCGCGGTCCCCGACTCAGCACTGCTTGGCC 1560   │ Exon 13 │
      501  G  L  S  I  S  Q  L  A  A  S  P  R  S  P  T  Q  H  C  L  A  520 └─────────┘

---------|---------|---------|---------|---------|---------|
     1561 AGGCCTACTTCACAGCTACCCCATGGCTCTCAGGCCTCCCCGGCCCAGGCACAGGAGTTC 1620   ┌─────────┐
      521  R  P  T  S  Q  L  P  H  G  S  Q  A  S  P  A  Q  A  Q  E  F  540   │ Exon 14 │
                                                                              └─────────┘
          ---------|---------|---------|---------|---------|---------|
     1621 CCTCTGGAGGCCCTATCTCCCACTTGAGGCTGACTGGCTAGATCTCCTGCTCTC      1680
      541  P  L  E  A  G  I  S  H  L  E  A  D  L  S  Q  T  S  L  V  L  560

---------|---------|---------|---------|---------|---------|
     1681 GAAACTCCATCGCCGAACAGCTGCAGGAGCTGCCTTTCACGCCTCTGCATGCCCCTATT 1740
      561  E  T  S  I  A  E  Q  L  Q  E  L  P  F  T  P  L  H  A  P  I  580

---------|---------|---------|---------|---------|---------|
     1741 GTTGTGGAACCCAGACCAGGAGCTCTGCAGGGCAGCCCTCGAGAGCCTCCATGGTGCTC 1800   ┌─────────┐
      581  V  V  G  T  Q  T  R  S  S  A  G  Q  P  S  R  A  S  M  V  L  600   │ Exon 15 │
                                                                              └─────────┘
          ---------|---------|---------|---------|---------|---------|
     1801 CTGCAGTCCTCCGGCTTTCCCGAGATTCTGGATGCCAATAAACAGCCAGCCGAGGCTGTC 1860
      601  L  Q  S  S  G  F  P  E  I  L  D  A  N  K  Q  P  A  E  A  V  620

---------|---------|---------|---------|---------|---------|
     1861 AGCGCTACAGAACCTGTGACGTTTAACCCTCAGAAGGAAGAATCAGATTGTCTACAAAGC 1920
      621  S  A  T  E  P  V  T  F  N  P  Q  K  E  E  S  D  C  L  Q  S  640

---------|---------|---------|---------|---------|---------|
     1921 AACGAGATGGTGCTACAGTTTCTTGCCTTTAGCAGAGTGGCTCAGGACTGCCGAGGAACA 1980
      641  N  E  M  V  L  Q  F  L  A  F  S  R  V  A  Q  D  C  R  G  T  660   ┌─────────┐
                                                                              │ Exon 16 │
          ---------|---------|---------|---------|---------|---------|      └─────────┘
     1981 TCATGGCCAAAGACTGTGTATTCACCTTCCAGTTCTACCGCTTCCACCCTGCAACGACC 2040
      661  S  W  P  K  T  V  Y  F  T  F  Q  F  Y  R  F  P  P  A  T  T  680

---------|---------|---------|---------|---------|---------|
     2041 CCACGAATTCAGTTGTCGAGCTGGATGAGGCAGGCCAGCCGTCTTCGGGCGCTCACC 2100
      681  P  R  L  Q  L  V  Q  L  D  E  A  G  Q  P  S  S  G  A  L  T  700
```

FIGURE 7 (cont.)

```
         ---------|---------|---------|---------|---------|---------|
   2101  CACATCCTGGTGCCTGTCAGCAGAGATGGCACCTTTGATGCTGGGTCTCCTGGCTTCCAG  2160
    701  H  I  L  V  P  V  S  R  D  G  T  F  D  A  G  S  P  G  F  Q   720

---------|---------|---------|---------|---------|---------|
   2161  CTGAGGTACATGGTGGGCCCTGGGTTCCTGAAGCCAGGTGAGCGGCGCTGCTTTGCCCGC  2220    Exon 17
    721  L  R  Y  M  V  G  P  G  F  L  K  P  G  E  R  R  C  F  A  R   740

---------|---------|---------|------F24|G2260A---|---------|
   2221  TACCTGGCCGTGCAGACCCTGCAGATTGACGTCTGGGACGAGACTCCCTGCTGCTCATC  2280
    741  Y  L  A  V  Q  T  L  Q  I  D  V  W  D     D  S  L  L  L  I   760

---------|---------|---------|---------|---------|---------|
   2281  GGATCTGCTGCCGTCCAGATGAAGCATCTGCTCCGCCAGGCCGGCCGCTCTGTCAGGCC  2340
    761  G  S  A  A  V  Q  M  K  H  L  L  R  Q  G  R  P  A  V  Q  A   780

---------|---------|---------|---------|---------|---------|
   2341  TCCCACGAGCTGGAGGTCGTGGCAACTGAATACGAGCAGGACAACATGGTGGTCAGTGGA  2400    Exon 18
    781  S  H  E  L  E  V  V  A  T  E  Y  E  Q  D  N  M  V  V  S  G   800

---------|---------|---------|---------|---------|---------|
   2401  GACATGCTGGGTTTCGGCCGTGTGAAGCCATCGGTGTGCATCGTGTGGTGAAGGGCCGG  2460
    801  D  M  L  G  F  G  R  V  K  P  I  G  V  H  S  V  V  K  G  R   820

---------|---------|---------|---------|---------|---------|
   2461  CTGCACCTGACTTTGCCAACGTTGGTCACCCGTGTGAACAGAAAGTGAGAGGTTGTAGC  2520
    821  L  H  L  T  L  A  N  V  G  H  P  C  E  Q  K  V  R  G  C  S   840

---------|---------|---------|---------|---------|---------|
   2521  ACATTGCCACCGTCCAGATCTCGGGTCATCTCAAACGATGGAGCCAGCCGCTTCTCTGGA  2580    Exon 19
    841  T  L  P  P  S  R  S  R  V  I  S  N  D  G  A  S  R  F  S  G   860

---------|---------|---------|---------|---------|---------|
   2581  GGCAGCCTCCTCACGACTGGAAGCTCAAGGCGAAACACGTGGTGCAAGCCACAGAAGCTG  2640
    861  G  S  L  L  T  T  G  S  S  R  R  K  H  V  V  Q  A  Q  K  L   880

---------|---------|---------|---------|---------|---------|
   2641  GCGGACGTGGACAGTGAGCTAGCTGCCATGCTACTGACACATGCCCGGCAGGGCAAGGGG  2700    Exon 20
    881  A  D  V  D  S  E  L  A  A  M  L  L  T  H  A  R  Q  G  K  G   900

---------|---------|---------|---------|---------|---------|
   2701  CCTCAGGACGTCTCACTCCGCGAGTCCGATGCCACCCGCAGGCGTAAGCTGGAGCGCATGAGG  2760
    901  P  Q  D  V  S  R  E  S  D  A  T  R  R  R  K  L  E  R  M  R   920

---------|---------|---------|---------|---------|---------|
   2761  TCTGTGCGGCTGCAGGAGGCTGGAGGAGACTTGGCTCGCCGCGGAGAGTGTCTTGCGG  2820
    921  S  V  R  L  Q  E  A  G  G  D  L  G  R  R  G  T  S  V  L  A   940

---------|---------|---------|---------|---------|---------|
   2821  CAGCAGAGCGTCCGCACACAGCACTTGCGGGACCTACAGGTCATCGCCGCCTACCGGGAA  2880    Exon 21
    941  Q  Q  S  V  R  T  Q  H  L  R  D  L  Q  V  I  A  A  Y  R  E   960

---------|---------|---------|---------|---------|---------|
   2881  CGCACGAAGGCCGAGAGCATCGCCAGCCTGCTGAGCCTGGCCATCACCACGGAGCACACG  2940
    961  R  T  K  A  E  S  I  A  S  L  L  S  L  A  I  T  T  E  H  T   980

---------|---------|---------|---------|---------|---------|
   2941  CTCCACGCCACGCTGGGGGTCGCCGAGTTCTTTGAGTTTGTGCTTAAGAACCCCCACAAC  3000
    981  L  H  A  T  L  G  V  A  E  F  F  E  F  V  L  K  N  P  H  N  1000

---------|---------|---------|---------|---------|---------|
   3001  ACACAGCACACGGTGACTGTGGAGATCGACAACCCCGAGCTCAGCGTCATCGTGGACAGT  3060
   1001  T  Q  H  T  V  T  V  E  I  D  N  P  E  L  S  V  I  V  D  S  1020

---------|---------|---------|---------|---------|---------|
   3061  CAGGAGTGGAGGGACTTCAAGTGCGCTGCCTGCCTTCACACACCGGTGGAGGAAGACATG  3120    Exon 22
   1021  Q  E  W  R  D  F  K  C  A  A  C  L  H  T  P  V  E  E  D  M  1040

---------|---------|---------|---------|---------|---------|
   3121  TTTCACCTGCGTGGCTCACTAGCCCCTCAGCTGTACCTGCGCCCACATGAAACCGCCCAC  3180
   1041  F  H  L  R  G  S  L  A  P  Q  L  Y  L  R  P  H  E  T  A  H  1060
```

FIGURE 7 (cont.)

```
       ---------|---------|---------|---------|---------|---------|
3181   GTGCCCTTCAAGTTCCAGAGCTTCTCCGCAGGGCAGCTGGCCATGGTGCAGGCCTCTCCT  3240
1061   V  P  F  K  F  Q  S  F  S  A  G  Q  L  A  M  V  Q  A  S  P   1080

---------|---------|---------|---------|---------|---------|
3241   GGGTTGAGCAACGAGAAGGGCATGGACGCCGTGTCCACCTTGGAAGTCCAGCGCAGTGCCC  3300      Exon 23
1081   G  L  S  N  E  K  G  M  D  A  V  S  P  W  K  S  S  A  V  P   1100

---------|---------|---------|---------|---------|---------|
3301   ACTAAACACGCCAAGCTCTTGTTCCAGCCAGTCCTGCAAGCCCATCCCTGTCTGTGC      3360
1101   T  K  H  A  K  V  L  F  R  A  S  G  G  K  P  I  A  V  L  C   1120      Exon 24

---------|---------|---------|---------|---------|---------|
3361   CTCCTGTCGAGCTGCAGCCCCACGTGGTGGACCAGGTCTTCCGCTTCTATCACCCGGAG    3420
1121   L  T  V  E  L  Q  P  H  V  V  D  Q  V  F  R  F  Y  H  P  E   1140

---------|---------|---------|---------|---------|---------|
3421   CTGCCTTCTGAAGAAGGCTATCCGCTTCCGCCTTGGCACAACTTCAGGTGCTCCG        3480
1141   L  S  F  L  K  K  A  I  R  L  P  P  W  H  T  F  P  G  A  P   1160      Exon 25

---------|---------|---------|---------|---------|---------|
3481   GTGGGAATGCTTGGTGAGGACCCCCCAGTCCATGTTCGCTGCAGCGACCCGAACGTCATC  3540
1161   V  G  M  L  G  E  D  P  P  V  H  V  R  C  S  D  P  N  V  I   1180

---------|---------|---------|---------|---------|---------|
3541   TGTGAGACCCAGAATGTGGGCCCTGGCGAACGCCGACATATTCTTAAGGTCGCTAGT      3600
1181   C  E  T  Q  N  V  G  P  G  E  P  R  D  I  F  L  K  V  A  S   1200      Exon 26

---------|---------|---------|---------|---------|---------|
3601   GGTCCAAGCCGAGAGAAGACCTCTTGTCAGATGTAGTGGATCGCTGGCTGGCG          3660
1201   G  P  S  P  E  I  K  D  F  F  V  I  Y  S  D  R  W  L  A      1220

---------|---------|---------|---------|---------|---------|
3661   ACACCCACACAGACGTGGCAGGTCTACCTCCACTCCCTGCAGCGCGTGGATGTCTCCTGC  3720
1221   T  P  T  Q  T  W  Q  V  Y  L  H  S  L  Q  R  V  D  V  S  C   1240      Exon 27

---------|---------|---------|---------|---------|---------|
3721   GTCGCAGGCCAGCTGACCCGCCTGTCCCTTGTCCTTCGGGGGACACAGACAGTGAGGAAA  3780
1241   V  A  G  Q  L  T  R  L  S  L  V  L  R  G  T  Q  T  V  R  K   1260

---------|---------|---------|---------|---------|---------|
3781   CTCACACCTTTCACCTCTCATCCCCAGGACCTCAACACAGACCCTAAAGCTGTCTTCGTC  3840
1261   V  R  A  F  T  S  H  P  Q  E  I  K  T  D  P  K  G  V  F  V   1280

---------|---------|---------|---------|---------|---------|
3841   CTGCCGCCTCGTGGTGTGCAGGACTTGCATGTGGGTGTGCGCCTTAGGGCTGTAGC       3900      Exon 28
1281   L  P  P  R  G  V  Q  D  L  H  V  G  V  R  P  L  R  A  G  S   1300

---------|---------|---------|---------|---------|---------|
3901   CGCTTCGTCCACCTCAACCTGGTGGACGTGGATTGCCACCAGCTGGTGGCGTCTGGCTG   3960
1301   R  F  V  H  L  N  L  V  D  V  D  C  H  Q  L  V  A  S  W  L   1320

---------|---------|---------|---------|---------|---------|
3961   GTGTGTCTGTGCCGCCAGCCCCTCATTTCAAAGGCCTTTGAGATCATGTTGGCTGCG      4020
1321   V  C  L  C  C  R  Q  P  L  I  S  K  A  F  E  I  M  L  A  A   1340

---------|---------|---------|---------|---------|---------|
4021   GGCGAAGGGAAGGGTGTCAACAAGAGGATCACCTACACCAACCCCTACCCCTCCCGGAGG  4080      Exon 29
1341   G  E  G  K  G  V  N  K  R  I  T  Y  T  N  P  Y  P  S  R  R   1360

---------|---------|---------|---------|---------|---------|
4081   ACATTCCACCTGCACAGCGACCACCCGGAGCTGCTGCGGTTCAGAGAGGACTCCTTCCAG  4140
1361   T  F  H  L  H  S  D  H  P  E  L  L  R  F  R  E  D  S  F  Q   1380

---------|---------|---------|---------|---------|---------|
4141   GTGGGCGGTGGAGAGACCTACACCATCGGCTTGCAGTTCGCCCAGTCAGAGAGTGGGT    4200
1381   V  G  G  G  E  T  Y  T  I  G  L  Q  F  A  P  S  Q  R  V  G   1400      Exon 30

---------|---------|---------|---------|---------|---------|
4201   GAGGAGGAGATCCTGATCTATATCAATGACCATGAGGACAAAAACGAAGAGGCATTTTGC  4260
1401   E  E  E  I  L  I  Y  I  N  D  H  E  D  K  N  E  E  A  F  C   1420
```

FIGURE 7 (cont.)

```
           ---------|---------|-
4261   GTGAAGGTCATCTACCAGTGA   4281
1421   V   K   V   I   Y   Q   *   1426
```

FIGURE 8

```
    GACGCGAGGCGGGTTCTTGCACTGAGTGTGCGGCGCGGTGCGCCGCCTTCCGAGGCTCCTCCCGCGGGTGGCAG      Exon 1
    CGGACGGGGCGCGCCCCTCGGCCAGTCCTCGGTCCTCAGGCTTGTGCGCTCCGTTGAGCACCGGCCGCCGGGCCT
    CTGGGTCCGTCGAGTGGAGACTCTCTGAAAAGCGTGGGCTCCGTGGCCTCCGGCGCGGCCGCGGCGGGCTCGGTC
    TCCTAGAT...
    ----------|----------|----------|----------|----------|----------|
  1 ATGAACGACTGGGAGAGGATCTTCACCCAAAACGTGCTGGTGCCCCCGCACCCACAGAGA       60
  1  M   N   D   W   E   R   I   F   T   Q   N   V   L   V   P   P   H   P   Q   R   20     Exon 2

----------|----------|----------|----------|----------|----------|
 61 GCCCGCCAGCCTTGGAAGGAATCACCGCATTCCAGTGTGTCATCAAGTGGCTGGATGGA    120
 21  A   R   Q   P   W   K   E   S   T   A   F   Q   C   V   I   K   W   L   D   G   40

----------|----------|----------|----------|----------|----------|
121 CCGGTAATTCGCCAGGGCGTGCTGGAGGTACTGTCAGAGGTTGAATGCCATCTGCGAGTG   180
 41  P   V   I   R   Q   G   V   L   E   V   L   S   E   V   E   C   H   L   R   V   60     Exon 3

----------|----------|----------|----------|----------|----------|
181 TCTTTCTTTGATGTCACCTACCGGCACTTCTTTGGGAGGACGTGGAAAACCACAGTGAAG   240
 61  S   F   F   D   V   T   Y   R   H   F   F   G   R   T   W   K   T   T   V   K   80

----------|----------|----------|----------|----------|----------|
241 CCGACGAAGAGACCGCCGTCCAGGATCGTCTTTAATGAGCCGATTTCACAATCC          300
 81  P   T   K   R   P   P   S   R   I   V   F   N   E   P   I   Y   F   H   T   S   100

----------|----------|----------|----------|----------|----------|
301 CTAAATCACCCATATTGTCGTGCTGTACAAAGTGGCGGAGGGCAAGAAACGGAT         360
101  I   N   H   P   E   I   V   A   V   V   E   V   V   A   E   G   K   K   R   D   120    Exon 4

----------|----------|----------|----------|----------|----------|
361 GGCAGCCTCCAGACATTGTCTCTGCGTTTGGAATTCTTCGATCTGTAGCAATCAGCCG     420
121  G   S   L   Q   T   L   S   C   G   F   G   I   L   R   I   F   S   N   Q   P   140

----------|----------|----------|----------|----------|----------|
421 GATTCTCCGATCTCGGCCTCGCAGGATAAAAGGTTGCGGCTGTACCATGGCACCCCCAGA   480    Exon 5
141  D   S   P   I   S   A   S   Q   D   K   R   L   R   L   Y   H   G   T   P   R   160

----------|----------|----------|----------|----------|----------|
481 GCCCTCCTGCACCCGCTTCTCCAGGACCCCGCAGAGCAAAACCGACACATGACCCTCATT   540
161  A   L   L   H   P   L   L   Q   D   P   A   E   Q   N   R   H   M   T   L   I   180

----------|----------|----------|----------|----------|----------|
541 GAGAACTGTAGCTTGCAGTACACGTTAAAGCCACACTCGCCTGAGCCGGCTTCAC        600
181  E   N   C   S   L   Q   Y   T   L   K   P   H   P   A   L   E   P   A   F   H   200    Exon 6

----------|----------|----------|----------|----------|----------|
601 CTTCTTCTCACAATCTTCTCTCTCTTTCACAATATACTCCCTGCTTCACCT             660
201  L   L   P   E   N   L   L   V   S   C   L   Q   Q   I   P   C   L   L   P   A   220

----------|----------|----------|----------|----------|----------|
661 CATGGAGAATCCGGCGACGCTCTCCGAAAGCCTCGCCTCCAGAAGCCCATCACGGGCAC    720
221  H   G   E   S   G   D   A   L   R   K   P   R   L   Q   K   P   I   T   G   H   240    Exon 7

----------|----------|----------|----------|----------|----------|
721 TTGGATGACTTATTCTTCACCCTGTACCCCTCCCTGGAGAAGTTTGAGGAAGAGCTGCTG   780
241  L   D   D   L   F   F   T   L   Y   P   S   L   E   K   F   E   E   E   L   L   260

----------|----------|----------|----------|----------|----------|
781 GAGCTCCACGTCCAGGACCACTTCCAGGAGGGATGTGGCCCACTGGACGGCGCGCTG      840
261  E   L   H   V   Q   D   H   F   Q   E   G   C   G   P   L   D   G   G   A   L   280

----------|----------|----------|----------|----------|----------|
841 GAGATTCTGGAGCGGCGCCTGCGCGTGGGCGTGCATAATGGCCTGGGCTTCGTGCAGCG   900     Exon 8
281  E   I   L   E   R   R   L   R   V   G   V   H   N   G   L   G   F   V   Q   R   300

```
 901 CGGCAGGTCGTGGTACTGGTGCCCGAGATGGATGTGGCCTTGACGCGCTCAGCTAGCTTC  960
 301  P  Q  V  V  V  L  V  P  E  M  D  V  A  L  T  R  S  A  S  F  320

---------|---------|---------|---------|---------|---------|
 961 AGCAGAAAAGTGGTCTCCTCTTCCAAGACAAGCTCCGGGAGCCAAGCTCTGGTTTTGAGA 1020
 321  S  R  K  V  V  S  S  S  K  T  S  S  G  S  Q  A  L  V  L  R  340     Exon 9

---------|---------|---------|---------|---------|---------|
1021 AGCCGCCTCCGCCTCCCAGAGATGGTCGGCCACCCTGCATTTGCGGTCATCTTCCAGCTG 1080
 341  S  R  L  R  L  P  E  M  V  G  H  P  A  F  A  V  I  F  Q  L  360

---------|---------|---------|---------|---------|---------|
1081 GAGTACGTGTTCAGCAGCCCTGCAGGAGTGGACGGCAATGCAGCTTCGGTCACCTCTCTG 1140
 361  E  Y  V  F  S  S  P  A  G  V  D  G  N  A  A  S  V  T  S  L  380     Exon 10

---------|---------|---------|---------|---------|---------|
1141 TCCAACCTGGCATGCATGCACATGGTCCGCTGGGCTGTCTGGAACCCCTTGCTGGAAGCT 1200
 381  S  N  L  A  C  M  H  M  V  R  W  A  V  W  N  P  L  L  E  A  400

---------|---------|---------|---------|---------|---------|
1201 GATTCTGGAAGGGTGACCCTGCCTCTGCAGGGTGGCATTCAGCCTAACCCCTCGCACTGT 1260
 401  D  S  G  R  V  T  L  P  L  Q  G  G  I  Q  P  N  P  S  H  C  420

---------|---------|---------|---------|---------|---------|
1261 CTGGTCTACAAGGTACCCTCAGCCAGCATGAGCTCTGAAGAGGTGAAGCAGGTGGAGTCG 1320
 421  L  V  Y  K  V  P  S  A  S  M  S  S  E  E  V  K  Q  V  E  S  440     Exon 11

---------|---------|---------|---------|---------|---------|
1321 GGTACACTCCGGTTCCAGTTCTCGCTGGGCTCAGAAGAACACCTGGATGCACCCACGGAG 1380
 441  G  T  L  R  F  Q  F  S  L  G  S  E  E  H  L  D  A  P  T  E  460

---------|---------|---------|---------|---------|---------|
1381 CCTGTCAGTGGCCCCAAAGTGGAGCGGCGGCCTTCCAGGAAACCACCCACGTCCCCTTCG 1440
 461  P  V  S  G  P  K  V  E  R  R  P  S  R  K  P  P  T  S  P  S  480

---------|---------|---------|---------|---------|---------|
1441 AGCCCGCCAGCACCAGTACTTGAGTTGTTGCTCCGAGAACTCACCTGTGGGACCA 1500
 481  S  P  P  A  P  V  P  R  V  L  A  A  P  Q  N  S  P  V  G  P  500     Exon 12

---------|---------|---------|---------|---------|---------|
1501 GGCTTGTCAATTTCCCAGCTGGCGGCCTCCCCGCGGTCCCCGACTCAGCACTGCTTGGCC 1560
 501  G  L  S  I  S  Q  L  A  A  S  P  R  S  P  T  Q  H  C  L  A  520     Exon 13

---------|---------|---------|---------|---------|---------|
1561 AGGCCTACTTCACAGCTACCCCATGGCTCTCAGGCCTCCCCGGCCCAGGCAGGGAGTTC 1620
 521  R  P  T  S  Q  L  P  H  G  S  Q  A  S  P  A  Q  A  Q  E  F  540

---------|---------|---------|---------|---------|---------|
1621 CCGTTGGAGGCCGGCATCTCCCACCTGGAAGCCGACCTGAGCCAGACTTCCCTGGTCCTG 1680
 541  P  L  E  A  G  I  S  H  L  E  A  D  L  S  Q  T  S  L  V  L  560     Exon 14

---------|---------|---------|---------|---------|---------|
1681 GAAACATCTATTGCAGAGCAGATACAGGAGCTGCCGTTCACGCCTTTGCATGCCCCTATT 1740
 561  E  T  S  I  A  E  Q  I  Q  E  L  P  F  T  P  L  H  A  P  I  580

---------|---------|---------|---------|---------|---------|
1741 GTTGGCACACAGACACGGAGCTCTGCAGGGCAGCCCTCGAGAGCCTCCATGGTGCTC 1800
 581  V  V  G  T  Q  T  R  S  S  A  G  Q  P  S  R  A  S  M  V  L  600     Exon 15

---------|---------|---------|---------|---------|---------|
1801 CTGCAGTCCTCCGGCTTTCCCGAGATTCTGGATGCCAATAAACAGCCAGCCGAGGCTGTC 1860
 601  L  Q  S  S  G  F  P  E  I  L  D  A  N  K  Q  P  A  E  A  V  620

---------|---------|---------|---------|---------|---------|
1861 AGCGCTACAGAACCTGTGACGTTTAACCCTCAGAAGGAAGAATCAGATTGTCTACAAAGC 1920
 621  S  A  T  E  P  V  T  F  N  P  Q  K  E  E  S  D  C  L  Q  S  640

---------|---------|---------|---------|---------|---------|
1921 AACGAGATGGTGCTACAGTTTCTTGCCTTTAGCAGAGTGGCCCAGGATTGCCGAGGAACA 1980
 641  N  E  M  V  L  Q  F  L  A  F  S  R  V  A  Q  D  C  R  G  T  660     Exon 16
```

FIGURE 8 (cont.)

```
         ---------|---------|---------|---------|---------|---------|
    1981 GCTATGGCCAAGCTGGGGAATCACCTGCCAGTCTACCGCTTCCACCGGAACGACG 2040
     661  S  W  P  K  T  V  Y  F  T  F  Q  F  Y  R  F  P  P  A  T  T  680

---------|---------|---------|---------|---------|---------|
    2041 CCACGATGCAGCTGGTCCAACTGGATGAGGCCTGCCAGCCAGCTCGTGCGCTTACC 2100
     681  P  R  L  Q  L  V  Q  L  D  E  A  C  Q  P  S  S  C  A  L  T  700

---------|---------|---------|---------|---------|---------|
    2101 CACATCCTGGTGCCTGTCAGCAGAGATGGCACCTTTGATGCTGGGTCTCCTGGCTTCCAG 2160
     701  H  I  L  V  P  V  S  R  D  G  T  F  D  A  G  S  P  G  F  Q  720

---------|---------|---------|---------|---------|---------|
    2161 CTGAGGTACATGGTGGGCCCTGGGTTCCTGAAGCCAGGTGAGCGGCGCTGCTTTGCCCGC 2220     Exon 17
     721  L  R  Y  M  V  G  P  G  F  L  K  P  G  E  R  R  C  F  A  R  740

---------|---------|---------|---------|---------|---------|
    2221 TACCTGGCCGTGCAGACCCTGCAGATTGACGTCTGGGACGGAGACTCCCTGCTGCTCATC 2280
     741  Y  L  A  V  Q  T  L  Q  I  D  V  W  D  G  D  S  L  L  L  I  760

---------|---------|---------|---------|---------|---------|
    2281 GGATCTGCTGCCGTCCAGATGAAGCATCTCCTGCGACAAGGCCGCCCTGTTCAGGCC 2340
     761  G  S  A  A  V  Q  M  K  H  L  L  R  Q  G  R  P  A  V  Q  A  780

---------|---------|---------|---------|---------|---------|
    2341 TCCACCGAGCTTGAGGTCGTGGCAACTGAATACGAGCAGGACAACATGGTGGTAAGTGGA 2400    Exon 18
     781  S  H  E  L  E  V  V  A  T  E  Y  E  Q  D  N  M  V  V  S  G  800

---------|---------|---------|---------|---------|---------|
    2401 GACATGCTGGGTTTCGGCCGGGTCAAGCCCATCGGCGTCCACTCGGTGGTGAAGGGCCGG 2460
     801  D  M  L  G  F  G  R  V  K  P  I  G  V  H  S  V  V  K  G  R  820

---------|---------|---------|---------|---------|---------|
    2461 CTGCACCTGACTGTGGCCAACGGGGTCACCCGTGTGAACAGAAAGTGAGAGGTTGTAGC 2520
     821  L  H  L  T  L  A  N  V  G  H  P  C  E  Q  K  V  R  G  C  S  840

---------|---------|---------|---------|---------|---------|
    2521 ACATTGCCACCGTCCAGATCTCGGGTCATCTCAAACGATGGAGCCAGCCGCTTCTCTGGA 2580     Exon 19
     841  T  L  P  P  S  R  S  R  V  I  S  N  D  G  A  S  R  F  S  G  860

---------|---------|---------|---------|---------|---------|
    2581 GGCAGCCTCCTCACGACTGGAAGCTCAAGGCGAAAGCATGTGGTGCAGGCACAGAAGCTG 2640
     861  G  S  L  L  T  T  G  S  S  R  R  K  H  V  V  Q  A  Q  K  L  880

---------|---------|---------|---------|---------|---------|
    2641 GCGGACGTGGACAGTGAGCTGGCTGCCATGCTGACGCACGCCCGGCAGGCAAGGGG 2700    Exon 20
     881  A  D  V  D  S  E  L  A  A  M  L  L  T  H  A  R  Q  G  K  G  900

---------|---------|---------|---------|---------|---------|
    2701 CCCAGGACGTGAGCCGGGAGTCGGATGCCACCCGGAGGCGTAAGCTGGAGCGGATGCGG 2760
     901  P  Q  D  V  S  R  E  S  D  A  T  R  R  R  K  L  E  R  M  R  920

---------|---------|---------|---------|---------|---------|
    2761 TCTGTGCGCCTGCAGGAGGCTGGCGGAGATTTGGGCCGGCGGGGCACCAGCGTGCTGGCG 2820
     921  S  V  R  L  Q  E  A  G  G  D  L  G  R  R  G  T  S  V  L  A  940

---------|---------|---------|---------|---------|---------|
    2821 CAGCAGAGCGTCCGCACACAGCACTTGCGGGACCTACAGGTCATCGCCGCCTACCGGGAA 2880    Exon 21
     941  Q  Q  S  V  R  T  Q  H  L  R  D  L  Q  V  I  A  A  Y  R  E  960

---------|---------|---------|---------|---------|---------|
    2881 CGCACGAAGGCCGAGAGCATCGCCAGCCTGCTGAGCCTGGCCATCACCACGGAGCACACG 2940
     961  R  T  K  A  E  S  I  A  S  L  L  S  L  A  I  T  T  E  H  T  980

---------|---------|---------|---------|---------|---------|
    2941 CTCCACGCCACGCTGGGGGTCGCCGAGTTCTTTGAGTTTGTGCTTAAGAACCCCCACAAC 3000
     981  L  H  A  T  L  G  V  A  E  F  F  E  F  V  L  K  N  P  H  N  1000

```
3001 ACACAGCACACGGTGACTGTGGAGATCGACAACCCCGAGCTCAGCGTCATCGTGGACAGT 3060
1001 T   Q   H   T   V   T   V   E   I   D   N   P   E   L   S   V   I   V   D   S   1020

---------|---------|---------|---------|---------|---------|
3061 CAGGAGTGGAGGGACTTCAAGGGTGCTGCTGGCCTTCACACACCTGTGGAGGAGGACATG 3120    Exon
1021 Q   E   W   R   D   F   K   G   A   A   G   L   H   T   P   V   E   E   D   M   1040    22

---------|---------|---------|---------|---------|---------|
3121 TTCCACCTGCGTGGCAGTCTGCCCCCAGCTCTACCTGCGCCCACACGAGACTGCCCAC 3180
1041 F   H   L   R   G   S   L   A   P   Q   L   Y   L   R   P   H   E   T   A   H   1060

---------|---------|---------|---------|---------|---------|
3181 GTCCCTTCAAGTTCAGCTTCTCTGCAGGGCAGCTGGCTATGGTCCAGGCCTCTCCT 3240    Exon 23
1061 V   P   F   K   F   Q   S   F   S   A   G   Q   L   A   M   V   Q   A   S   P   1080

---------|---------|---------F30↓3272delT--------|---------|---------|
3241 GGGTTGAGCAACGAGAAGGGCATGGACGCCGG-TCACCTTGGAAGTCCAGCGCAGTGCCC 3300
1081 G   L   S   N   E   K   G   M   D   A                                           1100

---------|---------|---------|---------|---------|---------|
3301 ACTAAACACGCCAAGCTCTTGTTCCAGCCACTGTGCAACGCCATCCGCTGTTTC 3360
1101                                                                                 1120    Exon 24

---------|---------|---------|---------|---------|---------|
3361 CTGA
1121
```

FIGURE 9

```
    GACGCGAGGCGGGTTCTTGGACTGAGTGTGCGGCGCGGTGCGCCGCCTTCCGAGGCTCCTCCCGCGG
    GTGGCAGCGGACGGGGCGCGCCCCTCGGCCAGTCCTCGGTCCTCAGGCTTGTGGCTCCGTTGAGCAC    Exon 1
    CGGCCGCCGGGCCTCTGGGTCCGTCGAGTGGAGACTCTCTGAAAAGCGTGGGCTCCGTGGCCTCCGG
    CGCGGCCGCGGCGGGTCGGTCTCCTAGATCACCCCGCGAGCCCGCGGACCCTCAGCCGCGCAGG
    ---------|---------|---------|---------|---------|---------|
  1 ATGAACGACTGGCACAGGATTTCACTCAAAACGTCCTTGTCCTCCCACACCTACAGAAGA           60
  1 M  N  D  W  H  R  I  F  T  Q  N  V  L  V  P  P  H  P  Q  R           20   Exon 2

---------|---------|---------|---------|---------|---------|
 61 GCGCGCCAGCCTTGGAAGGAATCCACGGCATCCAGTGTGTCCTCAAGTGGCTGGACGGA          120
 21 A  R  Q  P  W  K  E  S  T  A  F  Q  C  V  L  K  W  L  D  G           40

---------|---------|---------|---------|---------|---------|
121 CCCGTAATTAGCCACGGCGTGCTGGAGGTACTGTCAGAGGTTGAATGCCATCTGCGAGTG          180
 41 P  V  I  R  Q  G  V  L  E  V  L  S  E  V  E  C  H  L  R  V           60   Exon 3

---------|---------|---------|---------|---------|---------|
181 TCTTTCTTTGATGTCACCTACCGGCACTTCTTTGGGAGGACGTGGAAAACCACAGTGAAG          240
 61 S  F  F  D  V  T  Y  R  H  F  F  G  R  T  W  K  T  T  V  K           80

---------|---------|---------|---------|---------|---------|
241 CCGACGAAGAGACCGCCGTCCAGGATCGTCTTTAATGAGCCTCTGTATTTTCACACATCC          300
 81 P  T  K  R  P  P  S  R  I  V  F  N  E  P  L  Y  F  H  T  S          100

---------|---------|---------|---------|---------|---------|
301 CTAAACCACCCTCATATAGTGGCTGTGGTGGAAGTTGTCGCTGAGGGAAGAAGACGGGAT          360
101 L  N  H  P  H  I  V  A  V  V  E  V  V  A  E  G  K  K  R  D          120   Exon 4

---------|---------|---------|---------|---------|---------|
361 GGGAGCCTCCAGACATTGTCCTGTGGTTTTGGAATTCTTCGGATTTTCAGCAACCAGCCG          420
121 G  S  L  Q  T  L  S  C  G  F  G  I  L  R  I  F  S  N  Q  P          140

---------|---------|---------|---------|---------|---------|
421 GACTCTCCTATCTCTGCTTCCCAGGATAAAACGTTGCGGCTGTACCATGGCACCCCCAGA          480
141 D  S  P  I  S  A  S  Q  D  K  R  L  R  L  Y  H  G  T  P  R          160   Exon 5

---------|---------|---------|---------|---------|---------|
481 GCCCTCCTGCACCCGCTTCTCCAGGACCCCGCAGAGCAAAACAGACACATGACCCTCCTT          540
161 A  L  L  H  P  L  L  Q  D  P  A  E  Q  N  R  H  M  T  L  L          180

---------|---------|---------|---------|---------|---------|
541 GAGAACTGCAGCCTGCAGTACACGCTGAAGCCACACCCGGCGCTGGAGCCTGCGTTCCAC          600
181 E  N  C  S  L  Q  Y  T  L  K  P  H  P  A  L  E  P  A  F  H          200   Exon 6

---------|---------|---------|---------|---------|---------|
601 CTTCTGCCTGAGAACCTGCTGGTGTCTGGCCTGCAGCAGATTCCTGGCCTGCTTCCAGCT          660
201 L  L  P  E  N  L  L  V  S  G  L  Q  Q  I  P  G  L  L  P  A          220

---------|---------|---------|---------|---------|---------|
661 CATGGAGAATCCGGCGACGCTCTCCGAAAGCCTCGCCTCCAGAAGCCCATCACGGGGCAC          720
221 H  G  E  S  G  D  A  L  R  K  P  R  L  Q  K  P  I  T  G  H          240   Exon 7

---------|---------|---------|---------|---------|---------|
721 TTGGATGACTTATTCTTCACCCTGTACCCCTCCCTGGAGAAGTTTGAGGAAGAGCTGCTG          780
241 L  D  D  L  F  F  T  L  Y  P  S  L  E  K  F  E  E  E  L  L          260

---------|---------|---------|---------|---------|---------|
781 GAGCTCCACGTCCAGGACCACTTCCAGGAGGGATGTGGCCCACTGGATGGTGCTCTGG          840
261 E  L  H  V  Q  D  H  F  Q  E  G  C  G  P  L  D  G  A  L            280

---------|---------|---------|---------|---------|---------|
841 GAGATCCTGGAGCGGCGCCTGCGAGTGGGCGTCCACAATGGGCTGGGCTTCGTCCAGAGG          900
281 E  I  L  E  R  R  L  R  V  G  V  H  N  G  L  G  F  V  Q  R          300   Exon 8
```

FIGURE 9 (cont.)

```
           ---------|---------|---------|---------|---------|---------|
      901  CCGCAGGTGGTGGTACTCGTGCCTGAGATGGATGTGGCCTGACGCGCTCAGCTAGCTTC  960
      301  P  Q  V  V  V  L  V  P  E  M  D  V  A  L  T  R  S  A  S  F   320

---------|---------|---------|---------|---------|---------|
      961  AGTAGGAAAGTGGTCTCTTCTAAGACCAGCTCCGGGAGCCAAGCTCTGGTTTTGAGA  1020
      321  S  R  K  V  V  S  S  S  K  T  S  S  G  S  Q  A  L  V  L  R   340      Exon 9

---------|---------|---------|---------|---------|---------|
     1021  AGCCGCCTCCGCCTCCCAGAGATGGTCGGCCACCCTGCATTTGCGGTCATCTTCCAGCTG 1080
      341  S  R  L  R  L  P  E  M  V  G  H  P  A  F  A  V  I  F  Q  L   360

---------|---------|---------|---------|---------|---------|
     1081  GAGTACGTGTTCAGCAGCCCTGCAGGAGTGGACGGCAATGCAGCTTCGGTGACTCTCTG  1140
      361  E  Y  V  F  S  S  P  A  G  V  D  G  N  A  A  S  V  T  S  L   380      Exon 10

---------|---------|---------|---------|---------|---------|
     1141  TCCAACCTGGCATGCATGCACATGGTCCGCTGGGCTGTTGGAACCCCTTGCTGAAGCT  1200
      381  S  N  L  A  C  M  H  M  V  R  W  A  V  W  N  P  L  L  E  A   400

---------|---------|---------|---------|---------|---------|
     1201  GATTCTGGAAGGGTGACTCTGCCTCTCCAAGGTGGAATCCAGCCCAACCCTCGCCACTGT 1260
      401  D  S  G  R  V  T  L  P  L  Q  G  G  I  Q  P  N  P  S  H  C   420

---------|---------|---------|---------|---------|---------|
     1261  CTGGTTTACAAGGTACCGTAGCAGCATGAGCTCTGAAGAGGTGAAGCAGGTGGAGTCG  1320
      421  L  V  Y  K  V  P  S  A  S  M  S  S  E  E  V  K  Q  V  E  S   440      Exon 11

---------|F32||TC1334-1335AA
     1321  GGTACACTCCGGT
      441  G  T  L  R
```

FIGURE 10

```
       GACGCGAGGCGGGTTCTTGGACTGAGTGTGCGGCCGCGGTGCGCCGCCTTCCGAGGCTCCTCCCGCGGGTGGCAG
       CGGACGGGCGCGCCCCTCGGCCAGTCCTCGGTCCTCAGGCTTGTGGCTCCGTTGAGCACCGGCCGCCGGGCCT    Exon 1
       CTGGGTCCGTCGAGTGGACACTCTCTGAAAAGCGTGGGCTCCGTGGCCTCCGGCGCGGCCGCGGCGGGTCGGTC
       TCCTACA··························································
       ---------|---------|---------|---------|---------|---------|
     1 A··································································  60
     1 M  N  D  W  H  R  I  F  T  Q  N  V  L  V  P  P  H  P  Q  R            20    Exon 2

---------|---------|---------|---------|---------|---------|
    61 ································································  120
    21 A  R  Q  P  W  K  E  S  T  A  F  Q  C  V  L  K  W  L  D  C            40

---------|---------|---------|---------|---------|---------|
   121 ·······TTACCACGGCGTGCTGGAGGTACTGTCAGAGGTTGAATGCCATCTGCGAGTG            180
    41 P  V  I  R  Q  G  V  L  E  V  L  S  E  V  E  C  H  L  R  V            60    Exon 3

---------|---------|---------|---------|---------|---------|
   181 TCTTTCTTTGATGTCACCTACCGGCACTTCTTTGGGAGGACGTGGAAAACCACAGTGAAG           240
    61 S  F  F  D  V  T  Y  R  H  F  F  G  R  T  W  K  T  T  V  K            80

---------|---------|---------|---------|---------|---------|
   241 CCGACGAAGAGACCGCCGTCCAGGATCGTCTTTAATGAG·······················         300
    81 P  T  K  R  P  P  S  R  I  V  F  N  E  P  L  Y  F  H  T  S           100

---------|---------|---------|---------|---------|---------|
   301 ················································                      360
   101 L  N  H  P  I  V  A  V  V  E  V  V  A  E  G  K  K  R  D             120    Exon 4

---------|---------|---------|---------|---------|---------|
   361 ·······································································  420
   121 G  S  L  Q  T  L  S  C  G  F  G  I  L  R  I  F  S  N  Q  P           140

---------|---------|---------|---------|---------|---------|
   421 ·······························GTTGCGGCTGTACCATGGCACCCCCAGA           480
   141 D  S  P  I  S  A  S  Q  D  K  R  L  R  L  Y  H  G  T  P  R           160    Exon 5

---------|---------|---------|---------|---------|---------|
   481 GCCCTCCTGCACCCGCTTCTCCAGGACCCCGCAGAGC·························          540
   161 A  L  L  H  P  L  L  Q  D  P  A  E  Q  N  R  H  M  T  L  I           180

---------|---------|---------|---------|---------|---------|
   541 ·······································································  600
   181 E  N  C  S  L  Q  Y  T  L  K  P  H  P  A  L  E  P  A  F  H           200    Exon 6

---------|---------|---------|---------|---------|---------|
   601 ·······································································  660
   201 L  L  P  E  N  L  V  S  G  L  Q  Q  T  P  G  T  L  P  A             220

---------|---------|---------|---------|---------|---------|
   661 ·········GAATCGGCGACGCTCTCCGAAAGCCTCGCCTCCAGAAGCCCATCACGGGGCAC         720
   221 H  G  E  S  G  D  A  L  R  K  P  R  L  Q  K  P  I  T  G  H          240    Exon 7

---------|---------|---------|---------|---------|---------|
   721 TTGGATGACTTATTCTTCACCCTGTACCCCTCCCTGGAGAAGTTTGAGGAAGAGCTGCTG          780
   241 L  D  D  L  F  F  T  L  Y  P  S  L  E  K  F  E  E  E  L  L         260

---------|---------|---------|---------|---------|---------|
   781 GAGCTCCACGTCCAGGACCACTTCCAGGAG········································  840
   261 E  L  H  V  Q  D  H  F  Q  E  G  C  G  P  L  D  G  G  A  L         280

---------|---------|---------|---------|---------|---------|
   841 ·······································································  900
   281 E  I  L  E  R  R  L  R  V  G  V  H  N  G  L  G  F  V  Q  R         300    Exon 8

---------|---------|---------|---------|---------|---------|
   901 ·······································································  960
   301 P  Q  V  V  V  L  V  P  E  M  D  V  A  L  T  R  S  A  S  F         320

---------|---------|---------|---------|---------|---------|
   961 AGCAGGAAAGTGGT·························CTCCGGGAGCCAAGCTCTGGTTTTGAGA    1020
   321 S  R  K  V  V  S  S  S  K  T  S  S  G  S  Q  A  L  V  L  R         340    Exon 9
```

FIGURE 10 (cont.)

```
     ---------|---------|---------|---------|---------|---------|
1021 AGCCGCCTCCGCCTCCCAGAGATGGTCGGCCACCCTGCATTTGCGGTCATCTTCCAGCTG 1080
 341 S  R  L  R  L  P  E  M  V  G  H  P  A  F  A  V  I  F  Q  L  360

---------|---------|---------|---------|---------|---------|
1081 GAGTACGTGTTCAGCAGCCCTGCAGGAGTGGACGGCAATGGAGCTTCGGTGACTCTCTCG 1140
 361 E  Y  V  F  S  S  P  A  G  V  D  G  N  A  A  S  V  T  S  L  380

---------|---------|---------|---------|---------|---------|
1141 TCCAACCTGGCATGCATGCACATGGTCCGCTGGGCTGTTTGGAACCTCTTGCTGGAAGCT 1200
 381 S  N  L  A  C  M  H  M  V  R  W  A  V  W  N  P  L  L  E  A  400

---------|---------|---------|---------|---------|---------|
1201 GATTCTGGAAGGGTGACCCTGCCTCTGCAGGGTGGCATCCAGCCGAACCCTTCGCACTGT 1260
 401 D  S  G  R  V  T  L  P  L  Q  G  G  I  Q  P  N  P  S  H  C  420

---------|---------|---------|---------|---------|---------|
1261 CTGGTCTACAAGGTACCCTCAGCCAGCATGAGCTCTGAAGAGGTGAAGCAGGTGGAGTCG 1320
 421 L  V  Y  K  V  P  S  A  S  M  S  S  E  E  V  K  Q  V  E  S  440

---------|---------|---------|---------|---------|---------|
1321 GGTACACTCCGGTTCCAGTTCTCGCTGGGCTCAGAAGAACACCTGGATGCACCCACGGAG 1380
 441 G  T  L  R  F  Q  F  S  L  G  S  E  E  H  L  D  A  P  T  E  460

---------|---------|---------|---------|---------|---------|
1381 CCTGTCAGTGGCCCCAAAGTGGAGCGGCGGCCTTCCAGGAAACCACCCACGTCCCCTTCG 1440
 461 P  V  S  G  P  K  V  E  R  R  P  S  R  K  P  P  T  S  P  S  480

---------|---------|---------|---------|---------|---------|
1441 AGCCCGCCGGCCCCAGTACCTCGAGTCTTGTGGCCGCGCCAACTCACCTGTGGGACCA 1500
 481 S  P  P  A  P  V  P  R  V  L  A  A  P  Q  N  S  P  V  G  P  500

---------|---------|---------|---------|---------|---------|
1501 GGGTTGTCAATTTCCCAGCTGGCGGCCTCCCCGCGGTCCCCGACTCAGCACTGCTTGGCC 1560
 501 G  L  S  I  S  Q  L  A  A  S  P  R  S  P  T  Q  H  C  L  A  520

---------|---------|---------|---------|---------|---------|
1561 AGGCCTACTTCACAGCTACCCCATGGCTCTCAGGCCTCCCCGGCCCAGGCACAGGAGTTC 1620
 521 R  P  T  S  Q  L  P  H  G  S  Q  A  S  P  A  Q  A  Q  E  F  540

---------|---------|---------|---------|---------|---------|
1621 CCGTTGGAGGCGCTATCTCACTTGGAAGCTGACTTGAGCCAGACCTCCCTCGTCCTC 1680
 541 P  L  E  A  G  I  S  H  L  E  A  D  L  S  Q  T  S  L  V  L  560

---------|---------|---------|---------|---------|---------|
1681 GAACATCAATTGCAACAGTTACAGGAGCTGCCTTTCACGCCTTCATGCCCTATT 1740
 561 E  T  S  I  A  E  Q  L  Q  E  L  P  F  T  P  L  H  A  P  I  580

---------|---------|---------|---------|---------|---------|
1741 GTTGTGGGAACCCAGACCAGGAGCTCTGCAGGGCAGCCCTCGAGAGCCTCCATGGTGCTC 1800
 581 V  V  G  T  Q  T  R  S  S  A  G  Q  P  S  R  A  S  M  V  L  600

---------|---------|---------|---------|---------|---------|
1801 CTGCAGTCCTCCGGCTTTCCCGAGATTCTGGATGCCAATAAACAGCCAGCCGAGGCTGTC 1860
 601 L  Q  S  S  G  F  P  E  I  L  D  A  N  K  Q  P  A  E  A  V  620

---------|---------|---------|---------|---------|---------|
1861 AGCGCTACAGAACCTGTGACGTTTAACCCTCAGAAGGAAGAATCAGATTGTCTACAAAGC 1920
 621 S  A  T  E  P  V  T  F  N  P  Q  K  E  E  S  D  C  L  Q  S  640

---------|---------|---------|---------|--------F60|C1972T-|
1921 AACGAGATGGTGCTACAGTTTCTTGCCTTTAGCAGAGTGGCCCAGGACTGCGA
 641 N  E  M  V  L  Q  F  L  A  F  S  R  V  A  Q  D  C
```

Exon 10

Exon 11

Exon 12

Exon 13

Exon 14

Exon 15

Exon 16

FIGURE 11

```
      GACGCGAGGCGGGTTCTTGGACTGAGTGTGCGGCGCGGTGCGCCGCCTTCCGAGGCTCCTCCCGCGGGTCGCAG          Exon 1
      CGGACGGGGCGCGCCCTCGGCCAGTCCTCGGTCCTCAGGCTTGTCCTTCCGTTGAGCACCGGCCGCCGGGCCT
      CTGGGTCCGTCGAGTGGAGACTCTCTGAAAAGCGTGGGCTCCGTGGCCTCCGGCGCGGCCGCGGCGGGTCGGTC
      TCCTAG[...]

---------|---------|---------|---------|---------|---------|
    1 ATGAA[...]CACTG[...]AACA[...]TCT[...]CT[...]AA[...]CT[...]T[...]CT[...]CT[...]CACT[...]CACA[...]A  60
    1  M  N  D  W  E  R  I  F  T  Q  N  V  L  V  P  P  H  ?  Q  R   20        Exon 2

---------|---------|---------|---------|---------|---------|
   61 GC[...]GC[...]AG[...]T[...]GA[...]GA[...]TC[...]GC[...]CAT[...]C[...]G[...]G[...]CTCA[...]GC[...]GAC[...]A  120
   21  A  R  Q  P  W  K  E  S  T  A  F  Q  C  V  L  K  W  L  D  G   40

---------|---------|---------|---------|---------|---------|
  121 CC[...]GAATAGG[...]AGGCCGTGCTGGAGGTACTGTCAGAGGTTGAATGCCATCTGCGAGTG  180
   41  P  V  I  R  Q  G  V  L  E  V  L  S  E  V  E  C  H  L  R  V   60        Exon 3

---------|---------|---------|---------|---------|---------|
  181 TCTTTCTTTGATGTCACCTACCGGCACTTCTTTGGAGGACGTGGAAAACCACAGTGAAG  240
   61  S  F  F  D  V  T  Y  R  H  F  F  G  R  T  W  K  T  T  V  K   80

---------|---------|---------|---------|---------|---------|
  241 CCGACGAAGAGACCGCCGTCCAGGATCGTCTTTAATGAGC[...]C[...]T[...]A[...]T[...]CACACA[...]C  300
   81  P  T  K  R  P  P  S  R  I  V  F  N  E  P  L  Y  F  H  T  S   100

---------|---------|---------|---------|---------|---------|
  301 C[...]AACGCC[...]T[...]TC[...]CT[...]GT[...]CTGAACTC[...]GC[...]GCT[...]CTCA[...]AAG[...]C[...]AT  360
  101  L  N  H  P  E  I  V  A  V  V  E  V  V  A  E  G  K  K  R  D   120       Exon 4

---------|---------|---------|---------|---------|---------|
  361 G[...]GAG[...]CT[...]CAGAA[...]T[...]T[...]T[...]G[...]T[...]C[...]GAAT[...]CT[...]GAT[...]T[...]AG[...]A[...]A[...]C[...]G  420
  121  G  S  L  Q  T  L  S  C  G  F  G  I  L  R  I  F  S  N  Q  P   140

---------|---------|---------|---------|---------|---------|
  421 GAC[...]C[...]C[...]AT[...]T[...]T[...]C[...]T[...]C[...]AGCACAAA[...]GTTGCGGCTGTACCATGGCACCCCCAGA  480
  141  D  S  P  I  S  A  S  Q  D  K  R  L  R  L  Y  H  C  T  P  R   160       Exon 5

---------|---------|---------|---------|---------|---------|
  481 GCCCTCCTGCACCCGCTTCTCCAGGACCCCGCAGAGCAAA[...]CA[...]AC[...]A[...]CACTCTCATT  540
  161  A  L  L  H  P  L  L  Q  D  P  A  E  Q  N  R  H  M  T  L  I   180

---------|---------|---------|---------|---------|---------|
  541 GAGAA[...]CT[...]CAGCCTGC[...]G[...]TACACGCTGAA[...]GCC[...]C[...]CCGG[...]GCCTGG[...]GCT[...]CTTCCA[...]  600
  181  E  N  C  S  L  Q  Y  T  L  K  P  E  P  A  L  E  P  A  F  F   200       Exon 6

---------|---------|---------|---------|---------|---------|
  601 CT[...]CTTCC[...]AGAA[...]CT[...]CT[...]GC[...]GC[...]G[...]TCT[...]C[...]GCAGA[...]A[...]CC[...]GGCCTGCT[...]CC[...]GCT  660
  201  L  L  P  E  N  L  L  V  S  G  L  Q  Q  I  P  G  L  L  P  A   220

---------|---------|---------|---------|---------|---------|
  661 CA[...]G[...]AGAA[...]T[...]C[...]GCGACGCTCTCCGAAAGCCTCGCCTCCAGAAGCCCATCACGGGGCAC  720
  221  H  G  E  S  G  D  A  L  R  K  P  R  L  Q  K  P  I  T  G  E   240       Exon 7

---------|---------|---------|---------|---------|---------|
  721 TTGGATGACTTATTCTTCACCCTGTACCCCTCCCTGGAGAAGTTTGAGGAAGAGCTGCTG  780
  241  L  D  D  L  F  F  T  L  Y  P  S  L  E  K  F  E  E  E  L  L   260

---------|---------|---------|---------|---------|---------|
  781 GAGCTCCACGTCCAGGACCACTTCCAGGAG[...]G[...]P[...]GC[...]C[...]CT[...]GAC[...]GT[...]G[...]C[...]CTG  840
  261  E  L  H  V  Q  D  H  F  Q  E  G  C  G  P  L  D  G  G  A  L   280

---------|---------|---------|---------|---------|---------|
  841 GAGAT[...]CC[...]GGAGC[...]GGC[...]CC[...]G[...]GCGCGCGG[...]GCACAATGTGCGGCTGCTGCAGGG  900
  281  E  I  L  E  R  R  L  R  V  G  H  N  G  L  G  F  V  Q  R   300       Exon 8

---------|---------|---------|---------|---------|---------|
  901 G[...]G[...]CAGCTC[...]T[...]GCA[...]T[...]GC[...]CT[...]GACAT[...]CAT[...]GT[...]GCCTGAC[...]CG[...]T[...]AGCTAGCTC  960
```

---------|---------|---------|---------|---------|---------|
 961 AGCGGGAAAGTGGTCTCTTCAAGAACAGCTCCGGGAGCCAAGCTCTGGTTTTGAGA 1020
 321 S  R  K  V  V  S  S  S  K  T  S  S  G  S  Q  A  L  V  L  R  340   [Exon 9]

---------|---------|---------|---------|---------|---------|
1021 AGCCGCCTCCGCCTCCCAGAGATGGTCGGCCACCCTGCATTTGCGGTCATCTTCCAGCTG 1080
 341 S  R  L  R  L  P  E  M  V  G  H  P  A  F  A  V  I  F  Q  L  360

---------|---------|---------|---------|---------|---------|
1081 GAGTACGTGTTCAGCAGCCCTGCAGGAGTGGACGGCAATGCAGCTTCCGTCACTTCTTG 1140
 361 E  Y  V  F  S  S  P  A  C  V  D  C  N  A  A  S  V  T  S  L  380   [Exon 10]

---------|---------|---------|---------|---------|---------|
1141 TCAACCTGCATGCATGTCACAGATGGGTGGCTGTTGAACCCTGCTTGAAGCT 1200
 381 S  N  L  A  C  M  H  M  V  R  W  A  V  W  N  P  L  L  E  A  400

---------|---------|---------|---------|---------|---------|
1201 GATTCTGGAACGTGACCCTGCCTCTGCAGGGTGGATCGAGCCAATCCTCTCCGACTCT 1260
 401 D  S  G  R  V  T  L  P  L  Q  G  G  I  Q  P  N  P  S  H  C  420

---------|---------|---------|---------|---------|---------|
1261 CTGGTGTACAAGGTGCCCTCGGCCAGCATGAGCTCTGAAGAGGTGAAGCAGGTGGAGTCG 1320
 421 L  V  Y  K  V  P  S  A  S  M  S  S  E  E  V  K  Q  V  E  S  440   [Exon 11]

---------|---------|---------|---------|---------|---------|
1321 GGTACACTCCGGTTCCAGTTCTCGCTGGGCTCAGAAGAACACCTGGATGCACCCACGGAG 1380
 441 G  T  L  R  F  Q  F  S  L  G  S  E  E  H  L  D  A  P  T  E  460

---------|---------|---------|---------|---------|---------|
1381 CCTGTCAGTGGCCCCAAAGTGGAGCGGCGGCCTTCCAGGAAACCACCCACGTCCCCTTCG 1440
 461 P  V  S  G  P  K  V  E  R  R  P  S  R  K  P  P  T  S  P  S  480

---------|---------|---------|---------|---------|---------|
1441 AGCCCGCCAGCGTCAGTCCTGAGTCTGGCTGCCCGCAGAACTCCCCTGTGGGACCA 1500
 481 S  P  P  A  P  V  P  R  V  L  A  A  P  Q  N  S  P  V  G  P  500   [Exon 12]

---------|---------|---------|---------|---------|---------|
1501 GGGTTGTCAATTTCCCAGCTGGCGGCCTCCCCGCGGTCCCCGACTCAGCACTGCTTGGCC 1560
 501 G  L  S  I  S  Q  L  A  A  S  P  R  S  P  T  Q  H  C  L  A  520   [Exon 13]

---------|---------|---------|---------|---------|---------|
1561 AGGCCTACTTCACAGCTACCCCATGGCTCTCAGGCCTCCCCGGCCCAGGCAGGAGTTC 1620
 521 R  P  T  S  Q  L  P  H  G  S  Q  A  S  P  A  Q  A  Q  F  F  540

---------|---------|---------|---------|---------|---------|
1621 CCGTTGGAGGCAGGTATTTCCCATCTGGAAGCAATCGAGCCAGCTCCCTGGTCCTG 1680   [Exon 14]
 541 P  L  E  A  G  I  S  H  L  E  A  D  L  S  Q  T  S  L  V  L  560

---------|---------|---------|---------|---------|---------|
1681 GAAACATCAATTGCTGAACAGTTACAGGAGCTGCCGTTCACGCCTTTGCATGCCCCATT 1740
 561 E  T  S  I  A  E  Q  L  Q  E  L  P  F  T  P  L  H  A  P  I  580

---------|---------|---------|---------|---------|---------|
1741 GTGGGGGAACCCAGACCAGGAGCTCTGCAGGGCAGCCCTCGAGAGCCTCCATGGTGCTC 1800
 581 V  V  G  T  Q  T  R  S  S  A  G  Q  P  S  R  A  S  M  V  L  600   [Exon 15]

---------|---------|---------|---------|---------|---------|
1801 CTGCAGTCCTCCGGCTTTCCCGAGATTCTGGATGCCAATAAACAGCCAGCCGAGGCTGTC 1860
 601 L  Q  S  S  G  F  P  E  I  L  D  A  N  K  Q  P  A  E  A  V  620

---------|---------|---------|---------|---------|---------|
1861 AGCGCTACAGAACCTGTGACGTTTAACCCTCAGAAGGAAGAATCAGATTGTCTACAAAGC 1920
 621 S  A  T  E  P  V  T  F  N  P  Q  K  E  E  S  D  C  L  Q  S  640

---------|---------|---------|---------|---------|---------|
1921 AACGAGATGGTGCTACAGTTTCTTGCCTTTAGCAGAGTGGCCCAGGACTGTCGAGGAACA 1980
 641 N  E  M  V  L  Q  F  L  A  F  S  R  V  A  Q  D  C  R  G  T  660   [Exon 16]
```

FIGURE 11 (cont.)

```
         ---------|---------|---------|---------|---------|---------|
1981 TLATGCCAAAGACTGTTATTTACCTTCAGTTTACGTTTCCACTCCAGCACT 2040
 661  S   W   P   K   T   V   Y   F   T   F   Q   F   Y   R   F   P   P   A   T   T   680

F461↓C2044T
2041 CCATGA
 681  P   *
```

FIGURE 12

```
   GACGCGAGGCGGGTTCTTGGACTGAGTGTGCGGCGCGGTGCGCCGCCTTCCGAGGCTCCTCCCGCGGGTGGCAG
   CCCACCCCCCGCCCCCTCCCCCACTCCTCCCTCCTCAGCCTTTCTGCCTCCCTTCACCACCCCCCCCCCCCCT        Exon 1
   CTGGGTCCGTCGAGTGGAGACTCTCTGAAAAGCGTGGGCTCCGTGGCCTCCGGCGCGGCCGCGGCGGGTCGGTC
   TCCTAGATCATCGCGAAGCTCACCGCACCCTCAGCGCGCAGG
   ---------|---------|---------|---------|---------|---------|
   1 ATGAACGACTGGCACAGATCTTCACTCAAAACGTGCTGGTCCCTGCCCACCCACAGAGA 60
   1 M  N  D  W  H  R  I  F  T  Q  N  V  L  V  P  P  H  P  Q  R  20        Exon 2

---------|---------|---------|---------|---------|---------|
  61 GCGCGCCAGCCTTGGAAGGAATCGACGGCATTCAGTGTGTCCTCAAGTGGCTCGACGGA 120
  21 A  R  Q  P  W  K  E  S  T  A  F  Q  C  V  L  K  W  L  D  G  40

---------|---------|---------|---------|---------|---------|
 121 CCGGTAATTAGGCAGGGCGTGCTGGAGGTACTGTCAGAGGTTGAATGCCATCTGCGAGTG 180
  41 P  V  I  R  Q  G  V  L  E  V  L  S  E  V  E  C  H  L  R  V  60        Exon 3

---------|---------|---------|---------|---------|---------|
 181 TCTTTCTTTGATGTCACCTACCGGCACTTCTTTGGGAGGACGTGGAAAACCACAGTGAAG 240
  61 S  F  F  D  V  T  Y  R  H  F  F  G  R  T  W  K  T  T  V  K  80

---------|---------|---------|---------|---------|---------|
 241 CCGACGAAGAGACCGCCGTCCAGGATCGTCTTTAATGAGCCGTTGTATTTTCACACATCC 300
  81 P  T  K  R  P  P  S  R  I  V  F  N  E  P  L  Y  F  H  T  S  100

---------|---------|---------|---------|---------|---------|
 301 CTAAACCATCCTCATATCGTGGCTGTGGAAGTGGTGGCAGAGGCAAGAAATCCGAT 360
 101 L  N  H  P  H  I  V  A  V  V  E  V  V  A  E  G  K  K  R  D  120        Exon 4

---------|---------|---------|---------|---------|---------|
 361 GGTAGCCTCCAGACACTGTCTTGTCCTTGAATCTTTGGGATTCAGCAACCAGCCTG 420
 121 G  S  L  Q  T  L  S  C  C  F  C  I  L  R  I  F  S  N  Q  P  140

---------|---------|---------|---------|---------|---------|
 421 GACTCTCCTATCTCTGCTTCCCAGGACAAAAGGTTGCGGCTGTACCATGGCACCCCCAGA 480
 141 D  S  P  I  S  A  S  Q  D  K  R  L  R  L  Y  H  G  T  P  R  160        Exon 5

---------|---------|---------|---------|---------|---------|
 481 GCCCTCCTGCACCCGCTTCTCCAGGACCCCGCAGAGCAAAACAGACATATGACTCTCATT 540
 161 A  L  L  H  P  L  L  Q  D  P  A  E  Q  N  R  H  M  T  L  I  180

---------|---------|---------|---------|---------|---------|
 541 GAGAATTGCAGCCTGCAGTACACTCTCAAGCCTCATCCTGCCCTGCCAGCCTTCCTTCGAC 600
 181 E  N  C  S  L  Q  Y  T  L  K  P  H  P  A  L  P  A  F  H  200        Exon 6

---------|---------|---------|---------|---------|---------|
 601 CTGCTGCCTGAGAACCTTCTGGTGTCGGTCGGAGATACCTGGCTGTTCAGCT 660
 201 L  L  P  E  N  L  L  V  S  G  L  Q  Q  I  P  G  L  L  P  A  220

---------|---------|---------|---------|---------|---------|
 661 CACGGAGAATCGGCGACGCTCTCCGAAAGCCTCGCCTCCAGAAGCCCATCACGGGGCAC 720
 221 H  G  E  S  G  D  A  L  R  K  P  R  L  Q  K  P  I  T  G  H  240        Exon 7

---------|---------|---------|---------|---------|---------|
 721 TTGGATGACTTATTCTTCACCCTGTACCCCTCCCTGGAGAAGTTTGAGGAAGAGCTGCTG 780
 241 L  D  D  L  F  F  T  L  Y  P  S  L  E  K  F  E  E  E  L  L  260

---------|---------|---------|---------|---------|---------|
 781 GAGCTCCACGTCCAGGACCACTTCCAGGAGTGCGGCCCGCTGGACGGCGCGCTCCTC 840
 261 E  L  H  V  Q  D  H  F  Q  E  G  C  G  P  L  D  G  A  L  280

---------|---------|---------|---------|---------|---------|
 841 GAGATCCTCTTCAGGCGGCTGCGTGTTGGCGTGCACAATGGTCTGGCTTCGTGCAGAGG 900
 281 E  I  L  F  R  R  L  R  V  G  V  H  N  G  L  G  F  V  Q  R  300        Exon 8

```
 901 CGGCAGGTCGTGGTACTGGTGCCTGAGATGGATGTGGCCTTGACGCGGTCAGCGAGCTTC  960
 301  P  Q  V  V  V  L  V  P  E  M  D  V  A  L  T  R  S  A  S  F   320

---------|---------|---------|---------|---------|---------|
 961 AGCAGAAAGGTGTCTCTTCAAGACTAGCTCCGGGAGCCAAGCTCTGGTTTTGAGA 1020
 321  S  R  K  V  V  S  S  S  K  T  S  S  G  S  Q  A  L  V  L  R   340     Exon 9

---------|---------|---------|---------|---------|---------|
1021 AGCCGCCTCCGCCTCCCAGAGATGGTCGGCCACCCTGCATTTGCGGTCATCTTCCAGCTG 1080
 341  S  R  L  R  L  P  E  M  V  G  P  A  F  A  V  I  F  Q  L    360

---------|---------|---------|---------|---------|---------|
1081 GAGTACGTGTTCAGCAGCCCTGCAGGAGTGGACGGCAATGCAGCTGCGTCACTGCTGCG 1140
 361  E  Y  V  F  S  S  P  A  G  V  D  G  N  A  A  S  V  T  S  L   380     Exon 10

---------|---------|---------|---------|---------|---------|
1141 TCCAACCTGGCATGCATGCACATGGTCCGTGGGTGTTTGCAACCCCTTGCTGGAAGCT 1200
 381  S  N  L  A  C  M  H  M  V  R  W  A  V  W  N  P  L  L  E  A   400

---------|---------|---------|---------|---------|---------|
1201 GATTTGGAAGGTGTACTCCTTTTGCAGGTGGGATCAGCCTAACTCCTCGCACTGT 1260
 401  D  S  G  R  V  T  L  P  L  Q  G  G  I  Q  P  N  P  S  H  C   420

---------|---------|---------|---------|---------|---------|
1261 CTGCTCTACAAGGTACCTCAGCCAGCATGAGCTCTGAACACGTGAAGCAGGTGGAGTCG 1320
 421  L  V  Y  K  V  P  S  A  S  M  S  S  E  E  V  K  Q  V  E  S   440     Exon 11

---------|---------|---------|---------|---------|---------|
1321 GGTACACTCCGGTTCCAGTTCTCGCTGGGCTCAGAAGAACACCTGGATGCACCCACGGAG 1380
 441  G  T  L  R  F  Q  F  S  L  G  S  E  E  H  L  D  A  P  T  E   460

---------|---------|---------|---------|---------|---------|
1381 CCTGTCAGTGGCCCCAAAGTGGAGCGGCGGCCTTCCAGGAAACCACCCACGTCCCCTTCG 1440
 461  P  V  S  G  P  K  V  E  R  R  P  S  R  K  P  P  T  S  P  S   480

---------|---------|---------|---------|---------|---------|
1441 AGCCCGCCAGCAGTACTTGAGTTTGTGCAGAAACCCACTTTGTAGCCA 1500     Exon 12
 481  S  P  P  A  P  V  P  R  V  L  A  A  P  Q  N  S  P  V  G  P   500

---------|---------|---------|---------|---------|---------|
1501 CTCTTGTCAATTTCCCAGCTGGCGGCCTCCCCGCGGTCCCCGACTCAGCACTGCTTGGCC 1560     Exon 13
 501  C  L  S  I  S  Q  L  A  A  S  P  R  S  P  T  Q  H  C  L  A   520

---------|---------|---------|---------|---------|---------|
1561 AGGCCTACTTCACAGCTACCCCATGGCTCTCAGGCCTCCCCGGCCCAGGCAGGGAGTGC 1620
 521  R  P  T  S  Q  L  P  H  G  S  Q  A  S  P  A  Q  A  Q  E  F   540

---------|---------|---------|---------|---------|---------|
1621 CCGTGGCGAGGCGGCAGCCCCCACTGGAGGCCGACCTGAGCCAGACCTCCCTGGTGCTG 1680     Exon 14
 541  P  L  E  A  G  I  S  H  L  E  A  D  L  S  Q  T  S  L  V  L   560

---------|---------|---------|---------|---------|---------|
1681 GAAACATCGATTGCTGAACAGTTAGAGCTGCCGTTCACGCCTTGCATGCCCCATT 1740
 561  E  T  S  I  A  E  Q  L  E  L  P  F  T  P  L  H  A  P  I   580

---------|---------|---------|---------|---------|---------|
1741 GTTGTCGGAACCCAGACCAGGAGCTCTCCAGGCCACCCCTCGACAGCCTCCATGGTCCTC 1800     Exon 15
 581  V  V  G  T  Q  T  R  S  S  A  G  Q  P  S  R  A  S  M  V  L   600

---------|---------|---------|---------|---------|---------|
1801 CTGCAGTCCTCCGGCTTTCCCGAGATTCTGGATGCCAATAAACAGCCAGCCGAGGCTGTC 1860
 601  L  Q  S  S  G  F  P  E  I  L  D  A  N  K  Q  P  A  E  A  V   620

---------|---------|---------|---------|---------|---------|
1861 AGCGCTACAGAACCTGTGACGTTTAACCCTCAGAAGGAAGAATCAGATTGTCTACAAAGC 1920
 621  S  A  T  E  P  V  T  F  N  P  Q  K  E  E  S  D  C  L  Q  S   640

---------|---------|---------|---------|---------|---------|
1921 AACGAGATGGTGCTACAGTTTCTTGCCTTTAGCAGAGTGGCCCAGGATGCTGAGGAACA 1980
 641  N  E  M  V  L  Q  F  L  A  F  S  R  V  A  Q  D  C  R  G  T   660     Exon 16
```

FIGURE 12 (cont.)

```
         ---------|---------|---------|---------|---------|---------|
   1981  TCATGGCCAAAGCTGTGGATTCCACCTTCCAGTTCTACCGCTTCCCACCCGCAACGACG  2040
    661  S  W  P  K  T  V  Y  F  T  F  Q  F  Y  R  F  P  P  A  T  T    680

---------|---------|---------|---------|---------|---------|
   2041  TCACGACTGCAGCTGGTCCAGCTCGATGAGCGGCCAGCCAGTTCTGGCGCTTACC  2100
    681  P  R  L  Q  L  V  Q  L  D  E  A  G  Q  ?  S  S  G  A  L  T    700

---------|---------|---------|---------|---------|---------|
   2101  CACATCCTCCTCCTCTCACCACAAATCCACCTTCATCGCCCTCCCTGCCTTCCAG  2160
    701  H  I  L  V  P  V  S  R  D  G  T  F  D  A  G  S  P  G  F  Q    720

---------|---------|---------|---------|---------|---------|
   2161  CTGAGGTACATGGTGGGCCCTGGGTTCCTGAAGCCAGGTGAGCGGCGCTGCTTTGCCCGC  2220    Exon 17
    721  L  R  Y  M  V  G  P  G  F  L  K  P  G  E  R  R  C  F  A  R    740

---------|---------|---------|---------|---------|---------|
   2221  TACCTGGCCGTGCAGACCCTGCAGATTGACGTCTGGGACGGAGACTCCCTGCTGCTCATC  2280
    741  Y  L  A  V  Q  T  L  Q  I  D  V  W  D  G  D  S  L  L  L  I    760

---------|---------|---------|---------|---------|---------|
   2281  GGATCTGCTGCCGTCCAGATGAAGCATCTTCTGCGCCAAGCCCGCCCCGTCCAGCC  2340
    761  G  S  A  A  V  Q  M  K  H  L  L  R  Q  G  R  P  A  V  Q  A    780

---------|---------|---------|---------|---------|---------|                  Exon 18
   2341  TCCGAGGACTTGAGGTTGTCGCCAATGAATACGAGCAAGACAATATGGTGGTGAGTGGA  2400
    781  S  E  E  L  E  V  V  A  T  E  Y  E  Q  D  N  M  V  V  S  G    800

---------|---------|---------|---------|---------|---------|
   2401  GACATGCTGGGCTTTGGCCGCGTGAAGCCCATCGGCGTGCACAGTGTGGTGAAGGGCCGC  2460
    801  D  M  L  G  F  G  R  V  K  P  I  G  V  H  S  V  V  K  G  R    820

---------|---------|---------|---------|---------|---------|
   2461  CTGCACCTGACTTTGGCCAACCCGGTCACCCGTGTGAACAGAAAGTGAGAGGTTGTAGC  2520
    821  L  H  L  T  L  A  N  V  G  H  P  C  E  Q  K  V  R  G  C  S    840

---------|-------F461|C2542T-|---------|---------|---------|          Exon 19
   2521  ACATTGCCACCGTCCAGATCTAGGTCATCTCAAACGATGGAGCCAGCCGCTTCTCTGGA  2580
    841  T  L  P  P  S  R  S     V  I  S  N  D  G  A  S  R  F  S  G    860

---------|---------|---------|---------|---------|---------|
   2581  GGCAGCCTCCTCACGACTGGAAGCTCAAGGCGAAAAGAGGTGGTCCAAGCACAGAAACTG  2640
    861  G  S  L  L  T  T  G  S  S  R  R  K  E  V  V  Q  A  Q  K  L    880

---------|---------|---------|---------|---------|---------|          Exon 20
   2641  GCGGACGTGGACAGTGAGCTGGCCGCTATGCTGCTCACGCACGCTCGGCAGGGCAAGGGC  2700
    881  A  D  V  D  S  E  L  A  A  M  L  L  T  H  A  R  Q  G  K  G    900

---------|---------|---------|---------|---------|---------|
   2701  CCCCAGGACGTGAGCCGCGAGTCGGATGCCACCCGCAGGCGAAAGCTGGAGCGGATGAGG  2760
    901  P  Q  D  V  S  R  E  S  D  A  T  R  R  R  K  L  E  R  M  R    920

---------|---------|---------|---------|---------|---------|
   2761  TCAGTGCGCCTGCAGGAAGCAGGCGGCGACCTGGGAAGGCGAGGCACCAGCGTTCTCGCC  2820
    921  S  V  R  L  Q  E  A  G  G  D  L  G  R  R  G  T  S  V  L  A    940

---------|---------|---------|---------|---------|---------|
   2821  CAGCAGAGCGTCCGCACACAGCACTTGCGGGACCTACAGGTCATCGCCGCCTACCGGGAA  2880    Exon 21
    941  Q  Q  S  V  R  T  Q  H  L  R  D  L  Q  V  I  A  A  Y  R  E    960

---------|---------|---------|---------|---------|---------|
   2881  CGCACGAAGGCCGAGAGCATCGCCAGCCTGCTCAGCCTGGCCATCACCACGGAGCACACG  2940
    961  R  T  K  A  E  S  I  A  S  L  L  S  L  A  I  T  T  E  H  T    980

---------|---------|---------|---------|---------|---------|
   2941  CTCCACGCCACGCTGGGGGTCGCCGAGTTCTTTGAGTTTGTGCTTAAGAACCCCCACAAC  3000
    981  L  H  A  T  L  G  V  A  E  F  F  E  F  V  L  K  N  P  H  N   1000

```
3001 ACACAGCACACGGTGACTGTGGAGATCGACAACCCCGAGCTCAGCGTCATCGTGGACAGC 3060
1001  T  Q  H  T  V  T  V  E  I  D  N  P  E  L  S  V  I  V  D  S  1020

3061 CAGGAGTGGAGGGACTTTAAGGGTGCTGCTGGACACACACCTGTGGAGGAGGACATG 3120
1021  Q  E  W  R  D  F  K  G  A  A  G  L  H  T  P  V  E  E  D  M  1040

3121 TTCCATCTCCGTGGCAGCCTGGCCCAGCTGTATCTGCGCCCACGAGACAGCTCAT 3180
1041  F  H  L  R  G  S  L  A  P  Q  L  Y  L  R  P  H  E  T  A  H  1060

3181 GTGCCGTTCAAGTTCCAGTCTTTCAGCGGGCAGATCGCCATGGTCCAGGCCTCTCCT 3240
1061  V  P  F  K  F  Q  S  F  S  A  G  Q  I  A  M  V  Q  A  S  P  1080

3241 GGGTTGAGCAACGAGAAGGGCATGGACGCCGTGTCACCTTGGAAGTCCAGCGCAGTGCCC 3300
1081  G  L  S  N  E  K  G  M  D  A  V  S  P  W  K  S  S  A  V  P  1100

3301 ACTAAACACCCCAAGGTGCTGTTCAGGGCAGGCGGCAAGCCATCGCTGTGCTGTGC 3360
1101  T  K  H  A  K  V  L  F  R  A  S  G  G  K  P  I  A  V  L  C  1120

3361 CTGACTGTGGAGCTTCAGCCTCACGTTGTGGACCAGGTCTTCCGCTTCTATCACCCGGAG 3420
1121  L  T  V  E  L  Q  P  H  V  V  D  Q  V  F  R  F  Y  H  P  E  1140

3421 CTGTCTTTCTGAAGAAGGCCATCCGCTGCCGCCTGCCACACATTCCAGGTGCTCCG 3480
1141  L  S  F  L  K  K  A  I  R  L  P  P  W  H  T  P  G  A  P  1160

3481 GTGGGAATGCTTGGTGAGGACCCCCCAGTCCATGTTCGCTGCAGCGACCCGAACGTCATC 3540
1161  V  G  M  L  G  E  D  P  P  V  H  V  R  C  S  D  P  N  V  I  1180

3541 TGTGAGACCCAGAATGTGGGCCTGCAGGAACCGCGACATATTCTTAAGGTGGCCAGT 3600
1181  C  E  T  Q  N  V  G  P  G  E  P  R  D  I  F  L  K  V  A  S  1200

3601 GGTCCAAGCCCTGAGATAAAGGATTTCTTTGTCATTATTTACAGTGGATCGCTGGCTGGCG 3660
1201  G  P  S  P  E  I  K  D  F  F  V  I  I  Y  S  D  R  W  L  A  1220

3661 ACACCCACACAGACGTGGCAGGTCTACCTCCACTCCCTGCAGCGCGTGGATGTCTCCTGC 3720
1221  T  P  T  Q  T  W  Q  V  Y  L  H  S  L  Q  R  V  D  V  S  C  1240

3721 GTCCCAGGCCAGCTGACCCCCCTCTCCCTTCTCCTTCGCCCGACACAGACACTCACCAAA 3780
1241  V  A  G  Q  L  T  R  L  S  L  V  L  R  G  T  Q  T  V  R  K  1260

3781 GTGAGAGCTTTCACCTCTCATCCCCAGGAGCTGAAGACAGACCCAAAGGGTGTTTGTG 3840
1261  V  R  A  F  T  S  H  P  Q  E  L  K  T  D  P  K  G  V  F  V  1280

3841 CTGCCTCCTCGTGGTGTGCAGGACCTGCATGTGGGCGTCCGCCCTTAGGGCGGGAGC 3900
1281  L  P  P  R  G  V  Q  D  L  H  V  G  V  R  P  L  R  A  G  S  1300

3901 CGCTTCGTCCACCTGAACCTGGTGGATGTGGATTGCCAGCTGGTGGCCTCTGGCTC 3960
1301  R  F  V  H  L  N  L  V  D  V  D  C  H  Q  L  V  A  S  W  L  1320

3961 GTGTGCTGTGTGCCGTCAGCCTCATTTCCAAGGCCTTTGAGATCATGTTGGCTGCG 4020
1321  V  C  L  C  C  R  Q  P  L  I  S  K  A  F  E  I  M  L  A  A  1340

4021 GGCGAAGGGAAGGTGTCAACAAGAGGATCACCTACACCAACCCCTACCCCTCCCGGAGG 4080
1341  G  E  G  K  G  V  N  K  R  I  T  Y  T  N  P  Y  P  S  R  R  1360
```

Exon 22

Exon 23

Exon 24

Exon 25

Exon 26

Exon 27

Exon 28

Exon 29

FIGURE 12 (cont.)

```
         ---------|---------|---------|---------|---------|---------|
4081 ACATTCCACCTGCACAGCGACCACCCGGAGCTGCTGCGGTTCAGAGAGGACTCCTTCCAG 4140
1361  T  F  H  L  H  S  D  H  P  E  L  L  R  F  R  E  D  S  F  Q  1380

---------|---------|---------|---------|---------|---------|
4141 GTGGGGGGAGAGACCTACACCATCGGCTTGCAGTTTGCGCTAGTGAGAGTGGGT       4200
1381  V  G  G  G  E  T  Y  T  I  G  L  Q  F  A  P  S  Q  R  V  G  1400      Exon 30

```
     GACGCGAGGCGGGTTCTTGGACTGAGTGTGCGGCGCGGTGCGCCGCCTTCCGAGGCTCCTCCCGCGGGTGGCAG
     CGGACGGGGCGCGCCCTCGGCCAGTCCTCGGTCCTCAGGCTTGTGGCTCCGTTGAGCACCGGCCGCCGGCCT      Exon 1
     CTGGGTCCGTCGAGTGGAGACTCTCTGAAAAGCGTCGGCTCCGTGGCCTCCGGCGCGGCCGCGGCGGGTCGGTC
     TCCTAGATCACCGGGAAGCCGCGGGACCCTCAGCCGGGCAGG
     ---------|---------|---------|---------|---------|---------|
   1 ATGAACGACTGGCACACGATCTTCACCCAAAACGTGCTGGTGCCTCCACACCACAGAGA  60
   1 M  N  D  W  H  R  I  F  T  Q  N  V  L  V  P  P  H  P  Q  R   20          Exon 2

---------|---------|---------|---------|---------|---------|
  61 GGCGCCAGCCTGGAAGAATCCACGGCATCTAGTGTGCTCAAGTGGCTGGACGGA       120
  21 A  R  Q  P  W  K  E  S  T  A  F  Q  C  V  L  K  W  L  D  G   40

---------|---------|---------|---------|---------|---------|
 121 CCGGTAATTAGGCAGGGCGTGCTGGAGGTACTGTCAGAGGTTGAATGCCATCTGCGAGTG 180
  41 P  V  I  R  Q  G  V  L  E  V  L  S  E  V  E  C  H  L  R  V   60          Exon 3

---------|---------|---------|---------|---------|---------|
 181 TCTTTCTTTGATGTCACCTACCGGCACTTCTTTGGGAGGACGTGGAAAACCACAGTGAAG 240
  61 S  F  F  D  V  T  Y  R  H  F  F  C  R  T  W  K  T  T  V  K   80

---------|---------|---------|---------|---------|---------|
 241 CCGACGAAGAGACCGCCGTCCAGGATCGTCTTTAATGAGCCTCTTTATTTTCACACATCC 300
  81 P  T  K  R  P  P  S  R  I  V  F  N  E  P  L  Y  F  H  T  S  100

---------|---------|---------|---------|---------|---------|
 301 CTAAACCACCCTGAAATCGTAGCTGTTGTGGAAGTGGTCGCGGAAGGAAAGAAGCGGGAT 360
 101 L  N  H  P  E  I  V  A  V  V  E  V  V  A  E  G  K  K  R  D  120          Exon 4

---------|---------|---------|---------|---------|---------|
 361 GGCAGCCTCCAGACACTGTCCTGTGGCTTTGGAATTCTTCGGATCTTCAGCAACCAGCCG 420
 121 G  S  L  Q  T  L  S  C  G  F  G  I  L  R  I  F  S  N  Q  P  140

---------|---------|---------|---------|---------|---------|
 421 GACTCTCCTATTTCGGCTTCACAGGACAAAAGGTTGCGGCTGTACCATGGCACCCCCAGA 480     Exon 5
 141 D  S  P  I  S  A  S  Q  D  K  R  L  R  L  Y  F  G  T  P  R  160

---------|---------|---------|---------|---------|---------|
 481 GCCCTCCTGCACCCGCTTCTCCAGGACCCCGCAGAGCAAAACAGAGAATGACTCTCATT  540
 161 A  L  L  H  P  L  L  Q  D  P  A  E  Q  N  R  E  M  T  L  I  180

---------|---------|---------|---------|---------|---------|
 541 GAGAACTGCAGCCTGCAGTACACGCTGAAGCCACACCCGGCCCTGGAGCCTGCTTTCCAC 600     Exon 6
 181 E  N  C  S  L  Q  Y  T  L  K  P  H  P  A  L  E  P  A  F  H  200

---------|---------|---------|---------|---------|---------|
 601 CTCCTGCCGGAGAACCTCTGGTGCTCGTCTCAGGAGATACCAGGCTTGCTTCCAGCT     660
 201 L  L  P  E  N  L  L  V  S  G  L  Q  Q  I  P  G  L  L  P  A  220

---------|---------|---------|---------|---------|---------|
 661 CATGGAGAATCTGGCGACGCTCTCCGAAAGCCTCGCCTCCAGAAGCCCATCACGGGGCAC 720
 221 H  G  E  S  G  D  A  L  R  K  P  R  L  Q  K  P  I  T  G  H  240          Exon 7

---------|---------|---------|---------|---------|---------|
 721 TTGGATGACTTATTCTTCACCCTGTACCCCTCCCTGGAGAAGTTTGAGGAAGAGCTGCTG 780
 241 L  D  D  L  F  F  T  L  Y  P  S  L  E  K  F  E  E  E  L  L  260

---------|---------|---------|---------|---------|---------|
 781 GAGCTCCACGTCCAGGACCACTTCCAGGAGGGATGTGGACCTTTGGACGGTGCCCTGCTG 840
 261 E  L  H  V  Q  D  H  F  Q  E  G  C  G  P  L  D  G  A  L    280

---------|---------|---------|---------|---------|---------|
 841 GAGATCCTGGAGCGCCGCCTGCGCGTGGGCGTCCACAACGGTCTGGGCTTCGTCCAGCGG 900     Exon 8
 281 E  I  L  E  R  R  L  R  V  G  V  H  N  G  L  G  F  V  Q  R  300

---------|---------|---------|---------|---------|---------|
 901 CGCTAGCTCGTCCTGTCGCTCCAGATCGATGTGGCTTACGGCGTAGCTAGCTTC        960
```

---------|---------|---------|---------|---------|---------|
 961 ACGAGGAAACTGTGTCCTCTGCAAAGCACCTCCCGCACCCAACCTCTGCTTTTCACA 1020
 321 S  R  K  V  V  S  S  S  K  T  S  S  G  S  Q  A  L  V  L  R  340    Exon 9

---------|---------|---------|---------|---------|---------|
1021 AGCCGCCTCCGCCTCCCAGAGATGGTCGGCCACCCTGCATTTGCGGTCATCTTCCAGCTG 1080
 341 S  R  L  R  L  P  E  M  V  G  H  P  A  F  A  V  I  F  Q  L  360

---------|---------|---------|---------|---------|---------|
1081 GAGTACGTGTTCAGCAGCCCTGCAGGAGTGGACGGCAATGCAGCTTCGGTCACCTCTCTG 1140
 361 E  Y  V  F  S  S  P  A  G  V  D  G  N  A  A  S  V  T  S  L  380    Exon 10

---------|---------|---------|---------|---------|---------|
1141 TCAACCTGGCATGCATGCACATGGTGCGGTGGGCTGTTGAACCCTTGCTGGAAGCT 1200
 381 S  N  L  A  C  M  H  M  V  R  W  A  V  W  N  P  L  L  E  A  400

---------|---------|---------|---------|---------|---------|
1201 GATTCTGCAAGCGTCACCCTGCCTCTGCAGTGTTGTCTAGCCCAATCCCTGCACTGT 1260
 401 D  S  C  R  V  T  L  P  L  Q  C  C  I  Q  P  N  P  S  H  C  420

---------|---------|---------|---------|---------|---------|
1261 CTGGTCTACAAGGTGCCTTCGGCCTCCATGAGTTCTGAGGAGGTGAAGCAGGTGGAGTCG 1320
 421 L  V  Y  K  V  P  S  A  S  M  S  S  E  E  V  K  Q  V  E  S  440    Exon 11

---------|---------|---------|---------|---------|---------|
1321 GGTACACTCCGGTTCCAGTTCTCGCTGGGCTCAGAAGAACACCTGGATGCACCCACGGAG 1380
 441 G  T  L  R  F  Q  F  S  L  G  S  E  E  H  L  D  A  P  T  E  460

---------|---------|---------|---------|---------|---------|
1381 CCTGTCAGTGGCCCCAAAGTGGAGCGGCGGCCTTCCAGGAAACCACCCACGTCCCCTTCG 1440
 461 P  V  S  G  P  K  V  E  R  R  P  S  R  K  P  P  T  S  P  S  480

---------|---------|---------|---------|---------|---------|
1441 AGCCCGCCAGCCCAGTGCCTGGAGTCTGCTGCCCCAGAACTCTCCTGTGGGACCA 1500    Exon 12
 481 S  P  P  A  P  V  P  R  V  L  A  A  P  Q  N  S  P  V  G  P  500

---------|---------|---------|---------|---------|---------|
1501 GGGTTGTCAATTTCCCAGCTGGCGGCCTCCCCGCGGTCCCCGACTCAGCACTGCTTGGCC 1560    Exon 13
 501 G  L  S  I  S  Q  L  A  A  S  P  R  S  P  T  Q  H  C  L  A  520

---------|---------|---------|---------|---------|---------|
1561 AGGCCTACTTCACAGCTACCCCATGGCTCTCAGGCCTCCCCGGCCCAGGCAGAGGAGTTT 1620
 521 R  P  T  S  Q  L  P  H  G  S  Q  A  S  P  A  Q  A  E  F  540

---------|---------|---------|---------|---------|---------|
1621 CTGTTGGAGGCGGTATTTCTAACCTGAAGTCGAACTGAGCAGACTGCCTGCTCTT 1680    Exon 14
 541 P  L  E  A  G  I  S  H  L  E  A  D  L  S  Q  T  S  L  V  L  560

---------|---------|---------|---------|---------|---------|
1681 GAAACAGCCATCGCGAACAGTTACAGGAGCTGCCGTTCACGCCTTGCATGCCCTATT 1740
 561 E  T  S  I  A  E  Q  L  Q  E  L  P  F  T  P  L  H  A  P  I  580

---------|---------|---------|---------|---------|---------|
1741 GTGGTGGGAACCCAGACCAGGAGCTCTGCAGGGCAGCCCTCGAGAGCCTCCATGGTGCTC 1800    Exon 15
 581 V  V  G  T  Q  T  R  S  S  A  G  Q  P  S  R  A  S  M  V  L  600

---------|---------|---------|---------|---------|---------|
1801 CTGCAGTCCTCCGGCTTTCCCGAGATTCTGGATGCCAATAAACAGCCAGCCGAGGCTGTC 1860
 601 L  Q  S  S  G  F  P  E  I  L  D  A  N  K  Q  P  A  E  A  V  620

---------|---------|---------|---------|---------|---------|
1861 AGCGCTACAGAACCTGTGACGTTTAACCCTCAGAAGGAAGAATCAGATTGTCTACAAAGC 1920
 621 S  A  T  E  P  V  T  F  N  P  Q  K  E  E  S  D  C  L  Q  S  640

---------|---------|---------|---------|---------|---------|
1921 AACGAGATGGTGCTACAGTTTCTTGCCTTTAGCAGAGTTGCCCAGGACTGCCGGGCACA 1980
 641 N  E  M  V  L  Q  F  L  A  F  S  R  V  A  Q  D  C  R  G  T  660    Exon 16
```

FIGURE 13 (cont.)

```
      ---------|---------|---------|---------|---------|---------|
1981  TNATGTCNAAGNATCTGTATTTNACCTTCAGTTCTACTGCTTCCACTCCAACCACC 2040
 661  S  W  P  K  T  V  Y  F  T  F  Q  F  Y  R  F  P  P  A  T  T   680

---------|---------|---------|---------|---------|---------|
2041  CCNCGACTGNAGCTGNTCAGNTGANGNAGCNCGNCAGCCNACTCTGCNGCNCTGACN 2100
 681  P  R  L  Q  L  V  Q  L  D  E  A  C  Q  P  S  S  C  A  L  T   700

---------|---------|---------|---------|---------|---------|
2101  CACANCCTCGTGCCNGNCAGCAGAGANGGCACCTTCGANGCNGGTCTCCTGGCTTCCAG 2160
 701  H  I  L  V  ?  V  S  R  D  G  T  F  D  A  G  S  P  G  F  Q   720

---------|---------|---------|---------|---------|---------|
2161  CTGAGGTACATGGTGGGCCCTGGGTTCCTGAAGCCAGGTGAGCGGCGCTGCTTTGCCCGC 2220     Exon 17
 721  L  R  Y  M  V  G  P  G  F  L  K  P  G  E  R  R  C  F  A  R   740

---------|---------|---------|---------|---------|---------|
2221  TACCTGGCCCTGCAGACCCTGCAGATTGACGTCTGGGACGGAGACTCCCTGCTGCTCATC 2280
 741  Y  L  A  V  Q  T  L  Q  I  D  V  W  D  G  D  S  L  L  L  I   760

---------|---------|---------|---------|---------|---------|
2281  GGATCTGCTGCCGTCCAGATGAAGCNTCTCNTNCGNCAGGCNCGCCGGCTGTGCNAGGC 2340
 761  G  S  A  A  V  Q  M  K  H  L  L  R  Q  G  R  P  A  V  Q  A   780

---------|---------|---F622↓G2368T-----|---------|---------|             Exon 18
2341  TCCCACGNGGTNGANGTNGTNGCNAACTNAA
 781  S  H  E  L  E  V  V  A  T  *
```

Figure 14

Nucleotide sequence:

```
   1 ggttgctccc ggttgctaag aagactatga acaagtcaga gaacctgctg tttgctggtt
  61 catcattagc atcacaagtc catgctgctg ccgttaatgg agataagggt gctctacaga
 121 ggctcatcgt aggaaactct gctcttaaag acaagaaga tcagtttggg agaacaccac
 181 ttatgtattg cgtgttggct gacagattgg attgtgcaga tgctcttctg aaggcaggag
 241 cagatgtgaa taaaactgac catagccaga gaacagccct ccatcttgca gcccagaagg
 301 gaaattatcg tttcatgaaa ctcttactta cacgcagagc aaactggatg caaaaggatc
 361 tggaagagat gactcctttg cacttgacca cccggcacag gagccctaag tgtttggcac
 421 ttctgctgaa gtttatggca ccaggagaag tggatacaca ggataaaaac aagcaaacag
 481 ctctgcattg gagtgcctac tacaataacc ctgagcatgt gaagctgctc atcaagcatg
 541 attctaacat tgggattcct gatgttgaag gcaagatccc acttcactgg gcagccaacc
 601 ataaagatcc aagtgctgtt cacacagtga gatgcattct ggatgctgct ccaacagagt
 661 ctttactgaa ctggcaagac tacgagggtc gaactcctct tcactttgca gttgctgatg
 721 ggaatgtgac cgtggttgat gtcttgacct catatgaaag ctgcaatata acgtcttatg
 781 ataacttatt tcgaaccca ctgcactggg cagctttatt aggccatgca cagattgtcc
 841 atctcctttt agaaagaaat aagtctggaa ctatcccatc tgacagccaa ggagccacac
 901 ctttgcacta tgctgctcag agtaactttg ctgaaacggt taaagtgttt ttaaaacatc
 961 cttcagtgaa agatgattca gacctggaag gaagaacatc ctttatgtgg gcagctggca
1021 aaggcagtga tgatgtcctt agaactatgc tgagcttaaa atcggacata gatattaaca
1081 tggctgacaa atatggaggt acagctttgc atgctgctgc tctttctggc catgtcagca
1141 ccgtgaagtt attactggaa aataatgctc aagtagatgc tactgatgtt atgaaacata
1201 ctccactttt ccgagcctgt gagatgggac acaaagatgt gattcagaca ctcattaaag
1261 gtggagcaag ggtagatcta gttgaccaag atggacattc tcttctacat tgggcagcac
1321 tgggaggaaa tgctgatgtt tgccagatat aatagaaaa taagatcaat ccaaatgtcc
1381 aggattatgc aggaagaacc cctttgcagt gtgcagcata tggaggctat atcaactgca
1441 tggcagttct catggaaaac aatgcagacc ctaacattca agacaaagag ggaagaacag
1501 ctttgcattg gtcctgcaac aatggatacc ttgatgccat taaattactg ctagactttg
1561 ctgctttccc taatcagatg gaaaacaatg aagagagata cacacccctt gattatgctt
1621 tgcttggtga gcgccatgaa gtgatccagt tcatgttgga gcacggtgcc ctgtccatcg
1681 cagccataca agacatcgcc gccttcaaaa tccaagctgt ctacaaaggg tacaaggtca
1741 gaaaagcctt ccgagacagg aaaaatctcc tcatgaagca tgaacagttg agaaaagatg
1801 ctgctgccaa aaagcgagag aagaaaaaca acgaaaaga ggcagaacag caaaaaggaa
1861 ggcggagccc agattcctgc agacccagg cccttccctg tctgcctagc acccaggatg
1921 tgcccagcag gcagagccgg gccccagca agcagcctcc tgctggcaac gtggcccaag
1981 gccctgagcc aagagacagc agaggatctc caggagggtc tctaggcgga gccctccaga
2041 aggagcagca tgttcctca gatttgcagg gaacaaactc cagaaggcca aatgaaacag
2101 ccagagaaca ttctaaaggc caatctgctt gtgtccactt cagaccaat gaaggcagtg
2161 atggaagcag gcatccagca gttccctctg ttgagaagtc cagaggtgag acagctggcg
2221 atgagcggtg tgcaaagggg aaaggtttcg tgaagcagcc ctcctgtatc agggtggctg
2281 ggcctgatga aaaggagag gactccaggc gggcaggtgc aagccttcca ccgcacgata
2341 gccactggaa gcccagcagg cggcatgaca cagaacccaa ggccaaatgt gcccccccaga
2401 aaggcgcac tcaagagctc agaggaggaa ggtgctctcc ggctggttct agccgccctg
2461 gcagtgcccg gggggaggcg gtccatgctg ggcagaatcc tccccaccat cgtacaccaa
2521 gaaacaaagt gacacaagcc aagctcacag gagggctcta ttcacatttg ccacagagca
2581 cagaggagtt gaggtcagga gctaggaggc tggagacatc taccctgtcc gaggactttc
2641 aggtatctaa ggagactgat ccagcacctg gtccctctc tgggcagagt gtgaatattg
2701 accttctccc cgtagagctc cgactgcaga taattcagag agaacgaagg aggaaggagc
2761 tgtttcgcaa aaagaacaag gcagcagcag tcatccagcg cgcctggcga agctaccagc
2821 tcaggaagca cctgtcccac cttcggcata tgaagcagct tggagctgga gatgtggaca
```

FIGURE 14 (cont.)

```
2881 gatggaggca agagtctaca gcattgctcc tccaggtttg gaggaaggaa ctggaactaa
2941 aattcccca  aaccactgca gtaagcaagg cccccaagag tccatccaag ggcacctcag
3001 gcacaaagtc caccaagcac tcagtgctta agcaaatcta tggttgttct cacgaaggga
3061 aaatacatca tcctacaaga tctgtaaaag cctcttctgt gctgcgtctc aactcagtga
3121 gcaacctaca gtgtatacat ctccttgaga acagtggaag atcaaagaac ttttcttata
3181 acctgcaatc agctactcag ccaaaaaaca aaacaaaacc ttgactgcct atggaggaag
3241 actgtgttcg ggggagctgg catagctagt gcagagttca gattttctgc tgataatctt
3301 ttacaccttg ggaaaacttt aatatccgta cctgaaggct gattcaccta aaaatgtgtt
3361 aactgaaaga aaatgtcaga atgtttcctt tctgctctta cacagcattg ttttgtcaat
3421 caacacagcc tgcactgaaa ggacctgcat agactatgtc tgtgcaaagt gcctgagtgt
3481 ctgctttcac ctcagtctgt acagttggaa atgagaattc ataattaaca gcaaaatcta
3541 aggaaaacta aaataaaa
```

Amino acid sequence:

MNKSENLLFAGSSLASQVHAAAVNGDKGALQRLIVGNSALKDKE

DQFGRTPLMYCVLADRLDCADALLKAGADVNKTDHSQRTALHLAAQKGNYRFMKLLLT

RRANWMQKDLEEMTPLHLTTRHRSPKCLALLLKFMAPGEVDTQDKNKQTALHWSAYYN

NPEHVKLLIKHDSNIGIPDVEGKIPLHWAANHKDPSAVHTVRCILDAAPTESLLNWQD

YEGRTPLIIFAVADGNVTVVDVLTSYESCNITSYDNLFRTPLIIWAALLGIIAQIVIILLE

RNKSGTIPSDSQGATPLHYAAQSNFAETVKVFLKHPSVKDDSDLEGRTSFMWAAGKGS

DDVLRTMLSLKSDIDINMADKYGGTALHAAALSGHVSTVKLLLENNAQVDATDVMKHT

PLFRACEMGHKDVIQTLIKGGARVDLVDQDGHSLLHWAALGGNADVCQILIENKINPN

VQDYAGRTPLQCAAYGGYINCMAVLMENNADPNIQDKEGRTALHWSCNNGYLDAIKLL

LDFAAFPNQMENNEERYTPLDYALLGERHEVIQFMLEHGALSIAAIQDIAAFKIQAVY

KGYKVRKAFRDRKNLLMKHEQLRKDAAAKKREEENKRKEAEQQKGRRSPDSCRPQALP

CLPSTQDVPSRQSRAPSKQPPAGNVAQGPEPRDSRGSPGGSLGGALQKEQHVSSDLQG

TNSRRPNETAREHSKGQSACVHFRPNEGSDGSRHPGVPSVEKSRGETAGDERCAKGKG

FVKQPSCIRVAGPDEKGEDSRRAGASLPPHDSHWKPSRRHDTEPKAKCAPQKRRTQEL

RGGRCSPAGSSRPGSARGEAVHAGQNPPHHRTPRNKVTQAKLTGGLYSHLPQSTEELR

SGARRLETSTLSEDFQVSKETDPAPGPLSGQSVNIDLLPVELRLQIIQRERRRKELFR

KKNKAAAVIQRAWRSYQLRKIILSIILRIIMKQLGAGDVDRWRQESTALLLQVWRKELELK

FPQTTAVSKAPKSPSKGTSGTKSTKHSVLKQIYGCSHEGKIHHPTRSVKASSVLRLNS

VSNLQCIHLLENSGRSKNFSYNLQSATQPKNKTKP

Figure 16

Nucleotide sequence:

C2695T

Amino Acid sequence:

Nucleotide sequence:

1453delC

Amino Acid sequence:

Q485fsX509

Figure 18

Nucleotide sequence:

C1807T

Amino Acid sequence:

Nucleotide sequence:

C1186T

Amino Acid sequence:

Nucleotide sequence:

C1445G

Amino Acid sequence:

Nucleotide sequence:

2908delG

Amino Acid sequence:

E970fsX971

Figure 22

Nucleotide sequence:

C2719T

Amino Acid sequence:

Nucleotide sequence:

C2719T

Amino Acid sequence:

Nucleotide sequence:

2747insA

Amino Acid sequence:

K916fsX1002

Figure 25

Nucleotide sequence:

T1478C

Amino Acid sequence:

Figure 35
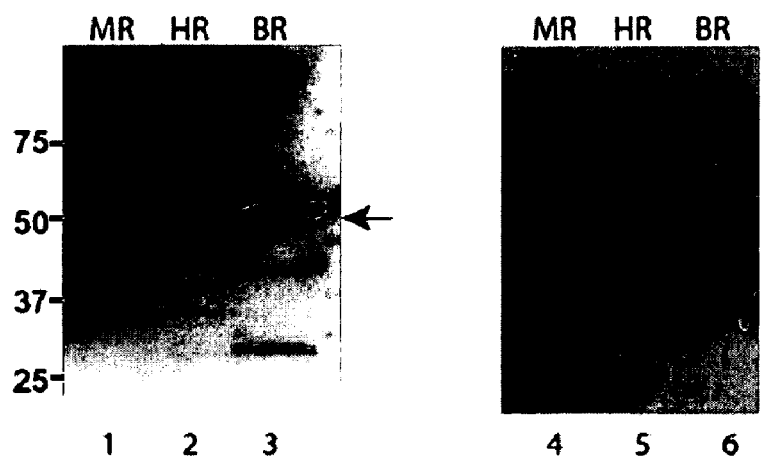
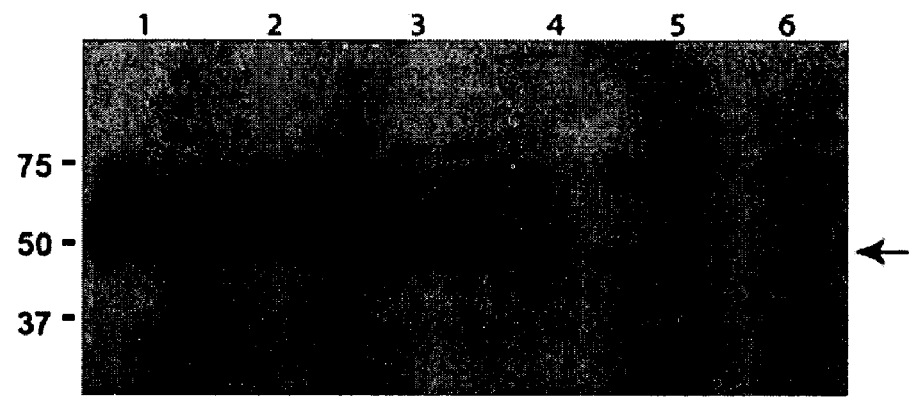

Figure 36
a
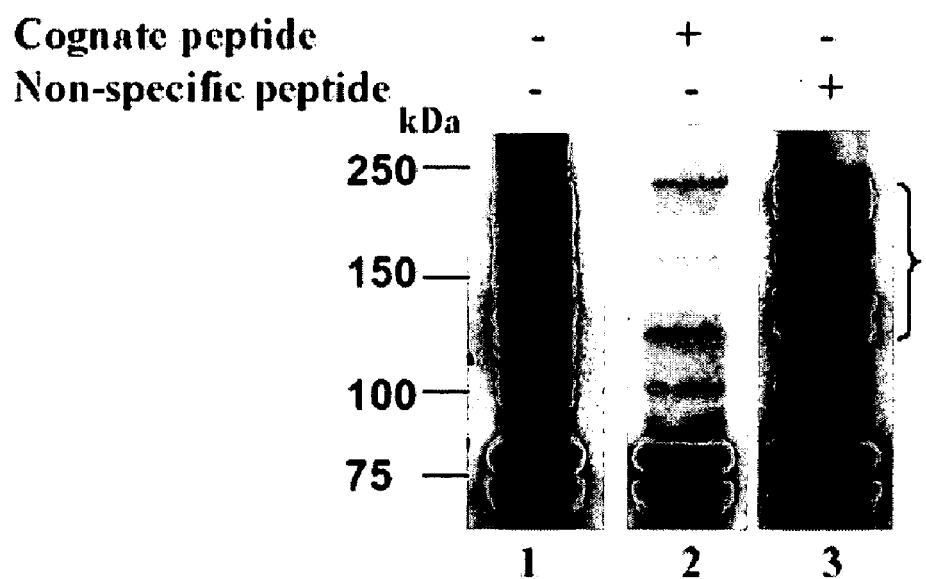
b
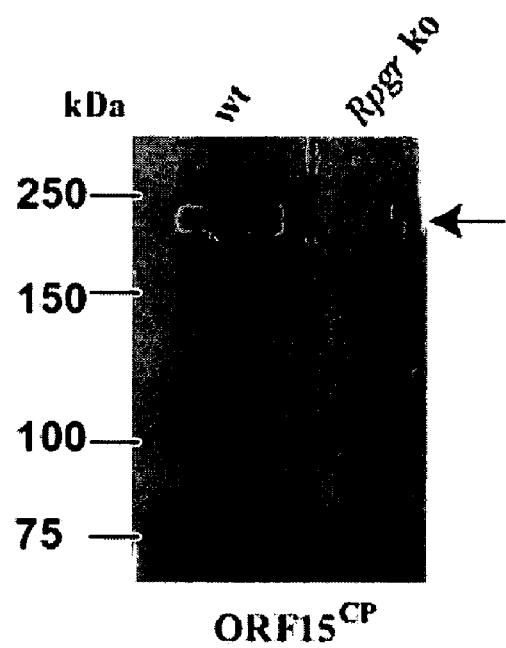
ORF15$^{CP}$

Figure 37

```
SEQ ID NO:82:

MKPTGTDPRILSIAAEVAKSPEQNVPVILLKLKEIINITPLGSSELKKIKQDIYCYDLIQYCLLVLSQDYSRIQGGWTTISQL
TQILSHCCVGLEPGEDAEEFYNELLPSAAENFLVLGRQLQTCFINAAKAEEKDELLHFFQIVTDSLFWLLGGHVELIQNVLQS
DHFLHLLQADNVQIGSAVMMLQNILQINSGDLLRIGRKALYSILDEVIFKLFSTPSPVIRSTATKLLLLMAESHQEILILLR
QSTCYKGLRRLLSKQETGTEFSQELRQLVGLLSPMVYQEVEEQKLHQAACLIQAYWKGFQTRKRLKKLPSAVIALQRSFRSKR
SKMLLEINRQKEEEDLKLQLQLQRQRAMRLSRELQLSMLEIVHPGQVEKHYREMEEKSALNIQKHWRGYRERKNFHQQRQSLI
EYKAAVTLQRAALKFLAKCRKKKKLFAPWRGLQELTDARRVELKKRVDDYVRRHLGSPMSDVVSRELHAQAQERLQHYFMGRA
LEERAQQHREALIAQISTNVEQLMKAPSLKEAEGKEPELFLSRSRPVAAKAKQAHLTTLKHIQAPWWKKLGEESGDEIDVPKD
ELSIELENLFIGGTKPP"
```

FIGURE 37 (cont.)

SEQ ID NO: 81

```
   1 cgcctccagg cccctteccg cgtcgcgacg cacgctgccc cggaaggccg cggcgctgta
  61 gtgcggcgcc ccaggttctt tagtggaaga acgcgaagcg aggatgagtg
>atccgtggag
 121 gcagtaacag gcgcggcgag ggagaagtga ttcccgaaga atcaaggctg
>ggccggaccc
>       181 ggtggcctgg caacagggta ataagagaaa tgaagccaac aggtacagac
>ccaaggatct
>       241 tatctatagc tgctgaagtt gcaaaaagcc ctgagcagaa tgtccctgtt
>atactgttga
>       301 agttaaaaga aataataaac atcacacctt taggaagctc agagttgaag
>aaaatcaaac
>       361 aagatatata ttgttatgat ctcattcaat attgcctctt ggtcctcagt
>caagattatt
>       421 ctcgaatcca gggtggttgg actacaattt cccagcttac acagatatta
>agccattgct
>       481 gtgtgggctt ggagccagga gaagatgcag aggaattta caatgaatta
>cttccatcag
>       541 ctgcagaaaa ttttctagtt ttggggagac aattacaaac atgttttatc
>aatgcagcta
>       601 aggctgaaga aaaagatgaa ttactacact ttttccaaat tgtgactgat
>tctctcttct
>       661 ggcttttggg aggccatgtt gaacttattc agaatgtact acaaagtgat
>catttcttac
>       721 atttactgca agctgacaat gtccaaatag gatctgcagt catgatgatg
>ctacagaata
>       781 tattacagat caacagtggt gatttactca gaataggaag aaaagccctg
>tattcaattt
>       841 tagatgaagt tattttcaag cttttttcaa ctcctagtcc agttataaga
>agtactgcta
>       901 caaaactcct actgttgatg gctgaatccc atcaggaaat tttgatttta
>ctgagacaaa
>       961 gtacctgcta caaaggactc agacgtctac taagtaaaca ggaaactggg
>actgaattca
>      1021 gtcaagaact tagacagctt gttggccttt taagcccaat ggtctatcag
>gaagtagaag
>      1081 agcagaaact acatcaagca gcatgcttga ttcaagccta ttggaagggt
>tttcagacaa
>      1141 gaaagagatt aaagaagctt ccatctgctg tgattgcttt gcagaggagt
>ttcagatcca
>      1201 aacgatcaaa gatgttgctg gagataaata ggcagaagga agaagaggac
>ctcaaattac
>      1261 aattgcaact tcaaagacag agagccatga gacttcccg agaattgcag
>ctgagtatgc
>      1321 tcgaaatagt tcatccaggt caggtggaga aacactatcg ggaaatggaa
>gagaaatcag
>      1381 cactgaatat ccagaaacat tggagagggt acagggaaag gaaaaatttt
>caccaacaga
>      1441 ggcagtctct catagagtat aaagcagctg tcacacttca aagagcagcg
>cttaaattcc
>      1501 tagcgaagtg ccgtaagaaa aagaaactat ttgctccttg gcgaggactc
>caagaactca
>      1561 ctgatgcacg ccgagttgaa ctgaagaaac gagtggatga ctatgtcaga
>agacatttgg
>      1621 gctctccaat gtcagatgtg gtcagtaggg agctccatgc ccaagctcaa
```

FIGURE 37 (cont.)

```
>gaacgactgc
>       1681 aacactactt tatgggcagg gccctagaag agcgagccca gcagcacaga
>gaagctctga
>       1741 tagcacagat cagcaccaac gttgaacagc taatgaaggc accaagtctg
>aaggaggcag
>       1801 aagggaaaga acctgagctc ttcctaagta gatccaggcc tgtggcagcc
>aaggccaagc
>       1861 aggcccatct cacaaccctg aagcacatac aagcaccctg gtggaagaag
>cttggagaag
>       1921 aatctggaga tgagattgat gttccaaagg atgagcttag tatagaatta
>gaaaatttat
>       1981 tcattggtgg aaccaaacca ccttagtgag taaccctaag aattgacaca
>aatctcatat
>       2041 tttaggagat tatattggtt ctgcctctgg catgctggta gactagggcc
>atcctaactt
>       2101 attattttcc agaggttctc ctccagacaa gacctgcagt aagcaaagag
>ttatattcta
>       2161 cctctctctc aatttctttt tcttttctc tgtatcctca tccttagcca
>cacacagatt
>       2221 tgtgtggctt ttattgtaga actaaactta gcatagtgtt ctgttgttta
>catgaagtgt
>       2281 gtttttcttt ggtttcttct gttttccaac taaatatttt tttctaaata
>aatattttca
>       2341 acaattgatt tgaaaaaaaa aaaaaaaaaa aaaaaaaaaa aaaaaaaaa aa
>//
>
```

FIGURE 37 (cont.)

SEQ ID NO: 83

```
   1 cgcctccagg ccccttcccg cgtcgcgacg cacgctgccc cggaaggccg cggcgctgta
  61 gtgcggcgcc ccaggttctt tagtggaaga acgcgaagcg aggatgagtg atccgtggag
 121 gcagtaacag gcgcggcgag ggagaagtga ttcccgaaga atcaaggctg ggccggaccc
 181 ggtggcctgg aacagggta ataagagaaa tgaagccaac aggtacagac ccaaggatct
 241 tatctatagc tgctgaagtt gcaaaaagcc ctgagcagaa tgtccctgtt atactgttga
 301 agttaaaaga aataataaac atcacacctt taggaagctc agagttgaag aaaatcaaac
 361 aagatatata ttgttatgat ctcattcaat attgcctctt ggtcctcagt caagattatt
 421 ctcgaatcca gggtggttgg actacaattt cccagcttac acagatatta agccattgct
 481 gtgtgggctt ggagccagga gaagatgcag aggaattta caatgaatta cttccatcag
 541 ctgcagaaaa ttttctagtt ttggggagac aattacaaac atgttttatc aatgcagcta
 601 aggctgaaga aaaagatgaa ttactacact ttccaaat tgtgactgat tctctcttct
 661 ggcttttggg aggccatgtt gaacttattc agaatgtact acaaagtgat catttcttac
 721 atttactgca agctgacaat gtccaaatag gatctgcagt catgatgatg ctacagaata
 781 tattacagat caacagtggt gatttactca gaataggaag aaaagccctg tattcaattt
 841 tagatgaagt tattttcaag cttttttcaa ctcctagtcc agttataaga agtactgcta
 901 caaaactcct actgttgatg gctgaatccc atcaggaaat tttgattta ctgagacaaa
 961 gtacctgcta caaaggactc agacgtctac taagtaaaca ggaaactggg actgaattca
1021 gtcaagaact tagacagctt gttggccttt taagcccaat ggtctatcag gaagtagaag
1081 agcagaaact acatcaagca gcatgcttga ttcaagccta ttggaagggt tttcagacaa
1141 gaaagagatt aaagaagctt ccatctgctg tgattgcttt gcagaggagt ttcagatcca
1201 aacgatcaaa gatgttgctg gagataaata ggcagaagga agaagaggac ctcaaattac
1261 aattgcaact tcaaagacag agagccatga gactttcccg agaattgcag ctgagtatgc
1321 tcgaaatagt tcatccaggt caggtggaga aacactatcg ggaaatggaa gagaaatcag
1381 cactgaatat ccagaaacat ggagagggt acaggaaag gaaaaatttt caccaacaga
1441 ggcagtctct catagagtat aaagcagctg tcacacttca aagagcagcg cttaaattcc
1501 tagcgaagtg ccgtaagaaa aagaaactat ttgctccttg gcgaggactc caagaactca
1561 ctgatgcacg ccgagttgaa ctgaagaaac gagtggatga ctatgtcaga agacatttgg
1621 gctctccaat gtcagatgtg gtcagtaggg agctccatgc ccaagctcaa
```

FIGURE 37 (cont.)

```
>gaacgactgc
>       1681 aacactactt tatgggcagg gccctagaag agcgagccca gcagcacaga
>gaagctctga
>       1741 tagcacagat cagcaccaac gttgaacagc taatgaaggc accaagtctg
>aaggaggcag
>       1801 aagggaaaga acctgagctc ttcctaagta gatccaggcc tgtggcagcc
>aaggccaagc
>       1861 aggcccatct cacaaccctg aagcacatac aagcaccctg gtggaagaag
>cttggagaag
>       1921 aatctggaga tgagattgat gttccaaagg atgagcttag tatagaatta
>gaaaatttat
>       1981 tcattggtgg aaccaaacca ccttagtgag taaccctaag aattgacaca
>aatctcatat
>       2041 tttaggagat tatattggtt ctgcctctgg catgctggta gactagggcc
>atcctaactt
>       2101 attattttcc agaggttctc ctccagacaa gacctgcagt aagcaaagag
>ttatattcta
>       2161 cctctctctc aattttcttt ttcttttctc tgtatcctca tccttagcca
>cacacagatt
>       2221 tgtgtggctt ttattgtaga actaaactta gcatagtgtt ctgttgttta
>catgaagtgt
>       2281 gtttttcttt ggtttcttct gttttccaac taaatatttt tttctaaata
>aatattttca
>       2341 acaattgatt tgaaaaaaaa aaaaaaaaaa aaaaaaaaaa aaaaaaaaaa aa
>//
```

FIGURE 37 (cont.)

SEQ ID NO: 84

```
   1 cgcctccagg ccccttcccg cgtcgcgacg cacgctgccc cggaaggccg cggcgctgta
  61 gtgcggcgcc ccaggttctt tagtggaaga acgcgaagcg aggatgagtg
>atccgtggag
 121 gcagtaacag gcgcggcgag ggagaagtga ttcccgaaga atcaaggctg
>ggccggaccc
>        181 ggtggcctgg caacagggta ataagagaaa tgaagccaac aggtacagac
>ccaaggatct
>        241 tatctatagc tgctgaagtt gcaaaaagcc ctgagcagaa tgtccctgtt
>atactgttga
>        301 agttaaaaga aataataaac atcacacctt taggaagctc agagttgaag
>aaaatcaaac
>        361 aagatatata ttgttatgat ctcattcaat attgcctctt ggtcctcagt
>caagattatt
>        421 ctcgaatcca gggtggttgg actacaattt cccagcttac acagatatta
>agccattgct
>        481 gtgtgggctt ggagccagga aagatgcag aggaatttta caatgaatta
>cttccatcag
>        541 ctgcagaaaa ttttctagtt ttggggagac aattacaaac atgttttatc
>aatgcagcta
>        601 aggctgaaga aaaagatgaa ttactacact ttttccaaat tgtgactgat
>tcttct
>        661 ggcttttggg aggccatgtt gaacttattc agaatgtact acaaagtgat
>catttcttac
>        721 atttactgca agctgacaat gtccaaatag gatctgcagt catgatgatg
>ctacagaata
>        781 tattacagat caacagtggt gatttactca gaataggaag aaaagccctg
>tattcaattt
>        841 tagatgaagt tattttcaag ctttttcaa ctcctagtcc agttataaga
>agtactgcta
>        901 caaaactcct actgttgatg gctgaatccc atcaggaaat tttgattta
>ctgagacaaa
>        961 gtacctgcta caaggactc agacgtctac taagtaaaca ggaaactggg
>actgaattca
>       1021 gtcaagaact tagacagctt gttggccttt taagcccaat ggtctatcag
>gaagtagaag
>       1081 agcagaaact acatcaagca gcatgcttga ttcaagccta ttggaagggt
>tttcagacaa
>       1141 gaaagagatt aaagaagctt ccatctgctg tgattgcttt gcagaggagt
>ttcagatcca
>       1201 aacgatcaaa gatgttgctg gagataaata ggcagaagga agaagaggac
>ctcaaattac
>       1261 aattgcaact tcaaagacag agagccatga dctttcccg agaattgcag
>ctgagtatgc
>       1321 tcgaaatagt tcatccaggt caggtggaga acactatcg ggaaatggaa
>gagaaatcag
>       1381 cactgaatat ccagaaacat tggagagggt acagggaaag gaaaaatttt
>caccaacaga
>       1441 ggcagtctct catagagtat aaagcagctg tcacacttca aagagcagcg
>cttaaattcc
>       1501 tagcgaagtg ccgtaagaaa agaaactat ttgctccttg gcgaggactc
>caagaactca
>       1561 ctgatgcacg ccgagttgaa ctgaagaaac gagtggatga ctatgtcaga
>agacatttgg
>       1621 gctctccaat gtcagatgtg gtcagtaggg agctccatgc ccaagctcaa
```

FIGURE 37 (cont.)

```
>gaacgactgc
>      1681 aacactactt tatgggcagg gccctagaag agcgagccca gcagcacaga
>gaagctctga
>      1741 tagcacagat cagcaccaac gttgaacagc taatgaaggc accaagtctg
>aaggaggcag
>      1801 aagggaaaga acctgagctc ttcctaagta gatccaggcc tgtggcagcc
>aaggccaagc
>      1861 aggcccatct cacaaccctg aagcacatac aagcaccctg gtggaagaag
>cttggagaag
>      1921 aatctggaga tgagattgat gttccaaagg atgagcttag tatagaatta
>gaaaatttat
>      1981 tcattggtgg aaccaaacca ccttagtgag taaccctaag aattgacaca
>aatctcatat
>      2041 tttaggagat tatattggtt ctgcctctgg catgctggta gactagggcc
>atcctaactt
>      2101 attattttcc agaggttctc ctccagacaa gacctgcagt aagcaaagag
>ttatattcta
>      2161 cctctctctc aattttcttt ttcttttctc tgtatcctca tccttagcca
>cacacagatt
>      2221 tgtgtggctt ttattgtaga actaaactta gcatagtgtt ctgttgttta
>catgaagtgt
>      2281 gttttctttt ggtttcttct gttttccaac taaatatttt tttctaaata
>aatattttca
>      2341 acaattgatt tgaaaaaaaa aaaaaaaaaa aaaaaaaaaa aaaaaaaaaa aa
>//
```

FIGURE 37 (cont.)

SEQ ID NO: 85

```
   1 cgcctccagg cccctteccg cgtcgcgacg cacgctgccc cggaaggccg cggcgctgta
  61 gtgcggcgcc ccaggttctt tagtggaaga acgcgaagcg aggatgagtg
>atccgtggag
 121 gcagtaacag gcgcggcgag ggagaagtga ttcccgaaga atcaaggctg
>ggccggaccc
>        181 ggtggcctgg caacagggta ataagagaaa tgaagccaac aggtacagac
>ccaaggatct
>        241 tatctatagc tgctgaagtt gcaaaaagcc ctgagcagaa tgtccctgtt
>atactgttga
>        301 agttaaaaga aataataaac atcacacctt taggaagctc agagttgaag
>aaaatcaaac
>        361 aagatatata ttgttatgat ctcattcaat attgcctctt ggtcctcagt
>caagattatt
>        421 ctcgaatcca gggtggttgg actacaattt cccagcttac acagatatta
>agccattgct
>        481 gtgtgggctt ggagccagga gaagatgcag aggaatttta caatgaatta
>cttccatcag
>        541 ctgcagaaaa ttttctagtt ttggggagac aattacaaac atgttttatc
>aatgcagcta
>        601 aggctgaaga aaaagatgaa ttactacact ttttccaaat tgtgactgat
>tcttct
>        661 ggcttttggg aggccatgtt gaacttattc agaatgtact acaaagtgat
>catttcttac
>        721 atttactgca agctgacaat gtccaaatag gatctgcagt catgatgatg
>ctacagaata
>        781 tattacagat caacagtggt gatttactca gaataggaag aaaagccctg
>tattcaattt
>        841 tagatgaagt tatttttcaag cttttttcaa ctcctagtcc agttataaga
>agtactgcta
>        901 caaaactcct actgttgatg gctgaatccc atcaggaaat tttgatttta
>ctgagacaaa
>        961 gtacctgcta caaaggactc agacgtctac taagtaaaca ggaaactggg
>actgaattca
>       1021 gtcaagaact tagctt gttggccttt taagcccaat ggtctatcag
>gaagtagaag
>       1081 agcagaaact acatcaagca gcatgcttga ttcaagccta ttggaagggt
>tttcagacaa
>       1141 gaaagagatt aaagaagctt ccatctgctg tgattgcttt gcagaggagt
>ttcagatcca
>       1201 aacgatcaaa gatgttgctg gagataaata ggcagaagga agaagaggac
>ctcaaattac
>       1261 aattgcaact tcaaagacag agagccatga gactttcccg agaattgcag
>ctgagtatgc
>       1321 tcgaaatagt tcatccaggt caggtggaga aacactatcg ggaaatggaa
>gagaaatcag
>       1381 cactgaatat ccagaaacat tggagagggt acagggaaag gaaaaatttt
>caccaacaga
>       1441 ggcagtctct catagagtat aaagcagctg tcacacttca aagagcagcg
>cttaaattcc
>       1501 tagcgaagtg ccgtaagaaa aagaaactat ttgctccttg gcgaggactc
>caagaactca
>       1561 ctgatgcacg ccgagttgaa ctgaagaaac gagtggatga ctatgtcaga
>agacatttgg
>       1621 gctctccaat gtcagatgtg gtcagtaggg agctccatgc ccaagctcaa
```

FIGURE 37 (cont.)

```
>gaacgactgc
>      1681 aacactactt tatgggcagg gccctagaag agcgagccca gcagcacaga
>gaagctctga
>      1741 tagcacagat cagcaccaac gttgaacagc taatgaaggc accaagtctg
>aaggaggcag
>      1801 aagggaaaga acctgagctc ttcctaagta gatccaggcc tgtggcagcc
>aaggccaagc
>      1861 aggcccatct cacaaccctg aagcacatac aagcaccctg gtggaagaag
>cttggagaag
>      1921 aatctggaga tgagattgat gttccaaagg atgagcttag tatagaatta
>gaaaatttat
>      1981 tcattggtgg aaccaaacca ccttagtgag taaccctaag aattgacaca
>aatctcatat
>      2041 tttaggagat tatattggtt ctgcctctgg catgctggta gactagggcc
>atcctaactt
>      2101 attattttcc agaggttctc ctccagacaa gacctgcagt aagcaaagag
>ttatattcta
>      2161 cctctctctc aattttcttt ttcttttctc tgtatcctca tccttagcca
>cacacagatt
>      2221 tgtgtggctt ttattgtaga actaaactta gcatagtgtt ctgttgttta
>catgaagtgt
>      2281 gttttctttt ggtttcttct gttttccaac taaatatttt tttctaaata
>aatattttca
>      2341 acaattgatt tgaaaaaaaa aaaaaaaaaa aaaaaaaaaa aaaaaaaaaa aa
>//
```

FIGURE 37 (cont.)

SEQ ID NO: 86

```
   1 cgcctccagg ccccttcccg cgtcgcgacg cacgctgccc cggaaggccg cggcgctgta
  61 gtgcggcgcc ccaggttctt tagtggaaga acgcgaagcg aggatgagtg atccgtggag
 121 gcagtaacag gcgcggcgag ggagaagtga ttcccgaaga atcaaggctg ggccggaccc
 181 ggtggcctgg caacagggta ataagagaaa tgaagccaac aggtacagac ccaaggatct
 241 tatctatagc tgctgaagtt gcaaaaagcc ctgagcagaa tgtccctgtt atactgttga
 301 agttaaaaga aataataaac atcacacctt taggaagctc agagttgaag aaaatcaaac
 361 aagatatata ttgttatgat ctcattcaat attgcctctt ggtcctcagt caagattatt
 421 ctcgaatcca gggtggttgg actacaattt cccagcttac acagatatta agccattgct
 481 gtgtgggctt ggagccagga gaagatgcag aggaatttta caatgaatta cttccatcag
 541 ctgcagaaaa ttttctagtt ttggggagac aattacaaac atgttttatc aatgcagcta
 601 aggctgaaga aaaagatgaa ttactacact ttttccaaat tgtgactgat tctctcttct
 661 ggcttttggg aggccatgtt gaacttattc agaatgtact acaaagtgat catttcttac
 721 atttactgca agctgacaat gtccaaatag gatctgcagt catgatgatg ctacagaata
 781 tattacagat caacagtggt gatttactca gaataggaag aaaagccctg tattcaattt
 841 tagatgaagt tattttcaag cttttttcaa ctcctagtcc agttataaga agtactgcta
 901 caaaactcct actgttgatg gctgaatccc atcaggaaat tttgattta ctgagacaaa
 961 gtacctgcta caaaggactc agacgtctac taagtaaaca ggaaactggg actgaattca
1021 gtcaagaact tagctt gttggccttt taagcccaat ggtctatcag gaagtagaag
1081 agcagaaact acatcaagca gcatgcttga ttcaagccta ttggaagggt tttcagacaa
1141 gaaagagatt aagaagctt ccatctgctg tgattgcttt gcagaggagt ttcagatcca
1201 aacgatcaaa gatgttgctg gagataaata ggcagaagga agaagaggac ctcaaattac
1261 aattgcaact tcaaagatag agagccatga gactttcccg agaattgcag ctgagtatgc
1321 tcgaaatagt tcatccaggt caggtggaga aacactatcg ggaaatggaa gagaaatcag
1381 cactgaatat ccagaaacat tggagagggt acagggaaag gaaaaatttt caccaacaga
1441 ggcagtctct catagagtat aaagcagctg tcacacttca aagagcagcg cttaaattcc
1501 tagcgaagtg ccgtaagaaa aagaaactat ttgctccttg gcgaggactc caagaactca
1561 ctgatgcacg ccgagttgaa ctgaagaaac gagtggatga ctatgtcaga agacatttgg
1621 gctctccaat gtcagatgtg gtcagtaggg agctccatgc ccaagctcaa
```

FIGURE 37 (cont.)

```
>gaacgactgc
>       1681 aacactactt tatgggcagg gccctagaag agcgagccca gcagcacaga
>gaagctctga
>       1741 tagcacagat cagcaccaac gttgaacagc taatgaaggc accaagtctg
>aaggaggcag
>       1801 aagggaaaga acctgagctc ttcctaagta gatccaggcc tgtggcagcc
>aaggccaagc
>       1861 aggcccatct cacaaccctg aagcacatac aagcaccctg gtggaagaag
>cttggagaag
>       1921 aatctggaga tgagattgat gttccaaagg atgagcttag tatagaatta
>gaaaatttat
>       1981 tcattggtgg aaccaaacca ccttagtgag taaccctaag aattgacaca
>aatctcatat
>       2041 tttaggagat tatattggtt ctgcctctgg catgctggta gactagggcc
>atcctaactt
>       2101 attattttcc agaggttctc ctccagacaa gacctgcagt aagcaaagag
>ttatattcta
>       2161 cctctctctc aattttcttt ttcttttctc tgtatcctca tccttagcca
>cacacagatt
>       2221 tgtgtggctt ttattgtaga actaaactta gcatagtgtt ctgttgttta
>catgaagtgt
>       2281 gtttttcttt ggtttcttct gttttccaac taaatatttt tttctaaata
>aatattttca
>       2341 acaattgatt tgaaaaaaaa aaaaaaaaaa aaaaaaaaaa aaaaaaaaa aa
>//
```

FIGURE 37 (cont.)

SEQ ID NO: 87

```
   1 cgcctccagg ccccttcccg cgtcgcgacg cacgctgccc cggaaggccg cggcgctgta
  61 gtgcggcgcc ccaggttctt tagtggaaga acgcgaagcg aggatgagtg
>atccgtggag
 121 gcagtaacag gcgcggcgag ggagaagtga ttcccgaaga atcaaggctg
>ggccggaccc
>        181 ggtggcctgg caacagggta ataagagaaa tgaagccaac aggtacagac
>ccaaggatct
>        241 tatctatagc tgctgaagtt gcaaaaagcc ctgagcagaa tgtccctgtt
>atactgttga
>        301 agttaaaaga aataataaac atcacacctt taggaagctc agagttgaag
>aaaatcaaac
>        361 aagatatata ttgttatgat ctcattcaat attgcctctt ggtcctcagt
>caagattatt
>        421 ctcgaatcca gggtggttgg actacaattt cccagcttac acagatatta
>agccattgct
>        481 gtgtgggctt ggagccagga gaagatgcag aggaatttta caatgaatta
>cttccatcag
>        541 ctgcagaaaa ttttctagtt ttggggagac aattacaaac atgttttatc
>aatgcagcta
>        601 aggctgaaga aaaagatgaa ttactacact ttttccaaat tgtgactgat
>tctctcttct
>        661 ggcttttggg aggccatgtt gaacttattc agaatgtact acaaagtgat
>catttcttac
>        721 atttactgca agctgacaat gtccaaatag gatctgcagt catgatgatg
>ctacagaata
>        781 tattacagat caacagtggt gatttactca gaataggaag aaaagccctg
>tattcaattt
>        841 tagatgaagt tattttcaag cttttttcaa ctcctagtcc agttataaga
>agtactgcta
>        901 caaaactcct actgttgatg gctgaatccc atcaggaaat tttgatttta
>ctgagacaaa
>        961 gtacctgcta caaaggactc agacgtctac taagtaaaca ggaaactggg
>actgaattca
>       1021 gtcaagaact tagacagctt gttggccttt taagcccaat ggtctatcag
>gaagtagaag
>       1081 agcagaaact acatcaagca gcatgcttga ttcaagccta ttggaagggt
>tttcagacaa
>       1141 gaaagagatt aaagaagctt ccatctgctg tgattgcttt gcagaggagt
>ttcagatcca
>       1201 aatgatcaaa gatgttgctg gagataaata ggcagaagga agaagaggac
>ctcaaattac
>       1261 aattgcaact tcaaagacag agagccatga gactttcccg agaattgcag
>ctgagtatgc
>       1321 tcgaaatagt tcatccaggt caggtggaga aacactatcg ggaaatggaa
>gagaaatcag
>       1381 cactgaatat ccagaaacat ggagagggt acagggaaag gaaaaatttt
>caccaacaga
>       1441 ggcagtctct catagagtat aaagcagctg tcacacttca aagagcagcg
>cttaaattcc
>       1501 tagcgaagtg ccgtaagaaa aagaaactat ttgctccttg gcgaggactc
>caagaactca
>       1561 ctgatgcacg ccgagttgaa ctgaagaaac gagtggatga ctatgtcaga
>agacatttgg
>       1621 gctctccaat gtcagatgtg gtcagtaggg agctccatgc ccaagctcaa
```

FIGURE 37 (cont.)

```
>gaacgactgc
>       1681 aacactactt tatgggcagg gccctagaag agcgagccca gcagcacaga
>gaagctctga
>       1741 tagcacagat cagcaccaac gttgaacagc taatgaaggc accaagtctg
>aaggaggcag
>       1801 aagggaaaga acctgagctc ttcctaagta gatccaggcc tgtggcagcc
>aaggccaagc
>       1861 aggcccatct cacaaccctg aagcacatac aagcaccctg gtggaagaag
>cttggagaag
>       1921 aatctggaga tgagattgat gttccaaagg atgagcttag tatagaatta
>gaaaatttat
>       1981 tcattggtgg aaccaaacca ccttagtgag taaccctaag aattgacaca
>aatctcatat
>       2041 tttaggagat tatattggtt ctgcctctgg catgctggta gactagggcc
>atcctaactt
>       2101 attattttcc agaggttctc ctccagacaa gacctgcagt aagcaaagag
>ttatattcta
>       2161 cctctctctc aattttcttt ttcttttctc tgtatcctca tccttagcca
>cacacagatt
>       2221 tgtgtggctt ttattgtaga actaaactta gcatagtgtt ctgttgttta
>catgaagtgt
>       2281 gttttctttt ggtttcttct gttttccaac taaatatttt tttctaaata
>aatattttca
>       2341 acaattgatt tgaaaaaaaa aaaaaaaaaa aaaaaaaaaa aaaaaaaaaa aa
>//
```

FIGURE 37 (cont.)

SEQ ID NO: 88

```
  1 cgcctccagg cccc ttcccg cgtcgcgacg cacgctgccc cggaaggccg cggcgctgta
 61 gtgcggcgcc ccaggttctt tagtggaaga acgcgaagcg aggatgagtg
>atccgtggag
121 gcagtaacag gcgcggcgag ggagaagtga ttcccgaaga atcaaggctg
>ggccggaccc
>       181 ggtggcctgg caacagggta ataagagaaa tgaagccaac aggtacagac
>ccaaggatct
>       241 tatctatagc tgctgaagtt gcaaaaagcc ctgagcagaa tgtccctgtt
>atactgttga
>       301 agttaaaaga aataataaac atcacacctt taggaagctc agagttgaag
>aaaatcaaac
>       361 aagatatata ttgttatgat ctcattcaat attgcctctt ggtcctcagt
>caagattatt
>       421 ctcgaatcca gggtggttgg actacaattt cccagcttac acagatatta
>agccattgct
>       481 gtgtgggctt ggagccagga gaagatgcag aggaatttta caatgaatta
>cttccatcag
>       541 ctgcagaaaa ttttctagtt ttggggagac aattacaaac atgttttatc
>aatgcagcta
>       601 aggctgaaga aaagatgaa ttactacact ttttccaaat tgtgactgat
>tctctcttct
>       661 ggcttttggg aggccatgtt gaacttattc agaatgtact acaaagtgat
>catttcttac
>       721 atttactgca agctgacaat gtccaaatag gatctgcagt catgatgatg
>ctacagaata
>       781 tattacagat caacagtggt gatttactca gaataggaag aaaagccctg
>tattcaattt
>       841 tagatgaagt tatttttcaag cttttttcaa ctcctagtcc agttataaga
>agtactgcta
>       901 caaaactcct actgttgatg gctgaatccc atcaggaaat tttgatttta
>ctgagacaaa
>       961 gtacctgcta caaggactc agacgtctac taagtaaaca ggaaactggg
>actgaattca
>      1021 gtcaagaact tagacagctt gttggccttt taagcccaat ggtctatcag
>gaagtagaag
>      1081 agcagaaact acatcaagca gcatgcttga ttcaagccta ttggaagggt
>tttcagacaa
>      1141 gaaagagatt aaagaagctt ccatctgctg tgattgcttt gcagaggagt
>ttcagatcca
>      1201 aacgatcaaa gatgttgctg gagataaata ggcagaagga agaagaggac
>ctcaaattac
>      1261 aattgcaact tcaaagacagag agagccatga cactttcccg agaattgcag
>ctgagtatgc
>      1321 tcgaaatagt tcatccaggt caggtggaga aacactatcg ggaaatggaa
>gagaaatcag
>      1381 cactgaatat ccagaaacat tggagagggt acagggaaag gaaaaatttt
>caccaacaga
>      1441 ggcagtctct catagagtat aaagcagctg tcacacttca aagagcagcg
>cttaaattcc
>      1501 tagcgaagtg ccgtaagaaa agaaactat ttgctccttg gcgaggactc
>caagaactca
>      1561 ctgatgcacg ccgagttgaa ctgaagaaac gagtggatga ctatgtcaga
>agacatttgg
>      1621 gctctccaat gtcagatgtg gtcagtaggg agctccatgc ccaagctcaa
```

FIGURE 37 (cont.)

```
>gaacgactgc
>       1681 aacactactt tatgggcagg gccctagaag agcgagccca gcagcacaga
>gaagctctga
>       1741 tagcacagat cagcaccaac gttgaacagc taatgaaggc accaagtctg
>aaggaggcag
>       1801 aagggaaaga acctgagctc ttcctaagta gatccaggcc tgtggcagcc
>aaggccaagc
>       1861 aggcccatct cacaaccctg aagcacatac aagcaccctg gtggaagaag
>cttggagaag
>       1921 aatctggaga tgagattgat gttccaaagg atgagcttag tatagaatta
>gaaaatttat
>       1981 tcattggtgg aaccaaacca ccttagtgag taaccctaag aattgacaca
>aatctcatat
>       2041 tttaggagat tatattggtt ctgcctctgg catgctggta gactagggcc
>atcctaactt
>       2101 attattttcc agaggttctc ctccagacaa gacctgcagt aagcaaagag
>ttatattcta
>       2161 cctctctctc aatttttcttt ttcttttctc tgtatcctca tccttagcca
>cacacagatt
>       2221 tgtgtggctt ttattgtaga actaaactta gcatagtgtt ctgttgttta
>catgaagtgt
>       2281 gtttttcttt ggtttcttct gttttccaac taaatatttt tttctaaata
>aatattttca
>       2341 acaattgatt tgaaaaaaaa aaaaaaaaaa aaaaaaaaaa aaaaaaaaaa aa
>//
```

FIGURE 37 (cont.)

SEQ ID NO: 89

```
1 cgcctccagg ccccttcccg cgtcgcgacg cacgctgccc cggaaggccg cggcgctgta
61 gtgcggcgcc ccaggttctt tagtggaaga acgcgaagcg aggatgagtg atccgtggag
121 gcagtaacag gcgcggcgag ggagaagtga ttcccgaaga atcaaggctg ggccggaccc
181 ggtggcctgg caacagggta ataagagaaa tgaagccaac aggtacagac ccaaggatct
241 tatctatagc tgctgaagtt gcaaaaagcc ctgagcagaa tgtccctgtt atactgttga
301 agttaaaaga aataataaac atcacacctt taggaagctc agagttgaag aaaatcaaac
361 aagatatata ttgttatgat ctcattcaat attgcctctt ggtcctcagt caagattatt
421 ctcgaatcca gggtggttgg actacaattt cccagcttac acagatatta agccattgct
481 gtgtgggctt ggagccagga aagatgcag aggaatttta caatgaatta cttccatcag
541 ctgcagaaaa ttttctagtt ttggggagac aattacaaac atgttttatc aatgcagcta
601 aggctgaaga aaaagatgaa ttactacact ttttccaaat tgtgactgat tctctcttct
661 ggcttttggg aggccatgtt gaacttattc agaatgtact acaaagtgat catttcttac
721 atttactgca agctgacaat gtccaaatag gatctgcagt catgatgatg ctacagaata
781 tattacagat caacagtggt gatttactca gaataggaag aaaagccctg tattcaattt
841 tagatgaagt tatttttcaag cttttttcaa ctcctagtcc agttataaga agtactgcta
901 caaaactcct actgttgatg gctgaatccc atcaggaaat tttgatttta ctgagacaaa
961 gtacctgcta caaaggactc agacgtctac taagtaaaca ggaaactggg actgaattca
1021 gtcaagaact tagacagctt gttggccttt taagcccaat ggtctatcag gaagtagaag
1081 agcagaaact acatcaagca gcatgcttga ttcaagccta ttggaagggt tttcagacaa
1141 gaaagagatt aaagaagctt ccatctgctg tgattgcttt gcagaggagt ttcagatcca
1201 aacgatcaaa gatgttgctg gagataaata ggcagaagga agaagaggac ctcaaattac
1261 aattgcaact tcaaagacag agagccatga gactttcccg agaattgcag ctgagtatgc
1321 tcgaaatagt tcatccaggt caggtggaga aacactatcg ggaaatggaa gagaaatcag
1381 cactgaatat ccagaaacat tggagagggt acaggaaag gaaaaatttt caccaacaga
1441 ggcagtctct catagagtat aaagcagctg tcacacttca aagagcagcg cttaaattcc
1501 tagcgaagtg ccgtaagaaa aagaaactat ttgctccttg gcgaggactc caagaactca
1561 ctgatgcacg ccgagttgaa ctgaagaaat gagtggatga ctatgtcaga agacatttgg
1621 gctctccaat gtcagatgtg gtcagtaggg agctccatgc ccaagctcaa
```

FIGURE 37 (cont.)

```
>gaacgactgc
>       1681 aacactactt tatgggcagg ccctagaag agcgagccca gcagcacaga
>gaagctctga
>       1741 tagcacagat cagcaccaac gttgaacagc taatgaaggc accaagtctg
>aaggaggcag
>       1801 aagggaaaga acctgagctc ttcctaagta gatccaggcc tgtggcagcc
>aaggccaagc
>       1861 aggcccatct cacaaccctg aagcacatac aagcaccctg gtggaagaag
>cttggagaag
>       1921 aatctggaga tgagattgat gttccaaagg atgagcttag tatagaatta
>gaaaatttat
>       1981 tcattggtgg aaccaaacca ccttagtgag taaccctaag aattgacaca
>aatctcatat
>       2041 tttaggagat tatattggtt ctgcctctgg catgctggta gactagggcc
>atcctaactt
>       2101 attattttcc agaggttctc ctccagacaa gacctgcagt aagcaaagag
>ttatattcta
>       2161 cctctctctc aattttcttt ttcttttctc tgtatcctca tccttagcca
>cacacagatt
>       2221 tgtgtggctt ttattgtaga actaaactta gcatagtgtt ctgttgttta
>catgaagtgt
>       2281 gttttctttt ggtttcttct gttttccaac taaatatttt tttctaaata
>aatattttca
>       2341 acaattgatt tgaaaaaaaa aaaaaaaaaa aaaaaaaaaa aaaaaaaaaa aa
>//
```

FIGURE 37 (cont.)

SEQ ID NO: 90

```
   1 cgcctccagg cccctteeeg cgtcgcgacg cacgctgccc cggaaggccg cggcgctgta
  61 gtgcggcgcc ccaggttctt tagtggaaga acgcgaagcg aggatgagtg atccgtggag
 121 gcagtaacag gcgcggcgag ggagaagtga ttcccgaaga atcaaggctg ggccggaccc
 181 ggtggcctgg caacagggta ataagagaaa tgaagccaac aggtacagac ccaaggatct
 241 tatctatagc tgctgaagtt gcaaaaagcc ctgagcagaa tgtccctgtt atactgttga
 301 agttaaaaga aataataaac atcacacctt taggaagctc agagttgaag aaaatcaaac
 361 aagatatata ttgttatgat ctcattcaat attgcctctt ggtcctcagt caagattatt
 421 ctcgaatcca gggtggttgg actacaattt cccagcttac acagatatta agccattgct
 481 gtgtgggctt ggagccagga gaagatgcag aggaatttta caatgaatta cttccatcag
 541 ctgcagaaaa ttttctagtt ttggggagac aattacaaac atgttttatc aatgcagcta
 601 aggctgaaga aaaagatgaa ttactacact ttttccaaat tgtgactgat tctctcttct
 661 ggcttttggg aggccatgtt gaacttattc agaatgtact acaaagtgat catttcttac
 721 atttactgca agctgacaat gtccaaatag gatctgcagt catgatgatg ctacagaata
 781 tattacagat caacagtggt gatttactca gaataggaag aaaagccctg tattcaattt
 841 tagatgaagt tattttcaag cttttttcaa ctcctagtcc agttataaga agtactgcta
 901 caaaactcct actgttgatg gctgaatccc atcaggaaat tttgatttta ctgagacaaa
 961 gtacctgcta caaaggactc agacgtctac taagtaaaca ggaaactggg actgaattca
1021 gtcaagaact tagacagctt gttggccttt taagcccaat ggtctatcag gaagtagaag
1081 agcagaaact acatcaagca gcatgcttga ttcaagccta ttggaagggt tttcagacaa
1141 gaaagagatt aaagaagctt ccatctgctg tgattgcttt gcagaggagt ttcagatcca
1201 aacgatcaaa gatgttgctg gagataaata ggcagaagga agaagaggac ctcaaattac
1261 aattgcaact tcaaagacag agagccatga gactttcccg agaattgcag ctgagtatgc
1321 tcgaaatagt tcatccaggt caggtggaga aacactatcg ggaaatggaa gagaaatcag
1381 cactgaatat ccagaaacat tggagagggt acagggaaag gaaaaatttt caccaacaga
1441 ggcagtctct catagagtat aaagcagctg tcacacttca aagagcagcg cttaaattcc
1501 tagcgaagtg ccgtaagaaa agaaactat ttgctccttg gcgaggactc caagaactca
1561 ctgatgcacg ccgagttgaa ctgaagaaac gagtggatga ctatgtcaga agacatttgg
1621 gctctccaat gtcagatgtg gtcagtaggg agctccatgc ccaagctcaa
```

FIGURE 37 (cont.)

```
>gaacgactgc
>       1681 aacactactt tatgggcagg gccctagaag agcgagccca gcagcaga
>gaagctctga
>       1741 tagcacagat cagcaccaac gttgaacagc taatgaaggc accaagtctg
>aaggaggcag
>       1801 aagggaaaga acctgagctc ttcctaagta gatccaggcc tgtggcagcc
>aaggccaagc
>       1861 aggcccatct cacaaccctg aagcacatac aagcaccctg gtggaagaag
>cttggagaag
>       1921 aatctggaga tgagattgat gttccaaagg atgagcttag tatagaatta
>gaaaatttat
>       1981 tcattggtgg aaccaaacca ccttagtgag taaccctaag aattgacaca
>aatctcatat
>       2041 tttaggagat tatattggtt ctgcctctgg catgctggta gactagggcc
>atcctaactt
>       2101 attattttcc agaggttctc ctccagacaa gacctgcagt aagcaaagag
>ttatattcta
>       2161 cctctctctc aattttcttt ttcttttctc tgtatcctca tccttagcca
>cacacagatt
>       2221 tgtgtggctt ttattgtaga actaaactta gcatagtgtt ctgttgttta
>catgaagtgt
>       2281 gttttctttt ggtttcttct gttttccaac taaatatttt tttctaaata
>aatattttca
>       2341 acaattgatt tgaaaaaaaa aaaaaaaaaa aaaaaaaaaa aaaaaaaaaa aa
>//
```

NPHP NUCLEIC ACIDS AND PROTEINS

The present invention is a continuation in part of U.S. patent application Ser. No. 10/648,512, filed Aug. 26, 2003 now abandoned, which claims priority to U.S. Provisional Patent Application Ser. No. 60/406,001, filed Aug. 26, 2002, the disclosure of which is hereby incorporated by reference in its entirety.

FIELD OF THE INVENTION

The present invention relates to Nephronophthisis, in particular to the NPHP5 protein (nephrocystin-5) and nucleic acids encoding the NPHP5 protein. The present invention also provides assays for the detection of NPHP5, and assays for detecting NPHP5 polymorphisms and mutations associated with disease states.

BACKGROUND OF THE INVENTION

Nephronophthisis (NPHP), an autosomal recessive cystic kidney disease, constitutes the most frequent genetic cause for end-stage renal disease (ESRD) in children and young adults. NPHP is a progressive hereditary kidney disease marked by anemia, polyuria, renal loss of sodium, progressing to chronic renal failure, tubular atrophy, interstitial fibrosis, glomerular sclerosis, and medullary cysts.

The most prominent histologic feature of NPHP consists of renal fibrosis, which in chronic renal failure, regardless of origin, represents the pathogenic event correlated most strongly to loss of renal function (Zeisberg et al., Hypertens. 10:315 [2001]). Therefore, NPHP has been considered a model disease for the development of renal fibrosis. The only treatment for NPHP is renal replacement therapy for survival (Smith et al., Am. J. Dis. Child. 69:369 [1945]; Fanconi et al., Helv. Paediatr. Acta. 6:1 [1951]; Hildebrandt, (1999) Juvenile nephronophthisis. In: Avner E, Holliday M, Barrat T (eds.) Pediatric Nephrology. Williams & Wilkins, Baltimore).

Three distinct gene loci for nephronophthisis, NPHP1 [MIM 256100], NPHP2 [MIM602088], and NPHP3 [MIM 604387], have been mapped to chromosomes 2q13 (Antignac et al., Nature Genet. 3:342 [1993]; Hildebrandt et al., Am J Hum Genet 53:1256-1261 [1993]), 9q22 (Haider et al., Am J Hum Genet 63:1404-1410 [1998], and 3q22 (Omran et al., Am J Hum Genet 66:118-127 [2000]), respectively. These disease variants share renal histology of interstitial infiltrations, renal tubular cell atrophy with cyst development, and renal interstitial fibrosis (Waldherr et al., Virchows Arch A Pathol Anat Histol 394:235-254 [1982]). The variants can be distinguished clinically by age of onset at ESRD. Renal failure develops at median ages of 1 year, 13 years, and 19 years, in NPHP2, NPHP1, and NPHP3, respectively (Omran et al., [2000], supra).

Clearly there is a great need for identification of the molecular basis of NPHP, as well as for improved diagnostics and treatments for NPHP.

SUMMARY OF THE INVENTION

The present invention relates to Nephronophthisis, in particular to the NPHP5 protein (nephroretinin or nephrocystin-4) and nucleic acids encoding the NPHP5 protein. The present invention also provides assays for the detection of NPHP5, and assays for detecting NPHP5 polymorphisms and mutations associated with disease states.

The present invention provides wild types and variant NPHP5 nucleic acid and amino acid sequences (e.g., those described by SEQ ID NOS: 81-90). The present invention further provides methods of identifying variant NPHP5 nucleic acid and amino acid sequences associated with disease states (e.g., Senior-Loken syndrome), as well as methods of screening for compounds that modulate NPHP5 activity or signaling.

Accordingly, in some embodiments, the present invention provides a method for detection of a variant NPHP5 polypeptide or nucleic acid in a subject, comprising: providing a biological sample (blood sample, a tissue sample, a urine sample, or an amniotic fluid sample) from a subject, wherein the biological sample comprises a NPHP5 polypeptide or nucleic acid; and detecting the presence or absence of a variant NPHP5 polypeptide or amino acid in the biological sample. In some embodiments, the variant NPHP5 polypeptide is a variant of SEQ ID NO:82 (e.g., encoded by a nucleic acid of SEQ ID NOS:83-90). In some embodiments, the presence of the variant nephroretinin polypeptide is indicative of Senior-Loken syndrome in the subject. In some embodiments, the subject is an embryo, a fetus, a newborn animal, or a young animal. In some embodiments, the animal is a human. In some embodiments, the detecting comprises differential antibody binding. In other embodiments, the detecting the presence of a variant NPHP5 nucleic acid comprises performing a nucleic acid hybridization assay.

The present invention further provides a kit comprising a reagent for detecting the presence or absence of a variant NPHP5 polypeptide or nucleic acid in a biological sample. In some embodiments, the kit further comprises instructions for using the kit for detecting the presence or absence of a variant NPHP5 polypeptide or nucleic acid in a biological sample. In some embodiments, the instructions further comprise instructions for diagnosing Senior-Loken syndrome in said subject based on the presence or absence of a variant nephroretinin polypeptide or nucleic acid. In some embodiments, the reagent is one or more antibodies. In other embodiments, the reagent is one or more nucleic acid probes (e.g., that hybridize to wild type or variant NPHP5 nucleic acids). In some embodiments, the variant NPHP5 polypeptide is a variant of SEQ ID NO:82 (e.g., encoded by a nucleic acid of SEQ ID NOS:83-90).

DESCRIPTION OF THE FIGURES

FIG. 1 shows haplotype results on chromosome 1p36 carried out for refining the NPHP4 locus in affected offspring from 3 consanguineous NPHP families. p-ter, telomeric; cen, centromeric; nd, not done.

FIG. 2A, genetic map position for microsatellites used in linkage mapping of NPHP4 (see FIG. 1). Published flanking markers are underlined (Schuermann et al., Am. J. Hum. Genet. 70:1240 [2002]. p-ter, telomeric; cen, centromeric. FIG. 2B, physical map distances of critical microsatellites relative to D1S2660. The secure 1.2 Mb critical interval (solid bar) and the 700 kb suggestive critical interval (stippled bar), are shown delimited by the newly identified secure flanking markers (asterisks) and suggestive flanking markers (double asterisks) defined by haplotype analysis (see FIG. 1). Below the axis known genes, predicted unknown genes, and the NPHP4 gene (alias Q9UFQ2) are represented as arrows in the direction of transcription. FIG. 2C, genomic organization of NPHP4 with exons indicated as vertical hatches and numbered. FIG. 2D, exon structure of NPHP4 cDNA. Black and white boxes represent the 30 exons encoding nephroretinin. The number of the first codon of each exon is indicated; exons beginning with the second or third base of a codon are indicated by "b" or "c", respectively. At the bottom locations of the 11 different mutations identified in 8 NPHP kindred are shown. fs, frameshift. FIG. 2E, NPHP4 mutations occurring homozygously in affecteds of 5 consanguineous families (underlined). Mutated nucleotides and altered amino acids are depicted on grey background.

FIG. 4 shows the nucleic acid (cDNA) (SEQ ID NO: 1) and amino acid (SEQ ID NO: 2) sequences of NPHP4.

FIG. 5 shows an alignment of human (SEQ ID NO: 2), mouse (SEQ ID NO: 3), and C. elegans (SEQ ID NO: 4) NPHP4 amino acid sequences.

FIG. 6 shows the nucleic acid (SEQ ID NO: 5) and amino acid (SEQ ID NO: 6) sequences of an exemplary NPHP4 variant found in family 3 (See Table 1).

FIG. 7 shows the nucleic acid (SEQ ID NO: 7) and amino acid (SEQ ID NO:8) sequences of an exemplary NPHP4 variant found in family 24 (See Table 1).

FIG. 8 shows the nucleic acid (SEQ ID NO: 9) and amino acid (SEQ ID NO:10) sequences of an exemplary NPHP4 variant found in family 30 (See Table 1).

FIG. 9 shows the nucleic acid (SEQ ID NO: 11) and amino acid (SEQ ID NO:12) sequences of an exemplary NPHP4 variant found in family 32 (See Table 1).

FIG. 10 shows the nucleic acid (SEQ ID NO: 13) and amino acid (SEQ ID NO:14) sequences of an exemplary NPHP4 variant found in family 60 (See Table 1).

FIG. 11 shows the nucleic acid (SEQ ID NO: 15) and amino acid (SEQ ID NO: 16) sequences of an exemplary NPHP4 variant found in family 461 (See Table 1).

FIG. 12 shows the nucleic acid (SEQ ID NO: 17) and amino acid (SEQ ID NO: 18) sequences of an additional exemplary NPHP4 variant found in family 461 (See Table 1).

FIG. 13 shows the nucleic acid (SEQ ID NO: 19) and amino acid (SEQ ID NO:20) sequences of an exemplary NPHP4 variant found in family 622 (See Table 1).

FIG. 14 shows the nucleic acid (cDNA) (SEQ ID NO: 21) and amino acid (SEQ ID NO: 22) sequences of inversin.

FIGS. 15a and 15d show mutations in INVS (nucleotide exchange and amino acid exchange) together with sequence traces for mutated sequences (top) and sequence from healthy controls (bottom). Family numbers are given above boxes. FIG. 15b shows the exon structure of INVS. FIG. 15c shows a representation of protein motifs found in inversin. aa, amino acid residues; Ank, ankyrin/swi6 motif D1, D box1 (Apc2-binding[23]); D2, D box2; IQ, calmodulin binding domains.

FIG. 16 depicts the specific nucleotide exchange (SEQ ID NO: 23) and resulting termination of the amino acid sequence (SEQ ID NO: 24) of an exemplary inversin variant found in family A6 (See Table 3).

FIG. 17 depicts a specific nucleotide deletion (SEQ ID NO: 25) and resulting termination of the amino acid sequence (SEQ ID NO: 26) of an exemplary inversin variant found in family A6 (See Table 3).

FIG. 18 depicts the specific nucleotide exchange (SEQ ID NO: 27) and resulting termination of the amino acid sequence (SEQ ID NO: 28) of an exemplary inversin variant found in family A8 (See Table 3).

FIG. 19 depicts the specific nucleotide exchange (SEQ ID NO: 29) and resulting termination of the amino acid sequence (SEQ ID NO: 30) of an exemplary inversin variant found in family A9 (See Table 3).

FIG. 20 depicts the specific nucleotide exchange (SEQ ID NO: 31) and resulting substitution in the amino acid sequence (SEQ ID NO: 32) of an exemplary inversin variant found in family A9 (See Table 3).

FIG. 21 depicts a specific nucleotide deletion (SEQ ID NO: 33) and resulting termination of the amino acid sequence (SEQ ID NO: 34) of an exemplary inversin variant found in family A10 (See Table 3).

FIG. 22 depicts the specific nucleotide exchange (SEQ ID NO: 35) and resulting termination of the amino acid sequence (SEQ ID NO: 36) of an exemplary inversin variant found in family A12 (See Table 3).

FIG. 23 depicts the specific nucleotide exchange (SEQ ID NO: 37) and resulting termination of the amino acid sequence (SEQ ID NO: 38) of an exemplary inversin variant found in family 868 (See Table 3).

FIG. 24 depicts a specific nucleotide insertion (SEQ ID NO: 39) and resulting termination of the amino acid sequence (SEQ ID NO: 40) of an exemplary inversin variant found in family 868 (See Table 3).

FIG. 25 depicts the specific nucleotide exchange (SEQ ID NO: 41) and resulting substitution in the amino acid sequence (SEQ ID NO: 42) of an exemplary inversin variant found in family A7 (See Table 3).

FIG. 31a shows the NPHP5 critical genetic region spanning 8.7 Mb between flanking markers D3S1575 and D3S1551 as annotated by GenomeBrowser. FIG. 31b shows the 8 different NPHP5 mutations detected in 16 individuals with SLSN (Table 5). FIG. 31c shows the exon structure of human NPHP5 cDNA drawn relative to scale bar. Positions of start codon (ATG) at nt +1 and of stop codon (TAG) are indicated. FIG. 31d shows representations of protein motifs are drawn to scale in relation to exon structure. Lines and arrows indicate relative positions of the mutations detected. IQ, IQ calmodulin-binding regions; CC, coiled-coil domain. FIG. 31e shows mutation detected in human NPHP5.

FIG. 32a shows that in yeast-two-hybrid direct interaction analysis, NPHP5 as bait interacts with calmodulin (CALM2) as prey, but not with NPHP1, inversin (NPHP2), NPHP3, NPHP4, NPHP5 (itself), RPGR, BBS1, BBS2 and BBS4-8 as prey. FIG. 32b shows colony growth on media deficient for leucine (-Leu) and tryptophan (-Trp). FIGS. 32c and 32d show coimmunoprecipitation of of NPHP5 with RPGR and calmodulin from bovine retinal extracts. Immunoblots of the proteins were probed with anti-RPGR antibody ORF15CP (FIG. 32c) or anti-NPHP5 antibody (FIG. 32d).

FIG. 33a shows a multiple tissue Northern blot with human adult poly (A)+ RNA was hybridized with a 1.8 kb NPHP5 human cDNA probe covering the complete coding region. FIG. 33b shows a β-actin control for poly(A)+ RNA loading.

FIG. 34 show amino acid sequence alignment for nephrocystin-5 (NPHP5) orthologs of mouse, rat, human, zebrafish, and *C. intestinalis*. *M.m., Mus musculus* (SEQ ID NO:113); *R.n., Rattus norvegicus* (SEQ ID NO:114); *H.s., Homo sapiens* (SEQ ID NO:115); *D.r., Danio rerio* (SEQ ID NO:116); *C.i., Ciona intestinalis* (SEQ ID NO:117).

FIG. 35 shows characterization of anti-NPHP5 antibody by immunoblot analysis. FIG. 35a shows an immunoblot of mouse (MR), human (HR), and bovine (BR) retinal protein extracts using anti-NPHP5 antibody (lanes 1-3). FIG. 35b shows expression of NPHP5 in different tissues and cell lines was examined using the anti-NPHP5 antibody.

FIG. 36 shows characterization of the anti-ORF15CP antibody. FIG. 36a: Bovine retinal protein extract (100 μg) was analyzed by SDS-PAGE, followed by immunoblotting using anti-ORF15CP antibody alone (lane 1) or after pre-incubated with 50-fold molar excess of the cognate (lane 2) or non-specific (lane 3) peptide. FIG. 36b shows immunoblot analysis of the wild-type (wt) and Rpgr knock out (ko) mouse (Hong et al. PNAS USA 97,3649-54,2000) retinal protein extracts using the ORF15CP antibody.

FIG. 37 shows the nucleic acid sequences of wild type (SEQ ID NO:81) and variant (SEQ ID NOS: 83-90), as well as wild type amino acid (SEQ ID NO:82) of NPHP5.

GENERAL DESCRIPTION OF THE INVENTION

Figure 2:
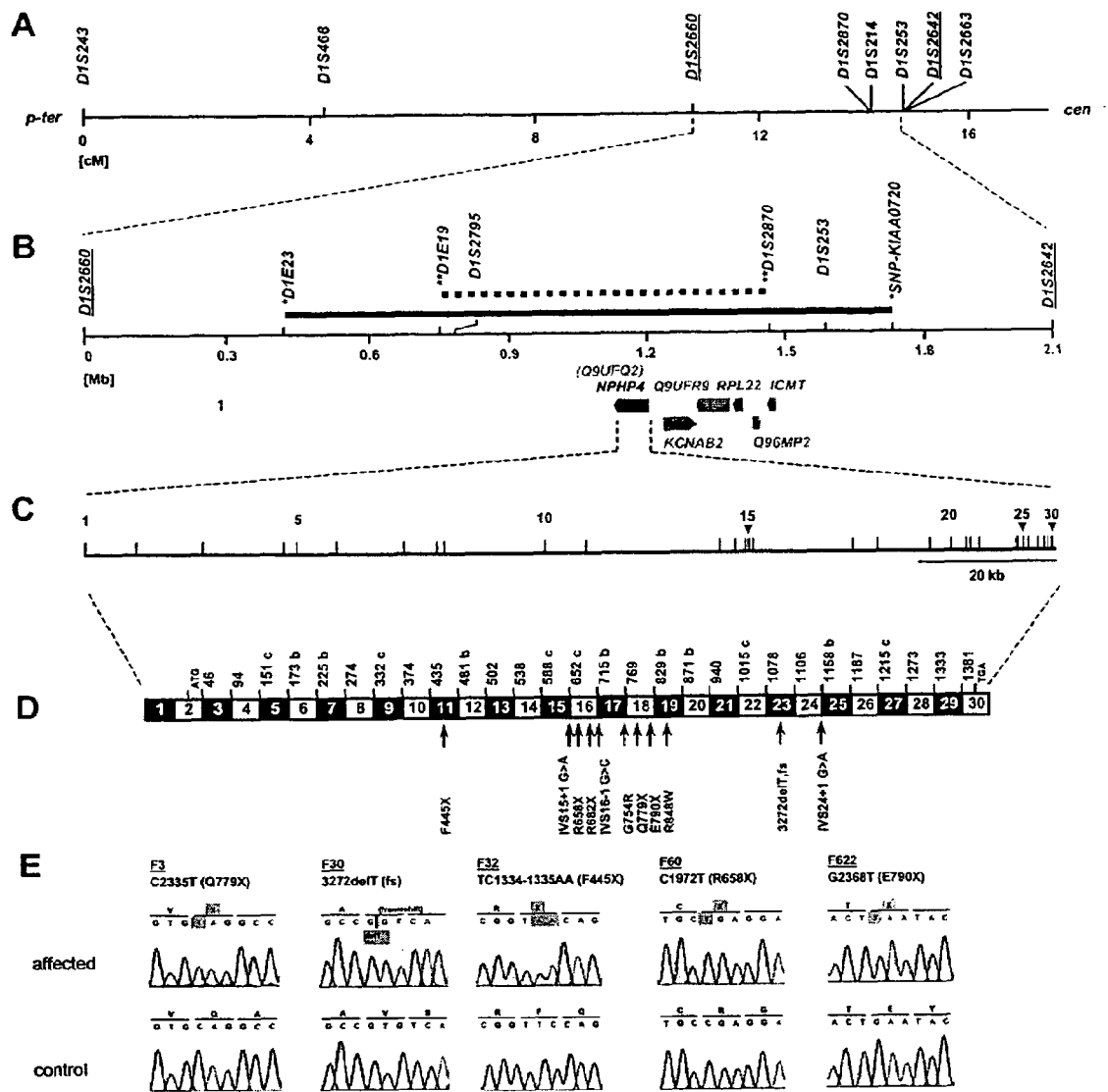
FIG. 2 shows the positional cloning strategy for the NPHP4 gene on human chromosome 1p36.

The gene for nephronophthisis type 1 (NPHP1) has been cloned by positional cloning (Hildebrandt et al., Nature Genet 17:149-153 [1997]). Its gene product, nephrocystin, represents a novel docking protein, which interacts with the signaling proteins p130Cas, tensin, focal adhesion kinase 2, and filamin A and B, which are involved in cell-cell and cell-matrix signaling of renal epithelial cells (Hildebrandt and Otto, J Am Soc Nephrol 11: 1753-1761 [2000]; Donaldson et al., Exp Cell Res 256:168-178 [2000]; Benzing et al., Proc Natl Acad Sci USA 98:9784-9789 [2001]; Donaldson et al., J Biol Chem 277:29028-29035 [2002]). The association of NPHP with autosomal recessive retinitis pigmentosa (RP), has been described as the so-called Senior-Løken syndrome (SLS [MIM 266900]) (Senior et al., Am J Ophthalmol 52:625-633 [1961]; Løken et al., Acta Paediatr 50:177-184 [1961]; each of which is herein incorporated by reference). In families with SLS, linkage has been demonstrated to the loci for NPHP1 and NPHP3 (Caridi et al., Am J Kidney Dis 32:1059-1062 [1998]; Omran et al., 2002, supra). Very recently, a new gene locus (NPHP4) for NPHP type 4 (Schuermann et al., Am. J. Hum. Genet. 70:1240 [2002]; herein incorporated by reference) has been identified and linkage of a large SLS kindred to this locus demonstrated.

Experiments conducted during the course of development of the present invention identified, by positional cloning, the gene (NPHP4) causing NPHP type 4, through demonstration of 9 likely loss-of-function mutations in 6 affected families. In addition, 2 loss of function mutations in patients from 2 families with SLS were detected. The conclusion that the gene cloned in the experiments described herein is the gene causing NPHP type 4 is based on identification, in 8 families with NPHP, of 9 distinct truncating mutations and 2 missense mutations, none of which occurred in over 92 healthy control individuals. Experiments conducted during the course of development of the present invention further demonstrated the presence of 2 homozygous truncating mutations also in 2 families with SLS (F3 and F60). A small percentage of patients also exhibit SLS in families with NPHP1 mutations (Caridi et al., Am. J. Kidney Disease 32:1059 [1998]) and in families linked to NPHP3 (Omran et al. 2002, surpa). For all 3 genes no distinction can be made on the basis of allelic differences between the NPHP phenotypes with and without RP. Therefore, it seems likely that a stochastic pleiotropic effect is responsible for the occurrence of RP in NPHP types 1, 3 and 4. Accordingly, in some embodiments, the present invention provides the NPHP4 nucleic acid and amino acid sequence, as well as disease related variants thereof.

NPHP4 is a novel gene, which is unrelated to any known gene families. It encodes a novel protein, "nephroretinin" or "nephrocystin-4". NPHP4, like NPHP1, is unique to the human genome, is conserved in *C. elegans*, and exhibits a broad expression pattern. Identification of the NPHP1 gene (Hildebrandt et al., Nature Genet. 17:149 [1997]) revealed nephrocystin as a novel docking protein, which interacts with p130Cas (Donaldson et al., Exp. Cell. Res. 256:168 [2000]; Hildebrandt and Otto, J. Am. Soc. Nephrol. 11:1753 [2000]), tensin, focal adhesion kinase 2 (Benzing et al., PNAS 98:9784 [2001]), and filamin A and B (Donaldson et al., 2002, supra), and which is involved in cell-cell and cell-matrix signaling. The present invention is not limited to a particular mechanism of action. Indeed, an understanding of the mechanism is not necessary to practice the present invention. Nonetheless, it is therefore likely that both nephroretinin and nephrocystin, interact within a novel shared pathogenic pathway. Thus, the present invention provides a novel gene with critical roles in renal tissue architecture and ophthalmic function.

Two additional gene loci have been mapped for NPHP. The locus NPHP3 associated with adolescent NPHP localizes to human chromosome 3q22 (Omran, et al., Am. J. Hum. Genet. 66, 118 [2000]), and NPHP2 associated with infantile NPHP resides on chromosome 9q21-q22 (Haider et al., Am. J. Hum. Genet. 63, 1404 [1998]). The kidney phenotype of NPHP2 combines features of NPHP, including tubular basement membrane disruption and renal interstitial fibrosis, with features of PKD (Gagnadoux et al., Pediatr. Nephrol. 3, 50 [1989]) including enlarged kidneys and widespread cyst development. During the course of development of the present invention, the human gene INVS was determined to be located in the NPHP2 critical genetic interval (Haider et al., Am. J. Hum. Genet. 63, 1404 [1998]).

In the inv/inv mouse model of insertional mutagenesis, a deletion of exons 3-11 of Invs encoding inversin causes a phenotype of cyst formation in enlarged kidneys, situs inversus and pancreatic islet cell dysplasia (Mochizuki et al., Nature 395, 177 [1998]; Morgan et al., Nat. Genet. 20, 149 [1998]). Histology of infantile NPHP2 and of the inv/inv mouse identified features resembling NPHP, namely interstitial fibrosis, mild interstitial cell infiltration, tubular cell atrophy, tubular cysts and periglomerular fibrosis. In addition, human NPHP2 and mouse inv/inv phenotypes showed features reminiscent of autosomal dominant PKD, such as kidney enlargement, absence of the tubular basement membrane irregularity characteristic of NPHP and presence of cysts also outside the medullary region.

Experiments conducted during the course of development of the present invention identified the gene (INVS) causing NPHP type 2, through demonstration of 8 likely loss-of-function mutations in 6 affected families. The conclusion that the gene identified in the experiments described herein is the gene causing NPHP type 2 is based on identification, in 7 families with NPHP, of 8 distinct truncating mutations and 2 missense mutations, none of which occurred in over 100 healthy control individuals.

Further experiments conducted during the course of development of the present invention demonstrated, by positional cloning, mutations in a novel evolutionarily conserved gene (NPHP5) as the most frequent cause of renal-retinal Senior-Loken syndrome (SLSN). NPHP5 encodes an IQ domain protein, nephrocystin-5. All 8 distinct recessive mutations detected in 16 SLSN families are predicted to generate a truncated nephrocystin-5 protein. Nephrocystin-5 interacts with calmodulin and is localized in primary cilia of renal epithelial cells. All individuals with NPHP5 mutations have RP. Hence, the interaction of nephrocystin-5 with RPGR (retinitis pigmentosa GTPase regulator), which is expressed in photoreceptor cilia and associated with 10-20% of RP, was examined. Nephrocystin-5, RPGR, and calmodulin can be coimmunoprecipitated from retinal extracts, and that these proteins localize to connecting cilia of photoreceptors. The studies provide a molecular link for kidney and eye involvement in this renal-retinal syndrome, and emphasize the central role of ciliary dysfunction in the pathogenesis of SLSN.

The findings that NPHP5 and RPGR coimmunoprecipitate and share localization to photoreceptors provide molecular evidence for a shared pathogenesis of the kidney and eye phenotypic changes in this renal-retinal syndrome. The present invention is not limited to a particular mechanism. Indeed, an understanding of the mechanism is not necessary to practice the present invention. Nonetheless, it is contemplated that, since primary cilia of renal epithelial cells and connecting cilia of photoreceptors are homologous subcellular structures, that NPHP5 and RPGR may participate in a common functional pathway of ciliary function. Mouse renal cystic phenotype pcy8 is caused by mutations in the orthologue of human NPHP38. Since pcy has recently become amenable to treatment with a vasopressin-2 receptor antagonist (Gattone et al., Nat Med 9:1323 2003), it is contemplated that the renal and retinal phenotypes of Nphp5 are responsive to this treatment.

All of the NPHP proteins thus identified are expressed in primary cilia (See e.g., Watnick et al., Nat Genet 34:355 2003), and share this features with genes mutated in retinitis, olfactory defects, obesity, infertility, etc. that are part of Bardet-Biedl syndrome/nephronophthisis (See e.g., Ansley et al., Nature 425:628, [2003]). Thus, the proteins and nucleic acids of the present invention find use the diagnosis, characterization, and treatment of a wide variety of diseases.

Definitions

To facilitate understanding of the invention, a number of terms are defined below. As used herein, the term "NPHP" "NPHPs" "NPHP proteins" and "NPHP nucleic acids" refers to any NPHP family member protein or nucleic acid. Example include, but are not limited to those described herein (e.g., NPHP2 (Inversin), NPHP3, NPHP4, and NPHP5).

As used herein, the term "NPHP4" or "nephroretinin" or "nephrocystin-4" when used in reference to a protein or nucleic acid refers to a protein or nucleic acid encoding a protein that, in some mutant forms, is correlated with nephronophthisis. The term NPHP4 encompasses both proteins that are identical to wild-type NPHP4 and those that are derived from wild type NPHP4 (e.g., variants of NPHP4 or chimeric genes constructed with portions of NPHP4 coding regions). In some embodiments, the "NPHP4" is the wild type nucleic acid (SEQ ID NO: 1) or amino acid (SEQ ID NO:2) sequence. In other embodiments, the "NPHP4" is a variant or mutant (e.g., including, but not limited to, the nucleic acid sequences described by SEQ ID NOS: 5, 7, 9, 11, 13, 15, 17, 19 and the amino acid sequences described by SEQ ID NOS: 6, 8, 10, 12, 14, 16, 18, and 20).

As used herein, the term "NPHP5" or "nephrocystin-5" when used in reference to a protein or nucleic acid refers to a protein or nucleic acid encoding a protein that, in some mutant forms, is correlated with nephronophthisis (e.g., the Senior-Loken syndrome variant). The term NPHP4 encompasses both proteins that are identical to wild-type NPHP5 and those that are derived from wild type NPHP5 (e.g., variants of NPHP5 or chimeric genes constructed with portions of NPHP5 coding regions). In some embodiments, the "NPHP5" is the wild type nucleic acid (SEQ ID NO: 81) or amino acid (SEQ ID NO:82) sequence. In other embodiments, the "NPHP5" is a variant or mutant (e.g., including, but not limited to, the nucleic acid sequences described by SEQ ID NOS: 83-90 and the amino acid sequences encoded by SEQ ID NOS: 83-90.

As used herein, the term "INVS" or "inversin" when used in reference to a protein or nucleic acid refers to a protein or nucleic acid encoding a protein that, in some mutant forms, is correlated with nephronophthisis. In some embodiments, the "inversin" is the wild type nucleic acid (SEQ ID NO: 21) or amino acid (SEQ ID NO:22) sequence. In other embodiments, the "inversin" is a variant or mutant (e.g., including, but not limited to, the nucleic acid sequences described by SEQ ID NOS: 23, 25, 27, 29, 31, 33, 35, 37, and 39 and the amino acid sequences described by SEQ ID NOS: 24, 26, 28, 30, 32, 34, 36, 38 and 40).

As used herein, the term "C-terminal truncation of SEQ ID NO:2 refers to a polypeptide comprising a portion of SEQ ID NO:2, wherein the portion comprises the N-terminus of SEQ ID NO:2. In preferred embodiments, the N-terminal portion comprises at least 200 amino acids, preferably at least 400 amino acids, and even more preferably at least 700 amino acids of SEQ ID NO:2. Exemplary C-terminal truncations of SEQ ID NO:2 include, but are not limited to, SEQ ID NOs: 6, 10, 12, 14, 16, and 20, and the term "C-terminal truncation of SEQ ID NO:22 refers to a polypeptide comprising a portion of SEQ ID NO:22, wherein the portion comprises the N-terminus of SEQ ID NO:22. In preferred embodiments, the N-terminal portion comprises at least 200 amino acids, preferably at least 400 amino acids, and even more preferably at least 700 amino acids of SEQ ID NO:22. Exemplary C-terminal truncations of SEQ ID NO:22 include, but are not limited to, SEQ ID NOs: 24, 26, 28, 30, 34, 36, 38 and 40.

As used herein, the terms "instructions for using said kit for said detecting the presence or absence of a variant nephroretinin polypeptide in a said biological sample" or "instructions for using said kit for said detecting the presence or absence of a variant inversin polypeptide in a said biological sample" includes instructions for using the reagents contained in the kit for the detection of variant and wild type nephroretinin and inversin polypeptides, respectfully. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4)Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., NPHP4). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "NPHP4 gene" refers to the full-length NPHP4 nucleotide sequence (e.g., contained in SEQ ID NO: 1). However, it is also intended that the term encompass fragments of the NPHP4 sequence, mutants (e.g., SEQ ID NOS: 5, 7, 9, 11, 13, 15, 17, 21, 23, and 25) as well as other domains within the full-length NPHP4 nucleotide sequence. Furthermore, the terms "NPHP4 nucleotide sequence" or "NPHP4 polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-"A-G-T-3'," is complementary to the sequence 3'-"T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.). Furthermore, when used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42 C when a probe of about 500 nucleotides in length is employed. The present invention is not limited to the hybridization of probes of about 500 nucleotides in length. The present invention contemplates the use of probes between approximately 10 nucleotides up to several thousand (e.g., at least 5000) nucleotides in length.

One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., NPHP4).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., the NPHP4 gene).

As used herein, the term "detection assay" refers to an assay for detecting the presence of absence of variant nucleic acid sequences (e.g., polymorphism or mutations) in a given allele of a particular gene (e.g., the NPHP4 gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos.

4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding NPHP4 includes, by way of example, such nucleic acid in cells ordinarily expressing NPHP4 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, NPHP4 antibodies are purified by removal of contaminating non-immunoglobulin proteins; they are also purified by the removal of immunoglobulin that does not bind NPHP4. The removal of non-immunoglobulin proteins and/or the removal of immunoglobulins that do not bind NPHP4 results in an increase in the percent of NPHP4-reactive immunoglobulins in the sample. In another example, recombinant NPHP4 polypeptides are expressed in bacterial host cells and the polypeptides are purified by the removal of host cell proteins; the percent of recombinant NPHP4 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced NPHP4 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding NPHP4 (e.g., SEQ ID NO:1) or fragments thereof may be employed as hybridization probes. In this case, the NPHP4 encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "membrane receptor protein" refers to membrane spanning proteins that bind a ligand (e.g., a hormone or neurotransmitter). As is known in the art, protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases is the tyrosine kinases (TKs), which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity. Tyrosine kinases can also be cytoplasmic, non-receptor-type enzymes and act as a downstream component of a signal transduction pathway.

As used herein, the term "signal transduction protein" refers to proteins that are activated or otherwise affected by ligand binding to a membrane or cytostolic receptor protein or some other stimulus. Examples of signal transduction protein include adenyl cyclase, phospholipase C, and G-proteins. Many membrane receptor proteins are coupled to G-proteins (i.e., G-protein coupled receptors (GPCRs); for a review, see Neer, 1995, Cell 80:249-257 [1995]). Typically, GPCRs contain seven transmembrane domains. Putative GPCRs can be identified on the basis of sequence homology to known GPCRs.

GPCRs mediate signal transduction across a cell membrane upon the binding of a ligand to an extracellular portion of a GPCR. The intracellular portion of a GPCR interacts with a G-protein to modulate signal transduction from outside to inside a cell. A GPCR is therefore said to be "coupled" to a G-protein. G-proteins are composed of three polypeptide subunits: an α subunit, which binds and hydrolyses GTP, and a dimeric βγ subunit. In the basal, inactive state, the G-protein exists as a heterotrimer of the α and βγ subunits. When the G-protein is inactive, guanosine diphosphate (GDP) is associated with the α subunit of the G-protein. When a GPCR is bound and activated by a ligand, the GPCR binds to the G-protein heterotrimer and decreases the affinity of the Gα subunit for GDP. In its active state, the G subunit exchanges GDP for guanine triphosphate (GTP) and active Gα subunit disassociates from both the receptor and the dimeric βγ subunit. The disassociated, active Gα subunit transduces signals to effectors that are "downstream" in the G-protein signaling pathway within the cell. Eventually, the G-protein's endogenous GTPase activity returns active G subunit to its inactive state, in which it is associated with GDP and the dimeric βγ subunit.

Numerous members of the heterotrimeric G-protein family have been cloned, including more than 20 genes encoding various Gα subunits. The various G subunits have been categorized into four families, on the basis of amino acid sequences and functional homology. These four families are termed $G\alpha_s$, $G\alpha_i$, $G\alpha_q$, and $G\alpha_{12}$. Functionally, these four families differ with respect to the intracellular signaling pathways that they activate and the GPCR to which they couple.

For example, certain GPCRs normally couple with $G\alpha_s$ and, through $G\alpha_s$, these GPCRs stimulate adenylyl cyclase activity. Other GPCRs normally couple with $GG\alpha_q$, and through $GG\alpha_q$, these GPCRs can activate phospholipase C (PLC), such as the β isoform of phospholipase C (i.e., PLCβ, Stermweis and Smrcka, Trends in Biochem. Sci. 17:502-506 [1992]).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "entering" as in "entering said genetic variation information into said computer" refers to transferring information to a "computer readable medium." Information may be transferred by any suitable method, including but not limited to, manually (e.g., by typing into a computer) or automated (e.g., transferred from another "computer readable medium" via a "processor").

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "computer implemented method" refers to a method utilizing a "CPU" and "computer readable medium."

DETAILED DESCRIPTION OF THE INVENTION

The present invention relates to Nephronophthisis, in particular to the NPHP proteins (e.g., nephrocystin-5) and nucleic acids encoding NPHP proteins. The present invention also provides assays for the detection of NPHP, and assays for detecting NPHP polymorphisms and mutations associated with disease states. The below descriptions pertains to all of the NPHP proteins and nucleic acids disclosed herein (e.g., NPHP2, NPHP3, NPNP4, and NPNP5). However, it is often illustrated with just one NPHP protein.

I. NPHP Polynucleotides

As described above, new genes associated with NPHP kidney disease have been discovered. Accordingly, the present invention provides nucleic acids encoding NPHP genes, homologs, variants (e.g., polymorphisms and mutants), including but not limited to, those described in SEQ ID NOs: 1, 21, and 81. In some embodiments, the present invention provide polynucleotide sequences that are capable of hybridizing to SEQ ID NO: 1, 21 and 81 under conditions of low to high stringency as long as the polynucleotide sequence capable of hybridizing encodes a protein that retains a biological activity of the naturally occurring NPHP. In some embodiments, the protein that retains a biological activity of naturally occurring NPHP is 70% homologous to wild-type NPHP, preferably 80% homologous to wild-type NPHP, more preferably 90% homologous to wild-type NPHP, and most preferably 95% homologous to wild-type NPHP. In preferred embodiments, hybridization conditions are based on the melting temperature ($T_m$) of the nucleic acid binding complex and confer a defined "stringency" as explained above (See e.g., Wahl, et al., Meth. Enzymol., 152:399-407 [1987], incorporated herein by reference).

In other embodiments of the present invention, additional alleles of NPHP are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Examples of the alleles of the present invention include those encoded by SEQ ID NOs:1, 21, and 81 (wild type) and disease alleles described herein (e.g., SEQ ID NOs: 5, 7, 9, 11, 13, 15, 17, 19, and 83-90).

In still other embodiments of the present invention, the nucleotide sequences of the present invention may be engineered in order to alter an NPHP coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of NPHP nucleic acids may be extended utilizing the nucleotide sequence (e.g., SEQ ID NOs: 1, 21 and 81) in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318-22 [1993]). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed NPHP sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., NPHP function) for such purposes as altering the biological activity (e.g., prevention of cystic kidney disease). Such modified peptides are considered functional equivalents of peptides having an activity of NPHP as defined herein. A modified peptide can be produced in which the nucleotide sequence encoding the polypeptide has been altered, such as by substitution, deletion, or addition. In particularly preferred embodiments, these modifications do not significantly reduce the biological activity of the modified NPHP. In other words, construct "X" can be evaluated in order to determine whether it is a member of the genus of modified or variant NPHP's of the present invention as defined functionally, rather than structurally. In preferred embodiments, the activity of variant NPHP4 polypeptides is evaluated by methods described herein (e.g., the generation of transgenic animals).

Moreover, as described above, variant forms of NPHP are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of NPHP disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a NPHP coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

II. NPHP Polypeptides

In other embodiments, the present invention provides NPHP polynucleotide sequences that encode NPHP polypeptide sequences. NPHP polypeptides (e.g., SEQ ID NOs: 2, 22, and 82) are described herein. Other embodiments of the present invention provide fragments, fusion proteins or functional equivalents of these NPHP proteins. In some embodiments, the present invention provides truncation mutants of NPHP4 (e.g., SEQ ID NOs: 6, 10, 12, 14, 16, and 20). In still other embodiment of the present invention, nucleic acid sequences corresponding to NPHP variants, homologs, and mutants may be used to generate recombinant DNA molecules that direct the expression of the NPHP variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO:1 that encode substantially the same or a functionally equivalent amino acid sequence, may be used to clone and express NPHP. In general, such polynucleotide sequences hybridize to SEQ ID NO:1 under conditions of high to medium stringency as described above. As will be understood by those of skill in the art, it may be advantageous to produce NPHP-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of NPHP expression or to produce recombinant RNA transcripts having desirable properties, such as a longer half-life, than transcripts produced from naturally occurring sequence.

1. Vectors for Production of NPHP

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 1, 5, 7, 9, 11, 13, 15, 17, and 19). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NO:1) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the $E.$ $coli$ lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in $E.$ $coli$).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of NPHP

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of NPHP

The present invention also provides methods for recovering and purifying NPHP from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NO: 1) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of NPHP

In addition, the present invention provides fragments of NPHP4 (i.e., truncation mutants, e.g., SEQ ID NOs: 6, 10, 12, 14, 16, and 20). As described above, truncations of NPHP4 were found in families with NPHP type 4 disease. In some embodiments of the present invention, when expression of a portion of the NPHP protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al., J. Bacteriol., 169:751 [1987]) and Salmonella typhimurium and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., E. coli or CM89 or S. cerivisiae), or in vitro by use of purified MAP.

5. Fusion Proteins Containing NPHP

The present invention also provides fusion proteins incorporating all or part of NPHP. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a NPHP protein. In some embodiments of the present invention, the VP6 capsid protein of rotavirus is used as an immunologic carrier protein for portions of the NPHP polypeptide, either in the monomeric form or in the form of a viral particle. In other embodiments of the present invention, the nucleic acid sequences corresponding to the portion of NPHP against which antibodies are to be raised can be incorporated into a fusion gene construct which includes coding sequences for a late vaccinia virus structural protein to produce a set of recombinant viruses expressing fusion proteins comprising a portion of NPHP as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of NPHP and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of NPHP is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the NPHP proteins can also be expressed and presented by bacterial cells.

In addition to utilizing fusion proteins to enhance immunogenicity, it is widely appreciated that fusion proteins can also facilitate the expression of proteins, such as the NPHP proteins of the present invention. Accordingly, in some embodiments of the present invention, NPHP can be generated as a glutathione-S-transferase (i.e., GST fusion protein). It is contemplated that such GST fusion proteins will enable easy purification of NPHP, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of NPHP, can allow purification of the expressed NPHP fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of NPHP

Still other embodiments of the present invention provide mutant or variant forms of NPHP (i.e., muteins). It is possible to modify the structure of a peptide having an activity of NPHP for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject NPHP proteins as defined herein. A modified peptide can be produced in which the amino acid sequence has been altered, such as by amino acid substitution, deletion, or addition.

Moreover, as described above, variant forms (e.g., mutants or polymorphic sequences) of the subject NPHP proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present NPHP proteins, as well as truncation mutants, and is especially useful for identifying potential variant sequences (i.e., mutants or polymorphic sequences) that are involved in kidney disease or resistance to kidney disease. The purpose of screening such combinatorial libraries is to generate, for example, novel NPHP variants that can act as either agonists or antagonists, or alternatively, possess novel activities all together.

Therefore, in some embodiments of the present invention, NPHP variants are engineered by the present method to provide altered (e.g., increased or decreased) biological activity. In other embodiments of the present invention, combinatorially-derived variants are generated which have a selective potency relative to a naturally occurring NPHP. Such proteins, when expressed from recombinant DNA constructs, can be used in gene therapy protocols.

Still other embodiments of the present invention provide NPHP variants that have intracellular half-lives dramatically different than the corresponding wild-type protein. For example, the altered protein can be rendered either more stable or less stable to proteolytic degradation or other cellular process that result in destruction of, or otherwise inactivate NPHP. Such variants, and the genes which encode them, can be utilized to alter the location of NPHP expression by modulating the half-life of the protein. For instance, a short half-life can give rise to more transient NPHP biological effects and, when part of an inducible expression system, can allow tighter control of NPHP levels within the cell. As above, such proteins, and particularly their recombinant nucleic acid constructs, can be used in gene therapy protocols.

In still other embodiments of the present invention, NPHP variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of NPHP homologs, variants or other related proteins are aligned, preferably to promote the highest homology possible. Such a population of variants can include, for example, NPHP homologs from one or more species, or NPHP variants from the same species but which differ due to mutation or polymorphisms. Amino acids that appear at each position of the aligned sequences are selected to create a degenerate set of combinatorial sequences.

In a preferred embodiment of the present invention, the combinatorial NPHP library is produced by way of a degenerate library of genes encoding a library of polypeptides which each include at least a portion of potential NPHP protein sequences. For example, a mixture of synthetic oligonucleotides can be enzymatically ligated into gene sequences such that the degenerate set of potential NPHP sequences are expressible as individual polypeptides, or alternatively, as a set of larger fusion proteins (e.g., for phage display) containing the set of NPHP sequences therein.

There are many ways by which the library of potential NPHP homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential NPHP sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; each of which is herein incorporated by reference; as well as U.S. Pat. Nos. 5,223,409, 5,198,346, and 5,096,815; each of which is incorporated herein by reference).

It is contemplated that the NPHP nucleic acids (e.g., SEQ ID NOs:1, 21, and 81, and fragments and variants thereof) can be utilized as starting nucleic acids for directed evolution. These techniques can be utilized to develop NPHP variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1:17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for NPHP activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370:324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for NPHP activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of NPHP homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of NPHP

In an alternate embodiment of the invention, the coding sequence of NPHP is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire NPHP amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431A Peptide Synthesizer (Perkin Elmer) in accordance with the instructions provided by the manufacturer. Additionally, the amino acid sequence of NPHP, or any part thereof, may be altered during direct synthesis and/or combined using chemical methods with other sequences to produce a variant polypeptide.

III. Detection of NPHP Alleles

In some embodiments, the present invention provides methods of detecting the presence of wild type or variant (e.g., mutant or polymorphic) NPHP nucleic acids or polypeptides. The detection of mutant NPHP finds use in the diagnosis of disease (e.g., NPHP type 4, Senior-Loken syndrome or type 2 disease).

A. NPHP Alleles

In some embodiments, the present invention includes alleles of NPHP4, NPHP5 and inversin that increase a patient's susceptibility to NPHP type 4, Senior-Loken syndromw or type 2 kidney disease (e.g., including, but not limited to, SEQ ID NOs: 5, 7, 9, 11, 13, 15, 17, 19, 23, 25, 27, 29, 33, 35, 37, 39, and 83-90; also see Examples 1, 2 and 7). However, the present invention is not limited to the mutations described in SEQ ID NOs: 5, 7, 9, 11, 13, 15, 17, 19, 23, 25, 27, 29, 33, 35, 37, 83-90 and 39. Any mutation that results in the undesired phenotype (e.g., kidney disease) is within the scope of the present invention.

B. Detection of NPHP Alleles

Accordingly, the present invention provides methods for determining whether a patient has an increased susceptibility NPHP type 4, Senior-Loken syndrome or type 2 kidney disease by determining whether the individual has a variant NPHP allele. In other embodiments, the present invention provides methods for providing a prognosis of increased risk for kidney disease to an individual based on the presence or absence of one or more variant alleles of NPHP. In preferred embodiments, the variation causes a truncation of the NPHP protein.

A number of methods are available for analysis of variant (e.g., mutant or polymorphic) nucleic acid sequences. Assays for detection variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

1. Direct sequencing Assays

In some embodiments of the present invention, variant sequences are detected using a direct sequencing technique. In these assays, DNA samples are first isolated from a subject using any suitable method. In some embodiments, the region of interest is cloned into a suitable vector and amplified by growth in a host cell (e.g., a bacteria). In other embodiments, DNA in the region of interest is amplified using PCR.

Following amplification, DNA in the region of interest (e.g., the region containing the SNP or mutation of interest) is sequenced using any suitable method, including but not limited to manual sequencing using radioactive marker nucleotides, or automated sequencing. The results of the sequencing are displayed using any suitable method. The sequence is examined and the presence or absence of a given SNP or mutation is determined.

2. PCR Assay

In some embodiments of the present invention, variant sequences are detected using a PCR-based assay. In some embodiments, the PCR assay comprises the use of oligonucleotide primers that hybridize only to the variant or wild type allele of NPHP (e.g., to the region of polymorphism or mutation). Both sets of primers are used to amplify a sample of DNA. If only the mutant primers result in a PCR product, then the patient has the mutant NPHP allele. If only the wild-type primers result in a PCR product, then the patient has the wild type allele of NPHP.

3. Mutational detection by dHPLC

In some embodiments of the present invention, variant sequences are detected using a PCR-based assay with consecutive detection of nucleotide variants by dHPLC (denaturing high performance liquid chromatography). Exemplary systems and Methods for dHPLC include, but are not limited to, WAVE (Transgenomic, Inc; Omaha, Nebr.) or VARIAN equipment (Palo Alto, Calif.).

4. Fragment Length Polymorphism Assays In some embodiments of the present invention, variant sequences are detected using a fragment length polymorphism assay. In a fragment length polymorphism assay, a unique DNA banding pattern based on cleaving the DNA at a series of positions is generated using an enzyme (e.g., a restriction enzyme or a CLEAVASE I [Third Wave Technologies, Madison, Wis.] enzyme). DNA fragments from a sample containing a SNP or a mutation will have a different banding pattern than wild type.

a. RFLP Assay

In some embodiments of the present invention, variant sequences are detected using a restriction fragment length polymorphism assay (RFLP). The region of interest is first isolated using PCR. The PCR products are then cleaved with restriction enzymes known to give a unique length fragment for a given polymorphism. The restriction-enzyme digested PCR products are separated by agarose gel electrophoresis and visualized by ethidium bromide staining. The length of the fragments is compared to molecular weight markers and fragments generated from wild-type and mutant controls.

b. CFLP Assay

In other embodiments, variant sequences are detected using a CLEAVASE fragment length polymorphism assay (CFLP; Third Wave Technologies, Madison, Wis.; See e.g., U.S. Pat. Nos. 5,843,654; 5,843,669; 5,719,208; and 5,888,780; each of which is herein incorporated by reference). This assay is based on the observation that when single strands of DNA fold on themselves, they assume higher order structures that are highly individual to the precise sequence of the DNA molecule. These secondary structures involve partially duplexed regions of DNA such that single stranded regions are juxtaposed with double stranded DNA hairpins. The CLEAVASE I enzyme, is a structure-specific, thermostable nuclease that recognizes and cleaves the junctions between these single-stranded and double-stranded regions.

The region of interest is first isolated, for example, using PCR. Then, DNA strands are separated by heating. Next, the reactions are cooled to allow intrastrand secondary structure to form. The PCR products are then treated with the CLEAVASE I enzyme to generate a series of fragments that are unique to a given SNP or mutation. The CLEAVASE enzyme treated PCR products are separated and detected (e.g., by agarose gel electrophoresis) and visualized (e.g., by ethidium bromide staining). The length of the fragments is compared to molecular weight markers and fragments generated from wild-type and mutant controls.

5. Hybridization Assays

In preferred embodiments of the present invention, variant sequences are detected a hybridization assay. In a hybridization assay, the presence of absence of a given SNP or mutation is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition or low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given SNP or mutation. The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given SNP or mutation are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target DNA molecules by determining which of the DNA capture probes hybridize, with complementary DNA in the test sample (e.g., a PCR amplified gene of interest). An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding, In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

DNA probes unique for the SNP or mutation of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., DNA). Hybridization is detected using any suitable method.

c. Enzymatic Detection of Hybridization

In some embodiments of the present invention, hybridization is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific DNA and RNA sequences by using structure-specific enzymes to cleave a complex formed by the hybridization of overlapping oligonucleotide probes. Elevated temperature and an excess of one of the probes enable multiple probes to be cleaved for each target sequence present without temperature cycling. These cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified genomic DNA. The isolated DNA sample is contacted with the first probe specific either for a SNP/mutation or wild type sequence and allowed to hybridize. Then a secondary probe, specific to the first probe, and containing the fluorescein label, is hybridized and the enzyme is added. Binding is detected by using a fluorescent plate reader and comparing the signal of the test sample to known positive and negative controls.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labeled antibody specific for biotin).

6. Mass Spectroscopy Assay

In some embodiments, a MassARRAY system (Sequenom, San Diego, Calif.) is used to detect variant sequences (See e.g., U.S. Pat. Nos. 6,043,031; 5,777,324; and 5,605,798; each of which is herein incorporated by reference). DNA is isolated from blood samples using standard procedures. Next, specific DNA regions containing the mutation or SNP of interest, about 200 base pairs in length, are amplified by PCR. The amplified fragments are then attached by one strand to a solid surface and the non-immobilized strands are removed by standard denaturation and washing. The remaining immobilized single strand then serves as a template for automated enzymatic reactions that produce genotype specific diagnostic products.

Very small quantities of the enzymatic products, typically five to ten nanoliters, are then transferred to a SpectroCHIP array for subsequent automated analysis with the SpectroREADER mass spectrometer. Each spot is preloaded with light absorbing crystals that form a matrix with the dispensed diagnostic product. The MassARRAY system uses MALDI-TOF (Matrix Assisted Laser Desorption Ionization—Time of Flight) mass spectrometry. In a process known as desorption, the matrix is hit with a pulse from a laser beam. Energy from the laser beam is transferred to the matrix and it is vaporized resulting in a small amount of the diagnostic product being expelled into a flight tube. As the diagnostic product is charged when an electrical field pulse is subsequently applied to the tube they are launched down the flight tube towards a detector. The time between application of the electrical field pulse and collision of the diagnostic product with the detector is referred to as the time of flight. This is a very precise measure of the product's molecular weight, as a molecule's mass correlates directly with time of flight with smaller molecules flying faster than larger molecules. The entire assay is completed in less than one thousandth of a second, enabling samples to be analyzed in a total of 3-5 second including repetitive data collection. The SpectroTYPER software then calculates, records, compares and reports the genotypes at the rate of three seconds per sample.

7. Detection of Variant NPHP Proteins

In other embodiments, variant (e.g., truncated) NPHP polypeptides are detected (e.g., including, but not limited to, those described in SEQ ID NOs: 6, 8, 10, 12, 14, 16, 18, 20, 24, 26, 28, 30, 34, 36, 38 and 40). Any suitable method may be used to detect truncated or mutant NPHP polypeptides including, but not limited to, those described below.

a) Cell Free Translation

For example, in some embodiments, cell-free translation methods from Ambergen, Inc. (Boston, Mass.) are utilized. Ambergen, Inc. has developed a method for the labeling, detection, quantitation, analysis and isolation of nascent proteins produced in a cell-free or cellular translation system without the use of radioactive amino acids or other radioactive labels. Markers are aminoacylated to tRNA molecules. Potential markers include native amino acids, non-native amino acids, amino acid analogs or derivatives, or chemical moieties. These markers are introduced into nascent proteins from the resulting misaminoacylated tRNAs during the translation process.

One application of Ambergen's protein labeling technology is the gel free truncation test (GFTT) assay (See e.g., U.S. Pat. No. 6,303,337, herein incorporated by reference). In some embodiments, this assay is used to screen for truncation mutations in a TSC1 or TSC2 protein. In the GFTT assay, a marker (e.g., a fluorophore) is introduced to the nascent protein during translation near the N-terminus of the protein. A second and different marker (e.g., a fluorophore with a different emission wavelength) is introduced to the nascent protein near the C-terminus of the protein. The protein is then separated from the translation system and the signal from the markers is measured. A comparison of the measurements from the N and C terminal signals provides information on the fraction of the molecules with C-terminal truncation (i.e., if the normalized signal from the C-terminal marker is 50% of the signal from the N-terminal marker, 50% of the molecules have a C-terminal truncation).

b) Antibody Binding

In still further embodiments of the present invention, antibodies (See below for antibody production) are used to determine if an individual contains an allele encoding a variant NPHP gene. In preferred embodiments, antibodies are utilized that discriminate between variant (i.e., truncated proteins); and wild-type proteins (SEQ ID NOs: 2, 82 and 22). In some particularly preferred embodiments, the antibodies are directed to the C-terminus of NPHP proteins. Proteins that are recognized by the N-terminal, but not the C-terminal antibody are truncated. In some embodiments, quantitative immunoassays are used to determine the ratios of C-terminal to N-terminal antibody binding. In other embodiments, identification of variants of NPHP is accomplished through the use of antibodies that differentially bind to wild type or variant forms of NPHP proteins.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the result of the immunoassay is utilized. In other embodiments, the immunoassay described in U.S. Pat. Nos. 5,599,677 and 5,672,480; each of which is herein incorporated by reference.

8. Kits for Analyzing Risk of NPHP Diseases

The present invention also provides kits for determining whether an individual contains a wild-type or variant (e.g., mutant or polymorphic) allele of NPHP4, NPHP5, inversin, or NPHP3. In some embodiments, the kits are useful for determining whether the subject is at risk of developing NPHP type 4, Senior-Loken type 3 or type 2 disease. The diagnostic kits are produced in a variety of ways. In some embodiments, the kits contain at least one reagent for specifically detecting a mutant NPHP allele or protein. In preferred embodiments, the kits contain reagents for detecting a truncation in the NPHP4, NPHP5, inversin or NPHP3 gene. In preferred embodiments, the reagent is a nucleic acid that hybridizes to nucleic acids containing the mutation and that does not bind to nucleic acids that do not contain the mutation. In other preferred embodiments, the reagents are primers for amplifying the region of DNA containing the mutation. In still other embodiments, the reagents are antibodies that preferentially bind either the wild-type or truncated NPHP4, NPHP5, inversin or NPHP3 proteins.

In some embodiments, the kit contains instructions for determining whether the subject is at risk for developing NPHP type 4, Senior-Loken syndrome, type 3 or type 2 disease. In preferred embodiments, the instructions specify that risk for developing NPHP type 4, type 3 Senior-Loken syndrome or type 2 disease is determined by detecting the presence or absence of a mutant NPHP4, NPHP3, NPHP5, or inversin allele in the subject, wherein subjects having an mutant (e.g., truncated) allele are at greater risk for NPHP disease.

The presence or absence of a disease-associated mutation in a NPHP4, NPHP5, NPHP3 or inversin gene can be used to make therapeutic or other medical decisions. For example, couples with a family history of NPHP may choose to conceive a child via in vitro fertilization and pre-implantation genetic screening. In this case, fertilized embryos are screened for mutant (e.g., disease associated) alleles of the NPHP4, NPHP5, NPHP3 or inversin gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a NPHP4, NPHP3, NPHP5, or inversin allele known to be associated with kidney disease allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packages in any suitable manner, typically with the elements in a single container or various containers as necessary along with a sheet of instructions for carrying out the test. In some embodiments, the kits also preferably include a positive control sample.

9. Bioinformatics

In some embodiments, the present invention provides methods of determining an individual's risk of developing NPHP disease based on the presence of one or more variant alleles of NPHP4, NPHP5, NPHP3 or inversin. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting NPHP type 4, type3, Senior-Loken syndrome or type 2 disease associated with a given polymorphism, as well as the sequences). In some embodiments, one of the computers stores application programs (e.g., for analyzing the results of detection assays). Results are then delivered to the user (e.g., via one of the computers or via the internet.

For example, in some embodiments, a computer-based analysis program is used to translate the raw data generated by the detection assay (e.g., the presence, absence, or amount of a given NPHP allele or polypeptide) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant NPHP4, NPHP3, NPHP5, or inversin genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing NPHP or a diagnosis of NPHP) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

IV. Generation of NPHP Antibodies

The present invention provides isolated antibodies or antibody fragments (e.g., FAB fragments). Antibodies can be generated to allow for the detection of an NPHP protein. The antibodies may be prepared using various immunogens. In one embodiment, the immunogen is a human NPHP peptide to generate antibodies that recognize a human NPHP protein. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against NPHP. For the production of antibody, various host animals can be immunized by injection with the peptide corresponding to the NPHP epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward NPHP, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Kohler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., *in Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing NPHP specific single chain antibodies. An additional embodiment of the invention utilizes the techniques described for the construction of Fab expression libraries (Huse et al., Science 246:1275-1281 [1989]) to allow rapid and easy identification of monoclonal Fab fragments with the desired specificity for NPHP.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

Additionally, using the above methods, antibodies can be generated that recognize the variant forms of NPHP proteins, while not recognizing the wild type forms of the NPHP proteins.

The foregoing antibodies can be used in methods known in the art relating to the localization and structure of NPHP proteins (e.g., for Western blotting, immunoprecipitaion and immunocytochemistry), measuring levels thereof in appropriate biological samples, etc. The antibodies can be used to detect NPHP proteisn in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human NPHP proteisn using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of NPHP detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of NPHP or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of NPHP. Such antibodies can also be used diagnostically to measure abnormal expression of NPHP proteins, or the aberrant formation of protein complexes, which may be indicative of a disease state.

V. Gene Therapy Using NPHP

The present invention also provides methods and compositions suitable for gene therapy to alter NPHP protein expression, production, or function. As described above, the present invention provides human NPHP genes and provides methods of obtaining NPHP genes from other species. Thus, the methods described below are generally applicable across many species. In some embodiments, it is contemplated that the gene therapy is performed by providing a subject with a wild-type allele of NPHP (i.e., an allele that does not contain a NPHP disease causing polymorphisms or mutations). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mavl, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. Nos. 4,797,368; 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+en-vAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

VI. Transgenic Animals Expressing Exogenous NPHP Genes and Homologs, Mutants, and Variants Thereof The present invention contemplates the generation of transgenic animals comprising an exogenous NPHP gene or homologs, mutants, or variants thereof. In preferred embodiments, the transgenic animal displays an altered phenotype as compared to wild-type animals. In some embodiments, the altered phenotype is the overexpression of mRNA for a NPHP gene as compared to wild-type levels of NPHP expression. In other embodiments, the altered phenotype is the decreased expression of mRNA for an endogenous NPHP gene as compared to wild-type levels of endogenous NPHP expression. In some preferred embodiments, the transgenic animals comprise mutant (e.g., truncated) alleles of NPHP. Methods for analyzing the presence or absence of such phenotypes include Northern blotting, mRNA protection assays, and RT-PCR. In other embodiments, the transgenic mice have a knock out mutation of the NPHP gene. In preferred embodiments, the transgenic animals display a NPHP disease phenotype.

Such animals find use in research applications (e.g., identifying signaling pathways involved in NPHP), as well as drug screening applications (e.g., to screen for drugs that prevents NPHP disease. For example, in some embodiments, test compounds (e.g., a drug that is suspected of being useful to treat NPHP disease) and control compounds (e.g., a placebo) are administered to the transgenic animals and the control animals and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which the LRRs of NPHP4 are deleted). Methods for homologous recombination are described in U.S. Pat. No. 5,614,396, incorporated herein by reference.

VIII. Drug Screening Using NPHP

As described herein, it is contemplated that nephroretinin, inversin and nephrocystin interact within a novel shared pathogenic pathway (e.g., as shown in Examples 3-5). Accordingly, in some embodiments, the isolated nucleic acid sequences of NPHP4 (e.g., SEQ ID NOS: 1, 5, 7, 9, 11, 13, 15, 17, and 19), NPHP5 (e.g., SEQ ID NOs: 81 and 83-90) and inversin (e.g., SEQ ID Nos: 24, 26, 28, 30, 34, 36, 38 and 40) are used in drug screening applications for compounds that alter (e.g., enhance) signaling within the pathway.

A. Identification of Binding Partners

In some embodiments, binding partners of NPHP amino acids are identified. In some embodiments, the NPHP4 nucleic acid sequence (e.g., SEQ ID NOS: 1, 5, 7, 9, 11, 13, 15, 17, and 19), NPHP5 (e.g., SEQ ID NOs: 81 and 83-90), and inversin nucleic acid sequences (e.g., SEQ ID Nos: 21, 23, 25, 27, 29, 33, 35, 37 and 39) or fragments thereof are used in yeast two-hybrid screening assays. For example, in some embodiments, the nucleic acid sequences are subcloned into pGPT9 (Clontech, La Jolla, Calif.) to be used as a bait in a yeast-2-hybrid screen for protein-protein interaction of a human fetal kidney cDNA library (Fields and Song *Nature* 340:245 -246, 1989; herein incorporated by reference). In other embodiments, phage display is used to identify binding partners (Parmley and Smith *Gene* 73 : 305-318, [1988]; herein incorporated by reference).

B. Drug Screening

The present invention provides methods and compositions for using NPHP proteins as a target for screening drugs that can alter, for example, interaction between NPHPs and their binding partners (e.g., those identified using the above methods)

In one screening method, the two-hybrid system is used to screen for compounds (e.g., drug) capable of altering (e.g., inhibiting) NPHP function(s) or inversin function(s) (e.g., interaction with a binding partner) in vitro or in vivo. In one embodiment, a GAL4 binding site, linked to a reporter gene such as lacZ, is contacted in the presence and absence of a candidate compound with a GAL4 binding domain linked to a NPHP fragment and a GAL4 transactivation domain II linked to a binding partner fragment. Expression of the reporter gene is monitored and a decrease in the expression is an indication that the candidate compound inhibits the interaction of NPHP with the binding partner. Alternately, the effect of candidate compounds on the interaction of NPHPs with other proteins (e.g., proteins known to interact directly or indirectly with the binding partner) can be tested in a similar manner.

In another screening method, candidate compounds are evaluated for their ability to alter NPHP signaling by contacting NPHPs, binding partners, binding partner-associated proteins, or fragments thereof, with the candidate compound and determining binding of the candidate compound to the peptide. The protein or protein fragments is/are immobilized using methods known in the art such as binding a GST-NPHP or a GST-inversin fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., E. coli XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate NPHP physiological effects (e.g., kidney disease).

In another screening method, one of the components of the NPHP /binding partner signaling system, is immobilized. Polypeptides can be immobilized using methods known in the art, such as adsorption onto a plastic microtiter plate or specific binding of a GST-fusion protein to a polymeric bead containing glutathione. For example, GST-NPHP is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of the NPHP with the other peptide. A variation of this method allows for the screening of compounds that are capable of disrupting a previously-formed protein/protein complex. For example, in some embodiments a complex comprising NPHP or fragments thereof bound to another peptide is immobilized as described above and contacted with a candidate compound. The dissolution of the complex by the candidate compound correlates with the ability of the compound to disrupt or inhibit the interaction between NPHP and the other peptide.

Another technique for drug screening provides high throughput screening for compounds having suitable binding affinity to NPHP peptides and is described in detail in WO 84/03564, incorporated herein by reference. Briefly, large numbers of different small peptide test compounds are synthesized on a solid substrate, such as plastic pins or some other surface. The peptide test compounds are then reacted with NPHP peptides and washed. Bound NPHP peptides are then detected by methods well known in the art.

Another technique uses NPHP antibodies, generated as discussed above. Such antibodies capable of specifically binding to NPHP peptides compete with a test compound for binding to NPHPs. In this manner, the antibodies can be used to detect the presence of any peptide that shares one or more antigenic determinants of the NPHP peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with NPHPs and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding NPHP variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, IP3, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DAB-CYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by NPHP in operable association with a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to NPHPs of the present invention, have an inhibitory (or stimulatory) effect on, for example, NPHP expression or activity, or have a stimulatory or inhibitory effect on, for example, the expression or activity of a NPHP. Compounds thus identified can be used to modulate the activity of target gene products (e.g., NPHP genes) either directly or indirectly in a therapeutic protocol, to elaborate the biological function of the target gene product, or to identify compounds that disrupt normal target gene interactions. Compounds which stimulate the activity of a variant NPHP or mimic the activity of a non-functional variant are particularly useful in the treatment of cystic kidney diseases (e.g., NPHP).

In one embodiment, the invention provides assays for screening candidate or test compounds that are substrates of a NPHP protein or polypeptide or a biologically active portion thereof. In another embodiment, the invention provides assays for screening candidate or test compounds that bind to or modulate the activity of a NPHP protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a NPHP protein or biologically active portion thereof is contacted with a test compound, and the ability of the test compound to modulate NPHP activity is determined. Determining the ability of the test compound to modulate NPHP activity can be accomplished by monitoring, for example, changes in enzymatic activity. The cell, for example, can be of mammalian origin.

The ability of the test compound to modulate NPHP binding to a compound, e.g., a NPHP substrate, can also be evaluated. This can be accomplished, for example, by coupling the compound, e.g., the substrate, with a radioisotope or enzymatic label such that binding of the compound, e.g., the substrate, to NPHP can be determined by detecting the labeled compound, e.g., substrate, in a complex.

Alternatively, the NPHP is coupled with a radioisotope or enzymatic label to monitor the ability of a test compound to modulate NPHP binding to a NPHP substrate. For example, compounds (e.g., substrates) can be labeled with $^{125}I$, $^{35}S$ $^{14}C$ or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a NPHP substrate) to interact with NPHP with or without the labeling of any of the interactants can be evaluated. For example, a microphysiormeter can be used to detect the interaction of a compound with a NPHP without the labeling of either the compound or the NPHP (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and an NPHP.

In yet another embodiment, a cell-free assay is provided in which a NPHP protein or biologically active portion thereof is contacted with a test compound and the ability of the test compound to bind to the NPHP protein or a biologically active portion thereof is evaluated. Preferred biologically active portions of the NPHP proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the NPHP protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BlAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize NPHP, an anti-NPHP antibody or their target molecules to facilitate separation of complexed from non-complexed forms of one or both of the proteins, as well as to accommodate automation of the assay. Binding of a test compound to a NPHP protein, or interaction of a NPHP protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, glutathione-S-transferase-NPHP or glutathione-S-transferase-inversin fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or NPHP protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of NPHP binding or activity determined using standard techniques. Other techniques for immobilizing either NPHP protein or a target molecule on matrices include using conjugation of biotin and streptavidin. Biotinylated NPHP protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with NPHP proteins or target molecules but which do not interfere with binding of the NPHP protein to its target molecule. Such antibodies can be derivatized to the wells of the plate, and unbound target or NPHP protein trapped in the wells by antibody conjugation. Methods for detecting such complexes, in addition to those described above for the GST-immobilized complexes, include immunodetection of complexes using antibodies reactive with the NPHP protein or target molecule, as well as enzyme-linked assays which rely on detecting an enzymatic activity associated with the NPHP protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the NPHP protein or biologically active portion thereof with a known compound that binds the NPHP to form an assay mixture, contacting the assay mixture with a test compound, and determining the ability of the test compound to interact with a NPHP protein, wherein determining the ability of the test compound to interact with a NPHP protein includes determining the ability of the test compound to preferentially bind to NPHP or biologically active portion thereof, or to modulate the activity of a target molecule, as compared to the known compound.

To the extent that NPHP proteins can, in vivo, interact with one or more cellular or extracellular macromolecules, such as proteins, inhibitors of such an interaction are useful. A homogeneous assay can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, NPHP protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with NPHPs ("NPHP-binding proteins" or "NPHP-bp) and are involved in NPHP activity. Such NPHP-bps can be activators or inhibitors of signals by the NPHP proteins or targets as, for example, downstream elements of a NPHP-mediated signaling pathway.

Modulators of NPHP expression can also be identified. For example, a cell or cell free mixture is contacted with a candidate compound and the expression of NPHP mRNA or protein evaluated relative to the level of expression of NPHP mRNA or protein in the absence of the candidate compound. When expression of NPHP mRNA or protein is greater in the presence of the candidate compound than in its absence, the candidate compound is identified as a stimulator of NPHP mRNA or protein expression. Alternatively, when expression of NPHP is less (i.e., statistically significantly less) in the presence of the candidate compound than in its absence, the candidate compound is identified as an inhibitor of NPHP mRNA or protein expression. The level of NPHP mRNA or protein expression can be determined by methods described herein for detecting NPHP mRNA or protein.

A modulating agent can be identified using a cell-based or a cell free assay, and the ability of the agent to modulate the activity of a NPHP protein can be confirmed in vivo, e.g., in an animal such as an animal model for a disease (e.g., an animal with kidney disease; See e.g., Hildenbrandt and Otto, J. Am. Soc. Nephrol. 11:1753 [2000]).

C. Therapeutic Agents

This invention further pertains to novel agents identified by the above-described screening assays. Accordingly, it is within the scope of this invention to further use an agent identified as described herein (e.g., a NPHP modulating agent or mimetic, antibody, or binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments of cystic kidney disease (e.g., including, but not limited to, NPHP kidney disease).

IX. Pharmaceutical Compositions Containing NPHP Nucleic Acid, Peptides, and Analogs The present invention further provides pharmaceutical compositions which may comprise all or portions of NPHP polynucleotide sequences, NPHP polypeptides, inhibitors or antagonists of NPHP bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant NPHP alleles (e.g., NPHP kidney disease or RP). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, NPHP nucleotide and NPHP amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, NPHP polynucleotide sequences or NPHP amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of NPHP4, conditions indicated on the label may include treatment of condition related to apoptosis.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts NPHP levels.

A therapeutically effective dose refers to that amount of NPHP that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for NPHP4 than for the inhibitors of NPHP4. Administration to the bone marrow may necessitate delivery in a manner different from intravenous injections.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); BSA (bovine serum albumin); Fisher (Fisher Scientific, Pittsburgh, Pa.); Sigma (Sigma Chemical Co., St. Louis, Mo.); Promega (Promega Corp., Madison, Wis.); Perkin-Elmer (Perkin-Elmer/Applied Biosystems, Foster City, Calif.); Boehringer Mannheim (Boehringer Mannheim, Corp., Indianapolis, Ind.); Clonetech (Clonetech, Palo Alto, Calif.); Qiagen (Qiagen, Santa Clarita, Calif.); Stratagene (Stratagene Inc., La Jolla, Calif.); National Biosciences (National Biosciences Inc, Plymouth Minn.) and NEB (New England Biolabs, Beverly, Mass.), wt (wild-type); Ab (antibody); NPHP (nephronophthisis); SLS (Senior-Loken syndrome); RP (retinitis pigmentosa) and ESRD (end stage renal disease).

Example 1

A. Methods

Pedigree and Diagnosis

Blood samples and pedigrees were obtained following informed consent from patients with NPHP and their parents. Diagnostic criteria were (i) development of ESRD following a history of polyuria, polydipsia, and anemia; (ii) renal ultrasound compatible with NPHP. In all families with the exception of F461 the diagnosis of NPHP was confirmed by renal biopsy. ESRD developed within a range of 6-35 years with a median age of 22 years (Table 1). In SLS, the renal symptoms are associated with RP. Clinical data for SLS family F3 have been published previously (Polak et al., Am J Ophthalmol 95:487-494 [1983]; Schuermann et al., Am J Hum Genet 70:1240-1246 [2002]; herein incorporated by reference). All three affected siblings had RP suggestive of Leber amaurosis congenital. Ophthalmologic data for family F60 has been published (Fillastre et al., Clin Nephrol 5:14-19 [1976]; herein incorporated by reference) and comprises: In J.C. (Fillastre et al. 1976, supra) amblyopia and rotary nystagmus with grossly impaired vision starting age 8 months, and on findoscopy retino-choroidal atrophy surrounded by pigment. In individuals M.C.B. and M.M.B. there were abnormal ERG findings with diminished amplitude (Fillastre et al. 1976, supra).

Haplotype and Mutational Analysis

The "screening markers" used for haplotype analysis consisted of microsatellites markers D1S2845, D1S2660, D1S2795, D1S2870, D1S2642, D1S214, D1S2663, D1S1612 (in pter to cen orientation) (Dib et al., Nature 380: 152 [1996]). Novel microsatellite markers were generated by searching for di-, tri-, and tetra-nucleotide repeats using the BLAST program on human genomic sequence in the interval between flanking markers D1S2660 and D1S2642. Preparation of genomic DNA and haplotype analysis were performed as described previously (Schuermann et al. 2002, supra). Mutational analysis was performed using exon-flanking primers as described previously (Schuermann et al. 1996). Markers are shown in Table 2.

TABLE 2

Primer sequences (from 5' to 3') used in exon amplification for mutational analysis of NPHP4.

| Exon | Forward Primer | Reverse Primer | Product Size (bp) |
|---|---|---|---|
| 1 | gtcggacatgcaaatcagg (SEQ ID NO:43) | aggctctggccaacactg (SEQ ID NO:73) | 439 |
| 2 | aagccttcaggattgctgtg (SEQ ID NO:44) | catccatctgttaactggaagc (SEQ ID NO:74) | 319 |
| 3 | acatggcctgccagtgac (SEQ ID NO:45) | cctggacccacaagtctgag (SEQ ID NO:75) | 346 |
| 4 | acgtgtaggaaggcggtctc (SEQ ID NO:46) | gacgagcagttaaaccaccatag (SEQ ID NO:76) | 649 |
| 5 | gaggcctccatgtgctttc (SEQ ID NO:47) | gctaaaggtggggaacactc (SEQ ID NO:77) | 209 |
| 6 | tgaccctcattgagaactgc (SEQ ID NO:48) | gtgccttcaaggtttcactg (SEQ ID NO:78) | 217 |
| 7 | ttgtgctctgtctgggagtc (SEQ ID NO:49) | catcagatgcggggtctc (SEQ ID NO:79) | 439 |
| 8 | ctcccccagggacttctg (SEQ ID NO:50) | cctgacatgcacaaatgacc (SEQ ID NO:80) | 335 |
| 9 | ttctgacagtggtcgacgtg (SEQ ID NO:51) | tgcccactacatttatcctcac (SEQ ID NO:103) | 279 |
| 10 | cactgttgatttcccctctc (SEQ ID NO:52) | gcaaacatatttgtgaactttgc (SEQ ID NO:104) | 343 |
| 11 | ttcctggttggatcgttctg (SEQ ID NO:53) | cgacgattatcttacaaatgtgg (SEQ ID NO:105) | 329 |
| 12 | aggcctgtggagacctgac (SEQ ID NO:54) | ggggacagagggttttcttg (SEQ ID NO:106) | 232 |
| 13 | catgttgggagctttgtgg (SEQ ID NO:55) | gacaggcacagtgcaaaaac (SEQ ID NO:107) | 262 |
| 14 | atctgagcaccgttggttg (SEQ ID NO:56) | gggttcacaaggtccaacag (SEQ ID NO:108) | 295 |
| 15 | ggtttccacagggaggtg (SEQ ID NO:57) | aggtcagaacctcagcgaag (SEQ ID NO:109) | 345 |

TABLE 2-continued

Primer sequences (from 5' to 3') used in exon amplification for mutational analysis of NPHP4.

| Exon | Forward Primer | Reverse Primer | Product Size (bp) |
|---|---|---|---|
| 16 | accatccctatgcaaacac (SEQ ID NO:58) | gcactggtcaccgtatgattc (SEQ ID NO:110) | 409 |
| 17 | gaccagagctgaaatctctt (SEQ ID NO:59) | acgctggaagcgtgactc (SEQ ID NO:111) | 315 |
| 18 | cacagtggctttcctgctg (SEQ ID NO:60) | cgagggagcccacactctac (SEQ ID NO:112) | 358 |
| 19 | tgtggtgggttgatctgttt (SEQ ID NO:61) | cactgacagcaccacgaatg (SEQ ID NO:91) | 332 |
| 20 | ccctggtgtctgctcctg (SEQ ID NO:62) | gaggcagggaaaggatgtg (SEQ ID NO:92) | 351 |
| 21 | agcaatagcccttgtggag (SEQ ID NO:63) | tctcgggcagaattcgag (SEQ ID NO:93) | 386 |
| 22 | tctctcccactcctctgagc (SEQ ID NO:64) | agggacactggtggagactg (SEQ ID NO:94) | 377 |
| 23 | tggcagtggtgtctctaagc (SEQ ID NO:65) | aggaggggagagaaggacac (SEQ ID NO:95) | 251 |
| 24 | ttggcaacagtggagatacg (SEQ ID NO:66) | catgaggccatctgtcacc (SEQ ID NO:96) | 342 |
| 25 | tcttgctgagcacctgtgac (SEQ ID NO:67) | aggatacccgtggggaag (SEQ ID NO:97) | 282 |
| 26 | cactcgctgcgtgtattagt (SEQ ID NO:68) | caagcccactttcaatccac (SEQ ID NO:98) | 268 |
| 27 | ccttgttggcctctcgtg (SEQ ID NO:69) | ccagctgaatgcccactg (SEQ ID NO:99) | 318 |
| 28 | ggaaccacccatgaccttg (SEQ ID NO:70) | cagtggtccgagtcacagg (SEQ ID NO:100) | 388 |
| 29 | cagggaatacttggaggaag (SEQ ID NO:71) | gaggaactcgctcctaaatgc (SEQ ID NO:101) | 310 |
| 30 | gcagagaggttgctggtgag (SEQ ID NO:72) | accgggcttgtgctgtag (SEQ ID NO:102) | 738 |

Northern Blot Analysis

A multiple tissue Northern blot with human adult poly(A)+ RNA (Clontech MTN7760-1) was hybridized with a NPHP4 DNA probe of 584 bp, derived from exon 30 (nt 4141-4724; see FIG. 4) generated by PCR amplification of human genomic DNA. The probe was labeled with [$^{32}$P]dCTP using Random Primers DNA Labeling System (Invitrogen). Hybridization was carried out at 68° C. using EXPRESSHYB solution (Clontech, Paolo Alto, Calif.). The final washing condition was 0.1×SSC, 0.1% SDS at 50° C. for 40 min.

Results

A gene locus (NPHP4) for NPHP type 4 was mapped by total genome search for linkage within a 2.1 Mb interval delimited by flanking markers D1S2660 and D1S2642 (Schuermann et al. 1996). To establish compatibility with linkage to NPHP4 in further kindred, 20 NPHP families with multiple affected children or parental consanguinity, in whom no mutation was present in the NPHP1 gene, were selected. In 8 families there was an association of NPHP with retinitis pigmentosa (RP). Haplotype analysis using 8 microsatellite markers covering the critical NPHP4 region (Schuermann et al. 2002, supra; herein incorporated by reference) was compatible with linkage to NPHP4 in 9 families, including 2 families with RP. To further refine the critical genetic interval of 2.1 Mb, high-resolution haplotype analysis was performed in these 9 families and the 7 families with linkage to NPHP4 published previously (Schuermann et al., 2002, supra). In 2 families (F3, F60) NPHP was associated with RP. Eight published (Dib et al. 1996, supra) and 38 newly generated microsatellite markers were used at an average marker density of 1 marker per 45 kb within the interval of flanking markers D1S2660 and D1S2642 (FIG. 1). Haplotype analysis, by the criterion of minimization of recombinants, clearly revealed erroneous inversion of sequence between markers D1S2795 and D1S244 in human genomic sequence data bases (www.ensembl.org).

Using high resolution haplotype data, the correct marker order at the NPHP4 locus was established as pter-<u>D1S2660</u>-D1S2795-D1S2633- D1S2870-D1S253-<u>D1S2642</u>-D1S214-D1S1612-D1S2663-D1S244-cen (flanking markers to NPHP4 underlined). A 22 kb sequence gap remaining in the interval D1S2660-D1S2795 was filled by use of CELERA human genomic sequence. In haplotype analysis, 3 consanguineous kindred yielded new key recombinants by the criterion of homozygosity by descent (Lander and Botstein, Science 236: 1567 [1987]) (FIG. 1). The NPHP4 critical genetic interval was thus refined to <1.2 Mb within secure borders based on a large kindred, and in addition, to <700 kb within suggestive borders based on 2 small families (FIG. 1, FIG. 2A, B). Within the 700 kb critical interval for NPHP4 there mapped 3 known genes (KCNAB2, RPL22, and ICMT), and 3 unknown genes (Q9UFQ2, Q9UFR9, and Q96MP2) (FIG. 2B). In addition, in the interval between Q9UFQ2 and flanking marker D1E19 (FIG. 2B) the program GENESCAN predicted approximately 40 non-annotated exons (www.ensembl.org). Mutational analysis was performed in affected individuals of the 16 families compatible with linkage to NPHP4, examining all 79 exons of the 3 known and 3 unknown genes by direct sequencing of the forward strands of exon-PCR products. While no mutations were detected in 5 of these genes, in Q9UFQ2 detected 11 distinct mutations were detected in 8 of the 16 families with NPHP (Table 1). In families F3 and F60 NPHP is associated with RP. In the affected individuals from all 8 families, mutations were shown to segregate from both parents (Table 1). All of these mutations were absent from 92-96 healthy control individuals. Nine of the 11 mutations detected represent very likely loss-of-function mutations: 5 were STOP codon, 1 frame shift, and 3 were obligatory splice consensus mutations (Table 1 and FIGS. 2D and 6-16.). Q9UFQ2 was thus identified as the gene causing NPHP type 4. The gene was termed NPHP4 and the respective gene product was called "nephroretinin" for its role in nephronophthisis and retinitis pigmentosa. In the 5 consanguineous families F3, F30, F32, F60, and F622, all mutations occurred in the homozygous state and represented STOP codon mutations and one frame shift mutation, truncating the protein in exons 18, 23, 11, 16, and 18, respectively (Table 1; FIG. 2D, E). In the 3 non-consanguineous families, 6 distinct compound heterozygous mutations were found. Four represented STOP codon or obligatory splice consensus mutations, truncating the gene product in exons 15, 16, 17, and 24. The missense mutations R848W and G754R affect amino acid residues conserved in mouse and cow. No mutations were detected in 8 families.

Figure 3:
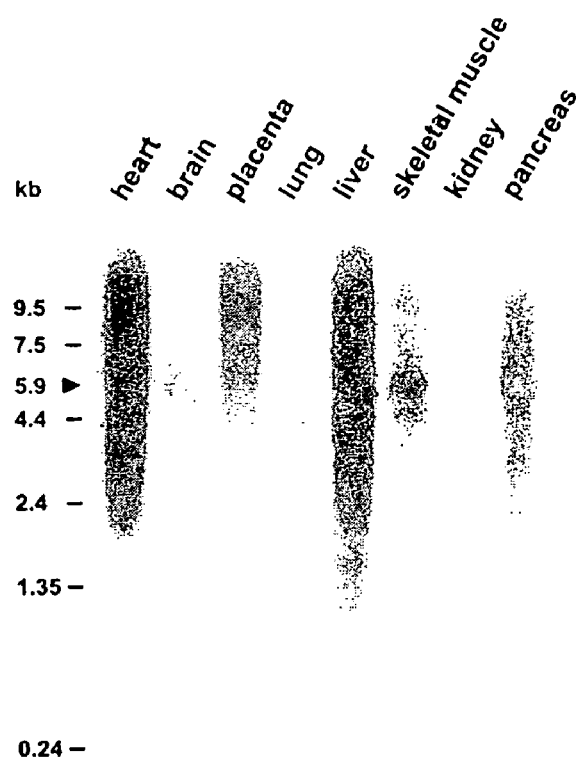
FIG. 3 shows Northern blot analysis of the NPHP4 expression pattern. Expression of a 5.9 kb transcript (arrowhead) is apparent in all tissues studied with highest expression in skeletal muscle.
Figure 15:
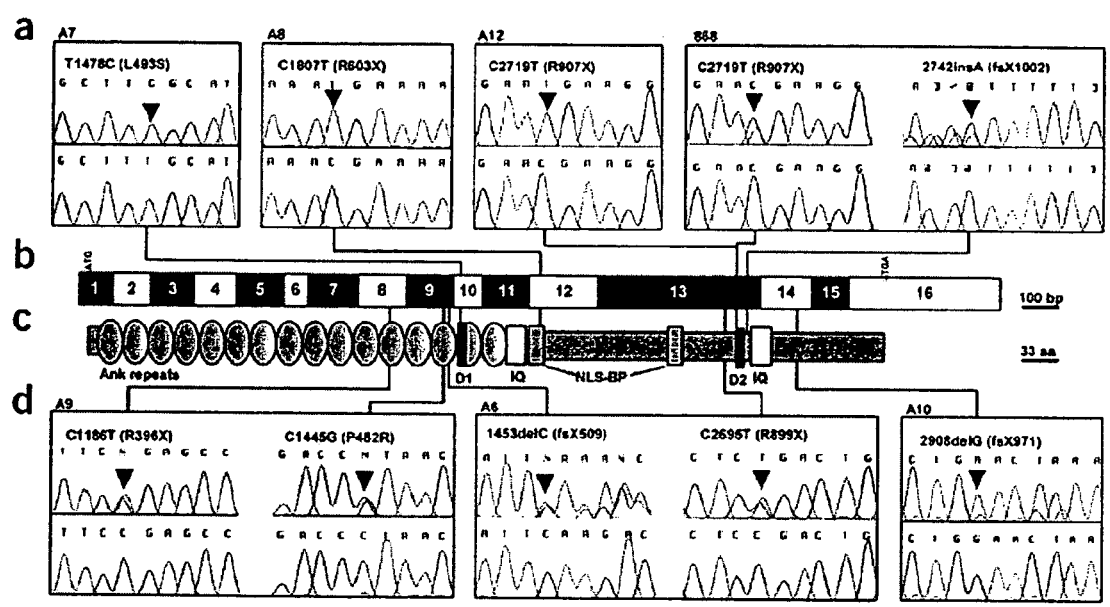
FIG. 15 shows mutations in INVS in individuals with NPHP2.

NPHP4 expression studies by northern blot analysis revealed a 5.9 kb transcript strongly expressed in human skeletal muscle, weakly in kidney, and in 6 additional tissues studied (FIG. 3). Northern dot blot analysis confirmed a widespread expression pattern in human adult and fetal tissues including testis. This broad expression pattern, with strong expression in skeletal muscle and testis corresponds well with the expression pattern described for the NPHP1 gene (Otto et al., J. Am. Soc. Nephrol. 11:270 [2000]).

Human genomic sequence of NPHP4 (KIAA0673) was assembled using the *homo sapiens* chromosome 1 working draft sequence segment NT_028054, which predicted 25 exons. Five additional 5' exons were identified using additional working draft sequence, the mRNA KIAA00673 and 57 human ESTs from the UniGene cluster Hs.106487. The genomic structure shown in FIGS. 2C, D and FIG. 4 was confirmed by human/mouse total genomic sequence comparison. The NPHP4 gene contains 30 exons encoding 1426 amino acids and extends over 130 kb, with splice sites that confirm to the canonical consensus gt-ag. An exception was found in intron 24, with gc-ag splicing, which occurs in 0.5% of mammalian splice sites (Burset et al., Nuc. Acid. Res. 29:255 [2001]). A polymorphism is known to be present at the intron 20 splice acceptor (tg for ag). Presence of exon 20 is supported by 3 human EST clones. Ten different splice variants have been suggested for KIAA0673 (See e.g., the Internet web site of NCBI).

The NPHP4 cDNA (FIG. 4) and deduced nephroretinin protein sequences were found to be novel, without any sequence similarity to known human cDNA or protein sequences. Therefore, NPHP4 encodes a hitherto unknown protein. As shown for the NPHP1 gene product nephrocystin (Hildebrandt et al., Nature Genet. 17:149 [1997]; Otto et al., J. Am. Soc. Nephrol. 11:270 [2000]), there was however strong sequence conservation for nephroretinin in evolution with 23% amino acid identity in a protein of *C. elegans* (FIG. 5). Translated EST sequences also demonstrated evolutionary conservation in mouse, cow, pig, zebrafish, *Xenopus laevis, Ascaris suum*, and *Halocynthia roretzi*. Sequence identity of the murine homologue was 78% (FIG. 5). Analysis of nephroretinin amino acid sequence provided no signal sequence, conserved domains, or predicted transmembrane regions. In the N-terminal half there was a putative nuclear localization signal (NLS), a glutamate-rich (E-rich) and a proline-rich (P-rich) domain. The latter two have also been found in nephrocystin (Otto et al., [2000], supra). No sequence similarity to nephrocystin was present. In addition, 2 serine rich (S-rich) sequences and a C-terminal endoplasmic reticulum membrane domain were found in human and murine nephroretinin sequences. Encoded by exons 15 and 16, there were was in nephroretinin a domain of unknown function (DUF339) with evolutionary conservation including prokaryotes and a 63 amino acid stretch with 30% sequence identity to a gas vesicle protein of *Halobacterium salinarium* (FIG. 5).

TABLE 1

| Family | Number of affecteds | ESRD at age | *Retinitis pigmentosa* | Origin | Parental consanguinity | Exon | Nucleotide change[b] | Effect on coding sequence | Segregation[c] |
|---|---|---|---|---|---|---|---|---|---|
| F3[a] | 3 | 28 y, 30 y, 35 y | yes | Turkey | yes | 18 | C2335T | Q779X | hom |
| F24 | 2 | ND | no | Germany | no | 17 | G2260A | G754R | P |
|  |  |  |  |  |  | 17 | IVS16 – 1G > C | Splice site | M |
| F30[a] | 3 | 18 y, 22 y, 22 y | no | Germany | yes | 23 | 3272delT | STOP at codon L1121 | hom |
| F32 | 2 | 19 y, 20 y, | no | India | yes | 11 | TC1334-1335AA | F445X | hom |
| F60 | 4 | 6 y, 10 y, 17 y, 22 y | yes | France | yes | 16 | C1972T | R658X | hom |
| F444[a] | 2 | 23 y, 33 y, | no | Finland | no | 15 | IVS15 + 1 G > A | Splice site | M |
|  |  |  |  |  |  | 24 | IVS24 + 1 G > A | Splice site | P |

TABLE 1-continued

| Family | Number of affecteds | ESRD at age | Retinitis pigmentosa | Origin | Parental consanguinity | Exon | Nucleotide change[b] | Effect on coding sequence | Segregation[c] |
|---|---|---|---|---|---|---|---|---|---|
| F461[a] | 3 | ND | no | France | no | 16 | C2044T | R682X | P |
|  |  |  |  |  |  | 19 | C2542T | R848W | M |
| F622 | 2 | 8 y, 9 y, | no | Afghanistan | yes | 18 | G2368T | E790X | hom |

[a]In these 4 families linkage to NPHP4 has been published previously (Schuermann et al. 2002).
[b]All mutations were absent from 92-96 healthy control subjects.
[c]M, maternal; P, paternal; hom, homozygous mutation inherited from both parents; ND, no data available.

Example 2

Mutations in INVS Cause NPHP2

Mutational analysis was performed on 16 exons of INVS in genomic DNA from nine affected individuals from seven different families with early onset of NPHP. One individual (from family A7) was included from the initial description (Gagnadoux et al., Pediatr. Nephrol. 3, 50 [1989]) of infantile NPHP (individual 5) and two affected siblings (VII-1 and VII-3 in family A12) from the Bedouin kindred (Haider et al., Am. J. Hum. Genet. 63, 1404 [1998]) in which the NPHP2 locus was first mapped (Table 3). Nine distinct recessive mutations were detected in INVS (Table 3 and FIG. 15). In six individuals, both mutated alleles were detected. In individual A10, only one heterozygous mutation was found.

Mutations in INVS (nucleotide exchange and amino acid exchange) are shown (FIG. 15a) together with sequence traces for mutated sequence (top) and sequence from healthy controls (bottom). Family numbers are given above boxes. If only one mutation is shown, it occurred in the homozygous state, except in individual A10, in whom only one mutation in the heterozygous state was detected. In individual 868, the 2742insA mutation is shown in the flipped version of the reverse strand. The exon structure of INVS is shown in FIG. 15b. Lines indicate relative positions and connect to mutations detected in INVS. Open and filled boxes represent INVS exons drawn relative to scale bar. Positions of start codon (ATG) at nucleotide +1 and of stop codon (TGA) are indicated. A representation of protein motifs drawn to scale parallel to exon structure is shown (FIG. 15c). Lines connect to point mutations detected, as shown in FIG. 15a and 15d).

Example 3

Inversin associates with nephrocystin in HEK293T cells and mouse tissue

Figure 26:
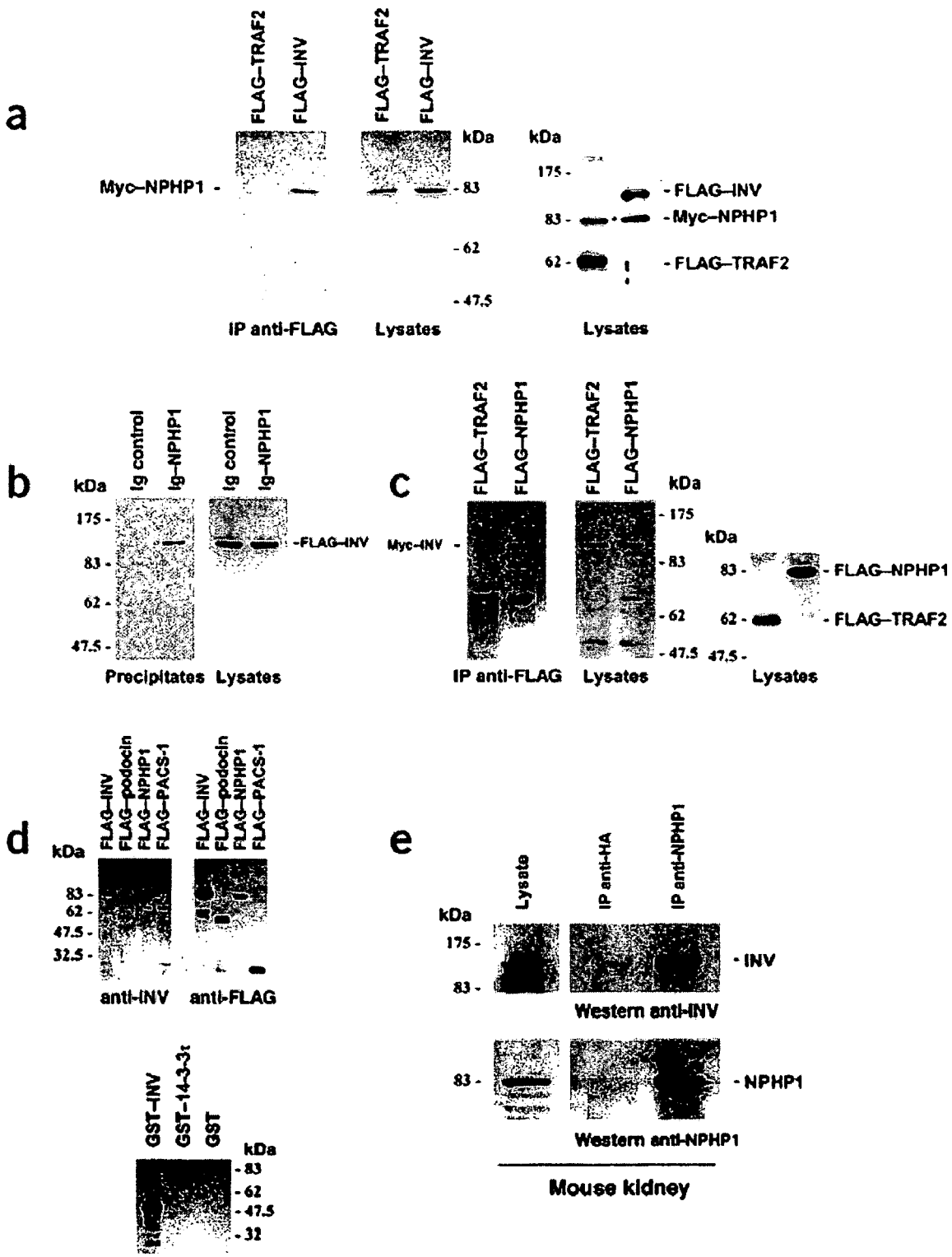
FIGS. 26a-26e show the association of inversin with nephrocystin in HEK 293T cells and in mouse tissue.

Myc-tagged nephrocystin (Myc-NPHP1) was coexpressed with N-terminally FLAG-tagged full-length inversin (FLAG-INV) or FLAG-tagged TRAF2 (FLAG-TRAF2) protein as a negative control. After immunoprecipitation with anti-FLAG antibody, coprecipitating nephrocystin was detected with nephrocystin-specific antiserum (FIG. 26a, left panel). Protein expression levels in cellular lysates were controlled by immunoblotting using a nephrocystin antibody (FIG. 26a, middle panel) or FLAG-specific and nephrocystin-specific antibodies (FIG. 26a, right panel). Molecular weight markers are shown in kDa. Full-length nephrocystin was fused to the CH2 and CH3 domains of human IgG1 and precipitated with protein G sepharose beads. FLAG-tagged inversin specifically coprecipitated with nephrocystin but not with control protein (CH2 and CH3 domains of human IgG1 without nephrocystin fusion) as shown with FLAG-specific antibody (FIG. 26b). FLAG-tagged nephrocystin or FLAG-tagged TRAF2 protein as a negative control was coexpressed with N-terminally Myc-tagged full-length inversin (Myc-INV). After immunoprecipitation with anti-FLAG antibody, coprecipitating inversin was detected with inversin-specific antiserum (FIG. 26c, left and middle panels). Appropriate controls were also run (FIG. 26c, right panel). A rabbit antiserum to a MBP-inversin fusion protein (amino acids 561-716 of mouse inversin) specifically recognized inversin (amino acids 1-716) expressed in HEK293T cells (FIG. 26d, left panel) but not the FLAG-tagged control proteins podocin (FLAG-podocin), nephrocystin (FLAG-NPHP1) or PACS-1 (FLAG-PACS-1, amino acids 85-280) (FIG. 26d, left panel). It also specifically recognized recombinant GST-inversin (amino acids 561-716) but not two other control GST fusion proteins (FIG. 26d, lower panel). To show endogenous nephrocystin-inversin interaction in vivo in mouse kidney, half of mouse kidney tissue lysates was immunoprecipitated with a control antibody to hemagglutinin (anti-HA), and the other half was precipitated with anti-nephrocystin antisera. Immobilized inversin was detected with the inversin-specific antisera (FIG. 26e, right upper panel). Precipitation of endogenous nephrocystin was confirmed by reprobing the blot for nephrocystin (FIG. 26e, right lower panel). Appropriate controls are also shown (FIG. 26e, left panels).

Example 4

β-tubulin is a Nephrocystin Interaction Partner

Figure 27:
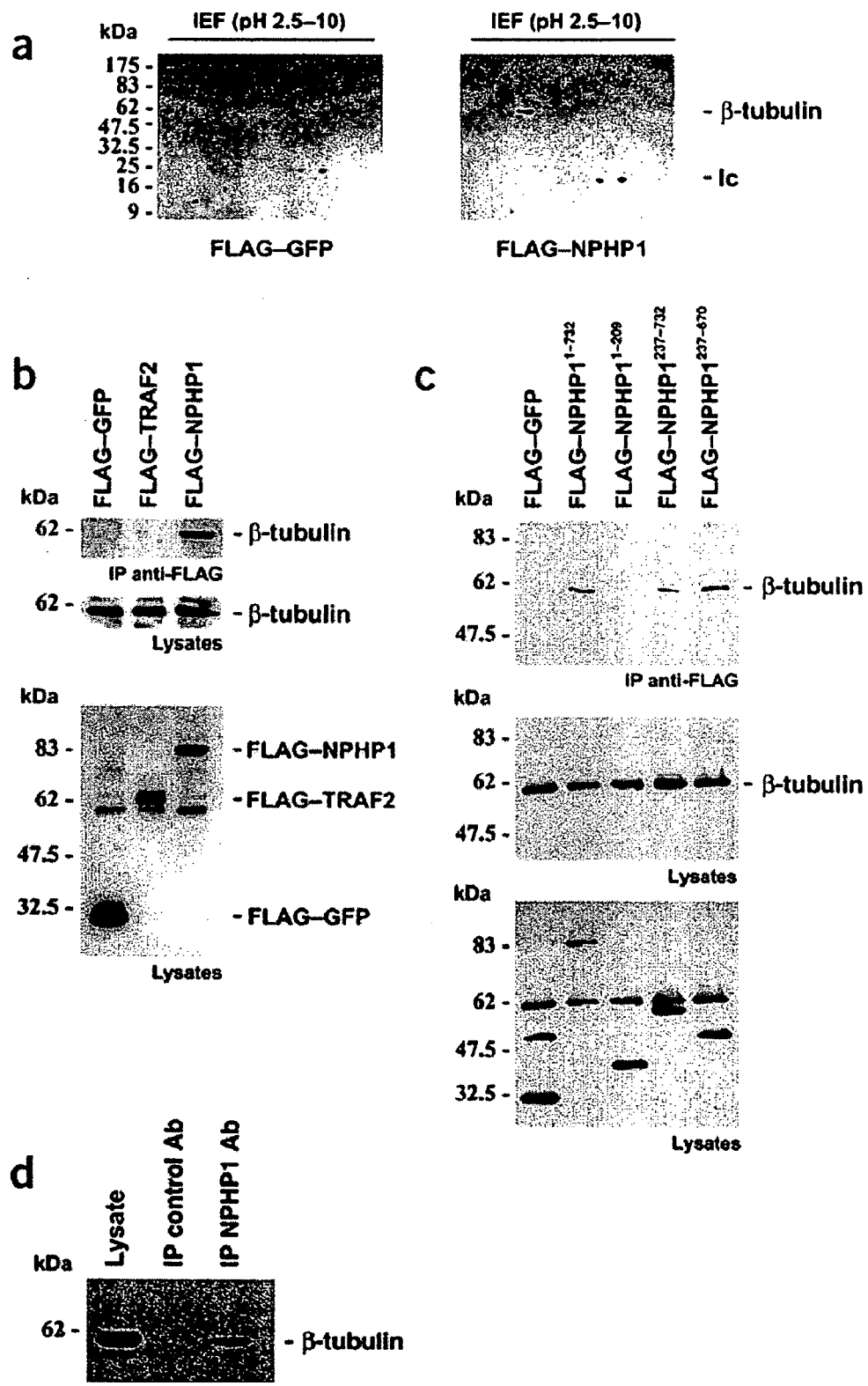
FIGS. 27a-27d show the molecular interaction of nephrocystin with β-tubulin.

In order to identify nephrocystin-interacting proteins, HEK 293T cells were transfected with the FLAG-tagged control protein GFP or FLAG-tagged nephrocystin. Specific association of β-tubulin with nephrocystin was confirmed by immunoblotting of 2D gels using anti β-tubulin antibody (FIG. 27a). Several FLAG-tagged nephrocystin truncations were generated to analyze the interaction of nephrocystin with β-tubulin. Endogenous β-tubulin precipitated with transfected full-length nephrocystin but not with the control proteins GFP or TRAF2 (FIG. 27b, upper panel). Expression of native β-tubulin in lysates is also shown (FIG. 27b, middle panel). The membrane depicted in FIG. 27b, middle panel, was reprobed with anti-FLAG antibody and shows that β-tubulin is still detected below the 62 kDa marker, confirming comparable expression levels of the FLAG-tagged proteins (FIG. 27b, lower panel). The interaction was mapped to a region of nephrocystin involving amino acids 237-670 (FIG. 27c, upper panel) with the expression levels of β-tubulin shown as a control (FIG. 27c, bottom panel). The membrane was reprobed with anti-FLAG antibody to confirm expression of the FLAG-tagged proteins in the lysates (FIG. 27c, lower panel). Endogenous β-tubulin coprecipitates with native nephrocystin in ciliated mCcd-K1 cells (FIG. 27d).

Example 5

Inversin and Nephrocystin Colocalize with β-tubulin to Cilia

Figure 28:
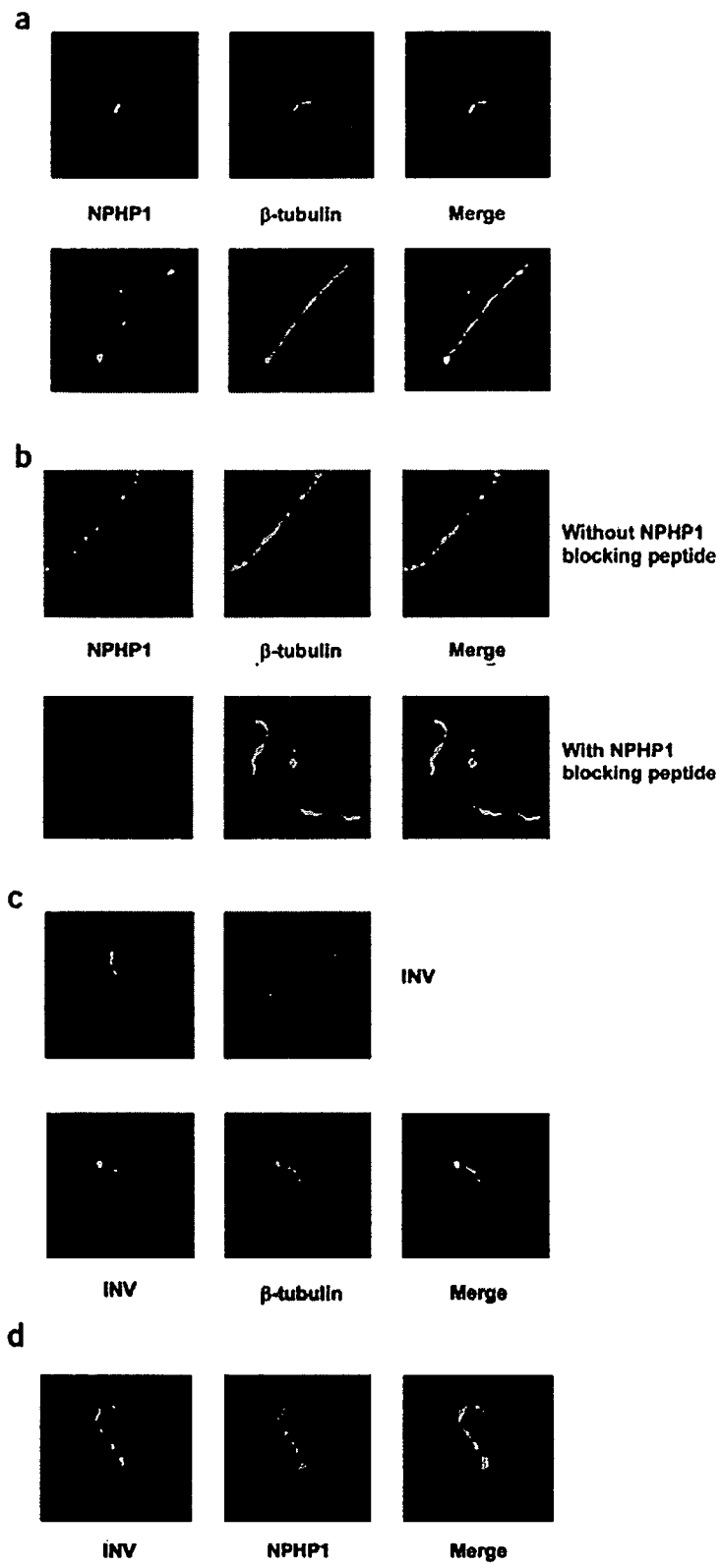
FIGS. 28a-28d show shows the co-localization of nephrocystin and inversin to primary cilia in renal tubular epithelial cells.

Nephrocystin and β-tubulin-4 colocalize in primary cilia of MDCK cells (FIG. 28a, upper and lower panels). Wild-type MDCK cells (clone II) were grown on coverslips at 100% confluence and cultivated for 7 d before the experiment to allow full polarization and cilia formation. Localization of nephrocystin was determined by immunofluorescence using nephrocystin-specific antibody with confocal images captured at the level of the apical membrane. Cells were costained with rabbit antibody to nephrocystin (FIG. 28a, left panels) and mouse antibody to β-tubulin-4 (FIG. 28a, middle panels) followed by the respective secondary antibodies. Specific localization of nephrocystin in primary cilia was confirmed by the use of blocking recombinant nephrocystin protein (FIG. 28b). Inversin localizes to primary cilia in MDCK cells (FIG. 28c). Localization of endogenous inversin was determined by immunofluorescence using inversin-specific antibody with confocal images captured at the level of the apical membrane. Cells were costained with mouse antibody to β-tubulin-4 and rabbit antibody to inversin followed by the respective secondary antibodies (FIG. 28c, lower panel). In additional stainings, the antibody to β-tubulin-4 was omitted to reduce potential spectral overlap between the inversin and β-tubulin-4 signals (FIG. 28c, upper panel). Partial colocalization of nephrocystin and inversin in primary cilia is observed (FIG. 28d). Localization of nephrocystin was determined by immunofluorescence using nephrocystin-specific antibody with confocal images captured at the level of the apical membrane. Cells were costained with goat antibody to inversin (FIG. 28d, left panel) and rabbit antibody to nephrocystin (FIG. 28d, middle panel) followed by the respective secondary antibodies. Partial colocalization is shown (FIG. 28d, right panel).

Example 6

Disruption of Zebrafish Invs Function Results in Renal Cyst Formation

Figure 29:
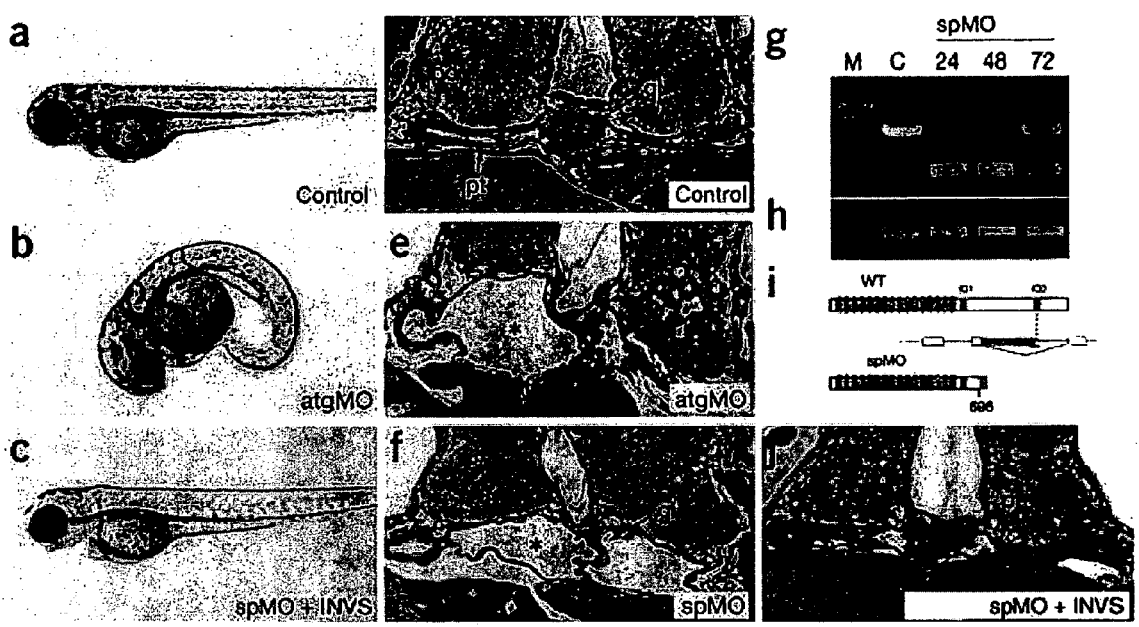
FIGS. 29a-29j show shows the disruption of zebrafish invs function results in renal cyst formation.
Figure 30:
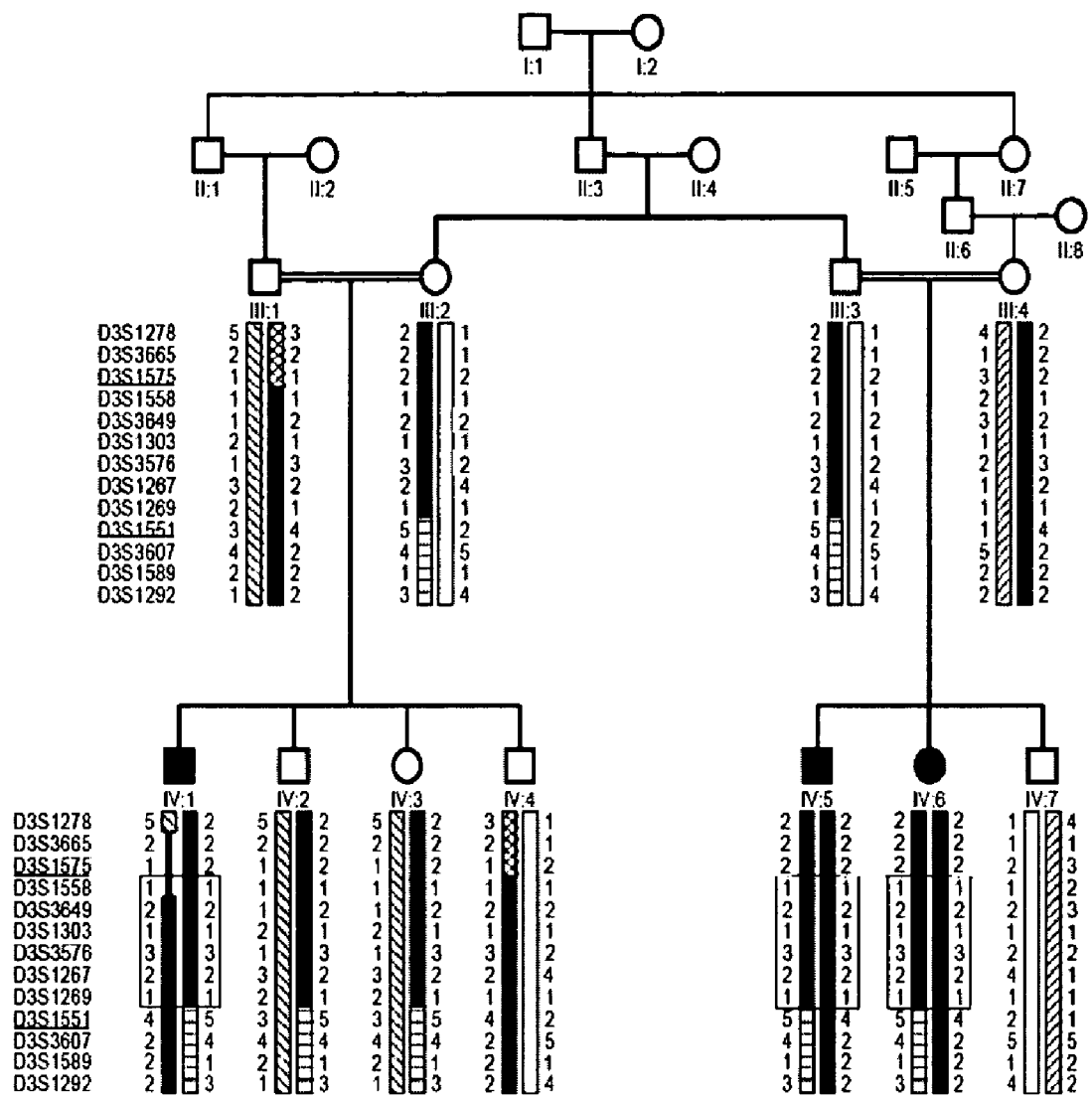
FIG. 30 shows a refinement of the NPHP5 gene locus by haplotype analysis in the consanguineous SLSN pedigree A132.

It was determined that embryos injected with a control, non-specific oligonucleotide have normal morphology (FIG. 29a) whereas embryos injected with atgMO and spMO have a pronounced ventral axis curvature at 3 d.p.f. (combined totals for atgMO and spMO: 432 of 479 injected embryos; 90%) (FIG. 29b). Coinjection of 100 pg mouse Invs mRNA with spMO completely rescued axis curvature defects (combined totals for atgMO and spMO: 363 of 381 mRNA+MO injected embryos were rescued; 95%).(FIG 29c). FIG. 29d shows a histological section of a 2.5-d.p.f. control embryo pronephros showing the midline glomerulus (G1), pronephric tubule (Pt) and pronephric duct (Pd). FIG. 29e shows an atgMO-injected 3-d.p.f. embryo showing cystic dilatation of pronephric tubules and glomerulus (indicated with an asterisk) lined with squamous epithelium. FIG. 29f shows that spMO similarly causes cystic maldevelopment of the pronephric tubules (marked with an asterisk). Molecular analysis of morpholino targeted invs splicing defects was performed. RT-PCR analysis of invs expression in 24-h.p.f. control injected embryos generates a 746-bp invs fragment encoding the C-terminal domain (FIG. 29g, lane C, nucleotides 2,233-2,979 of GenBank AF465261; lane M, φX174 markers). spMO-injected embryos analyzed with the same RT-PCR primers generate a 189-bp RT-PCR product representing a C-terminal invs deletion allele (FIG. 29g, lanes spMO; 24, 48 and 72 h.p.f.). Some recovery of wild-type (WT) mRNA is observed at 72 h.p.f. RT-PCR of ACTB mRNA on the same RNA samples as in FIG. 29g shows no effect of morpholino injection at any time point (FIG. 29h). FIG. 29i diagrams the effect of spMO on invs mRNA processing. Preventing normal splicing in the IQ2 domain recruits a cryptic splice donor in upstream invs coding sequence, the resulting out-of-frame fusion generates a C-terminally truncated invs mRNA at amino acid 696 with an altered 21 amino acid C terminus (FIG. 29i). Rescue of normal morphology by coinjected spMO and mouse Invs mRNA shows a normal pronephric duct structure (Pt) (FIG. 29j) as compared to the absence of any effect when the Invs mRNA was injected alone.

TABLE 3

| Family, (individual) | Ethnic origin | Nucleotide alteration(s)[a] | Alteration(s) in coding sequence | Exon, segregation[b] | Parental consanguinity | Renal cysts | Renal biopsy | Age at ESRD[c] | Situs inversus (other symptoms)[d] |
|---|---|---|---|---|---|---|---|---|---|
| A6 | France | C2695T | R899X | 13, het[e] | – | – | + | <2 y | – |
|  |  | 1453delC | Q485fsX509 | 9, het[e] |  |  |  |  |  |
| A8 | Turkey | C1807T | R603X | 12, hom[e] | + | – | + | 14 mo | + (VSD[f]) |
| A9 | France | C1186T | R396X | 8, het[e] | – | + | + | <2 y | – |
|  |  | C1445G | P482R | 9, het P |  |  |  |  |  |
| A10[g] | France | 2908delG | E970fsX971 | 14, het M | – | + | + | 12 mo | – |
| A12 (VII-1, VII-3) | Israel | C2719T | R907X | 13, hom M, P | + | + | (+, +) | (30 mo, 30 mo) | –, – (HT, HT) |
| 868 (II-1, II-2) | USA | C2719T | R907X | 13, het M | – | –[h] | (+, +) | (5 y, 4 y) | –, – (HT, HT) |
|  |  | 2747insA | K916fsX1002 | 13, het P |  |  |  |  |  |
| A7 | Portugal | T1478C | L493S | 10, hom[e] | + | ND | + | 5 y | – (HT) |

[a] All mutations were absent from at least 100 healthy control subjects.
[b] M, maternal; P, paternal; het, heterozygous; hom, homozygous mutation inherited from both parents; ND, no data available.
[c] ESRD, end-stage renal disease; mo, months.
[d] HT, arterial hypertension.
[e] Parent(s) not available for mutational analysis.
[f] VSD, cardiac ventricular septal defect.
[g] Only one mutation was detected in this individual.
[h] Hyperechogenicity noted as sign of incipient microcysts.

EXAMPLE 7

Identification and Characterization of NPHP5

A. Methods

Patients. Blood samples and pedigrees were obtained following informed consent from patients with NPHP and/or their parents. Approval for experiments on humans was obtained from the University of Michigan Institutional Review Board. In all patients the diagnosis of nephronophthisis was based on the following criteria: i) clinical course and renal ultrasound or renal biopsy were compatible with the diagnosis of NPHP/SLSN as judged by a (pediatric) nephrologist; ii) patients had entered end-stage renal disease; iii) retinitis pigmentosa was diagnosed by an ophthalmologist.

Linkage analysis. Genome wide homozygosity mapping was performed using the ABI Prism Linkage Mapping Set version 2 consisting of 400 microsatellite markers at an average spacing of 10 cM. The MLINK program of the LINKAGE software package was used to calculate two-point LOD scores assuming recessive inheritance with complete penetrance, a disease allele frequency of 0.001 and marker allele frequencies of 0.125. Mutation analysis. Total RNA was extracted from EBV transformed lymphoblast cell lines from two affected individuals from family A132 using TRIZOL Reagent (Invitrogen). RT-PCR was carried out using the SUPERSCRIPT III One-Step RT-PCR System (Invitrogen). The coding region was amplified (according to UCSC) of candidate genes ROPN1, HAPIP, TRAD, ITGB5, MUC13, DIRC2, AB033030, AB033063, and NPHP5 (KIAA0036) and sequenced the RT-PCR products directly on the ABI3700 sequencer (Applied Biosystems). After identifying a nonsense mutation in NPHP5, RT-PCR mutational analysis was performed using RNA from EBV-transformed lymphoblast cell lines of 48 isolated NPHP and 12 SLSN patients. Mutations were screened for by amplifying all 15 exons of NPHP5 by PCR using exon flanking primers (Table 6) in 24 individuals with isolated renal NPHP and 80 individuals with SLSN. Both strands of the PCR products were directly sequenced using the dideoxy chain termination method on an ABI capillary sequencer. Sequence data were analyzed using the MUTATION SURVEYOR (SoftGenetics) and SEQUENCHER (Gene Codes) Softwares.

Northern blot analysis. A human 12-lane multiple tissue northern (MTN) blot and a human multiple tissue expression (MTE) array blot were purchased from Clontech (Paolo Alto). As probe, full-length NPHP5 cDNA was amplified by PCR using cDNA from human mononuclear blood lymphocytes. The probe was radioactively labeled with 32P using the random primed DNA labeling kit (Roche). Hybridization was performed at 68° C. overnight in ExpressHyb solution (Clontech). The final washing condition was 0.1× sodium citrate and 0.1% SDS at 65° C. for 40 min. The filters were exposed the filters to X-ray film together with intensifying screens at −80° C. for 7 days. A β-actin cDNA probe was used as a loading control.

In situ hybridization. Whole-mount in situ hybridization was performed following a standard procedure with digoxigenin-labeled antisense riboprobes. The probes used were generated from a 1.9 kb Nphp5 mouse cDNA cloned in pCM-VSport6 using T7 RNA polymerase. Stained specimens were transferred in 50% glycerol prior to documentation. Constructs. Using RT-PCR, human full-length cDNAs of NPHP1, INVS, NPHP3, NPHP4, NPHP5, CALM2, BBS1, BBS2, BBS4, BBS5, BBS6, BBS7, BBS8, RPGR (non-ORF15 containing isoform) and a truncated version of calmodulin (aa 1-70) were generated by RT-PCR and cloned into the Gateway pENTR-TOPO vector (Invitrogen). After LR-clonase recombination, inserts were switched to destination vectors DEST22 (activation domain containing yeast-2-hybrid vector, Invitrogen) DEST32 (binding domain containing yeast-2-hybid vector, Invitrogen).

Yeast two-hybrid screening. Full-length NPHP5 cDNA was fused to the GAL4 DNA binding domain in the pDEST32 vector as bait and a human fetal brain expression library cloned into pPC86 GAL4 activation domain fusion vector was screened (Invitrogen #11386-018). Approximately $2 \times 10^6$ clones were screened after cotransforming plasmids into competent MaV203 yeast cells (lithium acetate method) and plated on -His, -Leu and -Trp restricted medium. 3-aminotriazole was included at 25 mM to suppress leaky growth from HIS3. Visible blue colored yeast colonies, grown on X-alpha-Gal containing plates, were further analysed. Plasmids of the transformants were directly sequenced after polymerase chain amplification or plasmid shuffling into E. coli. To test for direct yeast-2-hybrid interaction of the NPHP5 protein with calmodulin, NPHP proteins (nephrocystin 1-4), or Bardet Biedl proteins (BBS 1, 2, and BBS3-8), corresponding full-length cDNAs were cloned into the pENTR GATEWAY vector system (Invitrogen) and transferred to Gal4 activation domain (pDEST22) prey vector or Gal4 binding domain (pDEST32) bait vector. To confirm interaction, inserts were switched from prey to bait vector. Colony growth was compared to 2 negative control (respective plasmids without insert) and 4 positive control yeast strains for different interaction strength as provided by the kit.

Generation of antibodies to NPHP5 and RPGR. For rabbit immunization, a synthetic peptide corresponding to amino acid residues 566-582 (KKLGEESGDEIDVPKDE)(SEQ ID NO:82) of human NPHP5 was used, the sequence of which is identical to that of rat Nphp5 (one mismatch to mouse Nphp5). Peptide synthesis, KLH conjugation and affinity purification of immunserum was performed by Washington Biotechnology (Baltimore, MD). Final ELISA titer was 1:100,000,000. Antibody against calmodulin (sc-5537) was from Santa Cruz Biotechnologies. This antibody does not discriminate between CALM1, 2 or 3. (All three human CALM gene products are identical in amino acid sequence with the exception of a 3-amino acid insertion in calmodulin-3.) Antibody against acetylated tubulin was from Sigma (St. Louis, MO). Sheep anti-CALM antibody was from Bethyl Laboratories (Montgomery, TX). The rabbit polyclonal ORF15CP peptide antibody was generated against the amino-acid sequence 1100HKTYQKKSVTNTQGNGKE1117 (SEQ ID NO:118) of human RPGR14. The antibody was affinity purified using the cognate peptide. This ORF15CP antibody identified 5-6 bands with apparent molecular weight range of 100-250 kDa in mammalian retinas. The bands were abolished by pre-incubation with 50-fold molar excess of the relevant peptide, but not with an irrelevant peptide. In addition, the immunoreactive bands were not detected in the Rpgr knockout mouse retina (Hong et Al., Invest Opthalmol Vis Sci 43:3373 [2002]; Hong et al., Invest Opthalmol Vis Sci 44:2413 [2003](FIG. 36).

Coimmunoprecipitation from bovine retina. Five bovine retinae were resuspended in 1× phosphate-buffered saline (PBS) supplemented with complete protease inhibitor cocktail from Roche (Basel) and sonicated. The sonicate was centrifuged at 10,000×g for 15 min to remove debris. Immunoprecipitation followed by immunoblot analysis was performed as described previously (Cheng et al., Hum Mol. Genet 13:1563 [2004]). Immunofluorescence staining of MDCK cells. MDCK (strain II) were seeded onto Transwell filters (Corning, Corning, N.Y.) and grown seven days past confluence. After rinsing with ice-cold PBS, cells were fixed for 15 minutes at room temperature with 4% paraformaldehyde in PBS, pH 7.5 and permeabilized for 5 minutes at room temperature with 0.1% Triton X-100 in PBS. Filters were washed with PBS then blocked for at least 1 hour in PBS with 2% goat and/or donkey serum. Filters were incubated with primary antibodies in blocking solution at least 2 hours as indicated. Filters were washed three times in blocking solution at room temperature then incubated one hour at room temperature with secondary antibodies, Alexa Fluor 488 donkey anti-sheep, Alexa Fluor 594 goat anti-mouse (Molecular Probes, Eugene, Oreg.) and Cy5 conjugated goat anti-rabbit IgG (Jackson Immunoresearch, West Grove, Pa.) with and without primary antibodies as controls. Filters were mounted with ProLong antifade kit (Molecular Probes, Eugene, Oreg.) and confocal images were obtained with an Axiovert 100M Zeiss LSM 510 confocal microscope.

Microscopy of retina. For immunofluorescence microscopy, light-adapted mouse eyes were processed and examined as described (Gibbs et al., J. Cell Science 117:6383 [2004]). For immunoelectron microscopy, eyecups from light-adapted mouse and human were fixed by immersion in 0.1% glutaraldehyde+2% paraformaldehyde in 0.1 M cacodylate buffer, pH 7.4, processed and examined as described (Gibbs et al., supra). Negative controls included sections from the same retina incubated with 1 mg/ml of immunogen with the primary antibody.

B. Results

From a total of 57 genes within the critical genetic region, 9 were selected as candidates based on predicted functional domains (FIG. 2a). Mutational analysis was performed by direct sequencing of RT-PCR products from EBV transformed mononuclear cells of 2 affected individuals of family A132 (VI:1, IV:5). One of the 9 genes (KIAA0036) shared 2 putative "IQ calmodulin binding domains" with the NPHP2 gene product inversin (See above Examples). In this gene, in kindred A132 a homozygous truncating mutation was identified (Nucleotide C1381T; Residue R461X) that segregated with the affected status (Table 5 and FIG. 31b). Mutational analysis by direct sequencing of RT-PCR products of 48 additional individuals with isolated NPHP and 12 individuals with SLSN yielded 3 new truncating mutations of KIAA036 in 4 unrelated individuals with SLSN. Mutational screening was then performed of all 15 KIAA0036 exons in 24 additional unrelated individuals with NPHP and 80 unrelated individuals with SLSN. Altogether, 8 distinct KIAA0036 mutations were identified in a total of 16 SLSN individuals from different families (Table 5 and FIG. 31b-e).

Figure 33:
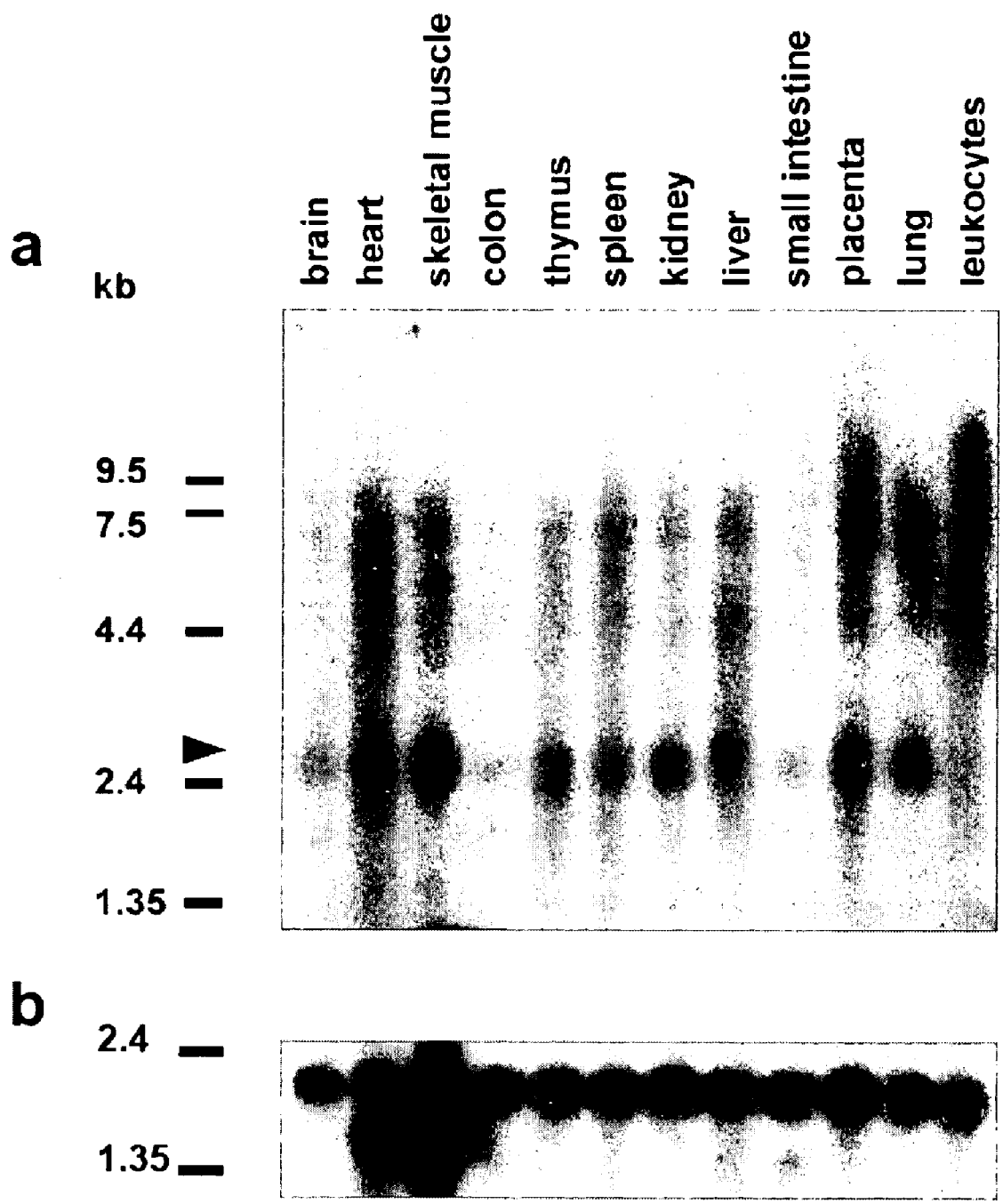
FIG. 33 shows Northern blot analysis of NPHP5.

All observed sequence changes were truncating mutations (i.e., nonsense mutations, small insertions or deletions), and no missense mutations were detected (Table 5 and FIG. 31b-e). Mutations were detected in exons 6, 9, 11, 13, or 14 (Table 5 and FIG. 31b-e). The wild type nucleic acid sequence of NPHP5 is described by SEQ ID NO:81 and the wild type amino acid sequence is described by SEQ ID NO:82 (FIG. 37). Variant nucleic acid sequences of NPHP5 are described by SEQ ID NOS: 83, 84, 85, 86, 87, 88, 89, and 90 (FIG. 37). All patients with mutations in KIAA0036 had both, nephronophthisis and RP, in contrast to patients with mutations in NPHP1, 2, 3 or 4, where only 10% of the patients exhibit RP8. Mutational analysis by RT-PCR in 48 patients with NPHP without RP revealed no mutations. No NPHP5 mutations were detected in the DNA from >155 healthy control individuals. Whenever DNA samples were available for testing, all mutations segregated from both parents (Table 5). KIAA0036 is thus a novel gene causing SLSN type 5. This gene was termed NPHP5 (alias SLSN5) and the respective gene product was called "nephrocystin-5 (NPHP5)". The NPHP5 gene spans 65,676 bp on human chromosome 3 (FIG. 31a). It consists of 15 exons. Exons 1 and 2 are not translated. Northern blot analysis revealed a major NPHP5 transcript of 2.6 kb that is ubiquitously expressed (FIG. 33). RNA dot blot analysis confirmed this pattern in human adult and fetal tissues, and in situ hybridization detected ubiquitous though weak expression during mouse embryonic development.

BLAST analysis of a genomic sequence database of the multicellular model organism Ciona intestinalis (sea squirt) (Dehal et al., Science 298:2157 [2002]), using the cDNA of the zebrafish NPHP5 ortholog as a query, identified a sequence (cieg034e08) orthologous to human NPHP5 (25% amino acid identity). Whole-mount in situ hybridization analysis of the nphp-5 Ciona intestinalis homolog showed ubiquitous expression at all stages of development studied (Web FIG. 1e-j). Unlike NPHP1, -2, and -411, a C. elegans ortholog was not identified for NPHP5.

Figure 31:
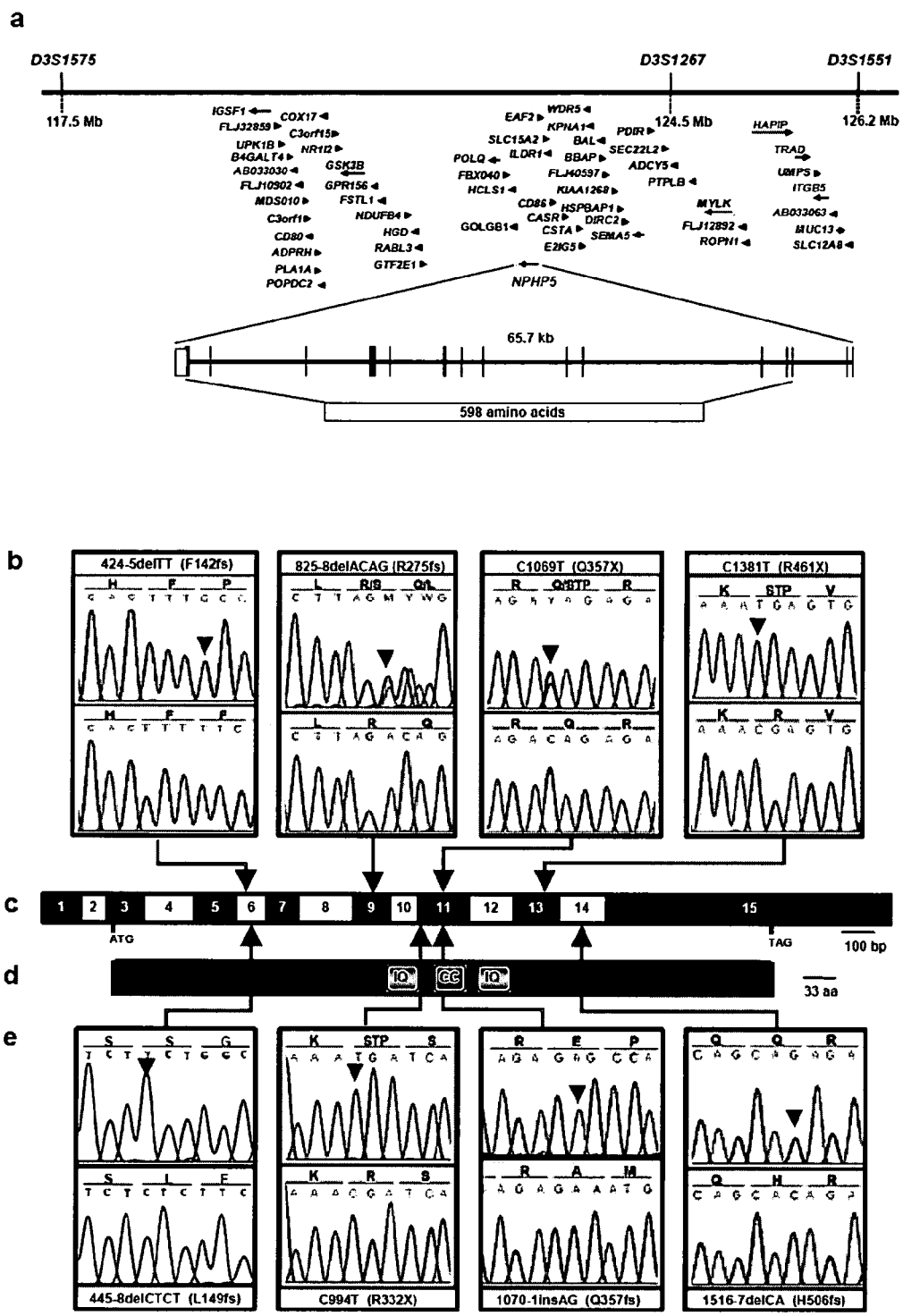
FIG. 31 shows the identification of the NPHP5 gene by direct mutational analysis in positional candidates.

The human full-length NPHP5 mRNA sequence encodes 598 amino acid residues with a predicted molecular weight of 69 kDa. Analysis of the deduced NPHP5 sequence yielded a putative coiled-coil domain (amino acid residues 340-373) (FIG. 31d), a feature that has also been found in NPHP1 gene product nephrocystin-1 (Otto et al., J Am Soc Nephrol. 11:270 [2000]). In addition, there are two IQ calmodulin binding regions, at amino acid positions 294-323 and 387-416, respectively (FIGS. 31d, 34). This is of interest, since the NPHP2 gene product (inversin) also contains two IQ calmodulin binding regions (Otto et al., Nat Genet. 34:413 [2003]).

Figure 32:
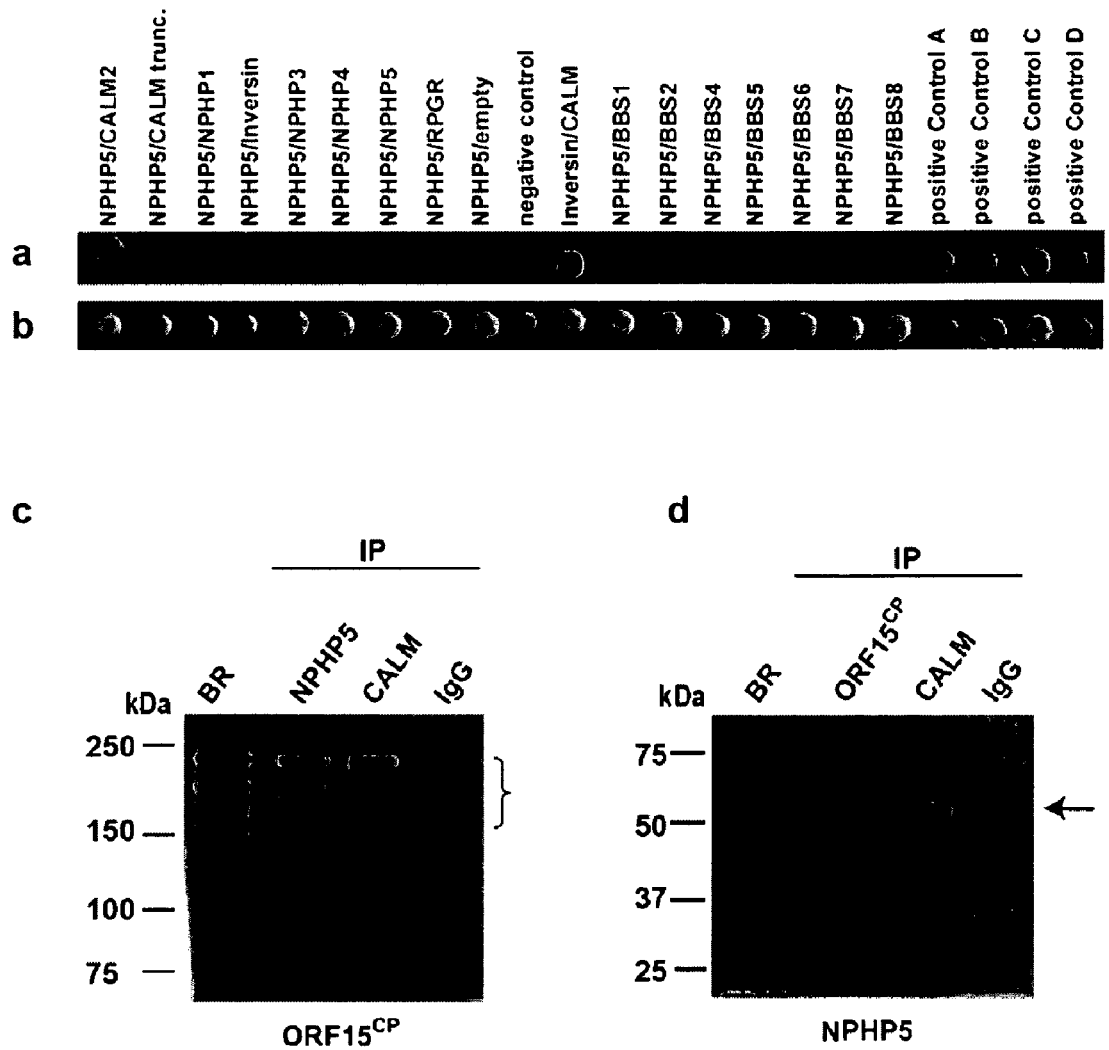
FIG. 32 shows that NPHP5 directly interacts with calmodulin and is in a complex with RPGR.

To determine whether calmodulin (CALM) physically interacts with NPHP5, a yeast-2-hybrid screen of a human fetal brain expression library was performed using a full-length human nephrocystin-5 construct as "bait". All 120 positive clones yielded calmodulin (CALM) sequence. No other direct binding partners were identified. The interaction of NPHP5 with CALM was further confirmed by yeast-2-hybrid assay and after switching "bait" and "prey" (FIG. 32a,b). Yeast-2-hybrid assays for other gene products mutated in renal cystic disease were also performed. The results were negative for NPHP1, 2, 3, and 4, for products of genes causing Bardet-Biedl syndrome (BBS1-8) (FIG. 3a,b), and for KIF3A.

To evaluate NPHP5-CALM interaction in vivo, and to identify additional members of NPHP5 protein complex, a polyclonal antibody against a human C-terminal NPHP5 peptide was raised. The antibody recognized a major protein of ~55 kDa in mouse and human retinal extracts and in mouse kidney extracts (FIG. 35a,b). Additional bands in bovine retina most likely represent alternatively spliced isoforms. The immunoreactive bands were completely blocked by preincubation with the cognate peptide but not by an irrelevant peptide (FIG. 35a). All patients with NPHP5 mutations exhibited RP in addition to the kidney disease.

Since NPHP1, 2, and 3 are expressed in primary cilia of renal epithelial cells (Olbrich et al., Nat Genet 34:455 [2003]; Otto et al., Nat Genet 34:413 [2003]) and since mutations in RPGR (which is expressed in photoreceptor cilia13) represent a major cause of X-linked RP (Vervoort et al., Nat Genet 25:462 [2000], it was evaluated whether NPHP5 interacts with the main retinal isoform of RPGR-ORF15. Coimmunoprecipitation (coIP) of endogenous NPHP5 from bovine retinal extracts was observed, using an anti-RPGR-ORF15CP antibody (FIG. 32c). Reverse coIP further confirmed that NPHP5 and RPGR are present in a multi-protein complex in the retina (FIG. 32d and FIG. 36). The yeast two-hybrid assay did not reveal an interaction between NPHP5 as "bait" and the non-ORF15 containing RPGR isoform (FIG. 32a) nor with the RPGR-ORF15 isoform, indicating that NPHP5 and RPGR do not physically interact. The direct NPHP5-CALM interaction detected by the direct yeast-2-hybrid assay (FIG. 32a) was confirmed as occurring in vivo by coIP from bovine retina extracts (FIG. 32c,d). NPHP1, 2, 3, and 4 are expressed in primary cilia of renal epithelial cells. Additionally, virtually all proteins encoded by genes that, if mutated, give rise to renal cystic disease, are expressed in primary cilia (Watnick et al., Nat Genet 34:355 [2003]. It was therefore investigated whether NPHP5 is similarly expressed in primary cilia of renal epithelial cells. Confocal laser microscopy images of renal epithelial MDCK cells using an anti-acetylated-tubulin antibody marked the primary cilia tubulin scaffold over its entire length. NPHP5 localized to these cilia in a dotted staining pattern, in a configuration similar to NPHP1 and NPHP2 (inversin). CALM partially colocalized with both, NPHP5 and tubulin, in apunctate pattern. At least one isoform of RPGR-ORF15 is localized in the analogous subcellular structure of the retina, the photoreceptor connecting cilium and in the outer segment (Hong et al., Invest Opthalmol Vis Sci 44:2413 [2003]; Roepman et al., Hum Mol Genet 9:2095 [2000]). The data are consistent with the finding that CALM is expressed in human photoreceptor connecting cilia (Cuenca et al., J. Neurocytol 31:649 [2002] and outer segments (Chen et al., PNAS 91:11757 [1994].

It was demonstrated by immunofluorescence and immunogold labeling that NPHP5 also localizes to the connecting cilia and outer segments of mouse and human photoreceptor cilia, thereby supporting its role in ciliary functions and its interaction with RPGR-ORF15. With sections of mouse retinas, there was significant immunolabeling of the photoreceptor outer segments as well as the connecting cilia, although the only significant immunogold labeling of human retinas was found in the connecting cilium (gold particle density+s.d. on human retinal sections was found to be 1.1+0.7 per μm2 for photoreceptor outer segments, 5.9+2.7 per μm2 for connecting cilia, and 0.6+0.7 per μm2 for the RPE, which represents only background tissue labeling). In comparing cilia among different tissues, the photoreceptor outer segment represents an amplified distal cilium.

TABLE 4

| Marker | Distance (in cM) | Lodscore at θ = | | | | | | $Z_{max}(\theta)$ |
|---|---|---|---|---|---|---|---|---|
| | | 0.00 | 0.05 | 0.10 | 0.20 | 0.30 | 0.40 | |
| D3S1278 | | −99.000 | 0.340 | 0.702 | 0.788 | 0.578 | 0.264 | 0.803 (θ = 0.15) |
| D3S3665 | 0.00 | 2.103 | 1.887 | 1.660 | 1.181 | 0.701 | 0.283 | 2.103 (θ = 0) |
| D3S1575[a] | 2.10 | −1.113 | 0.231 | 0.367 | 0.349 | 0.224 | 0.091 | 0.382 (θ = 0.15) |
| D3S1558 | 2.10 | 1.636 | 1.441 | 1.242 | 0.839 | 0.461 | 0.167 | 1.636 (θ = 0) |
| D3S3649 | 0.71 | 2.048 | 1.819 | 1.583 | 1.100 | 0.635 | 0.252 | 2.048 (θ = 0) |
| D3S1303 | 1.68 | 1.618 | 1.437 | 1.249 | 0.861 | 0.488 | 0.186 | 1.618 (θ = 0) |
| D3S3576 | 1.68 | 2.879 | 2.541 | 2.198 | 1.508 | 0.856 | 0.322 | 2.879 (θ = 0) |
| D3S1267[b] | 1.12 | 3.458[b] | 3.097 | 2.725 | 1.957 | 1.189 | 0.504 | 3.458[b] (θ = 0) |
| D3S1269 | 0.53 | 1.576 | 1.397 | 1.212 | 0.832 | 0.469 | 0.179 | 1.576 (θ = 0) |
| D3S1551[a] | 0.54 | 0.189 | 1.142 | 1.152 | 0.877 | 0.502 | 0.175 | 1.152 (θ = 0.10) |
| D3S3607 | 2.15 | −0.134 | 0.825 | 0.844 | 0.614 | 0.328 | 0.102 | 0.844 (θ = 0.10) |
| D3S1589 | 1.60 | −1.526 | −0.361 | −0.141 | 0.012 | 0.042 | 0.028 | 0.042 (θ = 0.30) |
| D3S1292 | 2.66 | −0.145 | 0.836 | 0.879 | 0.681 | 0.389 | 0.137 | 0.879 (θ = 0.10) |

[a]Markers that flank the NPHP5 critical genetic region within an 8.3 cM genetic and an 8.7 Mb physical interval are underlined.
[b]Maximum lod score and related marker are shown in bold; loci compatible with linkage are depicted on a shaded background.

TABLE 5

| Family (Individual) | Ethnic Origin | Nucleotide alteration(s)[a] | Alteration(s) in coding sequence | Exon (segregation)[b] | Parental consanguinity | Age at ESRD (years) | Age at diagnosis of RP (years) |
|---|---|---|---|---|---|---|---|
| F1 (II-1, II-2) | Germany | 424-425delTT | F142fsX147 | 6 (hom, M, nd) | + | 15, 12 | <3, <3 |
| F399 (II-1) | Germany | 424-425delTT | F142fsX147 | 6 (hom, nd, P) | − | 32 | 0.1 |
| F408 (II-1) | Switzerland | 424-425delTT | F142fsX147 | 6 (hom, nd, nd) | − | 8 | RP[d] |
| F409 (II-1) | Switzerland | 424-425delTT | F142fsX147 | 6 (hom, nd, nd) | − | 17 | RP[d] |
| F53 (II-2) | Germany | 445-448delCTCT | L149fsX170 | 6 (hom, M, P) | − | 16 | <1 |
| F269 (II-1) | Germany | 445-448delCTCT 825-828delACAG | L149feX170 R275fsX281 | 6 (het, nd, nd) 9 (het, nd, nd) | − | 37 | RP[d] |
| A19 (II-1) | Germany | 825-828delACAG C1069T | R275fsX281 Q357X | 9 (het, nd, nd) 11 (het, nd, nd) | − | <15 | <0.1 |
| F2 (II-1) | Italy | C994T | R332X | 11 (hom, nd, nd) | − | 9 | 0.4 |
| F189 (II-1) | Germany | C994T | R332X | 11 (hom, M, P) | + | <13 | RP[d] |
| F64 (II-3) | North Africa | 1070-1071insAG | Q357fsX360 | 11 (hom, M, P) | − | <20 | RP[d] |
| F1146 (II-1, II-2) | Belgium | 1070-1071insAG | Q357fsX360 | 11 (hom, M, P) | + | 12, >13[c] | 0.6, 1.5 |
| A132 (IV-1, IV-5, IV-6) | Turkey | C1381T | R461X | 13 (hom, M, P) | + | <12, <8, <6 | 0.1, 0.1, 0.1 |
| F50 (II-1, II-3) | Germany | 1516-1517delCA | H506fsX519 | 14 (hom, M, P) | − | 12, >13[c] | 0.1, 0.1 |
| F54 (II-1) | Germany | 1516-1517delCA | H506fsX519 | 14 (hom, nd, P) | − | <24 | RP[d] |

TABLE 5-continued

| Family (Individual) | Ethnic Origin | Nucleotide alteration(s)[a] | Alteration(s) in coding sequence | Exon (segregation)[b] | Parental consanguinity | Age at ESRD (years) | Age at diagnosis of RP (years) |
|---|---|---|---|---|---|---|---|
| F1175 (II-1) | Germany | 1516-1517delCA | H506fsX519 | 14 (hom, M, P) | – | 10 | 0.4 |
| F1298 (II-2) | Germany | 1516-1517delCA | H506fsX519 | 14 (hom, M, P) | – | 15 | 0.1 |

[a]All mutations were absent from at least 155 healthy control subjects.
[b]het heterozygous in affected individual; hom, homozygous in affected individual; M, mutation identified in mother; P, mutation identified in father; nd, no data or DNA available
[c]serum creatinine was 2.0 mg/dL age 13 years.
[d]retinitis pigmentosa present, but age of onset unknown.
ESRD, end-stage renal disease;
RP, retinitis pigmentosa The numbering shown in Table 5 is based on the cDNA sequence. SEQ ID NOs: 81 and 83-90 are mRNA sequences. Thus, the mutations are as follows:
633-634delTT
654-657delCTCT
1034-1037delACAG
C1278T
C1203T
1279-1280insAG
C1590T, and
1725-1726delCA, respectively.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

SEQUENCE LISTING

```
<160> NUMBER OF SEQ ID NOS: 117

<210> SEQ ID NO 1
<211> LENGTH: 4994
<212> TYPE: DNA
<213> ORGANISM: Homo sapiens

<400> SEQUENCE: 1
gacgcgaggc gggttcttgg actgagtgtg cggcgcggtg cgccgccttc cgaggctcct      60
cccgcgggtg gcaggcgacg gggcgcgccc ctcggccagt cctcggtcct caggcttgtg     120
gctccgttga gcaccggccg ccgggcctct gggtccgtcg agtggagact ctctgaaaag     180
cgtgggctcc gtggcctccg gcgcggccgc ggcgggtcgg tctcctagat catccgggaa     240
gcccacggga ccctcaggcg ggcaggatga acgactggca caggatcttc acccaaaacg     300
tgcttgtccc tccccaccca cagagagcgc gccagccttg gaaggaatcc acggcattcc     360
agtgtgtcct caagtggctg gacggaccgg taattaggca gggcgtgctg gaggtactgt     420
cagaggttga atgccatctg cgagtgtctt tctttgatgt cacctaccgg cacttctttg     480
ggaggacgtg gaaaaccaca gtgaagccga cgaagagacc gccgtccagg atcgtcttta     540
atgagccctt gtattttcac acatccctaa accaccctca tatcgtggct gtggtggaag     600
tggtcgctga gggcaagaaa cgggatggga gcctccagac attgtcctgt gggtttggaa     660
ttcttcggat cttcagcaac cagccggact ctcctatctc tgcttccag dacaaaaggt     720 tgcggctgta ccatggcacc cccagagccc tcctgcaccc gcttctccag gaccccgcag     780
agcaaaacag acacatgacc ctcattgaga actgcagcct gcagtacacg ctgaagccac     840
acccggccct ggagcctgcg ttccaccttc ttcctgagaa ccttctggtg tctggtctgc     900
```

-continued

```
agcagatacc tggcctgctt ccagctcatg gagaatccgg cgacgctctc cgaaagcctc    960
gcctccagaa gcccatcacg gggcacttgg atgacttatt cttcaccctg taccctccc    1020
tggagaagtt tgaggaagag ctgctggagc tccacgtcca ggaccacttc caggagggat   1080
gtggcccact ggacggtggt gccctggaga tcctggagcg cgcgcctgcgt gtgggcgtgc  1140
acaatggtct gggcttcgtg cagaggccgc aggtcgttgt actggtgcct gagatggatg   1200
tggccttgac gcgctcagct agcttcagca ggaaagtggt ctcctcttcc aagaccagct   1260
ccgggagcca agctctggtt ttgagaagcc gcctccgcct cccagagatg gtcggccacc   1320
ctgcatttgc ggtcatcttc cagctggagt acgtgttcag cagccctgca ggagtggacg   1380
gcaatgcagc ttcggtcacc tctctgtcca acctggcatg catgcacatg gtccgctggg   1440
ctgtttggaa cccccttgctg gaagctgatt ctggaagggt gaccctgcct ctgcagggtg  1500
ggatccagcc caaccctcg cactgtctgg tctacaaggt accctcagcc agcatgagct    1560
ctgaagaggt gaagcaggtg gagtcgggta cactccggtt ccagttctcg ctgggctcag   1620
aagaacacct ggatgcaccc acggagcctg tcagtggccc caaagtggag cggcggcctt   1680
ccaggaaacc acccacgtcc ccttcgagcc cgccagcgcc agtacctcga gttctcgctg   1740
ccccgcagaa ctcacctgtg ggaccagggt tgtcaatttc ccagctggcg gcctcccgc    1800
ggtccccgac tcagcactgc ttggccaggc ctacttcaca gctaccccat ggctctcagg   1860
cctcccggc ccaggcacag gagttcccgt tggaggccgg tatctcccac ctggaagccg    1920
acctgagcca gacctccctg gtcctggaaa catccattgc cgaacagtta caggagctgc   1980
cgttcacgcc tttgcatgcc cctattgttg tgggaaccca gaccaggagc tctgcagggc   2040
agccctcgag agcctccatg gtgctcctgc agtcctccgg ctttcccgag attctggatg   2100
ccaataaaca gccagccgag gctgtcagcg ctacagaacc tgtgacgttt aaccctcaga   2160
aggaagaatc agattgtcta caaagcaacg agatggtgct acagtttctt gcctttagca   2220
gagtggccca ggactgccga ggaacatcat ggccaaagac tgtgtatttc accttccagt   2280
tctaccgctt cccacccgca acgacgccac gactgcagct ggtccagctg gatgaggccg   2340
gccagcccag ctctggcgcc ctgacccaca tcctcgtgcc tgtgagcaga gatggcacct   2400
ttgatgctgg gtcctggc ttccagctga ggtacatggt gggccctggg ttcctgaagc     2460
caggtgagcg gcgctgctttt gcccgctacc tggccgtgca gaccctgcag attgacgtct   2520
gggacggaga ctccctgctg ctcatcggat ctgctgccgt ccagatgaag catctcctcc   2580
gccaaggccg gccggctgtg caggcctccc acgagcttga ggtcgtggca actgaatacg   2640
agcaggacaa catggtggtg agtggagaca tgctgggggtt tggccgcgtc aagcccatcg   2700
gcgtccactc ggtggtgaag ggccggctgc acctgacttt ggccaacgtg ggtcacccgt   2760
gtgaacagaa agtgagaggt tgtagcacat gccaccgtc cagatctcgg gtcatctcaa    2820
acgatggagc cagccgcttc tctggaggca gcctcctcac gactggaagc tcaaggcgaa   2880
aacacgtggt gcaagcacag aagctggcgg acgtggacag tgagctggct gccatgctac   2940
tgacccatgc ccggcagggc aaggggcccc aggacgtcag ccgcgagtcg gatgccaccc   3000
gcaggcgtaa gctggagcgg atgaggtctg tgcgcctgca ggaggccggg ggagacttgg   3060
gccggcgcgg gacgagcgtg ttggcgcagc agagcgtccg cacacagcac ttgcgggacc   3120
tacaggtcat cgccgcctac cgggaacgca cgaaggccga gagcatcgcc agcctgctga   3180
gcctggccat caccacggag cacacgctcc acgccacgct gggggtcgcc gagttctttg   3240
```

-continued

```
agtttgtgct taagaacccc cacaacacac agcacacggt gactgtggag atcgacaacc    3300
ccgagctcag cgtcatcgtg gacagtcagg agtggaggga cttcaagggt gctgctggcc    3360
tgcacacacc ggtggaggag gacatgttcc acctgcgtgg cagcctggcc cccagctct    3420
acctgcgccc ccacgagacc gcccacgtcc ccttcaagtt ccagagcttc tctgcagggc    3480
agctggccat ggtgcaggcc tctcctgggt tgagcaacga aagggcatg gacgccgtgt    3540
caccttggaa gtccagcgca gtgcccacta aacacgccaa ggtcttgttc cgagcgagtg    3600
gtggcaagcc catcgccgtg ctctgcctga ctgtggagct gcagcccac gtggtggacc    3660
aggtcttccg cttctatcac ccggagctct ccttcctgaa aaggccatc cgcctgccgc    3720
cctggcacac atttccaggt gctccggtgg aatgcttgg tgaggacccc ccagtccatg    3780
ttcgctgcag cgacccgaac gtcatctgtg agacccagaa tgtgggcccc ggggaaccac    3840
gggacatatt tctgaaggtg gccagtggtc aagcccgga gatcaaagac ttctttgtca    3900
tcatttactc ggatcgctgg ctggcgacac ccacacagag gtgcaggtc tacctccact    3960
ccctgcagcg cgtggatgtc tcctgcgtcg caggccagct gacccgcctg tcccttgtcc    4020
ttcggggac acagacagtg aggaaagtga gagctttcac ctctcatccc aggagctga    4080
agacagaccc caaaggtgtc ttcgtgctgc cgcctcgtgg ggtgcaggac ctgcatgttg    4140
gcgtgaggcc cctagggcc ggcagccgct ttgtccatct caacctggtg gacgtggatt    4200
gccaccagct ggtggcctcc tggctcgtgt gcctctgctg ccgccagccg ctcatctcca    4260
aggcctttga gatcatgttg gctgcgggcg aagggaaggg tgtcaacaag aggatcacct    4320
acaccaaccc ctaccctcc cggaggacat tccacctgca cagcgaccac ccggagctgc    4380
tgcggttcag agaggactcc ttccaggtcg ggggtggaga gacctacacc atcggcttgc    4440
agtttgcgcc tagtcagaga gtgggtgagg aggagatcct gatctacatc aatgaccatg    4500
aggacaaaaa cgaagaggca ttttgcgtga aggtcatcta ccagtgaggg cttgagggtg    4560
acgtccttcc tgcggcaccc agctggggcc tgtctgtgcc cctcctgccc tgcaggctgt    4620
cctccccgcc tctctgcagc ctttcacttc agtgcccacc tggctgacct gtgcacttgg    4680
ctgaggaagc agagaccgag cgctggtcat tttgtagtac ctgcatccag cttagctgct    4740
gctgacaccc agcaggcctg ggttccgtga gcgcgaactc cgtggtggtg ggtctggctc    4800
tggtgctgcc atctacgcat gtgggaccct cgttatcgct gttgctcaaa atgtatttta    4860
tgaatcatcc taaatgagaa aattatgttt ttcttactgg attttgtaca aacataatct    4920
attatttgct atgcaatatt ttatgctggt attatatctg tttttaaat tgttgaacaa    4980
aatactaaac tttt                                                    4994
```

<210> SEQ ID NO 2
<211> LENGTH: 1426
<212> TYPE: PRT
<213> ORGANISM: Homo sapiens

<400> SEQUENCE: 2

Met Asn Asp Trp His Arg Ile Phe Thr Gln Asn Val Leu Val Pro Pro
1               5                   10                  15

His Pro Gln Arg Ala Arg Gln Pro Trp Lys Glu Ser Thr Ala Phe Gln
            20                  25                  30

Cys Val Leu Lys Trp Leu Asp Gly Pro Val Ile Arg Gln Gly Val Leu
        35                  40                  45

Glu Val Leu Ser Glu Val Glu Cys His Leu Arg Val Ser Phe Phe Asp
    50                  55                  60

```
Val Thr Tyr Arg His Phe Phe Gly Arg Thr Trp Lys Thr Thr Val Lys
 65                  70                  75                  80

Pro Thr Lys Arg Pro Pro Ser Arg Ile Val Phe Asn Glu Pro Leu Tyr
                 85                  90                  95

Phe His Thr Ser Leu Asn His Pro His Ile Val Ala Val Val Glu Val
            100                 105                 110

Val Ala Glu Gly Lys Lys Arg Asp Gly Ser Leu Gln Thr Leu Ser Cys
        115                 120                 125

Gly Phe Gly Ile Leu Arg Ile Phe Ser Asn Gln Pro Asp Ser Pro Ile
    130                 135                 140

Ser Ala Ser Gln Asp Lys Arg Leu Arg Leu Tyr His Gly Thr Pro Arg
145                 150                 155                 160

Ala Leu Leu His Pro Leu Leu Gln Asp Pro Ala Glu Gln Asn Arg His
                165                 170                 175

Met Thr Leu Ile Glu Asn Cys Ser Leu Gln Tyr Thr Leu Lys Pro His
            180                 185                 190

Pro Ala Leu Glu Pro Ala Phe His Leu Leu Pro Glu Asn Leu Leu Val
        195                 200                 205

Ser Gly Leu Gln Gln Ile Pro Gly Leu Leu Pro Ala His Gly Glu Ser
    210                 215                 220

Gly Asp Ala Leu Arg Lys Pro Arg Leu Gln Lys Pro Ile Thr Gly His
225                 230                 235                 240

Leu Asp Asp Leu Phe Phe Thr Leu Tyr Pro Ser Leu Glu Lys Phe Glu
                245                 250                 255

Glu Glu Leu Leu Glu Leu His Val Gln Asp His Phe Gln Glu Gly Cys
            260                 265                 270

Gly Pro Leu Asp Gly Gly Ala Leu Glu Ile Leu Glu Arg Arg Leu Arg
        275                 280                 285

Val Gly Val His Asn Gly Leu Gly Phe Val Gln Arg Pro Gln Val Val
    290                 295                 300

Val Leu Val Pro Glu Met Asp Val Ala Leu Thr Arg Ser Ala Ser Phe
305                 310                 315                 320

Ser Arg Lys Val Val Ser Ser Lys Thr Ser Ser Gly Ser Gln Ala
                325                 330                 335

Leu Val Leu Arg Ser Arg Leu Arg Leu Pro Glu Met Val Gly His Pro
            340                 345                 350

Ala Phe Ala Val Ile Phe Gln Leu Glu Tyr Val Phe Ser Ser Pro Ala
        355                 360                 365

Gly Val Asp Gly Asn Ala Ala Ser Val Thr Ser Leu Ser Asn Leu Ala
    370                 375                 380

Cys Met His Met Val Arg Trp Ala Val Trp Asn Pro Leu Leu Glu Ala
385                 390                 395                 400

Asp Ser Gly Arg Val Thr Leu Pro Leu Gln Gly Gly Ile Gln Pro Asn
                405                 410                 415

Pro Ser His Cys Leu Val Tyr Lys Val Pro Ser Ala Ser Met Ser Ser
            420                 425                 430

Glu Glu Val Lys Gln Val Glu Ser Gly Thr Leu Arg Phe Gln Phe Ser
        435                 440                 445

Leu Gly Ser Glu Glu His Leu Asp Ala Pro Thr Glu Pro Val Ser Gly
    450                 455                 460

Pro Lys Val Glu Arg Arg Pro Ser Arg Lys Pro Pro Thr Ser Pro Ser
465                 470                 475                 480
```

-continued

```
Ser Pro Pro Ala Pro Val Pro Arg Val Leu Ala Ala Pro Gln Asn Ser
            485                 490                 495

Pro Val Gly Pro Gly Leu Ser Ile Ser Gln Leu Ala Ala Ser Pro Arg
            500                 505                 510

Ser Pro Thr Gln His Cys Leu Ala Arg Pro Thr Ser Gln Leu Pro His
            515                 520                 525

Gly Ser Gln Ala Ser Pro Ala Gln Ala Gln Glu Phe Pro Leu Glu Ala
            530                 535                 540

Gly Ile Ser His Leu Glu Ala Asp Leu Ser Gln Thr Ser Leu Val Leu
545                 550                 555                 560

Glu Thr Ser Ile Ala Glu Gln Leu Gln Glu Leu Pro Phe Thr Pro Leu
                565                 570                 575

His Ala Pro Ile Val Val Gly Thr Gln Thr Arg Ser Ser Ala Gly Gln
            580                 585                 590

Pro Ser Arg Ala Ser Met Val Leu Leu Gln Ser Ser Gly Phe Pro Glu
            595                 600                 605

Ile Leu Asp Ala Asn Lys Gln Pro Ala Glu Ala Val Ser Ala Thr Glu
610                 615                 620

Pro Val Thr Phe Asn Pro Gln Lys Glu Glu Ser Asp Cys Leu Gln Ser
625                 630                 635                 640

Asn Glu Met Val Leu Gln Phe Leu Ala Phe Ser Arg Val Ala Gln Asp
                645                 650                 655

Cys Arg Gly Thr Ser Trp Pro Lys Thr Val Tyr Phe Thr Phe Gln Phe
                660                 665                 670

Tyr Arg Phe Pro Pro Ala Thr Thr Pro Arg Leu Gln Leu Val Gln Leu
            675                 680                 685

Asp Glu Ala Gly Gln Pro Ser Ser Gly Ala Leu Thr His Ile Leu Val
            690                 695                 700

Pro Val Ser Arg Asp Gly Thr Phe Asp Ala Gly Ser Pro Gly Phe Gln
705                 710                 715                 720

Leu Arg Tyr Met Val Gly Pro Gly Phe Leu Lys Pro Gly Glu Arg Arg
                725                 730                 735

Cys Phe Ala Arg Tyr Leu Ala Val Gln Thr Leu Gln Ile Asp Val Trp
                740                 745                 750

Asp Gly Asp Ser Leu Leu Leu Ile Gly Ser Ala Ala Val Gln Met Lys
            755                 760                 765

His Leu Leu Arg Gln Gly Arg Pro Ala Val Gln Ala Ser His Glu Leu
            770                 775                 780

Glu Val Val Ala Thr Glu Tyr Glu Gln Asp Asn Met Val Val Ser Gly
785                 790                 795                 800

Asp Met Leu Gly Phe Gly Arg Val Lys Pro Ile Gly Val His Ser Val
                805                 810                 815

Val Lys Gly Arg Leu His Leu Thr Leu Ala Asn Val Gly His Pro Cys
            820                 825                 830

Glu Gln Lys Val Arg Gly Cys Ser Thr Leu Pro Pro Ser Arg Ser Arg
            835                 840                 845

Val Ile Ser Asn Asp Gly Ala Ser Arg Phe Ser Gly Gly Ser Leu Leu
            850                 855                 860

Thr Thr Gly Ser Ser Arg Arg Lys His Val Val Gln Ala Gln Lys Leu
865                 870                 875                 880

Ala Asp Val Asp Ser Glu Leu Ala Ala Met Leu Leu Thr His Ala Arg
                885                 890                 895

Gln Gly Lys Gly Pro Gln Asp Val Ser Arg Glu Ser Asp Ala Thr Arg
```

-continued

```
            900                 905                 910
Arg Arg Lys Leu Glu Arg Met Arg Ser Val Arg Leu Gln Glu Ala Gly
        915                 920                 925
Gly Asp Leu Gly Arg Arg Gly Thr Ser Val Leu Ala Gln Gln Ser Val
        930                 935                 940
Arg Thr Gln His Leu Arg Asp Leu Gln Val Ile Ala Ala Tyr Arg Glu
945                 950                 955                 960
Arg Thr Lys Ala Glu Ser Ile Ala Ser Leu Leu Ser Leu Ala Ile Thr
                965                 970                 975
Thr Glu His Thr Leu His Ala Thr Leu Gly Val Ala Gly Phe Phe Glu
            980                 985                 990
Phe Val Leu Lys Asn Pro His Asn Thr Gln His Thr Val Thr Val Glu
        995                 1000                1005
Ile Asp Asn Pro Glu Leu Ser Val Ile Val Asp Ser Gln Glu Trp
    1010                1015                1020
Arg Asp Phe Lys Gly Ala Ala Gly Leu His Thr Pro Val Glu Glu
    1025                1030                1035
Asp Met Phe His Leu Arg Gly Ser Leu Ala Pro Gln Leu Tyr Leu
    1040                1045                1050
Arg Pro His Glu Thr Ala His Val Pro Phe Lys Phe Gln Ser Phe
    1055                1060                1065
Ser Ala Gly Gln Leu Ala Met Val Gly Ala Ser Pro Gly Leu Ser
    1070                1075                1080
Asn Glu Lys Gly Met Asp Ala Val Ser Pro Trp Lys Ser Ser Ala
    1085                1090                1095
Val Pro Thr Lys His Ala Lys Val Leu Phe Arg Ala Ser Gly Gly
    1100                1105                1110
Lys Pro Ile Ala Val Leu Cys Leu Thr Val Glu Leu Gln Pro His
    1115                1120                1125
Val Val Asp Gln Val Phe Arg Phe Tyr His Pro Glu Leu Ser Phe
    1130                1135                1140
Leu Lys Lys Ala Ile Arg Leu Pro Pro Trp His Thr Phe Pro Gly
    1145                1150                1155
Ala Pro Val Gly Met Leu Gly Glu Asp Pro Pro Val His Val Arg
    1160                1165                1170
Cys Ser Asp Pro Asn Val Ile Cys Glu Thr Gln Asn Val Gly Pro
    1175                1180                1185
Gly Glu Pro Arg Asp Ile Phe Leu Lys Val Ala Ser Gly Pro Ser
    1190                1195                1200
Pro Glu Ile Lys Asp Phe Phe Val Ile Ile Tyr Ser Asp Arg Trp
    1205                1210                1215
Leu Ala Thr Pro Thr Gln Thr Trp Gln Val Tyr Leu His Ser Leu
    1220                1225                1230
Gln Arg Val Asp Val Ser Cys Val Ala Gly Gln Leu Thr Arg Leu
    1235                1240                1245
Ser Leu Val Leu Arg Gly Thr Gln Thr Val Arg Lys Val Arg Ala
    1250                1255                1260
Phe Thr Ser His Pro Gln Glu Leu Lys Thr Asp Pro Lys Gly Val
    1265                1270                1275
Phe Val Leu Pro Pro Arg Gly Val Gln Asp Leu His Val Gly Val
    1280                1285                1290
Arg Pro Leu Arg Ala Gly Ser Arg Phe Val His Leu Asn Leu Val
    1295                1300                1305
```

```
Asp Val Asp Cys His Gln Leu Val Ala Ser Trp Leu Val Cys Leu
    1310                1315                1320

Cys Cys Arg Gln Pro Leu Ile Ser Lys Ala Phe Glu Ile Met Leu
    1325                1330                1335

Ala Ala Gly Glu Gly Lys Gly Val Asn Lys Arg Ile Thr Tyr Thr
    1340                1345                1350

Asn Pro Tyr Pro Ser Arg Arg Thr Phe His Leu His Ser Asp His
    1355                1360                1365

Pro Glu Leu Leu Arg Phe Arg Glu Asp Ser Phe Gln Val Gly Gly
    1370                1375                1380

Gly Glu Thr Tyr Thr Ile Gly Leu Gln Phe Ala Pro Ser Gln Arg
    1385                1390                1395

Val Gly Glu Glu Glu Ile Leu Ile Tyr Ile Asn Asp His Glu Asp
    1400                1405                1410

Lys Asn Glu Glu Ala Phe Cys Val Lys Val Ile Tyr Gln
    1415                1420                1425

<210> SEQ ID NO 3
<211> LENGTH: 1366
<212> TYPE: PRT
<213> ORGANISM: Mus musculus

<400> SEQUENCE: 3

Met Gly Asp Trp His Arg Ala Phe Thr Gln Asn Thr Leu Val Pro Pro
  1               5                  10                  15

His Pro Gln Arg Ala Arg Gln Leu Gly Lys Glu Ser Thr Ala Phe Gln
                 20                  25                  30

Cys Ile Leu Lys Trp Leu Asp Gly Pro Leu Ile Lys Gln Gly Ile Leu
             35                  40                  45

Asp Met Leu Ser Glu Leu Glu Cys His Leu Arg Val Thr Leu Phe Asp
         50                  55                  60

Val Thr Tyr Lys His Phe Phe Gly Arg Thr Trp Lys Thr Thr Val Lys
 65                  70                  75                  80

Pro Thr Asn Gln Pro Ser Lys Gln Pro Pro Arg Ile Thr Phe Asn Glu
                 85                  90                  95

Pro Leu Tyr Phe His Thr Thr Leu Ser His Pro Ser Ile Val Ala Val
            100                 105                 110

Val Glu Val Val Thr Glu Gly Arg Lys Arg Asp Gly Thr Leu Gln Leu
        115                 120                 125

Leu Ser Cys Gly Phe Gly Ile Leu Arg Ile Phe Gly Asn Lys Pro Glu
    130                 135                 140

Ser Pro Thr Ser Ala Ala Gln Asp Lys Arg Leu Arg Leu Tyr His Gly
145                 150                 155                 160

Thr Pro Arg Ala Leu Leu His Pro Leu Leu Gln Asp Pro Ile Glu Gln
                165                 170                 175

Asn Lys Phe Met Arg Leu Met Glu Asn Cys Ser Leu Gln Tyr Thr Leu
            180                 185                 190

Lys Pro His Pro Pro Leu Glu Pro Ala Phe His Leu Leu Pro Glu Asn
        195                 200                 205

Leu Leu Val Ser Gly Phe Gln Gln Ile Pro Gly Leu Leu Pro Pro His
    210                 215                 220

Gly Asp Thr Gly Asp Ala Leu Arg Lys Pro Arg Phe Gln Lys Pro Thr
225                 230                 235                 240

Thr Trp His Leu Asp Asp Leu Phe Phe Thr Leu Tyr Pro Ser Leu Glu
```

-continued

```
                245                 250                 255
Lys Phe Glu Glu Glu Leu Val Gln Leu Leu Ile Ser Asp Arg Glu Gly
                260                 265                 270
Val Gly Leu Leu Asp Ser Gly Thr Leu Glu Val Leu Glu Arg Arg Leu
                275                 280                 285
His Val Cys Val His Asn Gly Leu Gly Phe Val Gln Arg Pro Gln Val
                290                 295                 300
Val Val Leu Val Pro Glu Met Asp Val Ala Leu Thr Arg Ser Ala Ser
305                 310                 315                 320
Phe Ser Arg Lys Ile Ser Ala Ser Ser Lys Asn Ser Ser Gly Asn Gln
                325                 330                 335
Ala Leu Val Leu Arg Ser His Leu Arg Leu Pro Glu Met Val Ser His
                340                 345                 350
Pro Ala Phe Ala Ile Val Phe Gln Leu Glu Tyr Val Phe Asn Ser Pro
                355                 360                 365
Ser Gly Ala Asp Gly Gly Ala Ser Ser Pro Thr Ser Ile Ser Ser Val
                370                 375                 380
Ala Cys Met His Met Val Arg Trp Ala Val Trp Asn Pro Asp Leu Glu
385                 390                 395                 400
Val Gly Pro Gly Lys Val Thr Leu Pro Leu Gln Gly Gly Val Gln Gln
                405                 410                 415
Asn Pro Ser Arg Cys Leu Val Tyr Lys Val Pro Ser Ala Ser Met Ser
                420                 425                 430
Ser Glu Glu Val Lys Gln Val Glu Ser Gly Thr Ile Gln Phe Gln Phe
                435                 440                 445
Ser Leu Ser Ser Asp Gly Pro Thr Glu His Ala Asn Gly Pro Arg Val
                450                 455                 460
Gly Arg Arg Ser Ser Arg Lys Met Pro Ala Ser Pro Ser Gln Glu Ser
465                 470                 475                 480
Val Leu Ser Glu Arg Val Ser His Leu Glu Ala Asp Leu Ser Gln Pro
                485                 490                 495
Ala Ser Leu Gln Gly Thr Pro Ala Val Glu His Leu Gln Glu Leu Pro
                500                 505                 510
Phe Thr Pro Leu His Ala Pro Ile Val Val Gly Ala Gln Thr Arg Ser
                515                 520                 525
Ser Arg Ser Gln Leu Ser Arg Ala Ala Met Val Leu Leu Gln Ser Ser
                530                 535                 540
Gly Phe Pro Glu Ile Leu Asp Ala Ser Gln Gln Pro Val Glu Ala Val
545                 550                 555                 560
Asn Pro Ile Asp Pro Val Arg Phe Asn Pro Gln Lys Glu Glu Ser Asp
                565                 570                 575
Cys Leu Arg Gly Asn Glu Ile Val Leu Gln Phe Leu Ala Phe Ser Arg
                580                 585                 590
Ala Ala Gln Asp Cys Pro Gly Thr Pro Trp Pro Gln Thr Val Tyr Phe
                595                 600                 605
Thr Phe Gln Phe Tyr Arg Phe Pro Pro Glu Thr Thr Pro Arg Leu Gln
                610                 615                 620
Leu Val Lys Leu Asp Gly Thr Gly Lys Ser Gly Ser Gly Ser Leu Ser
625                 630                 635                 640
His Ile Leu Val Pro Ile Asn Lys Asp Gly Ser Phe Asp Ala Gly Ser
                645                 650                 655
Pro Gly Leu Gln Leu Arg Tyr Met Val Asp Pro Gly Phe Leu Lys Pro
                660                 665                 670
```

```
Gly Glu Gln Arg Trp Phe Ala His Tyr Leu Ala Ala Gln Thr Leu Gln
            675                 680                 685

Val Asp Val Trp Asp Gly Asp Ser Leu Leu Ile Gly Ser Ala Gly
            690                 695                 700

Val Gln Met Lys His Leu Leu Arg Gln Gly Arg Pro Ala Val Gln Val
705                 710                 715                 720

Ser His Glu Leu Glu Val Val Ala Thr Glu Tyr Glu Gln Glu Met Met
            725                 730                 735

Ala Val Ser Gly Asp Val Ala Gly Phe Gly Ser Val Lys Pro Ile Gly
            740                 745                 750

Val His Thr Val Val Lys Gly Arg Leu His Leu Thr Leu Ala Asn Val
            755                 760                 765

Gly His Ala Cys Glu Pro Arg Ala Arg Gly Ser Asn Leu Leu Pro Pro
            770                 775                 780

Ser Arg Ser Arg Val Ile Ser Asn Asp Gly Ala Ser Phe Phe Ser Gly
785                 790                 795                 800

Gly Ser Leu Leu Ile Pro Gly Gly Pro Lys Arg Lys Arg Val Val Gln
            805                 810                 815

Ala Gln Arg Leu Ala Asp Val Asp Ser Glu Leu Ala Ala Met Leu Leu
            820                 825                 830

Thr His Thr Arg Ala Gly Gln Gly Pro Gln Ala Ala Gly Gln Glu Ala
            835                 840                 845

Asp Ala Val His Lys Arg Lys Leu Glu Arg Met Arg Leu Val Arg Leu
            850                 855                 860

Gln Glu Ala Gly Gly Asp Ser Asp Ser Arg Arg Ile Ser Leu Leu Ala
865                 870                 875                 880

Gln His Ser Val Arg Ala Gln His Ser Arg Asp Leu Gln Val Ile Asp
            885                 890                 895

Ala Tyr Arg Glu Arg Thr Lys Ala Glu Ser Ile Ala Gly Val Leu Ser
            900                 905                 910

Gln Ala Ile Thr Thr His His Thr Leu Tyr Ala Thr Leu Gly Thr Ala
            915                 920                 925

Glu Phe Phe Glu Phe Ala Leu Lys Asn Pro His Asn Thr Gln His Thr
            930                 935                 940

Val Ala Ile Glu Ile Asp Ser Pro Glu Leu Ser Ile Ile Leu Asp Ser
945                 950                 955                 960

Gln Glu Trp Arg Tyr Phe Lys Glu Ala Thr Gly Leu His Thr Pro Leu
            965                 970                 975

Glu Glu Asp Met Phe His Leu Arg Gly Ser Leu Ala Pro Gln Leu Tyr
            980                 985                 990

Leu Arg Pro Arg Glu Thr Ala His Ile Pro Leu Lys Phe Gln Ser Phe
            995                 1000                1005

Ser Val Gly Pro Leu Ala Pro Thr Gln Ala Pro Ala Glu Val Ile
            1010                1015                1020

Thr Glu Lys Asp Ala Glu Ser Gly Pro Leu Trp Lys Cys Ser Ala
            1025                1030                1035

Met Pro Thr Lys His Ala Lys Val Leu Phe Arg Val Glu Thr Gly
            1040                1045                1050

Gln Leu Ile Ala Val Leu Cys Leu Thr Val Glu Pro Gln Pro His
            1055                1060                1065

Val Val Asp Gln Val Phe Arg Phe Tyr His Pro Glu Leu Thr Phe
            1070                1075                1080
```

-continued

Leu Lys Lys Ala Ile Arg Leu Pro Pro Trp His Thr Leu Pro Gly
    1085                1090                1095

Ala Pro Val Gly Met Pro Gly Glu Asp Pro Val His Val Arg
    1100                1105                1110

Cys Ser Asp Pro Asn Val Ile Cys Glu Ala Gln Asn Val Gly Pro
    1115                1120                1125

Gly Glu Pro Arg Asp Val Phe Leu Lys Val Ala Ser Gly Pro Ser
    1130                1135                1140

Pro Glu Ile Lys Asp Phe Phe Val Val Ile Tyr Ala Asp Arg Trp
    1145                1150                1155

Leu Ala Val Pro Val Gln Thr Trp Gln Val Cys Leu His Ser Leu
    1160                1165                1170

Gln Arg Val Asp Val Ser Cys Val Ala Gly Gln Leu Thr Arg Leu
    1175                1180                1185

Ser Leu Val Leu Arg Gly Thr Gln Thr Val Arg Lys Val Arg Ala
    1190                1195                1200

Phe Thr Ser His Pro Gln Glu Leu Lys Thr Asp Pro Ala Gly Val
    1205                1210                1215

Phe Val Leu Pro Pro His Gly Val Gln Asp Leu His Val Gly Val
    1220                1225                1230

Arg Pro Arg Arg Ala Gly Ser Arg Phe Val His Leu Asn Leu Val
    1235                1240                1245

Asp Ile Asp Tyr His Gln Leu Val Ala Ser Trp Leu Val Cys Leu
    1250                1255                1260

Ser Cys Arg Gln Pro Leu Ile Ser Lys Ala Phe Glu Ile Thr Met
    1265                1270                1275

Ala Ala Gly Asp Glu Lys Gly Thr Asn Lys Arg Ile Thr Tyr Thr
    1280                1285                1290

Asn Pro Tyr Pro Ser Arg Arg Thr Tyr Arg Leu His Ser Asp Arg
    1295                1300                1305

Pro Glu Leu Leu Arg Phe Lys Glu Asp Ser Phe Gln Val Ala Gly
    1310                1315                1320

Gly Glu Thr Tyr Thr Ile Gly Leu Arg Phe Leu Pro Ser Gly Ser
    1325                1330                1335

Ala Gly Gln Glu Glu Ile Leu Ile Tyr Ile Asn Asp His Glu Asp
    1340                1345                1350

Lys Asn Glu Glu Thr Phe Cys Val Lys Val Leu Tyr Gln
    1355                1360                1365

<210> SEQ ID NO 4
<211> LENGTH: 1196
<212> TYPE: PRT
<213> ORGANISM: Caenorhabditis elegans

<400> SEQUENCE: 4

Met Ser Val Asn Asp Trp Tyr Ser Leu Phe Leu Ala Asn Arg Pro Val
1               5                   10                  15

Glu Met Lys Arg Asn Val Ser Arg Gly Thr Lys Ala Leu Cys Tyr Ser
                20                  25                  30

Met Phe Ile Ser Asn Leu Thr Ser Pro Gln Thr Leu Tyr Phe Tyr Ser
            35                  40                  45

Ile Ile Asn Ser Arg Asp Val Leu Leu Ile Leu Glu Phe Val Glu Glu
        50                  55                  60

Gly Ser Asp Glu Ile Asn Gly Arg Thr Phe Glu Asn Pro Lys Ser Thr
65                  70                  75                  80

-continued

```
Lys Ile Thr Ala Pro Ala Thr Ser Val Gly Trp Phe Ser Thr His Ile
                85                  90                  95

Glu Lys Lys Thr Pro Val Glu Ile Ser Asn Thr Lys Ile Phe Asp Ile
            100                 105                 110

Phe Gly Gly Thr Pro Lys Leu Leu Ile Phe Asp Lys Glu Thr Val Leu
        115                 120                 125

Lys Pro Val Gly Asn Val Glu Cys Thr Tyr Asn Ile Phe Glu Met Pro
    130                 135                 140

Pro Ile Phe Phe Gln Cys Leu Pro Glu Phe Cys Ile Val Cys Asp Lys
145                 150                 155                 160

Asp Ile Ile Pro Gly Ile Ile Lys Asp Ser Ser Asp Glu Trp Trp Leu
                165                 170                 175

Ser Thr Pro Lys Glu Met Pro Thr Ile Pro Ala Ala Ile Asp Ala Ile
            180                 185                 190

Val Ile Gln Phe Lys Asn Asn Val Pro Glu Leu Glu Lys Gln Ile Thr
        195                 200                 205

His Asp Ile Glu Lys Glu Trp Ala Leu Lys Glu Gly Gly Thr Leu Lys
    210                 215                 220

Pro Lys Ala Ile Ile Met Asp Arg Lys Leu Arg Ile Gly Val His Asn
225                 230                 235                 240

Gly Tyr Thr Tyr Val Thr Glu Pro Phe Thr Val Asp Leu Glu Ile Ile
                245                 250                 255

Ser Ser Asn Ala Gly Asp Thr Leu Arg Ser Arg Lys Lys Pro Ile Asp
            260                 265                 270

Phe Gly Lys Ser Ser Asn Trp Glu Glu Gln Leu Leu Phe Gln Ala Ala
        275                 280                 285

Gly Asn Pro Arg Leu Ala Leu Arg Asn Leu Tyr Ala Asp Pro Arg Met
    290                 295                 300

Ala Ile Ile Phe Leu Leu Glu Tyr Thr Phe His Arg Glu Asp Asn Gln
305                 310                 315                 320

Ser Leu Asn Gln Thr Ile Leu Ile Gly Trp Ala Ala Trp Thr Pro Phe
                325                 330                 335

Ser Asp Gly Ala Phe Ser Gly Lys Glu Val Glu Thr Arg Val Ser Phe
            340                 345                 350

Val Gly Gly Pro Arg Pro Asn Pro Glu Gly Val Leu Cys Tyr Lys Asn
        355                 360                 365

Val Leu Asn Gln Pro Asp Ser Leu Lys Pro Leu Asn Glu Lys Leu Glu
    370                 375                 380

Ile Phe Val Asp Phe Lys Phe Tyr Glu Asn Gly Arg Ser Val His Asn
385                 390                 395                 400

Thr Pro Thr Ser Arg Arg Ala Ala Asp Ser Ala Arg Val Gln Thr Gly
                405                 410                 415

Arg Ser Gly Asp Asn Gly Gln Ser Ala Arg Ser Asn Arg Lys Ser Val
            420                 425                 430

Lys Ile Glu Thr Pro Arg Ser Pro Glu Asn Ser Asn Arg Phe Pro Ala
        435                 440                 445

Leu Val Asp Thr Gly Arg Ser Val Ser Ser Val Asp Glu Leu Arg Ser
    450                 455                 460

Ile Asn Glu Asp Leu Asn Arg Phe Ile Glu Glu Pro Met Glu Ile Pro
465                 470                 475                 480

Val Gln Asp Val Val Ala Lys Lys Pro Val Glu Glu Pro Leu Pro
                485                 490                 495
```

```
Ile Thr Ser Val Tyr Lys Ile Pro Phe Asp Glu Leu Lys Pro Ile Asn
            500                 505                 510

Phe Pro Arg Ser Ala His Ser Met Phe Ala Arg Gln Asn Phe Thr Gln
            515                 520                 525

Leu Lys Asp Arg Asn Gly Ser Pro Pro Asn Thr Glu Asp Val Thr Leu
            530                 535                 540

Lys Thr Ile Ile Asp Met Lys Arg Glu Gln Leu Asp Arg Leu Ile Thr
545                 550                 555                 560

Ser His Val Tyr Phe Gln Phe Ile Ala Phe Lys Gln Leu Ala Ala Pro
                565                 570                 575

Asp Ala Arg Met Ile Lys Lys Leu Phe Phe Thr Ile Gly Phe Tyr Arg
            580                 585                 590

Phe Pro Asp Ile Thr Thr Glu Ser Met Leu Leu Thr Ser Met Glu Lys
            595                 600                 605

Gly Glu Pro Thr Leu Leu Thr Arg Leu Asp Lys Asn Gly Asn Ser Asp
            610                 615                 620

Val Ile Ala Ser Pro Gly Phe Ile Ala Lys Tyr Ile Ile Glu Gly Glu
625                 630                 635                 640

Glu Ser Lys Ala Asp Phe Leu Asp Phe Met Ala Ser Gly His Ala Thr
                645                 650                 655

Ile Asp Val Trp Asp Ser Asp Ser Leu Ile His Leu Gly Ser Thr Ile
            660                 665                 670

Val Pro Ile Lys Asn Leu Tyr Arg Arg Gly Arg Glu Ala Val Gln Leu
            675                 680                 685

Phe Ile Gln Cys Pro Val Val Asp Thr Ser Leu Asp Thr Ser Ser Lys
            690                 695                 700

Ala Gly Ala Phe Leu Tyr Met Arg Val Ala Asn Ile Gly Phe Pro Ser
705                 710                 715                 720

Gly Asn Thr Tyr Asp Leu Ser Ser Ser Ser Ser Leu Thr Thr Thr
                725                 730                 735

Arg Ser Asn Val Asn Ser Gly Gln Gly Thr Val Val Arg Arg Leu Thr
            740                 745                 750

Ser Ser Ile Arg Leu Asn Glu Glu Gly Pro His Ser Tyr Arg Ile His
            755                 760                 765

Ala Lys Pro Leu Pro Gly Asn Ser Gly Val Gly Leu Asp Arg Phe Leu
            770                 775                 780

Thr Ala Gln Arg Leu Asp Ile Gln Gln Arg His Glu Gln Leu Phe Asn
785                 790                 795                 800

Glu Asn Ser Leu Asp Lys Ile Arg Gln Trp Asn Asp Leu Lys Glu Gly
                805                 810                 815

Phe Asn Phe Ser Asp Asn Lys Glu Ile Ala Gln Lys Phe Ile Phe Glu
            820                 825                 830

Glu Glu Leu Ala Ala Tyr Lys Lys Leu Arg Tyr Glu Ser Lys Pro Ala
            835                 840                 845

Lys Leu Leu Glu Ala Val Phe Lys Gly Ile Thr Ser Cys His Gln Ile
850                 855                 860

Asn Pro Ser Phe Gly Glu Lys Val Phe Phe Glu Phe Pro Leu Glu Asn
865                 870                 875                 880

Tyr Asn Ser Glu Pro Ile Asn Cys Thr Ile Glu Phe Asp Asp Glu Ala
                885                 890                 895

Leu Lys Pro Val Phe Asp Ala Glu Glu Trp Lys Phe Tyr Lys Thr Val
            900                 905                 910

Asn Lys Val Thr Thr Pro Ser Glu Lys Gln Met Met Arg Gln Thr Thr
```

```
                        915                 920                 925
Asp Arg Ile Glu Ile Cys Leu Gln Pro Gly Asp Val Leu Phe Ile Pro
    930                 935                 940

Phe Ile Tyr Asp Ala Phe Phe Pro Asn Asp Ala Phe Asn Met Tyr
945                 950                 955                 960

Ser Thr Lys Val Val Phe Arg Arg Trp Asp Thr Lys Glu Pro Leu Ala
                965                 970                 975

Ile Leu Asp Leu His Val His Arg Arg Asn Phe Leu Leu Gln His Ser
            980                 985                 990

Val Thr Phe Ile Cys Glu Thr Ser  Gly Asn Trp Glu Lys  Gln Leu Val
            995                 1000                1005

Leu Pro  Pro Met Ala Arg Asp  Arg Arg Val Leu Ser  Cys Arg Cys
1010                1015                1020

Ser Asp  Pro Ser Val Arg Leu  Thr Val Arg Asn Ala  Thr Leu Gln
1025                1030                1035

Gln Ile  Val Gly Phe Thr Thr  Tyr Ser Gly Glu Thr  Asn Asp Arg
1040                1045                1050

Lys Thr  Phe Leu Leu Leu Met  Tyr Ser Asp His Tyr  Gln Thr Arg
1055                1060                1065

Leu Met  Ala Thr Trp Lys Ile  Thr Ile Leu Pro Phe  Phe Asn Val
1070                1075                1080

Asp Val  Arg Ser Ile Val Gly  Gln Thr Thr Arg Leu  His Leu Leu
1085                1090                1095

Val His  Arg Arg Ser Glu His  Asp Gly Val Pro Asp  Asp Leu Leu
1100                1105                1110

Lys Val  Tyr Thr Ala Ser Gly  Cys Met Lys Val Val  Asp Ser Val
1115                1120                1125

Leu Thr  Glu Arg Thr Pro Thr  Ala Thr Ile Asp Phe  Thr Pro Asn
1130                1135                1140

Phe Ile  Gly Thr Lys Lys Leu  Val Val Ser Val Val  Asn Thr Asn
1145                1150                1155

Thr Leu  Lys Leu Glu Arg Gly  Phe Leu Val Tyr Gly  Lys Ser Glu
1160                1165                1170

Ala Pro  Arg Ile Thr Gln Lys  Phe Val Ile Gln Ile  Pro Ser Ser
1175                1180                1185

Asp Glu  Ala Ile Arg Lys Val  Cys
1190                1195

<210> SEQ ID NO 5
<211> LENGTH: 2603
<212> TYPE: DNA
<213> ORGANISM: Homo sapiens

<400> SEQUENCE: 5
gacgcgaggc gggttcttgg actgagtgtg cggcgcggtg cgccgccttc cgaggctcct    60
cccgcgggtg gcagcggacg gggcgcgccc ctcggccagt cctcggtcct caggcttgtg   120
gctccgttga gcaccggccg ccgggcctct gggtccgtcg agtggagact ctctgaaaag   180
cgtgggctcc gtggcctccg gcgcggccgc ggcgggtcgg tctcctagat catccgggaa   240
gcccacggga ccctcaggcg ggcaggatga acgactggca caggatcttc acccaaaacg   300
tgcttgtccc tccccaccca cagagagcgc gccagccttg gaaggaatcc acggcattcc   360
agtgtgtcct caagtggctg acgaccggg taattaggca gggcgtgctg gaggtactgt    420
cagaggttga atgccatctg cgagtgtctt tctttgatgt cacctaccgg cacttctttg   480
```

-continued

```
ggaggacgtg gaaaaccaca gtgaagccga cgaagagacc gccgtccagg atcgtcttta    540
atgagccctt gtattttcac acatccctaa accaccctca tatcgtggct gtggtggaag    600
tggtcgctga gggcaagaaa cgggatggga gcctccagac attgtcctgt gggtttggaa    660
ttcttcggat cttcagcaac cagccggact ctcctatctc tgcttcccag gacaaaaggt    720
tgcggctgta ccatggcacc cccagagccc tcctgcaccc gcttctccag gaccccgcag    780
agcaaaacag acacatgacc ctcattgaga actgcagcct gcagtacacg ctgaagccac    840
acccggccct ggagcctgcg ttccaccttc ttcctgagaa ccttctggtg tctggtctgc    900
agcagatacc tggcctgctt ccagctcatg gagaatccgg cgacgctctc cgaaagcctc    960
gcctccagaa gcccatcacg gggcacttgg atgacttatt cttcaccctg taccccctccc   1020 tggagaagtt tgaggaagag ctgctggagc tccacgtcca ggaccacttc caggagggat   1080
gtggcccact ggacggtggt gccctggaga tcctggagcg cgcgcctgcgt gtgggcgtgc   1140 acaatggtct gggcttcgtg cagaggccgc aggtcgttgt actggtgcct gagatggatg   1200
tggccttgac gcgctcagct agcttcagca ggaaagtggt ctcctcttcc aagaccagct   1260
ccgggagcca agctctggtt tgagaagcc gcctccgcct cccagagatg gtcggccacc   1320
ctgcatttgc ggtcatcttc cagctggagt acgtgttcag cagccctgca ggagtggacg   1380
gcaatgcagc ttcggtcacc tctctgtcca acctggcatg catgcacatg gtccgctggg   1440
ctgtttggaa ccccttgctg gaagctgatt ctggaagggt gaccctgcct ctgcagggtg   1500
ggatccagcc caaccctcg cactgtctgg tctacaaggt accctcagcc agcatgagct   1560
ctgaagaggt gaagcaggtg gagtcgggta cactccggtt ccagttctcg ctgggctcag   1620
aagaacacct ggatgcaccc acggagcctg tcagtggccc caaagtggag cggcggcctt   1680
ccaggaaacc acccacgtcc ccttcgagcc cgccagcgcc agtacctcga gttctcgctg   1740
ccccgcagaa ctcacctgtg ggaccagggt tgtcaatttc ccagctggcg gcctccccgc   1800
ggtccccgac tcagcactgc ttggccaggc ctacttcaca gctaccccat ggctctcagg   1860 cctcccggc ccaggcacag gagttcccgt tggaggccgg tatctcccac ctggaagccg   1920
acctgagcca gacctccctg gtcctggaaa catccattgc cgaacagtta caggagctgc   1980
cgttcacgcc tttgcatgcc cctattgttg tgggaaccca gaccaggagc tctgcagggc   2040
agccctcgag agcctccatg gtgctcctgc agtcctccgg cttccccgag attctggatg   2100
ccaataaaca gccagccgag gctgtcagcg ctacagaacc tgtgacgttt aaccctcaga   2160
aggaagaatc agattgtcta caaagcaacg agatggtgct acagtttctt gcctttagca   2220
gagtggccca ggactgccga ggaacatcat ggccaaagac tgtgtatttc accttccagt   2280
tctaccgctt cccacccgca acgacgccac gactgcagct ggtccagctg gatgaggccg   2340
gccagcccag ctctggcgcc ctgacccaca tcctcgtgcc tgtgagcaga gatggcacct   2400
ttgatgctgg gtctcctggc ttccagctga ggtacatggt gggccctggg ttcctgaagc   2460
caggtgagcg cgcgctgcttt gcccgctacc tggccgtgca gacctgcag attgacgtct   2520 gggacggaga ctccctgctg ctcatcggat ctgctgccgt ccagatgaag catctcctcc   2580
gccaaggccg gccggctgtg tag                                             2603
```

<210> SEQ ID NO 6
<211> LENGTH: 779
<212> TYPE: PRT
<213> ORGANISM: Homo sapiens
<220> FEATURE:

<221> NAME/KEY: misc_feature
<222> LOCATION: (779)..(779)
<223> OTHER INFORMATION: Xaa can be any naturally occurring amino acid

<400> SEQUENCE: 6

```
Met Asn Asp Trp His Arg Ile Phe Thr Gln Asn Val Leu Val Pro Pro
1               5                   10                  15

His Pro Gln Arg Ala Arg Gln Pro Trp Lys Glu Ser Thr Ala Phe Gln
            20                  25                  30

Cys Val Leu Lys Trp Leu Asp Gly Pro Val Ile Arg Gln Gly Val Leu
        35                  40                  45

Glu Val Leu Ser Glu Val Glu Cys His Leu Arg Val Ser Phe Phe Asp
    50                  55                  60

Val Thr Tyr Arg His Phe Phe Gly Arg Thr Trp Lys Thr Thr Val Lys
65                  70                  75                  80

Pro Thr Lys Arg Pro Pro Ser Arg Ile Val Phe Asn Glu Pro Leu Tyr
                85                  90                  95

Phe His Thr Ser Leu Asn His Pro His Ile Val Ala Val Val Glu Val
            100                 105                 110

Val Ala Glu Gly Lys Lys Arg Asp Gly Ser Leu Gln Thr Leu Ser Cys
        115                 120                 125

Gly Phe Gly Ile Leu Arg Ile Phe Ser Asn Gln Pro Asp Ser Pro Ile
    130                 135                 140

Ser Ala Ser Gln Asp Lys Arg Leu Arg Leu Tyr His Gly Thr Pro Arg
145                 150                 155                 160

Ala Leu Leu His Pro Leu Leu Gln Asp Pro Ala Glu Gln Asn Arg His
                165                 170                 175

Met Thr Leu Ile Glu Asn Cys Ser Leu Gln Tyr Thr Leu Lys Pro His
            180                 185                 190

Pro Ala Leu Glu Pro Ala Phe His Leu Leu Pro Glu Asn Leu Leu Val
        195                 200                 205

Ser Gly Leu Gln Gln Ile Pro Gly Leu Leu Pro Ala His Gly Glu Ser
    210                 215                 220

Gly Asp Ala Leu Arg Lys Pro Arg Leu Gln Lys Pro Ile Thr Gly His
225                 230                 235                 240

Leu Asp Asp Leu Phe Phe Thr Leu Tyr Pro Ser Leu Glu Lys Phe Glu
                245                 250                 255

Glu Glu Leu Leu Glu Leu His Val Gln Asp His Phe Gln Glu Gly Cys
            260                 265                 270

Gly Pro Leu Asp Gly Gly Ala Leu Glu Ile Leu Glu Arg Arg Leu Arg
        275                 280                 285

Val Gly Val His Asn Gly Leu Gly Phe Val Gln Arg Pro Gln Val Val
    290                 295                 300

Val Leu Val Pro Glu Met Asp Val Ala Leu Thr Arg Ser Ala Ser Phe
305                 310                 315                 320

Ser Arg Lys Val Val Ser Ser Ser Lys Thr Ser Ser Gly Ser Gln Ala
                325                 330                 335

Leu Val Leu Arg Ser Arg Leu Arg Leu Pro Glu Met Val Gly His Pro
            340                 345                 350

Ala Phe Ala Val Ile Phe Gln Leu Glu Tyr Val Phe Ser Ser Pro Ala
        355                 360                 365

Gly Val Asp Gly Asn Ala Ala Ser Val Thr Ser Leu Ser Asn Leu Ala
    370                 375                 380

Cys Met His Met Val Arg Trp Ala Val Trp Asn Pro Leu Leu Glu Ala
```

```
385                 390                 395                 400
Asp Ser Gly Arg Val Thr Leu Pro Leu Gln Gly Gly Ile Gln Pro Asn
                405                 410                 415
Pro Ser His Cys Leu Val Tyr Lys Val Pro Ala Ser Met Ser Ser Ser
                420                 425             430
Glu Glu Val Lys Gln Val Glu Ser Gly Thr Leu Arg Phe Gln Phe Ser
            435                 440                 445
Leu Gly Ser Glu Glu His Leu Asp Ala Pro Thr Glu Pro Val Ser Gly
        450                 455                 460
Pro Lys Val Glu Arg Arg Pro Ser Arg Lys Pro Pro Thr Ser Pro Ser
465                 470                 475                 480
Ser Pro Pro Ala Pro Val Pro Arg Val Leu Ala Ala Pro Gln Asn Ser
                485                 490                 495
Pro Val Gly Pro Gly Leu Ser Ile Ser Gln Leu Ala Ala Ser Pro Arg
            500                 505                 510
Ser Pro Thr Gln His Cys Leu Ala Arg Pro Thr Ser Gln Leu Pro His
            515                 520                 525
Gly Ser Gln Ala Ser Pro Ala Gln Ala Gln Glu Phe Pro Leu Glu Ala
        530                 535                 540
Gly Ile Ser His Leu Glu Ala Asp Leu Ser Gln Thr Ser Leu Val Leu
545                 550                 555                 560
Glu Thr Ser Ile Ala Glu Gln Leu Gln Glu Leu Pro Phe Thr Pro Leu
                565                 570                 575
His Ala Pro Ile Val Val Gly Thr Gln Thr Arg Ser Ser Ala Gly Gln
                580                 585                 590
Pro Ser Arg Ala Ser Met Val Leu Leu Gln Ser Ser Gly Phe Pro Glu
            595                 600                 605
Ile Leu Asp Ala Asn Lys Gln Pro Ala Glu Ala Val Ser Ala Thr Glu
        610                 615                 620
Pro Val Thr Phe Asn Pro Gln Lys Glu Glu Ser Asp Cys Leu Gln Ser
625                 630                 635                 640
Asn Glu Met Val Leu Gln Phe Leu Ala Phe Ser Arg Val Ala Gln Asp
                645                 650                 655
Cys Arg Gly Thr Ser Trp Pro Lys Thr Val Tyr Phe Thr Phe Gln Phe
                660                 665                 670
Tyr Arg Phe Pro Pro Ala Thr Thr Pro Arg Leu Gln Leu Val Gln Leu
            675                 680                 685
Asp Glu Ala Gly Gln Pro Ser Ser Gly Ala Leu Thr His Ile Leu Val
        690                 695                 700
Pro Val Ser Arg Asp Gly Thr Phe Asp Ala Gly Ser Pro Gly Phe Gln
705                 710                 715                 720
Leu Arg Tyr Met Val Gly Pro Phe Leu Lys Pro Gly Glu Arg Arg
                725                 730                 735
Cys Phe Ala Arg Tyr Leu Ala Val Gln Thr Leu Gln Ile Asp Val Trp
            740                 745                 750
Asp Gly Asp Ser Leu Leu Leu Ile Gly Ser Ala Ala Val Gln Met Lys
        755                 760                 765
His Leu Leu Arg Gln Gly Arg Pro Ala Val Xaa
    770                 775

<210> SEQ ID NO 7
<211> LENGTH: 4994
<212> TYPE: DNA
<213> ORGANISM: Homo sapiens
```

```
<400> SEQUENCE: 7
gacgcgaggc gggttcttgg actgagtgtg cggcgcggtg cgccgccttc cgaggctcct      60
cccgcgggtg gcagcggacg gggcgcgccc ctcggccagt cctcggtcct caggcttgtg     120
gctccgttga gcaccggccg ccgggcctct gggtccgtcg agtggagact ctctgaaaag     180
cgtgggctcc gtggcctccg cgcggccgc ggcgggtcgg tctcctagat catccgggaa      240
gcccacggga ccctcaggcg ggcaggatga acgactggca caggatcttc acccaaaacg     300
tgcttgtccc tccccaccca cagagagcgc gccagccttg gaaggaatcc acggcattcc     360
agtgtgtcct caagtggctg gacggaccgg taattaggca gggcgtgctg gaggtactgt     420
cagaggttga atgccatctg cgagtgtctt tctttgatgt cacctaccgg cacttctttg     480
ggaggacgtg gaaaaccaca gtgaagccga cgaagagacc gccgtccagg atcgtcttta     540
atgagccctt gtattttcac acatccctaa accaccctca tatcgtggct gtggtggaag     600
tggtcgctga gggcaagaaa cgggatggga gcctccagac attgtcctgt gggtttggaa     660
ttcttcggat cttcagcaac cagccggact ctcctatctc tgcttcccag acaaaaggt     720
tgcggctgta ccatggcacc cccagagccc tcctgcaccc gcttctccag gaccccgcag     780
agcaaaacag acacatgacc ctcattgaga actgcagcct gcagtacacg ctgaagccac     840
acccggccct ggagcctgcg ttccaccttc ttcctgagaa ccttctggtg tctggtctgc     900
agcagatacc tggcctgctt ccagctcatg gagaatccgg cgacgctctc cgaaagcctc     960
gcctccagaa gcccatcacg gggcacttgg atgacttatt cttcaccctg tacccctccc    1020
tggagaagtt tgaggaagag ctgctggagc tccacgtcca ggaccacttc caggagggat    1080
gtggcccact ggacggtggt gccctggaga tcctggagcg cgcctgcgt gtgggcgtgc     1140
acaatggtct gggcttcgtg cagaggccgc aggtcgttgt actggtgcct gagatggatg    1200
tggccttgac gcgctcagct agcttcagca ggaaagtggt ctcctcttcc aagaccagct    1260
ccgggagcca agctctggtt ttgagaagcc gcctccgcct cccagagatg gtcggccacc    1320
ctgcatttgc ggtcatcttc cagctggagt acgtgttcag cagccctgca ggagtggacg    1380
gcaatgcagc ttcggtcacc tctctgtcca acctggcatg catgcacatg gtccgctggg    1440
ctgtttggaa ccccttgctg gaagctgatt ctggaagggt gaccctgcct ctgcagggtg    1500
ggatccagcc caaccctcg cactgtctgg tctacaaggt accctcagcc agcatgagct     1560
ctgaagaggt gaagcaggtg gagtcgggta cactccggtt ccagttctcg ctgggctcag    1620
aagaacacct ggatgcaccc acggagcctg tcagtggccc caaagtggag cggcggcctt    1680
ccaggaaacc acccacgtcc ccttcgagcc cgccagcgcc agtacctcga gttctcgctg    1740
ccccgcagaa ctcacctgtg ggaccagggt tgtcaatttc ccagctggcg gcctccccgc    1800
ggtccccgac tcagcactgc ttggccaggc ctacttcaca gctacccat ggctctcagg     1860
cctccccggc ccaggcacag gagttcccgt tggaggccgg tatctcccac ctggaagccg    1920
acctgagcca gacctccctg gtcctggaaa catccattgc cgaacagtta caggagctgc    1980
cgttcacgcc tttgcatgcc cctattgttg tgggaaccca gaccaggagc tctgcagggc    2040
agccctcgag agcctccatg gtgctcctgc agtcctccgg cttcccgag attctggatg    2100
ccaataaaca gccagccgag gctgtcagcg ctacagaacc tgtgacgttt aaccctcaga    2160
aggaagaatc agattgtcta caaagcaacg agatggtgct acagtttctt gcctttagca    2220
gagtggccca ggactgccga ggaacatcat ggccaaagac tgtgtatttc accttccagt    2280
```

```
tctaccgctt cccacccgca acgacgccac gactgcagct ggtccagctg gatgaggccg   2340
gccagcccag ctctggcgcc ctgacccaca tcctcgtgcc tgtgagcaga gatggcacct   2400
ttgatgctgg gtctcctggc ttccagctga ggtacatggt gggccctggg ttcctgaagc   2460
caggtgagcg gcgctgcttt gcccgctacc tggccgtgca gaccctgcag attgacgtct   2520
gggacagaga ctccctgctg ctcatcggat ctgctgccgt ccagatgaag catctcctcc   2580
gccaaggccg gccggctgtg caggcctccc acgagcttga ggtcgtggca actgaatacg   2640
agcaggacaa catggtggtg agtggagaca tgctggggtt tggccgcgtc aagcccatcg   2700
gcgtccactc ggtggtgaag ggccggctgc acctgacttt ggccaacgtg ggtcacccgt   2760
gtgaacagaa agtgagaggt tgtagcacat tgccaccgtc cagatctcgg gtcatctcaa   2820
acgatggagc cagccgcttc tctgaggca gcctcctcac gactggaagc tcaaggcgaa    2880
aacacgtggt gcaagcacag aagctggcgg acgtggacag tgagctggct gccatgctac   2940
tgacccatgc ccggcagggc aaggggcccc aggacgtcag ccgcgagtcg gatgccaccc   3000
gcaggcgtaa gctggagcgg atgaggtctg tgcgcctgca ggaggccggg ggagacttgg   3060
gccgcgcgg gacgagcgtg ttggcgcagc agagcgtccg cacacagcac ttgcgggacc    3120
tacaggtcat cgccgcctac cgggaacgca cgaaggccga gagcatcgcc agcctgctga   3180
gcctggccat caccacggag cacacgctcc acgccacgct gggggtcgcc gagttctttg   3240
agtttgtgct taagaacccc cacaacacac agcacacggt gactgtggag atcgacaacc   3300
ccgagctcag cgtcatcgtg gacagtcagg agtggagggg cttcaagggt gctgctggcc   3360
tgcacacacc ggtggaggag gacatgttcc acctgcgtgg cagcctggcc ccccagctct   3420
acctgcgccc ccacgagacc gcccacgtcc ccttcaagtt ccagagcttc tctgcagggc   3480
agctggccat ggtgcaggcc tctcctgggt tgagcaacga aagggcatg gacgccgtgt    3540
caccttggaa gtccagcgca gtgcccacta aacacgccaa ggtcttgttc cgagcgagtg   3600
gtggcaagcc catcgccgtg ctctgcctga ctgtggagct gcagcccac gtggtggacc    3660
aggtcttccg cttctatcac ccggagctct ccttcctgaa gaaggccatc cgcctgccgc   3720
cctggcacac atttccaggt gctccggtgg gaatgcttgg tgaggacccc ccagtccatg   3780
ttcgctgcag cgacccgaac gtcatctgtg agacccagaa tgtgggcccc ggggaaccac   3840
gggacatatt tctgaaggtg gccagtggtc caagcccgga gatcaaagac ttctttgtca   3900
tcatttactc ggatcgctgg ctggcgacac ccacacagac gtggcaggtc tacctccact   3960
ccctgcagcg cgtggatgtc tcctgcgtcg caggccagct gacccgcctg tcccttgtcc   4020
ttcgggggac acagacagtg aggaaagtga gagctttcac ctctcatccc caggagctga   4080
agacagaccc caaaggtgtc ttcgtgctgc cgcctcgtgg ggtgcaggac ctgcatgttg   4140
gcgtgaggcc ccttagggcc ggcagccgct ttgtccatct caacctggtg gacgtggatt   4200
gccaccagct ggtggcctcc tggctcgtgt gcctctgctg ccgccagccg ctcatctcca   4260
aggcctttga gatcatgttg gctgcgggcg aagggaaggg tgtcaacaag aggatcacct   4320
acaccaaccc ctaccccctcc cggaggacat tccacctgca cagcgaccac ccggagctgc   4380
tgcggttcag agaggactcc ttccaggtcg ggggtggaga gacctacacc atcggcttgc   4440
agtttgcgcc tagtcagaga gtgggtgagg aggagatcct gatctacatc aatgaccatg   4500
aggacaaaaa cgaagaggca ttttgcgtga aggtcatcta ccagtgaggg cttgagggtg   4560
acgtccttcc tgcggcaccc agctgggggcc tgtctgtgcc cctcctgccc tgcaggctgt   4620
cctccccgcc tctctgcagc cttttcactt cagtgcccacc tggctgacct gtgcacttgg   4680
```

-continued

```
ctgaggaagc agagaccgag cgctggtcat tttgtagtac ctgcatccag cttagctgct    4740
gctgacaccc agcaggcctg ggttccgtga gcgcgaactc cgtggtggtg ggtctggctc    4800
tggtgctgcc atctacgcat gtgggaccct cgttatcgct gttgctcaaa atgtatttta    4860
tgaatcatcc taaatgagaa aattatgttt ttcttactgg attttgtaca aacataatct    4920
attatttgct atgcaatatt ttatgctggt attatatctg tttttttaaat tgttgaacaa    4980 aatactaaac tttt                                                      4994
```

<210> SEQ ID NO 8
<211> LENGTH: 1426
<212> TYPE: PRT
<213> ORGANISM: Homo sapiens

<400> SEQUENCE: 8

```
Met Asn Asp Trp His Arg Ile Phe Thr Gln Asn Val Leu Val Pro Pro
1               5                   10                  15

His Pro Gln Arg Ala Arg Gln Pro Trp Lys Glu Ser Thr Ala Phe Gln
            20                  25                  30

Cys Val Leu Lys Trp Leu Asp Gly Pro Val Ile Arg Gln Gly Val Leu
        35                  40                  45

Glu Val Leu Ser Glu Val Glu Cys His Leu Arg Val Ser Phe Phe Asp
    50                  55                  60

Val Thr Tyr Arg His Phe Phe Gly Arg Thr Trp Lys Thr Thr Val Lys
65                  70                  75                  80

Pro Thr Lys Arg Pro Pro Ser Arg Ile Val Phe Asn Glu Pro Leu Tyr
                85                  90                  95

Phe His Thr Ser Leu Asn His Pro His Ile Val Ala Val Val Glu Val
            100                 105                 110

Val Ala Glu Gly Lys Lys Arg Asp Gly Ser Leu Gln Thr Leu Ser Cys
        115                 120                 125

Gly Phe Gly Ile Leu Arg Ile Phe Ser Asn Gln Pro Asp Ser Pro Ile
    130                 135                 140

Ser Ala Ser Gln Asp Lys Arg Leu Arg Leu Tyr His Gly Thr Pro Arg
145                 150                 155                 160

Ala Leu Leu His Pro Leu Leu Gln Asp Pro Ala Glu Gln Asn Arg His
                165                 170                 175

Met Thr Leu Ile Glu Asn Cys Ser Leu Gln Tyr Thr Leu Lys Pro His
            180                 185                 190

Pro Ala Leu Glu Pro Ala Phe His Leu Leu Pro Glu Asn Leu Leu Val
        195                 200                 205

Ser Gly Leu Gln Gln Ile Pro Gly Leu Leu Pro Ala His Gly Glu Ser
    210                 215                 220

Gly Asp Ala Leu Arg Lys Pro Arg Leu Gln Lys Pro Ile Thr Gly His
225                 230                 235                 240

Leu Asp Asp Leu Phe Phe Thr Leu Tyr Pro Ser Leu Glu Lys Phe Glu
                245                 250                 255

Glu Glu Leu Leu Glu Leu His Val Gln Asp His Phe Gln Glu Gly Cys
            260                 265                 270

Gly Pro Leu Asp Gly Gly Ala Leu Glu Ile Leu Glu Arg Arg Leu Arg
        275                 280                 285

Val Gly Val His Asn Gly Leu Gly Phe Val Gln Arg Pro Gln Val Val
    290                 295                 300

Val Leu Val Pro Glu Met Asp Val Ala Leu Thr Arg Ser Ala Ser Phe
```

-continued

```
              305                 310                 315                 320
Ser Arg Lys Val Val Ser Ser Lys Thr Ser Ser Gly Ser Gln Ala
                325                 330                 335

Leu Val Leu Arg Ser Arg Leu Arg Leu Pro Glu Met Val Gly His Pro
                340                 345                 350

Ala Phe Ala Val Ile Phe Gln Leu Glu Tyr Val Phe Ser Ser Pro Ala
                355                 360                 365

Gly Val Asp Gly Asn Ala Ala Ser Val Thr Ser Leu Ser Asn Leu Ala
        370                 375                 380

Cys Met His Met Val Arg Trp Ala Val Trp Asn Pro Leu Leu Glu Ala
385                 390                 395                 400

Asp Ser Gly Arg Val Thr Leu Pro Leu Gln Gly Gly Ile Gln Pro Asn
                405                 410                 415

Pro Ser His Cys Leu Val Tyr Lys Val Pro Ser Ala Ser Met Ser Ser
                420                 425                 430

Glu Glu Val Lys Gln Val Glu Ser Gly Thr Leu Arg Phe Gln Phe Ser
                435                 440                 445

Leu Gly Ser Glu Glu His Leu Asp Ala Pro Thr Glu Pro Val Ser Gly
        450                 455                 460

Pro Lys Val Glu Arg Arg Pro Ser Arg Lys Pro Pro Thr Ser Pro Ser
465                 470                 475                 480

Ser Pro Pro Ala Pro Val Pro Arg Val Leu Ala Ala Pro Gln Asn Ser
                485                 490                 495

Pro Val Gly Pro Gly Leu Ser Ile Ser Gln Leu Ala Ala Ser Pro Arg
                500                 505                 510

Ser Pro Thr Gln His Cys Leu Ala Arg Pro Thr Ser Gln Leu Pro His
                515                 520                 525

Gly Ser Gln Ala Ser Pro Ala Gln Ala Gln Glu Phe Pro Leu Glu Ala
        530                 535                 540

Gly Ile Ser His Leu Glu Ala Asp Leu Ser Gln Thr Ser Leu Val Leu
545                 550                 555                 560

Glu Thr Ser Ile Ala Glu Gln Leu Gln Glu Leu Pro Phe Thr Pro Leu
                565                 570                 575

His Ala Pro Ile Val Val Gly Thr Gln Thr Arg Ser Ser Ala Gly Gln
                580                 585                 590

Pro Ser Arg Ala Ser Met Val Leu Leu Gln Ser Ser Gly Phe Pro Glu
                595                 600                 605

Ile Leu Asp Ala Asn Lys Gln Pro Ala Glu Ala Val Ser Ala Thr Glu
        610                 615                 620

Pro Val Thr Phe Asn Pro Gln Lys Glu Glu Ser Asp Cys Leu Gln Ser
625                 630                 635                 640

Asn Glu Met Val Leu Gln Phe Leu Ala Phe Ser Arg Val Ala Gln Asp
                645                 650                 655

Cys Arg Gly Thr Ser Trp Pro Lys Thr Val Tyr Phe Thr Phe Gln Phe
                660                 665                 670

Tyr Arg Phe Pro Pro Ala Thr Thr Pro Arg Leu Gln Leu Val Gln Leu
                675                 680                 685

Asp Glu Ala Gly Gln Pro Ser Ser Gly Ala Leu Thr His Ile Leu Val
        690                 695                 700

Pro Val Ser Arg Asp Gly Thr Phe Asp Ala Gly Ser Pro Gly Phe Gln
705                 710                 715                 720

Leu Arg Tyr Met Val Gly Pro Gly Phe Leu Lys Pro Gly Glu Arg Arg
                725                 730                 735
```

```
Cys Phe Ala Arg Tyr Leu Ala Val Gln Thr Leu Gln Ile Asp Val Trp
        740                 745                 750

Asp Arg Asp Ser Leu Leu Leu Ile Gly Ser Ala Ala Val Gln Met Lys
        755                 760                 765

His Leu Leu Arg Gln Gly Arg Pro Ala Val Gln Ala Ser His Glu Leu
        770                 775                 780

Glu Val Val Ala Thr Glu Tyr Glu Gln Asp Asn Met Val Val Ser Gly
785                 790                 795                 800

Asp Met Leu Gly Phe Gly Arg Val Lys Pro Ile Gly Val His Ser Val
                805                 810                 815

Val Lys Gly Arg Leu His Leu Thr Leu Ala Asn Val Gly His Pro Cys
        820                 825                 830

Glu Gln Lys Val Arg Gly Cys Ser Thr Leu Pro Pro Ser Arg Ser Arg
        835                 840                 845

Val Ile Ser Asn Asp Gly Ala Ser Arg Phe Ser Gly Gly Ser Leu Leu
        850                 855                 860

Thr Thr Gly Ser Ser Arg Arg Lys His Val Val Gln Ala Gln Lys Leu
865                 870                 875                 880

Ala Asp Val Asp Ser Glu Leu Ala Ala Met Leu Leu Thr His Ala Arg
                885                 890                 895

Gln Gly Lys Gly Pro Gln Asp Val Ser Arg Glu Ser Asp Ala Thr Arg
        900                 905                 910

Arg Arg Lys Leu Glu Arg Met Arg Ser Val Arg Leu Gln Glu Ala Gly
        915                 920                 925

Gly Asp Leu Gly Arg Arg Gly Thr Ser Val Leu Ala Gln Gln Ser Val
        930                 935                 940

Arg Thr Gln His Leu Arg Asp Leu Gln Val Ile Ala Ala Tyr Arg Glu
945                 950                 955                 960

Arg Thr Lys Ala Glu Ser Ile Ala Ser Leu Leu Ser Leu Ala Ile Thr
                965                 970                 975

Thr Glu His Thr Leu His Ala Thr Leu Gly Val Ala Glu Phe Phe Glu
        980                 985                 990

Phe Val Leu Lys Asn Pro His Asn Thr Gln His Thr Val Thr Val Glu
        995                 1000                1005

Ile Asp Asn Pro Glu Leu Ser Val Ile Val Asp Ser Gln Glu Trp
        1010                1015                1020

Arg Asp Phe Lys Gly Ala Ala Gly Leu His Thr Pro Val Glu Glu
        1025                1030                1035

Asp Met Phe His Leu Arg Gly Ser Leu Ala Pro Gln Leu Tyr Leu
        1040                1045                1050

Arg Pro His Glu Thr Ala His Val Pro Phe Lys Phe Gln Ser Phe
        1055                1060                1065

Ser Ala Gly Gln Leu Ala Met Val Gln Ala Ser Pro Gly Leu Ser
        1070                1075                1080

Asn Glu Lys Gly Met Asp Ala Val Ser Pro Trp Lys Ser Ser Ala
        1085                1090                1095

Val Pro Thr Lys His Ala Lys Val Leu Phe Arg Ala Ser Gly Gly
        1100                1105                1110

Lys Pro Ile Ala Val Leu Cys Leu Thr Val Glu Leu Gln Pro His
        1115                1120                1125

Val Val Asp Gln Val Phe Arg Phe Tyr His Pro Glu Leu Ser Phe
        1130                1135                1140
```

| | | | | | | | | | | |
|---|---|---|---|---|---|---|---|---|---|---|
| Leu | Lys<br>1145 | Lys | Ala | Ile | Arg<br>1150 | Leu | Pro | Pro | Trp | His<br>1155 | Thr | Phe | Pro | Gly |
| Ala | Pro<br>1160 | Val | Gly | Met | Leu<br>1165 | Gly | Glu | Asp | Pro | Val<br>1170 | His | Val | Arg |
| Cys | Ser<br>1175 | Asp | Pro | Asn | Val<br>1180 | Ile | Cys | Glu | Thr | Gln<br>1185 | Asn | Val | Gly | Pro |
| Gly | Glu<br>1190 | Pro | Arg | Asp | Ile<br>1195 | Phe | Leu | Lys | Val | Ala<br>1200 | Ser | Gly | Pro | Ser |
| Pro | Glu<br>1205 | Ile | Lys | Asp | Phe<br>1210 | Phe | Val | Ile | Ile | Tyr<br>1215 | Ser | Asp | Arg | Trp |
| Leu | Ala<br>1220 | Thr | Pro | Thr | Gln<br>1225 | Thr | Trp | Gln | Val | Tyr<br>1230 | Leu | His | Ser | Leu |
| Gln | Arg<br>1235 | Val | Asp | Val | Ser<br>1240 | Cys | Val | Ala | Gly | Gln<br>1245 | Leu | Thr | Arg | Leu |
| Ser | Leu<br>1250 | Val | Leu | Arg | Gly<br>1255 | Thr | Gln | Thr | Val | Arg<br>1260 | Lys | Val | Arg | Ala |
| Phe | Thr<br>1265 | Ser | His | Pro | Gln<br>1270 | Glu | Leu | Lys | Thr | Asp<br>1275 | Pro | Lys | Gly | Val |
| Phe | Val<br>1280 | Leu | Pro | Pro | Arg<br>1285 | Gly | Val | Gln | Asp | Leu<br>1290 | His | Val | Gly | Val |
| Arg | Pro<br>1295 | Leu | Arg | Ala | Gly<br>1300 | Ser | Arg | Phe | Val | His<br>1305 | Leu | Asn | Leu | Val |
| Asp | Val<br>1310 | Asp | Cys | His | Gln<br>1315 | Leu | Val | Ala | Ser | Trp<br>1320 | Leu | Val | Cys | Leu |
| Cys | Cys<br>1325 | Arg | Gln | Pro | Leu<br>1330 | Ile | Ser | Lys | Ala | Phe<br>1335 | Glu | Ile | Met | Leu |
| Ala | Ala<br>1340 | Gly | Glu | Gly | Lys<br>1345 | Gly | Val | Asn | Lys | Arg<br>1350 | Ile | Thr | Tyr | Thr |
| Asn | Pro<br>1355 | Tyr | Pro | Ser | Arg<br>1360 | Arg | Thr | Phe | His | Leu<br>1365 | His | Ser | Asp | His |
| Pro | Glu<br>1370 | Leu | Leu | Arg | Phe<br>1375 | Arg | Glu | Asp | Ser | Phe<br>1380 | Gln | Val | Gly | Gly |
| Gly | Glu<br>1385 | Thr | Tyr | Thr | Ile<br>1390 | Gly | Leu | Gln | Phe | Ala<br>1395 | Pro | Ser | Gln | Arg |
| Val | Gly<br>1400 | Glu | Glu | Glu | Ile<br>1405 | Leu | Ile | Tyr | Ile | Asn<br>1410 | Asp | His | Glu | Asp |
| Lys | Asn<br>1415 | Glu | Glu | Ala | Phe<br>1420 | Cys | Val | Lys | Val | Ile<br>1425 | Tyr | Gln |

<210> SEQ ID NO 9
<211> LENGTH: 3629
<212> TYPE: DNA
<213> ORGANISM: Homo sapiens

<400> SEQUENCE: 9

```
gacgcgaggc gggttcttgg actgagtgtg cggcgcggtg cgccgccttc cgaggctcct       60
cccgcgggtg gcagcggacg gggcgcgccc ctcggccagt cctcggtcct caggcttgtg      120
gctccgttga gcaccggccg ccgggcctct gggtccgtcg agtggagact ctctgaaaag      180
cgtgggctcc gtggcctccg cgcggccgc ggcgggtcgg tctcctagat catccgggaa       240
gcccacggga ccctcaggcg ggcaggatga acgactggca caggatcttc acccaaaacg      300
tgcttgtccc tccccaccca cagagagcgc gccagccttg gaaggaatcc acggcattcc      360
agtgtgtcct caagtggctg gacggaccgg taattaggca gggcgtgctg gaggtactgt      420
```

```
cagaggttga atgccatctg cgagtgtctt tctttgatgt cacctaccgg cacttctttg    480
ggaggacgtg gaaaaccaca gtgaagccga cgaagagacc gccgtccagg atcgtcttta    540
atgagccctt gtattttcac acatccctaa accaccctca tatcgtggct gtggtggaag    600
tggtcgctga gggcaagaaa cgggatggga gcctccagac attgtcctgt gggtttggaa    660
ttcttcggat cttcagcaac cagccggact ctcctatctc tgcttcccag gacaaaaggt    720
tgcggctgta ccatggcacc cccagagccc tcctgcaccc gcttctccag gaccccgcag    780
agcaaaacag acacatgacc ctcattgaga actgcagcct gcagtacacg ctgaagccac    840
acccggccct ggagcctgcg ttccaccttc ttcctgagaa ccttctggtg tctggtctgc    900
agcagatacc tggcctgctt ccagctcatg agaatccgg cgacgctctc cgaaagcctc     960
gcctccagaa gccatcacg gggcacttgg atgacttatt cttcaccctg tacccctccc    1020
tggagaagtt tgaggaagag ctgctggagc tccacgtcca ggaccacttc caggagggat    1080
gtggcccact ggacgtggt gccctggaga tcctggagcg cgcctgcgt gtgggcgtgc      1140 acaatggtct gggcttcgtg cagaggccgc aggtcgttgt actggtgcct gagatggatg    1200
tggccttgac gcgctcagct agcttcagca ggaaagtggg ctcctcttcc aagaccagct    1260
ccgggagcca agctctggtt ttgagaagcc gcctccgcct cccagagatg gtcggccacc    1320
ctgcatttgc ggtcatcttc cagctggagt acgtgttcag cagccctgca ggagtggacg    1380
gcaatgcagc ttcggtcacc tctctgtcca acctggcatg catgcacatg gtccgctggg    1440
ctgtttggaa ccccttgctg gaagctgatt ctggaagggt gaccctgcct ctgcagggtg    1500
ggatccagcc caaccctcg cactgtctgg tctacaaggt accctcagcc agcatgagct     1560
ctgaagaggt gaagcaggtg gagtcgggta cactccggtt ccagttctcg ctgggctcag    1620
aagaacacct ggatgcaccc acggagcctg tcagtggccc caaagtggag cggcggcctt    1680
ccaggaaacc acccacgtcc ccttcgagcc cgccagcgcc agtacctcga gttctcgctg    1740
ccccgcagaa ctcacctgtg ggaccagggt tgtcaatttc ccagctggcg gcctccccgc    1800 ggtcccccgac tcagcactgc ttggccaggc ctacttcaca gctacccat ggctctcagg     1860 cctccccggc ccaggcacag gagttcccgt tggaggccgg tatctcccac ctggaagccg    1920
acctgagcca gacctccctg gtcctggaaa catccattgc cgaacagtta caggagctgc    1980
cgttcacgcc tttgcatgcc cctattgttg tgggaaccca gaccaggagc tctgcagggc    2040
agccctcgag agcctccatg gtgctcctgc agtcctccgg cttctcccgag attctggatg    2100 ccaataaaca gccagccgag gctgtcagcg ctacagaacc tgtgacgttt aaccctcaga    2160
aggaagaatc agattgtcta caaagcaacg agatggtgct acagtttctt gcctttagca    2220
gagtggccca ggactgccga ggaacatcat ggccaaagac tgtgtatttc accttccagt    2280
tctaccgctt cccacccgca acgacgccac gactgcagct ggtccagctg atgaggccg     2340 gccagcccag ctctggcgcc ctgacccaca tcctcgtgcc tgtgagcaga gatggcacct    2400
ttgatgctgg gtctcctggc ttccagctga ggtacatggt gggccctggg ttcctgaagc    2460
caggtgagcg cgcgctgcttt gcccgctacc tggccgtgca gaccctgcag attgacgtct    2520
gggacggaga ctccctgctg ctcatcggat ctgctgccgt ccagatgaag catctcctcc    2580
gccaaggccg gccggctgtg caggcctccc acgagcttga ggtcgtggca actgaatacg    2640
agcaggacaa catggtggtg agtggagaca tgctggggtt tggccgcgtc aagcccatcg    2700
gcgtccactc ggtggtgaag ggccggctgc acctgacttt ggccaacgtg ggtcacccgt    2760
gtgaacagaa agtgagaggt tgtagcacat tgccaccgtc cagatctcgg gtcatctcaa    2820
```

```
acgatggagc cagccgcttc tctggaggca gcctcctcac gactggaagc tcaaggcgaa    2880
aacacgtggt gcaagcacag aagctggcgg acgtggacag tgagctggct gccatgctac    2940
tgacccatgc ccggcagggc aaggggcccc aggacgtcag ccgcgagtcg gatgccaccc    3000
gcaggcgtaa gctggagcgg atgaggtctg tgcgcctgca ggaggccggg ggagacttgg    3060
gccggcgcgg gacgagcgtg ttggcgcagc agagcgtccg cacacagcac ttgcgggacc    3120
tacaggtcat cgccgcctac cgggaacgca cgaaggccga gagcatcgcc agcctgctga    3180
gcctggccat caccacggag cacacgctcc acgccacgct gggggtcgcc gagttctttg    3240
agtttgtgct taagaacccc cacaacacac agcacacggt gactgtggag atcgacaacc    3300
ccgagctcag cgtcatcgtg gacagtcagg agtggaggga cttcaagggt gctgctggcc    3360
tgcacacacc ggtggaggag gacatgttcc acctgcgtgg cagcctggcc ccccagctct    3420
acctgcgccc ccacgagacc gcccacgtcc ccttcaagtt ccagagcttc tctgcagggc    3480
agctggccat ggtgcaggcc tctcctgggt tgagcaacga aagggcatg gacgccggtc    3540 accttggaag tccagcgcag tgcccactaa acacgccaag gtcttgttcc gagcgagtgg    3600
tggcaagccc atcgccgtgc tctgcctga                                     3629
```

<210> SEQ ID NO 10  
<211> LENGTH: 1121  
<212> TYPE: PRT  
<213> ORGANISM: Homo sapiens  
<220> FEATURE:  
<221> NAME/KEY: misc_feature  
<222> LOCATION: (1121)..(1121)  
<223> OTHER INFORMATION: Xaa can be any naturally occurring amino acid

<400> SEQUENCE: 10

```
Met Asn Asp Trp His Arg Ile Phe Thr Gln Asn Val Leu Val Pro Pro
1               5                   10                  15

His Pro Gln Arg Ala Arg Gln Pro Trp Lys Glu Ser Thr Ala Phe Gln
            20                  25                  30

Cys Val Leu Lys Trp Leu Asp Gly Pro Val Ile Arg Gln Gly Val Leu
        35                  40                  45

Glu Val Leu Ser Glu Val Glu Cys His Leu Arg Val Ser Phe Phe Asp
    50                  55                  60

Val Thr Tyr Arg His Phe Phe Gly Arg Thr Trp Lys Thr Thr Val Lys
65                  70                  75                  80

Pro Thr Lys Arg Pro Pro Ser Arg Ile Val Phe Asn Glu Pro Leu Tyr
                85                  90                  95

Phe His Thr Ser Leu Asn His Pro His Ile Val Ala Val Val Glu Val
            100                 105                 110

Val Ala Glu Gly Lys Lys Arg Asp Gly Ser Leu Gln Thr Leu Ser Cys
        115                 120                 125

Gly Phe Gly Ile Leu Arg Ile Phe Ser Asn Gln Pro Asp Ser Pro Ile
    130                 135                 140

Ser Ala Ser Gln Asp Lys Arg Leu Arg Leu Tyr His Gly Thr Pro Arg
145                 150                 155                 160

Ala Leu Leu His Pro Leu Leu Gln Asp Pro Ala Glu Gln Asn Arg His
                165                 170                 175

Met Thr Leu Ile Glu Asn Cys Ser Leu Gln Tyr Thr Leu Lys Pro His
            180                 185                 190

Pro Ala Leu Glu Pro Ala Phe His Leu Leu Pro Glu Asn Leu Leu Val
        195                 200                 205
```

-continued

```
Ser Gly Leu Gln Gln Ile Pro Gly Leu Leu Pro Ala His Gly Glu Ser
    210                 215                 220
Gly Asp Ala Leu Arg Lys Pro Arg Leu Gln Lys Pro Ile Thr Gly His
225                 230                 235                 240
Leu Asp Asp Leu Phe Phe Thr Leu Tyr Pro Ser Leu Glu Lys Phe Glu
                245                 250                 255
Glu Glu Leu Leu Glu Leu His Val Gln Asp His Phe Gln Glu Gly Cys
            260                 265                 270
Gly Pro Leu Asp Gly Gly Ala Leu Glu Ile Leu Glu Arg Arg Leu Arg
        275                 280                 285
Val Gly Val His Asn Gly Leu Gly Phe Val Gln Arg Pro Gln Val Val
    290                 295                 300
Val Leu Val Pro Glu Met Asp Val Ala Leu Thr Arg Ser Ala Ser Phe
305                 310                 315                 320
Ser Arg Lys Val Val Ser Ser Lys Thr Ser Ser Gly Ser Gln Ala
                325                 330                 335
Leu Val Leu Arg Ser Arg Leu Arg Leu Pro Glu Met Val Gly His Pro
            340                 345                 350
Ala Phe Ala Val Ile Phe Gln Leu Glu Tyr Val Phe Ser Ser Pro Ala
        355                 360                 365
Gly Val Asp Gly Asn Ala Ala Ser Val Thr Ser Leu Ser Asn Leu Ala
    370                 375                 380
Cys Met His Met Val Arg Trp Ala Val Trp Asn Pro Leu Leu Glu Ala
385                 390                 395                 400
Asp Ser Gly Arg Val Thr Leu Pro Leu Gln Gly Gly Ile Gln Pro Asn
                405                 410                 415
Pro Ser His Cys Leu Val Tyr Lys Val Pro Ser Ala Ser Met Ser Ser
            420                 425                 430
Glu Glu Val Lys Gln Val Glu Ser Gly Thr Leu Arg Phe Gln Phe Ser
        435                 440                 445
Leu Gly Ser Glu Glu His Leu Asp Ala Pro Thr Glu Pro Val Ser Gly
    450                 455                 460
Pro Lys Val Glu Arg Arg Pro Ser Arg Lys Pro Pro Thr Ser Pro Ser
465                 470                 475                 480
Ser Pro Pro Ala Pro Val Pro Arg Val Leu Ala Ala Pro Gln Asn Ser
                485                 490                 495
Pro Val Gly Pro Gly Leu Ser Ile Ser Gln Leu Ala Ala Ser Pro Arg
            500                 505                 510
Ser Pro Thr Gln His Cys Leu Ala Arg Pro Thr Ser Gln Leu Pro His
        515                 520                 525
Gly Ser Gln Ala Ser Pro Ala Gln Ala Gln Glu Phe Pro Leu Glu Ala
    530                 535                 540
Gly Ile Ser His Leu Glu Ala Asp Leu Ser Gln Thr Ser Leu Val Leu
545                 550                 555                 560
Glu Thr Ser Ile Ala Glu Gln Leu Gln Glu Leu Pro Phe Thr Pro Leu
                565                 570                 575
His Ala Pro Ile Val Val Gly Thr Gln Thr Arg Ser Ser Ala Gly Gln
            580                 585                 590
Pro Ser Arg Ala Ser Met Val Leu Leu Gln Ser Ser Gly Phe Pro Glu
        595                 600                 605
Ile Leu Asp Ala Asn Lys Gln Pro Ala Glu Ala Val Ser Ala Thr Glu
    610                 615                 620
```

-continued

```
Pro Val Thr Phe Asn Pro Gln Lys Glu Glu Ser Asp Cys Leu Gln Ser
625             630                 635                 640

Asn Glu Met Val Leu Gln Phe Leu Ala Phe Ser Arg Val Ala Gln Asp
                645                 650                 655

Cys Arg Gly Thr Ser Trp Pro Lys Thr Val Tyr Phe Thr Phe Gln Phe
            660                 665                 670

Tyr Arg Phe Pro Pro Ala Thr Thr Pro Arg Leu Gln Leu Val Gln Leu
        675                 680                 685

Asp Glu Ala Gly Gln Pro Ser Ser Gly Ala Leu Thr His Ile Leu Val
690                 695                 700

Pro Val Ser Arg Asp Gly Thr Phe Asp Ala Gly Ser Pro Gly Phe Gln
705                 710                 715                 720

Leu Arg Tyr Met Val Gly Pro Gly Phe Leu Lys Pro Gly Glu Arg Arg
                725                 730                 735

Cys Phe Ala Arg Tyr Leu Ala Val Gln Thr Leu Gln Ile Asp Val Trp
            740                 745                 750

Asp Gly Asp Ser Leu Leu Leu Ile Gly Ser Ala Ala Val Gln Met Lys
        755                 760                 765

His Leu Leu Arg Gln Gly Arg Pro Ala Val Gln Ala Ser His Glu Leu
770                 775                 780

Glu Val Val Ala Thr Glu Tyr Glu Gln Asp Asn Met Val Val Ser Gly
785                 790                 795                 800

Asp Met Leu Gly Phe Gly Arg Val Lys Pro Ile Gly Val His Ser Val
                805                 810                 815

Val Lys Gly Arg Leu His Leu Thr Leu Ala Asn Val Gly His Pro Cys
            820                 825                 830

Glu Gln Lys Val Arg Gly Cys Ser Thr Leu Pro Pro Ser Arg Ser Arg
        835                 840                 845

Val Ile Ser Asn Asp Gly Ala Ser Arg Phe Ser Gly Gly Ser Leu Leu
850                 855                 860

Thr Thr Gly Ser Ser Arg Arg Lys His Val Val Gln Ala Gln Lys Leu
865                 870                 875                 880

Ala Asp Val Asp Ser Glu Leu Ala Ala Met Leu Leu Thr His Ala Arg
                885                 890                 895

Gln Gly Lys Gly Pro Gln Asp Val Ser Arg Glu Ser Asp Ala Thr Arg
            900                 905                 910

Arg Arg Lys Leu Glu Arg Met Arg Ser Val Arg Leu Gln Glu Ala Gly
        915                 920                 925

Gly Asp Leu Gly Arg Arg Gly Thr Ser Val Leu Ala Gln Gln Ser Val
930                 935                 940

Arg Thr Gln His Leu Arg Asp Leu Gln Val Ile Ala Ala Tyr Arg Glu
945                 950                 955                 960

Arg Thr Lys Ala Glu Ser Ile Ala Ser Leu Leu Ser Leu Ala Ile Thr
                965                 970                 975

Thr Glu His Thr Leu His Ala Thr Leu Gly Val Ala Glu Phe Phe Glu
            980                 985                 990

Phe Val Leu Lys Asn Pro His Asn  Thr Gln His Thr Val  Thr Val Glu
        995                 1000                1005

Ile Asp  Asn Pro Glu Leu Ser  Val Ile Val Asp Ser  Gln Glu Trp
    1010                1015                1020

Arg Asp  Phe Lys Gly Ala Ala  Gly Leu His Thr Pro  Val Glu Glu
    1025                1030                1035

Asp Met  Phe His Leu Arg Gly  Ser Leu Ala Pro Gln  Leu Tyr Leu
```

-continued

```
                     1040                1045                1050
       Arg Pro His Glu Thr Ala His Val Pro Phe Lys Phe Gln Ser Phe
           1055                1060                1065

Ser Ala Gly Gln Leu Ala Met Val Gln Ala Ser Pro Gly Leu Ser
           1070                1075                1080

Asn Glu Lys Gly Met Asp Ala Gly His Leu Gly Ser Pro Ala Gln
           1085                1090                1095

Cys Pro Leu Asn Thr Pro Arg Ser Cys Ser Glu Arg Val Val Ala
           1100                1105                1110

Ser Pro Ser Pro Cys Ser Ala Xaa
           1115                1120
```

<210> SEQ ID NO 11
<211> LENGTH: 1601
<212> TYPE: DNA
<213> ORGANISM: Homo sapiens

<400> SEQUENCE: 11

```
gacgcgaggc gggttcttgg actgagtgtg cggcgcggtg cgccgccttc cgaggctcct      60
cccgcgggtg gcagcggacg gggcgcgccc ctcggccagt cctcggtcct caggcttgtg     120
gctccgttga gcaccggccg ccgggcctct gggtccgtcg agtggagact ctctgaaaag     180
cgtgggctcc gtggcctccg gcgcggccgc ggcgggtcgg tctcctagat catccgggaa     240
gcccacggga ccctcaggcg ggcaggatga cgactggca caggatcttc acccaaaacg      300
tgcttgtccc tccccaccca cagagagcgc gccagccttg gaaggaatcc acggcattcc     360
agtgtgtcct caagtggctg gacggaccgg taattaggca gggcgtgctg gaggtactgt     420
cagaggttga atgccatctg cgagtgtctt tctttgatgt cacctaccgg cacttctttg     480
ggaggacgtg gaaaaccaca gtgaagccga cgaagagacc gccgtccagg atcgtctttta    540
atgagccctt gtattttcac acatccctaa accacccctca tatcgtggct gtggtggaag     600
tggtcgctga gggcaagaaa cgggatggga gcctccagac attgtcctgt gggtttggaa     660
ttcttcggat cttcagcaac cagccggact ctcctatctc tgcttcccag acaaaaggt      720
tgcggctgta ccatggcacc cccagagccc tcctgcaccc gcttctccag daccccgcag     780
agcaaaacag acacatgacc ctcattgaga actgcagcct gcagtacacg ctgaagccac     840
acccggccct ggagcctgcg ttccaccttc ttcctgagaa ccttctggtg tctggtctgc     900
agcagatacc tggcctgctt ccagctcatg gagaatccgg cgacgctctc cgaaagcctc     960
gcctccagaa gcccatcacg ggcacttggg atgacttatt cttcaccctg taccccctccc   1020
tggagaagtt tgaggaagag ctgctggagc tccacgtcca ggaccacttc caggagggat    1080
gtggcccact ggacggtggt gccctggaga tcctggagcg gcgcctgcgt gtgggcgtgc    1140
acaatggtct gggcttcgtg cagaggccgc aggtcgttgt actggtgcct gagatggatg    1200
tggccttgac gcgctcagct agcttcagca ggaaagtggt ctcctcttcc aagaccagct    1260
ccggagccca agctctggtt ttgagaagcc gcctccgcct cccagagatg gtcggccacc    1320
ctgcatttgc ggtcatcttc cagctggagt acgtgttcag cagccctgca ggagtggacg    1380
gcaatgcagc ttcggtcacc tctctgtcca acctggcatg catgcacatg gtccgctggg    1440
ctgtttggaa ccccttgctg gaagctgatt ctggaagggt gaccctgcct ctgcagggtg    1500
ggatccagcc caaccctcg cactgtctgg tctacaaggt accctcagcc agcatgagct     1560
ctgaagaggt gaagcaggtg gagtcgggta cactccggta a                       1601
```

```
<210> SEQ ID NO 12
<211> LENGTH: 445
<212> TYPE: PRT
<213> ORGANISM: Homo sapiens
<220> FEATURE:
<221> NAME/KEY: misc_feature
<222> LOCATION: (445)..(445)
<223> OTHER INFORMATION: Xaa can be any naturally occurring amino acid

<400> SEQUENCE: 12

Met Asn Asp Trp His Arg Ile Phe Thr Gln Asn Val Leu Val Pro Pro
1               5                   10                  15

His Pro Gln Arg Ala Arg Gln Pro Trp Lys Glu Ser Thr Ala Phe Gln
            20                  25                  30

Cys Val Leu Lys Trp Leu Asp Gly Pro Val Ile Arg Gln Gly Val Leu
        35                  40                  45

Glu Val Leu Ser Glu Val Glu Cys His Leu Arg Val Ser Phe Phe Asp
    50                  55                  60

Val Thr Tyr Arg His Phe Phe Gly Arg Thr Trp Lys Thr Thr Val Lys
65                  70                  75                  80

Pro Thr Lys Arg Pro Pro Ser Arg Ile Val Phe Asn Glu Pro Leu Tyr
                85                  90                  95

Phe His Thr Ser Leu Asn His Pro His Ile Val Ala Val Val Glu Val
            100                 105                 110

Val Ala Glu Gly Lys Lys Arg Asp Gly Ser Leu Gln Thr Leu Ser Cys
        115                 120                 125

Gly Phe Gly Ile Leu Arg Ile Phe Ser Asn Gln Pro Asp Ser Pro Ile
    130                 135                 140

Ser Ala Ser Gln Asp Lys Arg Leu Arg Leu Tyr His Gly Thr Pro Arg
145                 150                 155                 160

Ala Leu Leu His Pro Leu Leu Gln Asp Pro Ala Glu Gln Asn Arg His
                165                 170                 175

Met Thr Leu Ile Glu Asn Cys Ser Leu Gln Tyr Thr Leu Lys Pro His
            180                 185                 190

Pro Ala Leu Glu Pro Ala Phe His Leu Leu Pro Glu Asn Leu Leu Val
        195                 200                 205

Ser Gly Leu Gln Gln Ile Pro Gly Leu Leu Pro Ala His Gly Glu Ser
    210                 215                 220

Gly Asp Ala Leu Arg Lys Pro Arg Leu Gln Lys Pro Ile Thr Gly His
225                 230                 235                 240

Leu Asp Asp Leu Phe Phe Thr Leu Tyr Pro Ser Leu Glu Lys Phe Glu
                245                 250                 255

Glu Glu Leu Leu Glu Leu His Val Gln Asp His Phe Gln Glu Gly Cys
            260                 265                 270

Gly Pro Leu Asp Gly Gly Ala Leu Glu Ile Leu Glu Arg Arg Leu Arg
        275                 280                 285

Val Gly Val His Asn Gly Leu Gly Phe Val Gln Arg Pro Gln Val Val
    290                 295                 300

Val Leu Val Pro Glu Met Asp Val Ala Leu Thr Arg Ser Ala Ser Phe
305                 310                 315                 320

Ser Arg Lys Val Val Ser Ser Lys Thr Ser Ser Gly Ser Gln Ala
                325                 330                 335

Leu Val Leu Arg Ser Arg Leu Arg Leu Pro Glu Met Val Gly His Pro
            340                 345                 350

Ala Phe Ala Val Ile Phe Gln Leu Glu Tyr Val Phe Ser Ser Pro Ala
```

```
              355                 360                 365
Gly Val Asp Gly Asn Ala Ala Ser Val Thr Ser Leu Ser Asn Leu Ala
    370                 375                 380

Cys Met His Met Val Arg Trp Ala Val Trp Asn Pro Leu Leu Glu Ala
385                 390                 395                 400

Asp Ser Gly Arg Val Thr Leu Pro Leu Gln Gly Gly Ile Gln Pro Asn
                405                 410                 415

Pro Ser His Cys Leu Val Tyr Lys Val Pro Ser Ala Ser Met Ser Ser
                420                 425                 430

Glu Glu Val Lys Gln Val Glu Ser Gly Thr Leu Arg Xaa
                435                 440                 445

<210> SEQ ID NO 13
<211> LENGTH: 2240
<212> TYPE: DNA
<213> ORGANISM: Homo sapiens

<400> SEQUENCE: 13
gacgcgaggc gggttcttgg actgagtgtg cggcgcggtg cgccgccttc cgaggctcct      60
cccgcgggtg gcagcggacg gggcgcgccc ctcggccagt cctcggtcct caggcttgtg     120
gctccgttga gcaccggccg ccgggcctct gggtccgtcg agtggagact ctctgaaaag     180
cgtgggctcc gtggcctccg cgcggccgc ggcgggtcgg tctcctagat catccgggaa     240
gcccacggga ccctcaggcg ggcaggatga acgactggca caggatcttc acccaaaacg     300
tgcttgtccc tccccaccca cagagagcgc gccagccttg gaaggaatcc acggcattcc     360
agtgtgtcct caagtggctg gacggaccgg taattaggca gggcgtgctg gaggtactgt     420
cagaggttga atgccatctg cgagtgtctt ctttgatgt cacctaccgg cacttctttg     480
ggaggacgtg gaaaaccaca gtgaagccga cgaagagacc gccgtccagg atcgtcttta     540
atgagccctt gtattttcac acatccctaa accaccctca tatcgtggct gtggtggaag     600
tggtcgctga gggcaagaaa cgggatggga gcctccagac attgtcctgt gggtttggaa     660
ttcttcggat cttcagcaac cagccggact ctcctatctc tgcttcccag acaaaaggt     720
tgcggctgta ccatggcacc cccagagccc tcctgcaccc gcttctccag gaccccgcag     780
agcaaaacag acacatgacc ctcattgaga actgcagcct gcagtacacg ctgaagccac     840
acccggccct ggagcctgcg ttccaccttc ttcctgagaa ccttctggtg tctggtctgc     900
agcagatacc tggcctgctt ccagctcatg gagaatccgg cgacgctctc cgaaagcctc     960
gcctccagaa gcccatcacg ggcacttgg atgacttatt cttcaccctg taccctctcc    1020
tggagaagtt tgaggaagag ctgctggagc tccacgtcca ggaccacttc caggagggat    1080
gtggcccact ggacggtggt gccctggaga tcctggagcg gcgcctgcgt gtgggcgtgc    1140
acaatggtct gggcttcgtg cagaggccgc aggtcgttgt actggtgcct gagatggatg    1200
tggccttgac gcgctcagct agcttcagca ggaaagtggt ctcctcttcc aagaccagct    1260
ccggagccca agctctggtt ttgagaagcc gcctccgcct cccagagatg gtcggccacc    1320
ctgcatttgc ggtcatcttc cagctggagt acgtgttcag cagccctgca ggagtggacg    1380
gcaatgcagc ttcggtcacc tctctgtcca acctggcatg catgcacatg gtccgctggg    1440
ctgtttggaa ccccttgctg gaagctgatt ctggaagggt gaccctgcct ctgcagggtg    1500
ggatccagcc caaccctcg cactgtctgg tctacaaggt accctcagcc agcatgagct    1560
ctgaagaggt gaagcaggtg gagtcgggta cactccggtt ccagttctcg ctgggctcag    1620
```

-continued

```
aagaacacct ggatgcaccc acggagcctg tcagtggccc caaagtggag cggcggcctt  1680
ccaggaaacc acccacgtcc ccttcgagcc cgccagcgcc agtacctcga gttctcgctg  1740
ccccgcagaa ctcacctgtg ggaccagggt tgtcaatttc ccagctggcg gcctccccgc  1800
ggtccccgac tcagcactgc ttggccaggc ctacttcaca gctaccccat ggctctcagg  1860
cctccccggc ccaggacag gagttcccgt tggaggccgg tatctcccac ctggaagccg  1920
acctgagcca gacctccctg gtcctggaaa catccattgc cgaacagtta caggagctgc  1980
cgttcacgcc tttgcatgcc cctattgttg tgggaaccca gaccaggagc tctgcagggc  2040
agccctcgag agcctccatg gtgctcctgc agtcctccgg cttccccgag attctggatg  2100
ccaataaaca gccagccgag gctgtcagcg ctacagaacc tgtgacgttt aaccctcaga  2160
aggaagaatc agattgtcta caaagcaacg agatggtgct acagtttctt gcctttagca  2220
gagtggccca ggactgctga                                              2240
```

<210> SEQ ID NO 14
<211> LENGTH: 658
<212> TYPE: PRT
<213> ORGANISM: Homo sapiens
<220> FEATURE:
<221> NAME/KEY: misc_feature
<222> LOCATION: (658)..(658)
<223> OTHER INFORMATION: Xaa can be any naturally occurring amino acid

<400> SEQUENCE: 14

```
Met Asn Asp Trp His Arg Ile Phe Thr Gln Asn Val Leu Val Pro Pro
1               5                   10                  15

His Pro Gln Arg Ala Arg Gln Pro Trp Lys Glu Ser Thr Ala Phe Gln
            20                  25                  30

Cys Val Leu Lys Trp Leu Asp Gly Pro Val Ile Arg Gln Gly Val Leu
        35                  40                  45

Glu Val Leu Ser Glu Val Glu Cys His Leu Arg Val Ser Phe Phe Asp
    50                  55                  60

Val Thr Tyr Arg His Phe Phe Gly Arg Thr Trp Lys Thr Thr Val Lys
65                  70                  75                  80

Pro Thr Lys Arg Pro Pro Ser Arg Ile Val Phe Asn Glu Pro Leu Tyr
                85                  90                  95

Phe His Thr Ser Leu Asn His Pro His Ile Val Ala Val Val Glu Val
            100                 105                 110

Val Ala Glu Gly Lys Lys Arg Asp Gly Ser Leu Gln Thr Leu Ser Cys
        115                 120                 125

Gly Phe Gly Ile Leu Arg Ile Phe Ser Asn Gln Pro Asp Ser Pro Ile
    130                 135                 140

Ser Ala Ser Gln Asp Lys Arg Leu Arg Leu Tyr His Gly Thr Pro Arg
145                 150                 155                 160

Ala Leu Leu His Pro Leu Leu Gln Asp Pro Ala Glu Gln Asn Arg His
                165                 170                 175

Met Thr Leu Ile Glu Asn Cys Ser Leu Gln Tyr Thr Leu Lys Pro His
            180                 185                 190

Pro Ala Leu Glu Pro Ala Phe His Leu Leu Pro Glu Asn Leu Leu Val
        195                 200                 205

Ser Gly Leu Gln Gln Ile Pro Gly Leu Leu Pro Ala His Gly Glu Ser
    210                 215                 220

Gly Asp Ala Leu Arg Lys Pro Arg Leu Gln Lys Pro Ile Thr Gly His
225                 230                 235                 240
```

```
Leu Asp Asp Leu Phe Phe Thr Leu Tyr Pro Ser Leu Glu Lys Phe Glu
            245                 250                 255

Glu Glu Leu Leu Glu Leu His Val Gln Asp His Phe Gln Glu Gly Cys
        260                 265                 270

Gly Pro Leu Asp Gly Gly Ala Leu Glu Ile Leu Glu Arg Arg Leu Arg
            275                 280                 285

Val Gly Val His Asn Gly Leu Gly Phe Val Gln Arg Pro Gln Val Val
        290                 295                 300

Val Leu Val Pro Glu Met Asp Val Ala Leu Thr Arg Ser Ala Ser Phe
305                 310                 315                 320

Ser Arg Lys Val Val Ser Ser Lys Thr Ser Ser Gly Ser Gln Ala
            325                 330                 335

Leu Val Leu Arg Ser Arg Leu Arg Leu Pro Glu Met Val Gly His Pro
            340                 345                 350

Ala Phe Ala Val Ile Phe Gln Leu Glu Tyr Val Phe Ser Ser Pro Ala
            355                 360                 365

Gly Val Asp Gly Asn Ala Ala Ser Val Thr Ser Leu Ser Asn Leu Ala
            370                 375                 380

Cys Met His Met Val Arg Trp Ala Val Trp Asn Pro Leu Leu Glu Ala
385                 390                 395                 400

Asp Ser Gly Arg Val Thr Leu Pro Leu Gln Gly Gly Ile Gln Pro Asn
            405                 410                 415

Pro Ser His Cys Leu Val Tyr Lys Val Pro Ser Ala Ser Met Ser Ser
            420                 425                 430

Glu Glu Val Lys Gln Val Glu Ser Gly Thr Leu Arg Phe Gln Phe Ser
            435                 440                 445

Leu Gly Ser Glu Glu His Leu Asp Ala Pro Thr Glu Pro Val Ser Gly
            450                 455                 460

Pro Lys Val Glu Arg Arg Pro Ser Arg Lys Pro Pro Thr Ser Pro Ser
465                 470                 475                 480

Ser Pro Pro Ala Pro Val Pro Arg Val Leu Ala Ala Pro Gln Asn Ser
            485                 490                 495

Pro Val Gly Pro Gly Leu Ser Ile Ser Gln Leu Ala Ala Ser Pro Arg
            500                 505                 510

Ser Pro Thr Gln His Cys Leu Ala Arg Pro Thr Ser Gln Leu Pro His
            515                 520                 525

Gly Ser Gln Ala Ser Pro Ala Gln Ala Gln Glu Phe Pro Leu Glu Ala
            530                 535                 540

Gly Ile Ser His Leu Glu Ala Asp Leu Ser Gln Thr Ser Leu Val Leu
545                 550                 555                 560

Glu Thr Ser Ile Ala Glu Gln Leu Gln Glu Leu Pro Phe Thr Pro Leu
            565                 570                 575

His Ala Pro Ile Val Val Gly Thr Gln Thr Arg Ser Ser Ala Gly Gln
            580                 585                 590

Pro Ser Arg Ala Ser Met Val Leu Leu Gln Ser Ser Gly Phe Pro Glu
            595                 600                 605

Ile Leu Asp Ala Asn Lys Gln Pro Ala Glu Ala Val Ser Ala Thr Glu
            610                 615                 620

Pro Val Thr Phe Asn Pro Gln Lys Glu Glu Ser Asp Cys Leu Gln Ser
625                 630                 635                 640

Asn Glu Met Val Leu Gln Phe Leu Ala Phe Ser Arg Val Ala Gln Asp
            645                 650                 655

Cys Xaa
```

<210> SEQ ID NO 15
<211> LENGTH: 2312
<212> TYPE: DNA
<213> ORGANISM: Homo sapiens

<400> SEQUENCE: 15

```
gacgcgaggc gggttcttgg actgagtgtg cggcgcggtg cgccgccttc cgaggctcct      60
cccgcgggtg gcagcggacg gggcgcgccc ctcggccagt cctcggtcct caggcttgtg     120
gctccgttga gcaccggccg ccgggcctct gggtccgtcg agtggagact ctctgaaaag     180
cgtgggctcc gtggcctccg gcgcggccgc ggcgggtcgg tctcctagat catccgggaa     240
gcccacggga ccctcaggcg ggcaggatga acgactggca caggatcttc acccaaaacg     300
tgcttgtccc tccccaccca cagagagcgc gccagccttg gaaggaatcc acggcattcc     360
agtgtgtcct caagtggctg gacggaccgg taattaggca gggcgtgctg gaggtactgt     420
cagaggttga atgccatctg cgagtgtctt tctttgatgt cacctaccgg cacttctttg     480
ggaggacgtg gaaaaccaca gtgaagccga cgaagagacc gccgtccagg atcgtcttta     540
atgagccctt gtattttcac acatccctaa accaccctca tatcgtggct gtggtggaag     600
tggtcgctga gggcaagaaa cgggatggga gcctccagac attgtcctgt gggtttggaa     660
ttcttcggat cttcagcaac cagccggact ctcctatctc tgcttcccag gacaaaaggt     720
tgcggctgta ccatggcacc cccagagccc tcctgcaccc gcttctccag gaccccgcag     780
agcaaaacag acacatgacc ctcattgaga actgcagcct gcagtacacg ctgaagccac     840
acccggccct ggagcctgcg ttccaccttc ttcctgagaa ccttctggtg tctggtctgc     900
agcagatacc tggcctgctt ccagctcatg agaatccgg cgacgctctc cgaaagcctc     960
gcctccagaa gcccatcacg gggcacttgg atgacttatt cttcaccctg tacccctccc    1020
tggagaagtt tgaggaagag ctgctggagc tccacgtcca ggaccacttc caggagggat    1080
gtggcccact ggacggtggt gccctggaga tcctggagcg gcgcctgcgt gtgggcgtgc    1140
acaatggtct gggcttcgtg cagaggccgc aggtcgttgt actggtgcct gagatggatg    1200
tggccttgac gcgctcagct agcttcagca ggaaagtggt ctcctcttcc aagaccagct    1260
ccgggagcca agctctggtt ttgagaagcc gcctccgcct cccagagatg gtcggccacc    1320
ctgcatttgc ggtcatcttc agctggagt acgtgttcag cagccctgca ggagtggacg    1380
gcaatgcagc ttcggtcacc tctctgtcca acctggcatg catgcacatg gtccgctggg    1440
ctgtttggaa cccccttgctg gaagctgatt ctggaagggt gaccctgcct ctgcagggtg    1500
ggatccagcc caacccctcg cactgtctgg tctacaaggt accctcagcc agcatgagct    1560
ctgaagaggt gaagcaggtg gagtcgggta cactccggtt ccagttctcg ctgggctcag    1620
aagaacacct ggatgcaccc acggagcctg tcagtggccc caaagtggag cggcggcctt    1680
ccaggaaacc acccacgtcc ccttcgagcc cgccagcgcc agtacctcga gttctcgctg    1740
ccccgcagaa ctcacctgtg ggaccagggt tgtcaatttc ccagctggcg gcctccccgc    1800
ggtccccgac tcagcactgc ttggccaggc ctacttcaca gctaccccat ggctctcagg    1860
cctcccggc ccaggcacag gagttccgt tggaggccgg tatctcccac ctggaagccg    1920
acctgagcca gacctccctg gtcctggaaa catccattgc cgaacagtta caggagctgc    1980
cgttcacgcc tttgcatgcc cctattgttg tgggaaccca gaccaggagc tctgcagggc    2040
agccctcgag agcctccatg gtgctcctgc agtcctccgg ctttcccgag attctggatg    2100
```

```
ccaataaaca gccagccgag gctgtcagcg ctacagaacc tgtgacgttt aaccctcaga    2160
aggaagaatc agattgtcta caaagcaacg agatggtgct acagtttctt gcctttagca    2220
gagtggccca ggactgccga ggaacatcat ggccaaagac tgtgtatttc accttccagt    2280
tctaccgctt cccacccgca acgacgccat ga                                  2312
```

<210> SEQ ID NO 16
<211> LENGTH: 682
<212> TYPE: PRT
<213> ORGANISM: Homo sapiens
<220> FEATURE:
<221> NAME/KEY: misc_feature
<222> LOCATION: (682)..(682)
<223> OTHER INFORMATION: Xaa can be any naturally occurring amino acid

<400> SEQUENCE: 16

```
Met Asn Asp Trp His Arg Ile Phe Thr Gln Asn Val Leu Val Pro Pro
1               5                   10                  15

His Pro Gln Arg Ala Arg Gln Pro Trp Lys Glu Ser Thr Ala Phe Gln
            20                  25                  30

Cys Val Leu Lys Trp Leu Asp Gly Pro Val Ile Arg Gln Gly Val Leu
        35                  40                  45

Glu Val Leu Ser Glu Val Glu Cys His Leu Arg Val Ser Phe Phe Asp
    50                  55                  60

Val Thr Tyr Arg His Phe Phe Gly Arg Thr Trp Lys Thr Val Lys
65                  70                  75                  80

Pro Thr Lys Arg Pro Pro Ser Arg Ile Val Phe Asn Glu Pro Leu Tyr
                85                  90                  95

Phe His Thr Ser Leu Asn His Pro His Ile Val Ala Val Val Glu Val
            100                 105                 110

Val Ala Glu Gly Lys Lys Arg Asp Gly Ser Leu Gln Thr Leu Ser Cys
        115                 120                 125

Gly Phe Gly Ile Leu Arg Ile Phe Ser Asn Gln Pro Asp Ser Pro Ile
    130                 135                 140

Ser Ala Ser Gln Asp Lys Arg Leu Arg Leu Tyr His Gly Thr Pro Arg
145                 150                 155                 160

Ala Leu Leu His Pro Leu Leu Gln Asp Pro Ala Glu Gln Asn Arg His
                165                 170                 175

Met Thr Leu Ile Glu Asn Cys Ser Leu Gln Tyr Thr Leu Lys Pro His
            180                 185                 190

Pro Ala Leu Glu Pro Ala Phe His Leu Leu Pro Glu Asn Leu Leu Val
        195                 200                 205

Ser Gly Leu Gln Gln Ile Pro Gly Leu Leu Pro Ala His Gly Glu Ser
    210                 215                 220

Gly Asp Ala Leu Arg Lys Pro Arg Leu Gln Lys Pro Ile Thr Gly His
225                 230                 235                 240

Leu Asp Asp Leu Phe Phe Thr Leu Tyr Pro Ser Leu Glu Lys Phe Glu
                245                 250                 255

Glu Glu Leu Leu Glu Leu His Val Gln Asp His Phe Gln Glu Gly Cys
            260                 265                 270

Gly Pro Leu Asp Gly Gly Ala Leu Glu Ile Leu Glu Arg Arg Leu Arg
        275                 280                 285

Val Gly Val His Asn Gly Leu Gly Phe Val Gln Arg Pro Gln Val Val
    290                 295                 300

Val Leu Val Pro Glu Met Asp Val Ala Leu Thr Arg Ser Ala Ser Phe
305                 310                 315                 320
```

```
Ser Arg Lys Val Val Ser Ser Lys Thr Ser Ser Gly Ser Gln Ala
            325                 330                 335

Leu Val Leu Arg Ser Arg Leu Arg Leu Pro Glu Met Val Gly His Pro
            340                 345                 350

Ala Phe Ala Val Ile Phe Gln Leu Glu Tyr Val Phe Ser Ser Pro Ala
            355                 360                 365

Gly Val Asp Gly Asn Ala Ala Ser Val Thr Ser Leu Ser Asn Leu Ala
            370                 375                 380

Cys Met His Met Val Arg Trp Ala Val Trp Asn Pro Leu Leu Glu Ala
385                 390                 395                 400

Asp Ser Gly Arg Val Thr Leu Pro Leu Gln Gly Ile Gln Pro Asn
            405                 410                 415

Pro Ser His Cys Leu Val Tyr Lys Val Pro Ser Ala Ser Met Ser Ser
            420                 425                 430

Glu Glu Val Lys Gln Val Glu Ser Gly Thr Leu Arg Phe Gln Phe Ser
            435                 440                 445

Leu Gly Ser Glu Glu His Leu Asp Ala Pro Thr Glu Pro Val Ser Gly
            450                 455                 460

Pro Lys Val Glu Arg Arg Pro Ser Arg Lys Pro Pro Thr Ser Pro Ser
465                 470                 475                 480

Ser Pro Pro Ala Pro Val Pro Arg Val Leu Ala Ala Pro Gln Asn Ser
            485                 490                 495

Pro Val Gly Pro Gly Leu Ser Ile Ser Gln Leu Ala Ala Ser Pro Arg
            500                 505                 510

Ser Pro Thr Gln His Cys Leu Ala Arg Pro Thr Ser Gln Leu Pro His
            515                 520                 525

Gly Ser Gln Ala Ser Pro Ala Gln Ala Gln Glu Phe Pro Leu Glu Ala
            530                 535                 540

Gly Ile Ser His Leu Glu Ala Asp Leu Ser Gln Thr Ser Leu Val Leu
545                 550                 555                 560

Glu Thr Ser Ile Ala Glu Gln Leu Gln Glu Leu Pro Phe Thr Pro Leu
            565                 570                 575

His Ala Pro Ile Val Val Gly Thr Gln Thr Arg Ser Ser Ala Gly Gln
            580                 585                 590

Pro Ser Arg Ala Ser Met Val Leu Leu Gln Ser Ser Gly Phe Pro Glu
            595                 600                 605

Ile Leu Asp Ala Asn Lys Gln Pro Ala Glu Ala Val Ser Ala Thr Glu
            610                 615                 620

Pro Val Thr Phe Asn Pro Gln Lys Glu Glu Ser Asp Cys Leu Gln Ser
625                 630                 635                 640

Asn Glu Met Val Leu Gln Phe Leu Ala Phe Ser Arg Val Ala Gln Asp
            645                 650                 655

Cys Arg Gly Thr Ser Trp Pro Lys Thr Val Tyr Phe Thr Phe Gln Phe
            660                 665                 670

Tyr Arg Phe Pro Pro Ala Thr Thr Pro Xaa
            675                 680

<210> SEQ ID NO 17
<211> LENGTH: 4994
<212> TYPE: DNA
<213> ORGANISM: Homo sapiens

<400> SEQUENCE: 17
gacgcgaggc gggttcttgg actgagtgtg cggcgcggtg cgccgccttc cgaggctcct    60
```

```
cccgcgggtg gcagcggacg gggcgcgccc ctcggccagt cctcggtcct caggcttgtg    120
gctccgttga gcaccggccg ccgggcctct gggtccgtcg agtggagact ctctgaaaag    180
cgtgggctcc gtggcctccg cgcggccgc ggcgggtcgg tctcctagat catccgggaa    240
gcccacggga ccctcaggcg ggcaggatga acgactggca caggatcttc acccaaaacg    300
tgcttgtccc tccccaccca cagagagcgc gccagccttg aaggaatcc acggcattcc     360 agtgtgtcct caagtggctg gacggaccgg taattaggca gggcgtgctg gaggtactgt    420
cagaggttga atgccatctg cgagtgtctt tctttgatgt cacctaccgg cacttctttg    480
ggaggacgtg gaaaaccaca gtgaagccga cgaagagacc gccgtccagg atcgtcttta    540
atgagccctt gtattttcac acatccctaa accaccctca tatcgtggct gtggtggaag    600
tggtcgctga gggcaagaaa cgggatggga gcctccagac attgtcctgt gggtttggaa    660
ttcttcggat cttcagcaac cagccggact ctcctatctc tgcttcccag acaaaaggt     720 tgcggctgta ccatggcacc cccagagccc tcctgcaccc gcttctccag gaccccgcag    780
agcaaaacag acacatgacc ctcattgaga actgcagcct gcagtacacg ctgaagccac    840
acccggccct ggagcctgcg ttccaccttc ttcctgagaa ccttctggtg tctggtctgc    900
agcagatacc tggcctgctt ccagctcatg gagaatccgg cgacgctctc cgaaagcctc    960
gcctccagaa gcccatcacg gggcacttgg atgacttatt cttcaccctg taccctcc     1020 tggagaagtt tgaggaagag ctgctggagc tccacgtcca ggaccacttc caggagggat    1080
gtggcccact ggacggtggt gccctggaga tcctggagcg gcgcctgcgt gtgggcgtgc    1140
acaatggtct gggcttcgtg cagaggccgc aggtcgttgt actggtgcct gagatggatg    1200
tggccttgac gcgctcagct agcttcagca ggaaagtggt ctcctcttcc aagaccagct    1260
ccgggagcca agctctggtt ttgagaagcc gcctccgcct cccagagatg gtcggccacc    1320
ctgcatttgc ggtcatcttc cagctggagt acgtgttcag cagccctgca ggagtggacg    1380
gcaatgcagc ttcggtcacc tctctgtcca acctggcatg catgcacatg gtccgctggg    1440
ctgtttggaa cccccttgctg gaagctgatt ctggaagggt gaccctgcct ctgcagggtg    1500
ggatccagcc caaccctcg cactgtctgg tctacaaggt accctcagcc agcatgagct    1560
ctgaagaggt gaagcaggtg gagtcgggta cactccggtt ccagttctcg ctgggctcag    1620
aagaacacct ggatgcaccc acggagcctg tcagtggccc caaagtggag cggcggcctt    1680
ccaggaaacc acccacgtcc ccttcgagcc cgccagcgcc agtacctcga gttctcgctg    1740
ccccgcagaa ctcacctgtg ggaccagggt tgtcaatttc ccagctggcg gcctcccgc    1800 ggtcccgac tcagcactgc ttggccaggc ctacttcaca gctacccat ggctctcagg     1860 cctccccggc ccaggcacag gagttcccgt tggaggccgg tatctcccac ctggaagccg    1920
acctgagcca gacctccctg gtcctggaaa catccattgc cgaacagtta caggagctgc    1980
cgttcacgcc tttgcatgcc cctattgttg tgggaaccca gaccaggagc tctgcagggc    2040
agccctcgag agcctccatg gtgctcctgc agtcctccgg ctttcccgag attctggatg    2100
ccaataaaca gccagccgag gctgtcagcg ctacagaacc tgtgacgttt aaccctcaga    2160
aggaagaatc agattgtcta caaagcaacg agatggtgct acagtttctt gcctttagca    2220
gagtggccca ggactgccga ggaacatcat ggccaaagac tgtgtatttc accttccagt    2280
tctaccgctt cccacccgca acgacgccac gactgcagct ggtccagctg gatgaggccg    2340
gccagcccag ctctggcgcc ctgacccaca tcctcgtgcc tgtgagcaga gatggcacct    2400
```

```
ttgatgctgg gtctcctggc ttccagctga ggtacatggt gggccctggg ttcctgaagc    2460
caggtgagcg gcgctgcttt gcccgctacc tggccgtgca gaccctgcag attgacgtct    2520
gggacggaga ctccctgctg ctcatcggat ctgctgccgt ccagatgaag catctcctcc    2580
gccaaggccg gccggctgtg caggcctccc acgagcttga ggtcgtggca actgaatacg    2640
agcaggacaa catggtggtg agtgagacat gctggggtt tggccgcgtc aagcccatcg    2700
gcgtccactc ggtggtgaag ggccggctgc acctgacttt ggccaacgtg ggtcacccgt    2760
gtgaacagaa agtgagaggt tgtagcacat gccaccgtc cagatcttgg gtcatctcaa    2820
acgatggagc cagccgcttc tctgaggca gcctcctcac gactggaagc tcaaggcgaa    2880
aacacgtggt gcaagcacag aagctggcgg acgtggacag tgagctggct gccatgctac    2940
tgacccatgc ccggcagggc aaggggcccc aggacgtcag ccgcgagtcg gatgccaccc    3000
gcaggcgtaa gctggagcgg atgaggtctg tgcgcctgca ggaggccggg ggagacttgg    3060
gccggcgcgg gacgagcgtg ttggcgcagc agagcgtccg cacacagcac ttgcgggacc    3120
tacaggtcat cgccgcctac cgggaacgca cgaaggccga gagcatcgcc agcctgctga    3180
gcctggccat caccacggag cacacgctcc acgccacgct gggggtcgcc gagttctttg    3240
agtttgtgct taagaacccc cacaacacac agcacacggt gactgtggag atcgacaacc    3300
ccgagctcag cgtcatcgtg gacagtcagg agtggaggga cttcaagggt gctgctggcc    3360
tgcacacacc ggtggaggag gacatgttcc acctgcgtgg cagcctggcc ccccagctct    3420
acctgcgccc ccacgagacc gcccacgtcc ccttcaagtt ccagagcttc tctgcagggc    3480
agctggccat ggtgcaggcc tctcctgggt tgagcaacga aagggcatg gacgccgtgt    3540 caccttggaa gtccagcgca gtgcccacta aacacgccaa ggtcttgttc cgagcgagtg    3600
gtggcaagcc catcgccgtg ctctgcctga ctgtggagct gcagcccac gtggtggacc    3660 aggtcttccg cttctatcac ccggagctct ccttcctgaa aaggccatc cgcctgccgc    3720 cctggcacac atttccaggt gctccggtgg gaatgcttgg tgaggacccc ccagtccatg    3780
ttcgctgcag cgacccgaac gtcatctgtg agacccagaa tgtgggcccc ggggaaccac    3840
gggacatatt tctgaaggtg gccagtggtc caagcccgga gatcaaagac ttctttgtca    3900
tcatttactc ggatcgctgg ctggcgacac ccacacagac gtggcaggtc tacctccact    3960
ccctgcagcg cgtggatgtc tcctgcgtcg caggccagct gacccgcctg tcccttgtcc    4020
ttcgggggac acagacagtg aggaaagtga gagctttcac ctctcatccc caggagctga    4080
agacagaccc caaaggtgtc ttcgtgctgc cgcctcgtgg ggtgcaggac ctgcatgttg    4140
gcgtgaggcc ccttagggcc ggcagccgct ttgtccatct caacctggtg gacgtggatt    4200
gccaccagct ggtggcctcc tggctcgtgt gcctctgctg ccgccagccg ctcatctcca    4260
aggcctttga gatcatgttg gctgcgggcg aagggaaggg tgtcaacaag aggatcacct    4320
acaccaaccc ctaccctcc cggaggacat tccacctgca cagcgaccac ccggagctgc    4380
tgcggttcag agaggactcc ttccaggtcg ggggtggaga gacctacacc atcggcttgc    4440
agtttgcgcc tagtcagaga gtgggtgagg aggagatcct gatctacatc aatgaccatg    4500
aggacaaaaa cgaagaggca ttttgcgtga aggtcatcta ccagtgaggg cttgagggtg    4560
acgtccttcc tgcggcaccc agctgggccc tgtctgtgcc cctcctgccc tgcaggctgt    4620
cctccccgcc tctctgcagc cttttcacttc agtgcccacc tggctgacct gtgcacttgg    4680
ctgaggaagc agagaccgag cgctggtcat tttgtagtac ctgcatccag cttagctgct    4740
gctgacaccc agcaggcctg ggttccgtga gcgcgaactc cgtggtggtg ggtctggctc    4800
```

-continued

```
tggtgctgcc atctacgcat gtgggaccct cgttatcgct gttgctcaaa atgtatttta    4860
tgaatcatcc taaatgagaa aattatgttt tccttactgg attttgtaca aacataatct    4920
attatttgct atgcaatatt ttatgctggt attatatctg tttttaaat tgttgaacaa     4980 aatactaaac tttt                                                       4994
```

<210> SEQ ID NO 18
<211> LENGTH: 1426
<212> TYPE: PRT
<213> ORGANISM: Homo sapiens

<400> SEQUENCE: 18

```
Met Asn Asp Trp His Arg Ile Phe Thr Gln Asn Val Leu Val Pro Pro
1               5                   10                  15

His Pro Gln Arg Ala Arg Gln Pro Trp Lys Glu Ser Thr Ala Phe Gln
            20                  25                  30

Cys Val Leu Lys Trp Leu Asp Gly Pro Val Ile Arg Gln Gly Val Leu
        35                  40                  45

Glu Val Leu Ser Glu Val Glu Cys His Leu Arg Val Ser Phe Phe Asp
    50                  55                  60

Val Thr Tyr Arg His Phe Phe Gly Arg Thr Trp Lys Thr Thr Val Lys
65                  70                  75                  80

Pro Thr Lys Arg Pro Pro Ser Arg Ile Val Phe Asn Glu Pro Leu Tyr
                85                  90                  95

Phe His Thr Ser Leu Asn His Pro His Ile Val Ala Val Glu Val
            100                 105                 110

Val Ala Glu Gly Lys Lys Arg Asp Gly Ser Leu Gln Thr Leu Ser Cys
        115                 120                 125

Gly Phe Gly Ile Leu Arg Ile Phe Ser Asn Gln Pro Asp Ser Pro Ile
    130                 135                 140

Ser Ala Ser Gln Asp Lys Arg Leu Arg Leu Tyr His Gly Thr Pro Arg
145                 150                 155                 160

Ala Leu Leu His Pro Leu Leu Gln Asp Pro Ala Glu Gln Asn Arg His
                165                 170                 175

Met Thr Leu Ile Glu Asn Cys Ser Leu Gln Tyr Thr Leu Lys Pro His
            180                 185                 190

Pro Ala Leu Glu Pro Ala Phe His Leu Leu Pro Glu Asn Leu Leu Val
        195                 200                 205

Ser Gly Leu Gln Gln Ile Pro Gly Leu Leu Pro Ala His Gly Glu Ser
    210                 215                 220

Gly Asp Ala Leu Arg Lys Pro Arg Leu Gln Lys Pro Ile Thr Gly His
225                 230                 235                 240

Leu Asp Asp Leu Phe Phe Thr Leu Tyr Pro Ser Leu Glu Lys Phe Glu
                245                 250                 255

Glu Glu Leu Leu Glu Leu His Val Gln Asp His Phe Gln Glu Gly Cys
            260                 265                 270

Gly Pro Leu Asp Gly Gly Ala Leu Glu Ile Leu Glu Arg Arg Leu Arg
        275                 280                 285

Val Gly Val His Asn Gly Leu Gly Phe Val Gln Arg Pro Gln Val Val
    290                 295                 300

Val Leu Val Pro Glu Met Asp Val Ala Leu Thr Arg Ser Ala Ser Phe
305                 310                 315                 320

Ser Arg Lys Val Val Ser Ser Lys Thr Ser Gly Ser Gln Ala
                325                 330                 335
```

```
Leu Val Leu Arg Ser Arg Leu Arg Leu Pro Glu Met Val Gly His Pro
            340                 345                 350

Ala Phe Ala Val Ile Phe Gln Leu Glu Tyr Val Phe Ser Ser Pro Ala
            355                 360                 365

Gly Val Asp Gly Asn Ala Ala Ser Val Thr Ser Leu Ser Asn Leu Ala
            370                 375                 380

Cys Met His Met Val Arg Trp Ala Val Trp Asn Pro Leu Leu Glu Ala
385                 390                 395                 400

Asp Ser Gly Arg Val Thr Leu Pro Leu Gln Gly Ile Gln Pro Asn
                405                 410                 415

Pro Ser His Cys Leu Val Tyr Lys Val Pro Ser Ala Ser Met Ser Ser
            420                 425                 430

Glu Glu Val Lys Gln Val Glu Ser Gly Thr Leu Arg Phe Gln Phe Ser
            435                 440                 445

Leu Gly Ser Glu Glu His Leu Asp Ala Pro Thr Glu Pro Val Ser Gly
            450                 455                 460

Pro Lys Val Glu Arg Arg Pro Ser Arg Lys Pro Pro Thr Ser Pro Ser
465                 470                 475                 480

Ser Pro Pro Ala Pro Val Pro Arg Val Leu Ala Ala Pro Gln Asn Ser
                485                 490                 495

Pro Val Gly Pro Gly Leu Ser Ile Ser Gln Leu Ala Ala Ser Pro Arg
            500                 505                 510

Ser Pro Thr Gln His Cys Leu Ala Arg Pro Thr Ser Gln Leu Pro His
            515                 520                 525

Gly Ser Gln Ala Ser Pro Ala Gln Ala Gln Glu Phe Pro Leu Glu Ala
            530                 535                 540

Gly Ile Ser His Leu Glu Ala Asp Leu Ser Gln Thr Ser Leu Val Leu
545                 550                 555                 560

Glu Thr Ser Ile Ala Glu Gln Leu Gln Glu Leu Pro Phe Thr Pro Leu
                565                 570                 575

His Ala Pro Ile Val Val Gly Thr Gln Thr Arg Ser Ser Ala Gly Gln
            580                 585                 590

Pro Ser Arg Ala Ser Met Val Leu Leu Gln Ser Ser Gly Phe Pro Glu
            595                 600                 605

Ile Leu Asp Ala Asn Lys Gln Pro Ala Glu Ala Val Ser Ala Thr Glu
            610                 615                 620

Pro Val Thr Phe Asn Pro Gln Lys Glu Glu Ser Asp Cys Leu Gln Ser
625                 630                 635                 640

Asn Glu Met Val Leu Gln Phe Leu Ala Phe Ser Arg Val Ala Gln Asp
                645                 650                 655

Cys Arg Gly Thr Ser Trp Pro Lys Thr Val Tyr Phe Thr Phe Gln Phe
            660                 665                 670

Tyr Arg Phe Pro Pro Ala Thr Thr Pro Arg Leu Gln Leu Val Gln Leu
            675                 680                 685

Asp Glu Ala Gly Gln Pro Ser Ser Gly Ala Leu Thr His Ile Leu Val
            690                 695                 700

Pro Val Ser Arg Asp Gly Thr Phe Asp Ala Gly Ser Pro Gly Phe Gln
705                 710                 715                 720

Leu Arg Tyr Met Val Gly Pro Gly Phe Leu Lys Pro Gly Glu Arg Arg
                725                 730                 735

Cys Phe Ala Arg Tyr Leu Ala Val Gln Thr Leu Gln Ile Asp Val Trp
            740                 745                 750
```

-continued

```
Asp Gly Asp Ser Leu Leu Ile Gly Ser Ala Ala Val Gln Met Lys
        755                 760                 765

His Leu Leu Arg Gln Gly Arg Pro Ala Val Gln Ala Ser His Glu Leu
        770                 775                 780

Glu Val Val Ala Thr Glu Tyr Glu Gln Asp Asn Met Val Val Ser Gly
785                 790                 795                 800

Asp Met Leu Gly Phe Gly Arg Val Lys Pro Ile Gly Val His Ser Val
                805                 810                 815

Val Lys Gly Arg Leu His Leu Thr Leu Ala Asn Val Gly His Pro Cys
                820                 825                 830

Glu Gln Lys Val Arg Gly Cys Ser Thr Leu Pro Pro Ser Arg Ser Trp
            835                 840                 845

Val Ile Ser Asn Asp Gly Ala Ser Arg Phe Ser Gly Gly Ser Leu Leu
        850                 855                 860

Thr Thr Gly Ser Ser Arg Arg Lys His Val Val Gln Ala Gln Lys Leu
865                 870                 875                 880

Ala Asp Val Asp Ser Glu Leu Ala Ala Met Leu Leu Thr His Ala Arg
                885                 890                 895

Gln Gly Lys Gly Pro Gln Asp Val Ser Arg Glu Ser Asp Ala Thr Arg
            900                 905                 910

Arg Arg Lys Leu Glu Arg Met Arg Ser Val Arg Leu Gln Glu Ala Gly
        915                 920                 925

Gly Asp Leu Gly Arg Arg Gly Thr Ser Val Leu Ala Gln Gln Ser Val
        930                 935                 940

Arg Thr Gln His Leu Arg Asp Leu Gln Val Ile Ala Ala Tyr Arg Glu
945                 950                 955                 960

Arg Thr Lys Ala Glu Ser Ile Ala Ser Leu Leu Ser Leu Ala Ile Thr
                965                 970                 975

Thr Glu His Thr Leu His Ala Thr Leu Gly Val Ala Glu Phe Phe Glu
                980                 985                 990

Phe Val Leu Lys Asn Pro His Asn Thr Gln His Thr Val Thr Val Glu
        995                 1000                1005

Ile Asp Asn Pro Glu Leu Ser Val Ile Val Asp Ser Gln Glu Trp
    1010                1015                1020

Arg Asp Phe Lys Gly Ala Ala Gly Leu His Thr Pro Val Glu Glu
    1025                1030                1035

Asp Met Phe His Leu Arg Gly Ser Leu Ala Pro Gln Leu Tyr Leu
    1040                1045                1050

Arg Pro His Glu Thr Ala His Val Pro Phe Lys Phe Gln Ser Phe
    1055                1060                1065

Ser Ala Gly Gln Leu Ala Met Val Gln Ala Ser Pro Gly Leu Ser
    1070                1075                1080

Asn Glu Lys Gly Met Asp Ala Val Ser Pro Trp Lys Ser Ser Ala
    1085                1090                1095

Val Pro Thr Lys His Ala Lys Val Leu Phe Arg Ala Ser Gly Gly
    1100                1105                1110

Lys Pro Ile Ala Val Leu Cys Leu Thr Val Glu Leu Gln Pro His
    1115                1120                1125

Val Val Asp Gln Val Phe Arg Phe Tyr His Pro Glu Leu Ser Phe
    1130                1135                1140

Leu Lys Lys Ala Ile Arg Leu Pro Pro Trp His Thr Phe Pro Gly
    1145                1150                1155

Ala Pro Val Gly Met Leu Gly Glu Asp Pro Pro Val His Val Arg
```

```
                1160                1165                1170
    Cys Ser Asp Pro Asn Val Ile Cys Glu Thr Gln Asn  Val Gly Pro
        1175                1180                1185

Gly Glu Pro Arg Asp Ile Phe Leu Lys Val Ala Ser  Gly Pro Ser
        1190                1195                1200

Pro Glu Ile Lys Asp Phe Phe Val Ile Ile Tyr Ser  Asp Arg Trp
        1205                1210                1215

Leu Ala Thr Pro Thr Gln Thr Trp Gln Val Tyr Leu  His Ser Leu
        1220                1225                1230

Gln Arg Val Asp Val Ser Cys Val Ala Gly Gln Leu  Thr Arg Leu
        1235                1240                1245

Ser Leu Val Leu Arg Gly Thr Gln Thr Val Arg Lys  Val Arg Ala
        1250                1255                1260

Phe Thr Ser His Pro Gln Glu Leu Lys Thr Asp Pro  Lys Gly Val
        1265                1270                1275

Phe Val Leu Pro Pro Arg Gly Val Gln Asp Leu His  Val Gly Val
        1280                1285                1290

Arg Pro Leu Arg Ala Gly Ser Arg Phe Val His Leu  Asn Leu Val
        1295                1300                1305

Asp Val Asp Cys His Gln Leu Val Ala Ser Trp Leu  Val Cys Leu
        1310                1315                1320

Cys Cys Arg Gln Pro Leu Ile Ser Lys Ala Phe Glu  Ile Met Leu
        1325                1330                1335

Ala Ala Gly Glu Gly Lys Gly Val Asn Lys Arg Ile  Thr Tyr Thr
        1340                1345                1350

Asn Pro Tyr Pro Ser Arg Arg Thr Phe His Leu His  Ser Asp His
        1355                1360                1365

Pro Glu Leu Leu Arg Phe Arg Glu Asp Ser Phe Gln  Val Gly Gly
        1370                1375                1380

Gly Glu Thr Tyr Thr Ile Gly Leu Gln Phe Ala Pro  Ser Gln Arg
        1385                1390                1395

Val Gly Glu Glu Glu Ile Leu Ile Tyr Ile Asn Asp  His Glu Asp
        1400                1405                1410

Lys Asn Glu Glu Ala Phe Cys Val Lys Val Ile Tyr  Gln
        1415                1420                1425

<210> SEQ ID NO 19
<211> LENGTH: 2636
<212> TYPE: DNA
<213> ORGANISM: Homo sapiens

<400> SEQUENCE: 19
gacgcgaggc gggttcttgg actgagtgtg cggcgcggtg cgccgccttc cgaggctcct      60
cccgcgggtg gcagcggacg gggcgcgccc ctcggccagt cctcggtcct caggcttgtg     120
gctccgttga gcaccggccg ccgggcctct gggtccgtcg agtggagact ctctgaaaag     180
cgtgggctcc gtggcctccg cgcggccgc ggcgggtcgg tctcctagat catccgggaa     240
gcccacggga ccctcaggcg ggcaggatga acgactggca caggatcttc acccaaaacg     300
tgcttgtccc tccccaccca cagagagcgc gccagccttg gaaggaatcc acggcattcc     360
agtgtgtcct caagtggctg gacggaccgg taattaggca gggcgtgctg gaggtactgt     420
cagaggttga atgccatctg cgagtgtctt tctttgatgt cacctaccgg cacttctttg     480
ggaggacgtg gaaaaccaca gtgaagccga cgaagagacc gccgtccagg atcgtcttta     540
```

```
atgagccctt gtattttcac acatccctaa accacccctca tatcgtggct gtggtggaag    600
tggtcgctga gggcaagaaa cgggatggga gcctccagac attgtcctgt gggtttggaa    660
ttcttcggat cttcagcaac cagccggact ctcctatctc tgcttcccag gacaaaaggt    720
tgcggctgta ccatggcacc cccagagccc tcctgcaccc gcttctccag gaccccgcag    780
agcaaaacag acacatgacc ctcattgaga actgcagcct gcagtacacg ctgaagccac    840
acccggccct ggagcctgcg ttccaccttc ttcctgagaa ccttctggtg tctggtctgc    900
agcagatacc tggcctgctt ccagctcatg gagaatccgg cgacgctctc cgaaagcctc    960
gcctccagaa gcccatcacg gggcacttgg atgacttatt cttcaccctg tacccctccc   1020
tggagaagtt tgaggaagag ctgctggagc tccacgtcca ggaccacttc caggagggat   1080
gtggcccact ggacggtggt gccctggaga tcctggagcg cgcctgcgt gtgggcgtgc    1140 acaatggtct gggcttcgtg cagaggccgc aggtcgttgt actggtgcct gagatggatg   1200
tggccttgac gcgctcagct agcttcagca ggaaagtggt ctcctcttcc aagaccagct   1260
ccgggagcca agctctggtt ttgagaagcc gcctccgcct cccagagatg gtcggccacc   1320
ctgcatttgc ggtcatcttc cagctggagt acgtgttcag cagccctgca ggagtggacg   1380
gcaatgcagc ttcggtcacc tctctgtcca acctggcatg catgcacatg gtccgctggg   1440
ctgtttggaa cccctgctg gaagctgatt ctggaagggt gaccctgcct ctgcagggtg    1500
ggatccagcc caacccctcg cactgtctgg tctacaaggt accctcagcc agcatgagct   1560
ctgaagaggt gaagcaggtg gagtcgggta cactccggtt ccagttctcg ctgggctcag   1620
aagaacacct ggatgcaccc acggagcctg tcagtggccc caaagtggag cggcggcctt   1680
ccaggaaacc acccacgtcc ccttcgagcc cgccagcgcc agtacctcga gttctcgctg   1740
ccccgcagaa ctcacctgtg ggaccagggt tgtcaatttc ccagctggcg gcctccccgc   1800
ggtccccgac tcagcactgc ttggccaggc ctacttcaca gctaccccat ggctctcagg   1860
cctccccggc ccaggcacag gagttcccgt tggaggccgg tatctcccac ctggaagccg   1920
acctgagcca gacctccctg gtcctggaaa catccattgc cgaacagtta caggagctgc   1980
cgttcacgcc tttgcatgcc cctattgttg tgggaaccca gaccaggagc tctgcagggc   2040
agccctcgag agcctccatg gtgctcctgc agtcctccgg cttccccgag attctggatg   2100
ccaataaaca gccagccgag gctgtcagcg ctacagaacc tgtgacgttt aaccctcaga   2160
aggaagaatc agattgtcta caaagcaacg agatggtgct acagtttctt gcctttagca   2220
gagtggccca ggactgccga ggaacatcat ggccaaagac tgtgtatttc accttccagt   2280
tctaccgctt cccacccgca acgacgccac gactgcagct ggtccagctg gatgaggccg   2340
gccagcccag ctctggcgcc ctgacccaca tcctcgtgcc tgtgagcaga gatggcacct   2400
ttgatgctgg gtctcctggc ttccagctga ggtacatggt gggccctggg ttcctgaagc   2460
caggtgagcg cgctgctttt gcccgctacc tggccgtgca gacctgcag attgacgtct   2520 gggacggaga ctccctgctg ctcatcggat ctgctgccgt ccagatgaag catctcctcc   2580
gccaaggccg gccggctgtg caggcctccc acgagcttga ggtcgtggca acttaa       2636
```

<210> SEQ ID NO 20
<211> LENGTH: 790
<212> TYPE: PRT
<213> ORGANISM: Homo sapiens
<220> FEATURE:
<221> NAME/KEY: misc_feature
<222> LOCATION: (790)..(790)
<223> OTHER INFORMATION: Xaa can be any naturally occurring amino acid

<400> SEQUENCE: 20

```
Met Asn Asp Trp His Arg Ile Phe Thr Gln Asn Val Leu Val Pro Pro
1               5                   10                  15
His Pro Gln Arg Ala Arg Gln Pro Trp Lys Glu Ser Thr Ala Phe Gln
            20                  25                  30
Cys Val Leu Lys Trp Leu Asp Gly Pro Val Ile Arg Gln Gly Val Leu
        35                  40                  45
Glu Val Leu Ser Glu Val Glu Cys His Leu Arg Val Ser Phe Phe Asp
    50                  55                  60
Val Thr Tyr Arg His Phe Phe Gly Arg Thr Trp Lys Thr Thr Val Lys
65                  70                  75                  80
Pro Thr Lys Arg Pro Pro Ser Arg Ile Val Phe Asn Glu Pro Leu Tyr
                85                  90                  95
Phe His Thr Ser Leu Asn His Pro His Ile Val Ala Val Val Glu Val
            100                 105                 110
Val Ala Glu Gly Lys Lys Arg Asp Gly Ser Leu Gln Thr Leu Ser Cys
        115                 120                 125
Gly Phe Gly Ile Leu Arg Ile Phe Ser Asn Gln Pro Asp Ser Pro Ile
    130                 135                 140
Ser Ala Ser Gln Asp Lys Arg Leu Arg Leu Tyr His Gly Thr Pro Arg
145                 150                 155                 160
Ala Leu Leu His Pro Leu Leu Gln Asp Pro Ala Glu Gln Asn Arg His
                165                 170                 175
Met Thr Leu Ile Glu Asn Cys Ser Leu Gln Tyr Thr Leu Lys Pro His
            180                 185                 190
Pro Ala Leu Glu Pro Ala Phe His Leu Leu Pro Glu Asn Leu Leu Val
        195                 200                 205
Ser Gly Leu Gln Gln Ile Pro Gly Leu Leu Pro Ala His Gly Glu Ser
    210                 215                 220
Gly Asp Ala Leu Arg Lys Pro Arg Leu Gln Lys Pro Ile Thr Gly His
225                 230                 235                 240
Leu Asp Asp Leu Phe Phe Thr Leu Tyr Pro Ser Leu Glu Lys Phe Glu
                245                 250                 255
Glu Glu Leu Leu Glu Leu His Val Gln Asp His Phe Gln Glu Gly Cys
            260                 265                 270
Gly Pro Leu Asp Gly Gly Ala Leu Glu Ile Leu Glu Arg Arg Leu Arg
        275                 280                 285
Val Gly Val His Asn Gly Leu Gly Phe Val Gln Arg Pro Gln Val Val
    290                 295                 300
Val Leu Val Pro Glu Met Asp Val Ala Leu Thr Arg Ser Ala Ser Phe
305                 310                 315                 320
Ser Arg Lys Val Val Ser Ser Lys Thr Ser Ser Gly Ser Gln Ala
                325                 330                 335
Leu Val Leu Arg Ser Arg Leu Arg Leu Pro Glu Met Val Gly His Pro
            340                 345                 350
Ala Phe Ala Val Ile Phe Gln Leu Glu Tyr Val Phe Ser Ser Pro Ala
        355                 360                 365
Gly Val Asp Gly Asn Ala Ala Ser Val Thr Ser Leu Ser Asn Leu Ala
    370                 375                 380
Cys Met His Met Val Arg Trp Ala Val Trp Asn Pro Leu Leu Glu Ala
385                 390                 395                 400
Asp Ser Gly Arg Val Thr Leu Pro Leu Gln Gly Gly Ile Gln Pro Asn
```

```
                405                 410                 415
Pro Ser His Cys Leu Val Tyr Lys Val Pro Ala Ser Met Ser Ser
            420                 425                 430

Glu Glu Val Lys Gln Val Glu Ser Gly Thr Leu Arg Phe Gln Phe Ser
            435                 440                 445

Leu Gly Ser Glu Glu His Leu Asp Ala Pro Thr Glu Pro Val Ser Gly
        450                 455                 460

Pro Lys Val Glu Arg Arg Pro Ser Arg Lys Pro Thr Ser Pro Ser
465                 470                 475                 480

Ser Pro Pro Ala Pro Val Pro Arg Val Leu Ala Ala Pro Gln Asn Ser
            485                 490                 495

Pro Val Gly Pro Gly Leu Ser Ile Ser Gln Leu Ala Ala Ser Pro Arg
        500                 505                 510

Ser Pro Thr Gln His Cys Leu Ala Arg Pro Thr Ser Gln Leu Pro His
        515                 520                 525

Gly Ser Gln Ala Ser Pro Ala Gln Ala Gln Glu Phe Pro Leu Glu Ala
        530                 535                 540

Gly Ile Ser His Leu Glu Ala Asp Leu Ser Gln Thr Ser Leu Val Leu
545                 550                 555                 560

Glu Thr Ser Ile Ala Glu Gln Leu Gln Glu Leu Pro Phe Thr Pro Leu
                565                 570                 575

His Ala Pro Ile Val Val Gly Thr Gln Thr Arg Ser Ser Ala Gly Gln
                580                 585                 590

Pro Ser Arg Ala Ser Met Val Leu Leu Gln Ser Ser Gly Phe Pro Glu
        595                 600                 605

Ile Leu Asp Ala Asn Lys Gln Pro Ala Glu Ala Val Ser Ala Thr Glu
        610                 615                 620

Pro Val Thr Phe Asn Pro Gln Lys Glu Glu Ser Asp Cys Leu Gln Ser
625                 630                 635                 640

Asn Glu Met Val Leu Gln Phe Leu Ala Phe Ser Arg Val Ala Gln Asp
                645                 650                 655

Cys Arg Gly Thr Ser Trp Pro Lys Thr Val Tyr Phe Thr Phe Gln Phe
                660                 665                 670

Tyr Arg Phe Pro Pro Ala Thr Thr Pro Arg Leu Gln Leu Val Gln Leu
        675                 680                 685

Asp Glu Ala Gly Gln Pro Ser Ser Gly Ala Leu Thr His Ile Leu Val
        690                 695                 700

Pro Val Ser Arg Asp Gly Thr Phe Asp Ala Gly Ser Pro Gly Phe Gln
705                 710                 715                 720

Leu Arg Tyr Met Val Gly Pro Gly Phe Leu Lys Pro Gly Glu Arg Arg
                725                 730                 735

Cys Phe Ala Arg Tyr Leu Ala Val Gln Thr Leu Gln Ile Asp Val Trp
            740                 745                 750

Asp Gly Asp Ser Leu Leu Leu Ile Gly Ser Ala Ala Val Gln Met Lys
            755                 760                 765

His Leu Leu Arg Gln Gly Arg Pro Ala Val Gln Ala Ser His Glu Leu
        770                 775                 780

Glu Val Val Ala Thr Xaa
785                 790

<210> SEQ ID NO 21
<211> LENGTH: 3558
<212> TYPE: DNA
<213> ORGANISM: Homo sapiens
```

<400> SEQUENCE: 21

```
ggttgctccc ggttgctaag aagactatga acaagtcaga gaacctgctg tttgctggtt      60
catcattagc atcacaagtc catgctgctg ccgttaatgg agataagggt gctctacaga     120
ggctcatcgt aggaaactct gctcttaaag acaaagaaga tcagtttggg agaacaccac     180
ttatgtattg cgtgttggct gacagattgg attgtgcaga tgctcttctg aaggcaggag     240
cagatgtgaa taaaactgac catagccaga gaacagccct ccatcttgca gcccagaagg     300
gaaattatcg tttcatgaaa ctcttactta cacgcagagc aaactggatg caaaaggatc     360
tggaagagat gactcctttg cacttgacca cccggcacag gagccctaag tgtttggcac     420
ttctgctgaa gttatggca ccaggagaag tggatacaca ggataaaaac aagcaaacag     480
ctctgcattg gagtgcctac tacaataacc ctgagcatgt gaagctgctc atcaagcatg     540
attctaacat tgggattcct gatgttgaag gcaagatccc acttcactgg gcagccaacc     600
ataaagatcc aagtgctgtt cacacagtga gatgcattct ggatgctgct ccaacagagt     660
ctttactgaa ctggcaagac tacgagggtc gaactcctct tcactttgca gttgctgatg     720
ggaatgtgac cgtggttgat gtcttgacct catatgaaag ctgcaatata acgtcttatg     780
ataacttatt tcgaacccca ctgcactggg cagctttatt aggccatgca cagattgtcc     840
atctcctttt agaaagaaat aagtctggaa ctatcccatc tgacagccaa ggagccacac     900
ctttgcacta tgctgctcag agtaactttg ctgaaacggt taaagtgttt ttaaaacatc     960
cttcagtgaa agatgattca gacctggaag gaagaacatc ctttatgtgg gcagctggca    1020
aaggcagtga tgatgtcctt agaactatgc tgagcttaaa atcggacata gatattaaca    1080
tggctgacaa atatgggagt acagctttgc atgctgctgc tctttctggc catgtcagca    1140
ccgtgaagtt attactggaa aataatgctc aagtagatgc tactgatgtt atgaaacata    1200
ctccactttt ccgagcctgt gagatgggac acaaagatgt gattcagaca ctcattaaag    1260
gtggagcaag ggtagatcta gttgaccaag atggacattc tcttctacat tgggcagcac    1320
tgggaggaaa tgctgatgtt tgccagatat aatagaaaa taagatcaat ccaaatgtcc    1380
aggattatgc aggaagaacc cctttgcagt gtgcagcata tggaggctat atcaactgca    1440
tggcagttct catggaaaac aatgcagacc ctaacattca agacaaagag ggaagaacag    1500
ctttgcattg gtcctgcaac aatggatacc ttgatgccat taaattactg ctagactttg    1560
ctgctttccc taatcagatg gaaaacaatg aagagagata cacacccctt gattatgctt    1620
tgcttggtga gcgccatgaa gtgatccagt tcatgttgga gcacggtgcc ctgtccatcg    1680
cagcccataca agacatcgcc gccttcaaaa tccaagctgt ctacaaaggg tacaaggtca    1740
gaaaagcctt ccgagacagg aaaaatctcc tcatgaagca tgaacagttg agaaaagatg    1800
ctgctgccaa aaagcgagag gaagaaaaca acgaaaaga ggcagaacag caaaaggaa     1860
ggcggagccc agattcctgc agaccccagg cccttccctg tctgcctagc acccaggatg    1920
tgcccagcag gcagagccgg gcccccagca agcagcctcc tgctggcaac gtggcccaag    1980
gccctgagcc aagagacagc agaggatctc caggagggtc tctaggcgga gccctccaga    2040
aggagcagca tgtttcctca gatttgcagg gaacaaactc cagaaggcca atgaaacag     2100
ccagagaaca ttctaaaggc caatctgctt gtgtccactt cagacccaat gaaggcagtg    2160
atggaagcag gcatccagga gttccctctg ttgagaagtc cagaggtgag acagctggcg    2220
atgagcggtg tgcaaagggg aaaggtttcg tgaagcagcc ctcctgtatc agggtggctg    2280
```

```
ggcctgatga gaaaggagag gactccaggc gggcaggtgc aagccttcca ccgcacgata    2340
gccactggaa gcccagcagg cggcatgaca cagaacccaa ggccaaatgt gccccccaga    2400
aaaggcgcac tcaagagctc agaggaggaa ggtgctctcc ggctggttct agccgccctg    2460
gcagtgcccg gggggaggcg gtccatgctg gcagaatcc tccccaccat cgtacaccaa     2520
gaaacaaagt gacacaagcc aagctcacag gagggctcta ttcacatttg ccacagagca    2580
cagaggagtt gaggtcagga gctaggaggc tggagacatc taccctgtcc gaggactttc    2640
aggtatctaa ggagactgat ccagcacctg gtcccctctc tgggcagagt gtgaatattg    2700
accttctccc cgtagagctc cgactgcaga taattcagag agaacgaagg aggaaggagc    2760
tgtttcgcaa aaagaacaag gcagcagcag tcatccagcg cgcctggcga agctaccagc    2820
tcaggaagca cctgtcccac cttcggcata tgaagcagct tggagctgga gatgtgggaca   2880 gatggaggca agagtctaca gcattgctcc tccaggtttg gaggaaggaa ctggaactaa    2940
aattccccca aaccactgca gtaagcaagg cccccaagag tccatccaag ggcacctcag    3000
gcacaaagtc caccaagcac tcagtgctta agcaaatcta tggttgttct cacgaaggga    3060
aaatacatca tcctacaaga tctgtaaaag cctcttctgt gctgcgtctc aactcagtga    3120
gcaacctaca gtgtatacat ctccttgaga acagtggaag atcaaagaac ttttcttata    3180
acctgcaatc agctactcag ccaaaaaaca aaacaaaacc ttgactgcct atggaggaag    3240
actgtgttcg ggggagctgg catagctagt gcagagttca gattttctgc tgataatctt    3300
ttacaccttg ggaaaacttt aatatccgta cctgaaggct gattcaccta aaaatgtgtt    3360
aactgaaaga aaatgtcaga atgtttcctt tctgctctta cacagcattg ttttgtcaat    3420
caacacagcc tgcactgaaa ggacctgcat agactatgtc tgtgcaaagt gcctgagtgt    3480
ctgctttcac ctcagtctgt acagttggaa atgagaattc ataattaaca gcaaaatcta    3540
aggaaaacta aaataaaa                                                  3558
```

<210> SEQ ID NO 22
<211> LENGTH: 1065
<212> TYPE: PRT
<213> ORGANISM: Homo sapiens

<400> SEQUENCE: 22

```
Met Asn Lys Ser Glu Asn Leu Leu Phe Ala Gly Ser Ser Leu Ala Ser
1               5                   10                  15

Gln Val His Ala Ala Ala Val Asn Gly Asp Lys Gly Ala Leu Gln Arg
            20                  25                  30

Leu Ile Val Gly Asn Ser Ala Leu Lys Asp Lys Glu Asp Gln Phe Gly
        35                  40                  45

Arg Thr Pro Leu Met Tyr Cys Val Leu Ala Asp Arg Leu Asp Cys Ala
    50                  55                  60

Asp Ala Leu Leu Lys Ala Gly Ala Asp Val Asn Lys Thr Asp His Ser
65                  70                  75                  80

Gln Arg Thr Ala Leu His Leu Ala Ala Gln Lys Gly Asn Tyr Arg Phe
                85                  90                  95

Met Lys Leu Leu Leu Thr Arg Arg Ala Asn Trp Met Gln Lys Asp Leu
            100                 105                 110

Glu Glu Met Thr Pro Leu His Leu Thr Thr Arg His Arg Ser Pro Lys
        115                 120                 125

Cys Leu Ala Leu Leu Leu Lys Phe Met Ala Pro Gly Glu Val Asp Thr
    130                 135                 140
```

```
Gln Asp Lys Asn Lys Gln Thr Ala Leu His Trp Ser Ala Tyr Tyr Asn
145                 150                 155                 160

Asn Pro Glu His Val Lys Leu Leu Ile Lys His Asp Ser Asn Ile Gly
            165                 170                 175

Ile Pro Asp Val Glu Gly Lys Ile Pro Leu His Trp Ala Ala Asn His
        180                 185                 190

Lys Asp Pro Ser Ala Val His Thr Val Arg Cys Ile Leu Asp Ala Ala
    195                 200                 205

Pro Thr Glu Ser Leu Leu Asn Trp Gln Asp Tyr Glu Gly Arg Thr Pro
210                 215                 220

Leu His Phe Ala Val Ala Asp Gly Asn Val Thr Val Asp Val Leu
225                 230                 235                 240

Thr Ser Tyr Glu Ser Cys Asn Ile Thr Ser Tyr Asp Asn Leu Phe Arg
                245                 250                 255

Thr Pro Leu His Trp Ala Ala Leu Leu Gly His Ala Gln Ile Val His
            260                 265                 270

Leu Leu Leu Glu Arg Asn Lys Ser Gly Thr Ile Pro Ser Asp Ser Gln
        275                 280                 285

Gly Ala Thr Pro Leu His Tyr Ala Ala Gln Ser Asn Phe Ala Glu Thr
290                 295                 300

Val Lys Val Phe Leu Lys His Pro Ser Val Lys Asp Asp Ser Asp Leu
305                 310                 315                 320

Glu Gly Arg Thr Ser Phe Met Trp Ala Ala Gly Lys Gly Ser Asp Asp
                325                 330                 335

Val Leu Arg Thr Met Leu Ser Leu Lys Ser Asp Ile Asp Ile Asn Met
            340                 345                 350

Ala Asp Lys Tyr Gly Gly Thr Ala Leu His Ala Ala Leu Ser Gly
        355                 360                 365

His Val Ser Thr Val Lys Leu Leu Leu Glu Asn Asn Ala Gln Val Asp
370                 375                 380

Ala Thr Asp Val Met Lys His Thr Pro Leu Phe Arg Ala Cys Glu Met
385                 390                 395                 400

Gly His Lys Asp Val Ile Gln Thr Leu Ile Lys Gly Gly Ala Arg Val
                405                 410                 415

Asp Leu Val Asp Gln Asp Gly His Ser Leu Leu His Trp Ala Ala Leu
            420                 425                 430

Gly Gly Asn Ala Asp Val Cys Gln Ile Leu Ile Glu Asn Lys Ile Asn
        435                 440                 445

Pro Asn Val Gln Asp Tyr Ala Gly Arg Thr Pro Leu Gln Cys Ala Ala
450                 455                 460

Tyr Gly Gly Tyr Ile Asn Cys Met Ala Val Leu Met Glu Asn Asn Ala
465                 470                 475                 480

Asp Pro Asn Ile Gln Asp Lys Glu Gly Arg Thr Ala Leu His Trp Ser
                485                 490                 495

Cys Asn Asn Gly Tyr Leu Asp Ala Ile Lys Leu Leu Leu Asp Phe Ala
            500                 505                 510

Ala Phe Pro Asn Gln Met Glu Asn Asn Glu Glu Arg Tyr Thr Pro Leu
        515                 520                 525

Asp Tyr Ala Leu Leu Gly Glu Arg His Glu Val Ile Gln Phe Met Leu
530                 535                 540

Glu His Gly Ala Leu Ser Ile Ala Ala Ile Gln Asp Ile Ala Ala Phe
545                 550                 555                 560

Lys Ile Gln Ala Val Tyr Lys Gly Tyr Lys Val Arg Lys Ala Phe Arg
```

-continued

```
                565                 570                 575
Asp Arg Lys Asn Leu Leu Met Lys His Glu Gln Leu Arg Lys Asp Ala
            580                 585                 590
Ala Ala Lys Lys Arg Glu Glu Glu Asn Lys Arg Lys Glu Ala Glu Gln
        595                 600                 605
Gln Lys Gly Arg Arg Ser Pro Asp Ser Cys Arg Pro Gln Ala Leu Pro
    610                 615                 620
Cys Leu Pro Ser Thr Gln Asp Val Pro Ser Arg Gln Ser Arg Ala Pro
625                 630                 635                 640
Ser Lys Gln Pro Pro Ala Gly Asn Val Ala Gln Gly Pro Glu Pro Arg
            645                 650                 655
Asp Ser Arg Gly Ser Pro Gly Gly Ser Leu Gly Gly Ala Leu Gln Lys
        660                 665                 670
Glu Gln His Val Ser Ser Asp Leu Gln Gly Thr Asn Ser Arg Arg Pro
    675                 680                 685
Asn Glu Thr Ala Arg Glu His Ser Lys Gly Gln Ser Ala Cys Val His
690                 695                 700
Phe Arg Pro Asn Glu Gly Ser Asp Gly Ser Arg His Pro Gly Val Pro
705                 710                 715                 720
Ser Val Glu Lys Ser Arg Gly Glu Thr Ala Gly Asp Glu Arg Cys Ala
            725                 730                 735
Lys Gly Lys Gly Phe Val Lys Gln Pro Ser Cys Ile Arg Val Ala Gly
        740                 745                 750
Pro Asp Glu Lys Gly Asp Ser Arg Arg Ala Gly Ala Ser Leu Pro
    755                 760                 765
Pro His Asp Ser His Trp Lys Pro Ser Arg Arg His Asp Thr Glu Pro
770                 775                 780
Lys Ala Lys Cys Ala Pro Gln Lys Arg Arg Thr Gln Glu Leu Arg Gly
785                 790                 795                 800
Gly Arg Cys Ser Pro Ala Gly Ser Ser Arg Pro Gly Ser Ala Arg Gly
            805                 810                 815
Glu Ala Val His Ala Gly Gln Asn Pro Pro His His Arg Thr Pro Arg
        820                 825                 830
Asn Lys Val Thr Gln Ala Lys Leu Thr Gly Gly Leu Tyr Ser His Leu
    835                 840                 845
Pro Gln Ser Thr Glu Glu Leu Arg Ser Gly Ala Arg Arg Leu Glu Thr
        850                 855                 860
Ser Thr Leu Ser Glu Asp Phe Gln Val Ser Lys Glu Thr Asp Pro Ala
865                 870                 875                 880
Pro Gly Pro Leu Ser Gly Gln Ser Val Asn Ile Asp Leu Leu Pro Val
            885                 890                 895
Glu Leu Arg Leu Gln Ile Ile Gln Arg Glu Arg Arg Lys Glu Leu
        900                 905                 910
Phe Arg Lys Lys Asn Lys Ala Ala Ala Val Ile Gln Arg Ala Trp Arg
    915                 920                 925
Ser Tyr Gln Leu Arg Lys His Leu Ser His Leu Arg His Met Lys Gln
        930                 935                 940
Leu Gly Ala Gly Asp Val Asp Arg Trp Arg Gln Glu Ser Thr Ala Leu
945                 950                 955                 960
Leu Leu Gln Val Trp Arg Lys Glu Leu Glu Leu Lys Phe Pro Gln Thr
            965                 970                 975
Thr Ala Val Ser Lys Ala Pro Lys Ser Pro Ser Lys Gly Thr Ser Gly
        980                 985                 990
```

```
Thr Lys Ser Thr Lys His Ser Val Leu Lys Gln Ile Tyr Gly Cys Ser
        995                 1000                1005

His Glu Gly Lys Ile His His Pro Thr Arg Ser Val Lys Ala Ser
    1010            1015                 1020

Ser Val Leu Arg Leu Asn Ser Val Ser Asn Leu Gln Cys Ile His
    1025                1030                1035

Leu Leu Glu Asn Ser Gly Arg Ser Lys Asn Phe Ser Tyr Asn Leu
    1040                1045                1050

Gln Ser Ala Thr Gln Pro Lys Asn Lys Thr Lys Pro
    1055                1060                1065

<210> SEQ ID NO 23
<211> LENGTH: 3558
<212> TYPE: DNA
<213> ORGANISM: Homo sapiens

<400> SEQUENCE: 23
ggttgctccc ggttgctaag aagactatga acaagtcaga gaacctgctg tttgctggtt      60
catcattagc atcacaagtc catgctgctg ccgttaatgg agataagggt gctctacaga     120
ggctcatcgt aggaaactct gctcttaaag acaaagaaga tcagtttggg agaacaccac     180
ttatgtattg cgtgttggct gacagattgg attgtgcaga tgctcttctg aaggcaggag     240
cagatgtgaa taaaactgac catagccaga gaacagccct ccatcttgca gcccagaagg     300
gaaattatcg tttcatgaaa ctcttactta cacgcagagc aaactggatg caaaaggatc     360
tggaagagat gactcctttg cacttgacca cccggcacag gagccctaag tgtttggcac     420
ttctgctgaa gttatggca ccaggagaag tggatacaca ggataaaaac aagcaaacag     480
ctctgcattg gagtgcctac tacaataacc ctgagcatgt gaagctgctc atcaagcatg     540
attctaacat tgggattcct gatgttgaag gcaagatccc acttcactgg gcagccaacc     600
ataaagatcc aagtgctgtt cacacagtga gatgcattct ggatgctgct ccaacagagt     660
ctttactgaa ctggcaagac tacgagggtc gaactcctct tcactttgca gttgctgatg     720
ggaatgtgac cgtggttgat gtcttgacct catatgaaag ctgcaatata acgtcttatg     780
ataacttatt tcgaaccccca ctgcactggg cagctttatt aggccatgca cagattgtcc     840
atctcctttt agaaagaaat aagtctggaa ctatcccatc tgacagccaa ggagccacac     900
ctttgcacta tgctgctcag agtaactttg ctgaaacggt taaagtgttt ttaaaacatc     960
cttcagtgaa agatgattca gacctggaag aagaacatcc ctttatgtgg gcagctggca    1020
aaggcagtga tgatgtcctt agaactatgc tgagcttaaa atcggacata gatattaaca    1080
tggctgacaa atatggaggt acagctttgc atgctgctgc tctttctggc catgtcagca    1140
ccgtgaagtt attactggaa ataatgctc aagtagatgc tactgatgtt atgaaacata    1200
ctccactttt ccgagcctgt gagatgggac acaaagatgt gattcagaca ctcattaaag    1260
gtggagcaag ggtagatcta gttgaccaag atggacattc tcttctacat tgggcagcac    1320
tgggaggaaa tgctgatgtt tgccagatat aatagaaaa taagatcaat ccaaatgtcc    1380
aggattatgc aggaagaacc cctttgcagt gtgcagcata tggaggctat atcaactgca    1440
tggcagttct catggaaaac aatgcagacc ctaacattca agacaaagag ggaagaacag    1500
ctttgcattg gtcctgcaac aatggatacc ttgatgccat taaattactg ctagactttg    1560
ctgctttccc taatcagatg gaaaacaatg aagagagata cacacccctt gattatgctt    1620
tgcttggtga gcgccatgaa gtgatccagt tcatgttgga gcacggtgcc ctgtccatcg    1680
```

```
cagccataca agacatcgcc gccttcaaaa tccaagctgt ctacaaaggg tacaaggtca    1740
gaaaagcctt ccgagacagg aaaaatctcc tcatgaagca tgaacagttg agaaaagatg    1800
ctgctgccaa aaagcgagag gaagaaaaca acgaaaaga ggcagaacag caaaaaggaa    1860
ggcggagccc agattcctgc agaccccagg cccttccctg tctgcctagc acccaggatg    1920
tgcccagcag gcagagccgg gccccagca agcagcctcc tgctggcaac gtggcccaag    1980
gccctgagcc aagagacagc agaggatctc caggagggtc tctaggcgga gccctccaga    2040
aggagcagca tgtttcctca gatttgcagg gaacaaactc cagaaggcca atgaaacag    2100
ccagagaaca ttctaaaggc caatctgctt gtgtccactt cagacccaat gaaggcagtg    2160
atggaagcag gcatccagga gttccctctg ttgagaagtc cagaggtgag acagctggcg    2220
atgagcggtg tgcaaagggg aaaggtttcg tgaagcagcc ctcctgtatc agggtggctg    2280
ggcctgatga aaaggagag gactccaggc gggcaggtgc aagccttcca ccgcacgata    2340
gccactggaa gcccagcagg cggcatgaca cagaacccaa ggccaaatgt gccccccaga    2400
aaaggcgcac tcaagagctc agaggaggaa ggtgctctcc ggctggttct agccgccctg    2460
gcagtgcccg gggggaggcg gtccatgctg ggcagaatcc tccccaccat cgtacaccaa    2520
gaaacaaagt gacacaagcc aagctcacag gagggctcta ttcacatttg ccacagagca    2580
cagaggagtt gaggtcagga gctaggaggc tggagacatc taccctgtcc gaggactttc    2640
aggtatctaa ggagactgat ccagcacctg gtccctctc tgggcagagt gtgaatattg    2700
accttctccc cgtagagctc tgactgcaga taattcagag agaacgaagg aggaaggagc    2760
tgtttcgcaa aaagaacaag gcagcagcag tcatccagcg cgcctggcga agctaccagc    2820
tcaggaagca cctgtcccac cttcggcata tgaagcagct ggagctgga gatgtggaca    2880
gatggaggca agagtctaca gcattgctcc tccaggtttg aggaaggaa ctggaactaa    2940
aattccccca aaccactgca gtaagcaagg ccccccaagag tccatccaag ggcacctcag    3000
gcacaaagtc caccaagcac tcagtgctta agcaaatcta tggttgttct cacgaaggga    3060
aaatacatca tcctacaaga tctgtaaaag cctcttctgt gctgcgtctc aactcagtga    3120
gcaacctaca gtgtatacat ctccttgaga acagtggaag atcaaagaac ttttcttata    3180
acctgcaatc agctactcag ccaaaaaaca aaacaaaacc ttgactgcct atggaggaag    3240
actgtgttcg ggggagctgg catagctagt gcagagttca gattttctgc tgataatctt    3300
ttacaccttg ggaaaacttt aatatccgta cctgaaggct gattcaccta aaaatgtgtt    3360
aactgaaaga aaatgtcaga atgtttcctt tctgctctta cacagcattg ttttgtcaat    3420
caacacagcc tgcactgaaa ggacctgcat agactatgtc tgtgcaaagt gcctgagtgt    3480
ctgctttcac ctcagtctgt acagttggaa atgagaattc ataattaaca gcaaaatcta    3540
aggaaaacta aaataaaa                                                 3558
```

<210> SEQ ID NO 24
<211> LENGTH: 898
<212> TYPE: PRT
<213> ORGANISM: Homo sapiens

<400> SEQUENCE: 24

```
Met Asn Lys Ser Glu Asn Leu Leu Phe Ala Gly Ser Ser Leu Ala Ser
1               5                   10                  15

Gln Val His Ala Ala Ala Val Asn Gly Asp Lys Gly Ala Leu Gln Arg
            20                  25                  30
```

-continued

```
Leu Ile Val Gly Asn Ser Ala Leu Lys Asp Lys Glu Asp Gln Phe Gly
         35                  40                  45

Arg Thr Pro Leu Met Tyr Cys Val Leu Ala Asp Arg Leu Asp Cys Ala
         50                  55                  60

Asp Ala Leu Leu Lys Ala Gly Ala Asp Val Asn Lys Thr Asp His Ser
 65                  70                  75                  80

Gln Arg Thr Ala Leu His Leu Ala Ala Gln Lys Gly Asn Tyr Arg Phe
                 85                  90                  95

Met Lys Leu Leu Leu Thr Arg Arg Ala Asn Trp Met Gln Lys Asp Leu
            100                 105                 110

Glu Glu Met Thr Pro Leu His Leu Thr Thr Arg His Arg Ser Pro Lys
            115                 120                 125

Cys Leu Ala Leu Leu Leu Lys Phe Met Ala Pro Gly Glu Val Asp Thr
            130                 135                 140

Gln Asp Lys Asn Lys Gln Thr Ala Leu His Trp Ser Ala Tyr Tyr Asn
145                 150                 155                 160

Asn Pro Glu His Val Lys Leu Leu Ile Lys His Asp Ser Asn Ile Gly
                165                 170                 175

Ile Pro Asp Val Glu Gly Lys Ile Pro Leu His Trp Ala Ala Asn His
            180                 185                 190

Lys Asp Pro Ser Ala Val His Thr Val Arg Cys Ile Leu Asp Ala Ala
            195                 200                 205

Pro Thr Glu Ser Leu Leu Asn Trp Gln Asp Tyr Glu Gly Arg Thr Pro
            210                 215                 220

Leu His Phe Ala Val Ala Asp Gly Asn Val Thr Val Val Asp Val Leu
225                 230                 235                 240

Thr Ser Tyr Glu Ser Cys Asn Ile Thr Ser Tyr Asp Asn Leu Phe Arg
                245                 250                 255

Thr Pro Leu His Trp Ala Ala Leu Leu Gly His Ala Gln Ile Val His
            260                 265                 270

Leu Leu Leu Glu Arg Asn Lys Ser Gly Thr Ile Pro Ser Asp Ser Gln
            275                 280                 285

Gly Ala Thr Pro Leu His Tyr Ala Ala Gln Ser Asn Phe Ala Glu Thr
            290                 295                 300

Val Lys Val Phe Leu Lys His Pro Ser Val Lys Asp Asp Ser Asp Leu
305                 310                 315                 320

Glu Gly Arg Thr Ser Phe Met Trp Ala Ala Gly Lys Gly Ser Asp Asp
                325                 330                 335

Val Leu Arg Thr Met Leu Ser Leu Lys Ser Asp Ile Asp Ile Asn Met
            340                 345                 350

Ala Asp Lys Tyr Gly Gly Thr Ala Leu His Ala Ala Leu Ser Gly
            355                 360                 365

His Val Ser Thr Val Lys Leu Leu Glu Asn Asn Ala Gln Val Asp
            370                 375                 380

Ala Thr Asp Val Met Lys His Thr Pro Leu Phe Arg Ala Cys Glu Met
385                 390                 395                 400

Gly His Lys Asp Val Ile Gln Thr Leu Ile Lys Gly Gly Ala Arg Val
                405                 410                 415

Asp Leu Val Asp Gln Asp Gly His Ser Leu Leu His Trp Ala Ala Leu
            420                 425                 430

Gly Gly Asn Ala Asp Val Cys Gln Ile Leu Ile Glu Asn Lys Ile Asn
            435                 440                 445

Pro Asn Val Gln Asp Tyr Ala Gly Arg Thr Pro Leu Gln Cys Ala Ala
```

-continued

```
            450                 455                 460
Tyr Gly Gly Tyr Ile Asn Cys Met Ala Val Leu Met Glu Asn Asn Ala
465                 470                 475                 480

Asp Pro Asn Ile Gln Asp Lys Glu Gly Arg Thr Ala Leu His Trp Ser
                485                 490                 495

Cys Asn Asn Gly Tyr Leu Asp Ala Ile Lys Leu Leu Leu Asp Phe Ala
                500                 505                 510

Ala Phe Pro Asn Gln Met Glu Asn Asn Glu Glu Arg Tyr Thr Pro Leu
            515                 520                 525

Asp Tyr Ala Leu Leu Gly Glu Arg His Glu Val Ile Gln Phe Met Leu
530                 535                 540

Glu His Gly Ala Leu Ser Ile Ala Ala Ile Gln Asp Ile Ala Ala Phe
545                 550                 555                 560

Lys Ile Gln Ala Val Tyr Lys Gly Tyr Lys Val Arg Lys Ala Phe Arg
                565                 570                 575

Asp Arg Lys Asn Leu Leu Met Lys His Glu Gln Leu Arg Lys Asp Ala
                580                 585                 590

Ala Ala Lys Lys Arg Glu Glu Glu Asn Lys Arg Lys Glu Ala Glu Gln
                595                 600                 605

Gln Lys Gly Arg Arg Ser Pro Asp Ser Cys Arg Pro Gln Ala Leu Pro
            610                 615                 620

Cys Leu Pro Ser Thr Gln Asp Val Pro Ser Arg Gln Ser Arg Ala Pro
625                 630                 635                 640

Ser Lys Gln Pro Pro Ala Gly Asn Val Ala Gln Gly Pro Glu Pro Arg
                645                 650                 655

Asp Ser Arg Gly Ser Pro Gly Gly Ser Leu Gly Gly Ala Leu Gln Lys
                660                 665                 670

Glu Gln His Val Ser Ser Asp Leu Gln Gly Thr Asn Ser Arg Arg Pro
            675                 680                 685

Asn Glu Thr Ala Arg Glu His Ser Lys Gly Gln Ser Ala Cys Val His
            690                 695                 700

Phe Arg Pro Asn Glu Gly Ser Asp Gly Ser Arg His Pro Gly Val Pro
705                 710                 715                 720

Ser Val Glu Lys Ser Arg Gly Glu Thr Ala Gly Asp Glu Arg Cys Ala
                725                 730                 735

Lys Gly Lys Gly Phe Val Lys Gln Pro Ser Cys Ile Arg Val Ala Gly
                740                 745                 750

Pro Asp Glu Lys Gly Glu Asp Ser Arg Arg Ala Gly Ala Ser Leu Pro
            755                 760                 765

Pro His Asp Ser His Trp Lys Pro Ser Arg Arg His Asp Thr Glu Pro
            770                 775                 780

Lys Ala Lys Cys Ala Pro Gln Lys Arg Arg Thr Gln Glu Leu Arg Gly
785                 790                 795                 800

Gly Arg Cys Ser Pro Ala Gly Ser Ser Arg Pro Gly Ser Ala Arg Gly
                805                 810                 815

Glu Ala Val His Ala Gly Gln Asn Pro Pro His His Arg Thr Pro Arg
                820                 825                 830

Asn Lys Val Thr Gln Ala Lys Leu Thr Gly Gly Leu Tyr Ser His Leu
                835                 840                 845

Pro Gln Ser Thr Glu Glu Leu Arg Ser Gly Ala Arg Arg Leu Glu Thr
            850                 855                 860

Ser Thr Leu Ser Glu Asp Phe Gln Val Ser Lys Glu Thr Asp Pro Ala
865                 870                 875                 880
```

```
Pro Gly Pro Leu Ser Gly Gln Ser Val Asn Ile Asp Leu Leu Pro Val
            885                 890                 895
Glu Leu
```

<210> SEQ ID NO 25
<211> LENGTH: 3557
<212> TYPE: DNA
<213> ORGANISM: Homo sapiens

<400> SEQUENCE: 25

| | | | | | |
|---|---|---|---|---|---|
| ggttgctccc | ggttgctaag | aagactatga | acaagtcaga | gaacctgctg | tttgctggtt | 60 |
| catcattagc | atcacaagtc | catgctgctg | ccgttaatgg | agataagggt | gctctacaga | 120 |
| ggctcatcgt | aggaaactct | gctcttaaag | acaaagaaga | tcagtttggg | agaacaccac | 180 |
| ttatgtattg | cgtgttggct | gacagattgg | attgtgcaga | tgctcttctg | aaggcaggag | 240 |
| cagatgtgaa | taaaactgac | catagccaga | gaacagccct | ccatcttgca | gcccagaagg | 300 |
| gaaattatcg | tttcatgaaa | ctcttactta | cacgcagagc | aaactggatg | caaaaggatc | 360 |
| tggaagagat | gactcctttg | cacttgacca | cccggcacag | gagccctaag | tgtttggcac | 420 |
| ttctgctgaa | gtttatggca | ccaggagaag | tggatacaca | ggataaaaac | aagcaaacag | 480 |
| ctctgcattg | gagtgcctac | tacaataacc | ctgagcatgt | gaagctgctc | atcaagcatg | 540 |
| attctaacat | tgggattcct | gatgttgaag | gcaagatccc | acttcactgg | gcagccaacc | 600 |
| ataaagatcc | aagtgctgtt | cacacagtga | atgcattct | ggatgctgct | ccaacagagt | 660 |
| ctttactgaa | ctggcaagac | tacgagggtc | gaactcctct | tcactttgca | gttgctgatg | 720 |
| ggaatgtgac | cgtggttgat | gtcttgacct | catatgaaag | ctgcaatata | acgtcttatg | 780 |
| ataacttatt | tcgaacccca | ctgcactggg | cagctttatt | aggccatgca | cagattgtcc | 840 |
| atctcctttt | agaaagaaat | aagtctggaa | ctatcccatc | tgcacagcca | ggagccacac | 900 |
| ctttgcacta | tgctgctcag | agtaactttg | ctgaaacggt | taaagtgttt | ttaaaacatc | 960 |
| cttcagtgaa | agatgattca | gacctggaag | gaagaacatc | ctttatgtgg | gcagctggca | 1020 |
| aaggcagtga | tgatgtcctt | agaactatgc | tgagcttaaa | atcggacata | gatattaaca | 1080 |
| tggctgacaa | atatgaggt | acagctttgc | atgctgctgc | tctttctggc | catgtcagca | 1140 |
| ccgtgaagtt | attactggaa | aataatgctc | aagtagatgc | tactgatgtt | atgaaacata | 1200 |
| ctccactttt | ccgagcctgt | gagatgggac | acaaagatgt | gattcagaca | ctcattaaag | 1260 |
| gtggagcaag | ggtagatcta | gttgaccaag | atggacattc | tcttctacat | tgggcagcac | 1320 |
| tgggaggaaa | tgctgatgtt | tgccagatat | taatagaaaa | taagatcaat | ccaaatgtcc | 1380 |
| aggattatgc | aggaagaacc | cctttgcagt | gtgcagcata | tggaggctat | atcaactgca | 1440 |
| tggcagttct | catggaaaac | aatgcagacc | ctaacattaa | gacaaagagg | gaagaacagc | 1500 |
| tttgcattgg | tcctgcaaca | atggatacct | tgatgccatt | aaattactgc | tagactttgc | 1560 |
| tgctttccct | aatcagatgg | aaaacaatga | agagagatac | acacccettg | attatgcttt | 1620 |
| gcttggtgag | cgccatgaag | tgatccagtt | catgttggag | cacggtgccc | tgtccatcgc | 1680 |
| agccatacaa | gacatcgccg | ccttcaaaat | ccaagctgtc | tacaaagggt | acaaggtcag | 1740 |
| aaaagccttc | cgagacagga | aaaatctcct | catgaagcat | gaacagttga | aaaagatgc | 1800 |
| tgctgccaaa | aagcgagagg | aagaaaacaa | acgaaaagag | gcagaacagc | aaaaaggaag | 1860 |
| gcggagccca | gattcctgca | gaccccaggc | ccttccctgt | ctgcctagca | cccaggatgt | 1920 |
| gcccagcagg | cagagccggg | cccccagcaa | gcagcctcct | gctggcaacg | tggcccaagg | 1980 |

-continued

```
ccctgagcca agagacagca gaggatctcc aggagggtct ctaggcggag ccctccagaa    2040
ggagcagcat gtttcctcag atttgcaggg aacaaactcc agaaggccaa atgaaacagc    2100
cagagaacat tctaaaggcc aatctgcttg tgtccacttc agacccaatg aaggcagtga    2160
tggaagcagg catccaggag ttccctctgt tgagaagtcc agaggtgaga cagctggcga    2220
tgagcggtgt gcaaagggga aaggtttcgt gaagcagccc tcctgtatca gggtggctgg    2280
gcctgatgag aaaggagagg actccaggcg ggcaggtgca agccttccac cgcacgatag    2340
ccactggaag cccagcaggc ggcatgacac agaacccaag gccaaatgtg cccccagaa    2400 aaggcgcact caagagctca gaggaggaag gtgctctccg gctggttcta gccgccctgg    2460
cagtgcccgg ggggaggcgg tccatgctgg gcagaatcct ccccaccatc gtacaccaag    2520
aaacaaagtg acacaagcca agctcacagg agggctctat tcacatttgc cacagagcac    2580
agaggagttg aggtcaggag ctaggaggct ggagacatct accctgtccg aggactttca    2640
ggtatctaag gagactgatc cagcacctgg tcccctctct gggcagagtg tgaatattga    2700
ccttctcccc gtagagctcc gactgcagat aattcagaga gaacgaagga ggaaggagct    2760
gtttcgcaaa aagaacaagg cagcagcagt catccagcgc gcctggcgaa gctaccagct    2820
caggaagcac ctgtcccacc ttcggcatat gaagcagctt ggagctggag atgtggacag    2880
atggaggcaa gagtctacag cattgctcct ccaggtttgg aggaaggaac tggaactaaa    2940
attcccccaa accactgcag taagcaaggc ccccaagagt ccatccaagg gcacctcagg    3000
cacaaagtcc accaagcact cagtgcttaa gcaaatctat ggttgttctc acgaagggaa    3060
aatacatcat cctacaagat ctgtaaaagc ctcttctgtg ctgcgtctca actcagtgag    3120
caacctacag tgtatacatc tccttgagaa cagtggaaga tcaaagaact tttcttataa    3180
cctgcaatca gctactcagc caaaaaacaa aacaaaacct tgactgccta tggaggaaga    3240
ctgtgttcgg gggagctggc atagctagtg cagagttcag attttctgct gataatcttt    3300
tacaccttgg gaaaacttta atatccgtac ctgaaggctg attcacctaa aaatgtgtta    3360
actgaaagaa aatgtcagaa tgtttccttt ctgctcttac acagcattgt tttgtcaatc    3420
aacacagcct gcactgaaag gacctgcata gactatgtct gtgcaaagtg cctgagtgtc    3480
tgctttcacc tcagtctgta cagttggaaa tgagaattca taattaacag caaaatctaa    3540
ggaaaactaa aataaaa                                                  3557
```

<210> SEQ ID NO 26
<211> LENGTH: 510
<212> TYPE: PRT
<213> ORGANISM: Homo sapiens

<400> SEQUENCE: 26

```
Met Asn Lys Ser Glu Asn Leu Leu Phe Ala Gly Ser Ser Leu Ala Ser
1               5                   10                  15

Gln Val His Ala Ala Val Asn Gly Asp Lys Gly Ala Leu Gln Arg
            20                  25                  30

Leu Ile Val Gly Asn Ser Ala Leu Lys Asp Lys Glu Asp Gln Phe Gly
        35                  40                  45

Arg Thr Pro Leu Met Tyr Cys Val Leu Ala Asp Arg Leu Asp Cys Ala
    50                  55                  60

Asp Ala Leu Leu Lys Ala Gly Ala Asp Val Asn Lys Thr Asp His Ser
65                  70                  75                  80

Gln Arg Thr Ala Leu His Leu Ala Ala Gln Lys Gly Asn Tyr Arg Phe
```

-continued

```
                85                  90                  95
Met Lys Leu Leu Leu Thr Arg Arg Ala Asn Trp Met Gln Lys Asp Leu
            100                 105                 110
Glu Glu Met Thr Pro Leu His Leu Thr Thr Arg His Arg Ser Pro Lys
            115                 120                 125
Cys Leu Ala Leu Leu Lys Phe Met Ala Pro Gly Glu Val Asp Thr
            130                 135                 140
Gln Asp Lys Asn Lys Gln Thr Ala Leu His Trp Ser Ala Tyr Tyr Asn
145                 150                 155                 160
Asn Pro Glu His Val Lys Leu Leu Ile Lys His Asp Ser Asn Ile Gly
            165                 170                 175
Ile Pro Asp Val Glu Gly Lys Ile Pro Leu His Trp Ala Ala Asn His
            180                 185                 190
Lys Asp Pro Ser Ala Val His Thr Val Arg Cys Ile Leu Asp Ala Ala
            195                 200                 205
Pro Thr Glu Ser Leu Leu Asn Trp Gln Asp Tyr Glu Gly Arg Thr Pro
            210                 215                 220
Leu His Phe Ala Val Ala Asp Gly Asn Val Thr Val Val Asp Val Leu
225                 230                 235                 240
Thr Ser Tyr Glu Ser Cys Asn Ile Thr Ser Tyr Asp Asn Leu Phe Arg
            245                 250                 255
Thr Pro Leu His Trp Ala Ala Leu Leu Gly His Ala Gln Ile Val His
            260                 265                 270
Leu Leu Leu Glu Arg Asn Lys Ser Gly Thr Ile Pro Ser Asp Ser Gln
            275                 280                 285
Gly Ala Thr Pro Leu His Tyr Ala Ala Gln Ser Asn Phe Ala Glu Thr
            290                 295                 300
Val Lys Val Phe Leu Lys His Pro Ser Val Lys Asp Ser Asp Leu
305                 310                 315                 320
Glu Gly Arg Thr Ser Phe Met Trp Ala Ala Gly Lys Gly Ser Asp Asp
            325                 330                 335
Val Leu Arg Thr Met Leu Ser Leu Lys Ser Asp Ile Asp Ile Asn Met
            340                 345                 350
Ala Asp Lys Tyr Gly Gly Thr Ala Leu His Ala Ala Leu Ser Gly
            355                 360                 365
His Val Ser Thr Val Lys Leu Leu Leu Glu Asn Asn Ala Gln Val Asp
            370                 375                 380
Ala Thr Asp Val Met Lys His Thr Pro Leu Phe Arg Ala Cys Glu Met
385                 390                 395                 400
Gly His Lys Asp Val Ile Gln Thr Leu Ile Lys Gly Gly Ala Arg Val
            405                 410                 415
Asp Leu Val Asp Gln Asp Gly His Ser Leu Leu His Trp Ala Ala Leu
            420                 425                 430
Gly Gly Asn Ala Asp Val Cys Gln Ile Leu Ile Glu Asn Lys Ile Asn
            435                 440                 445
Pro Asn Val Gln Asp Tyr Ala Gly Arg Thr Pro Leu Gln Cys Ala Ala
            450                 455                 460
Tyr Gly Gly Tyr Ile Asn Cys Met Ala Val Leu Met Glu Asn Asn Ala
465                 470                 475                 480
Asp Pro Asn Ile Lys Gln Asp Lys Glu Gly Arg Thr Ala Leu His Trp
            485                 490                 495
Ser Cys Asn Asn Gly Tyr Leu Asp Ala Ile Lys Leu Leu Leu
            500                 505                 510
```

<210> SEQ ID NO 27
<211> LENGTH: 3558
<212> TYPE: DNA
<213> ORGANISM: Homo sapiens

<400> SEQUENCE: 27

| | | | | | |
|---|---|---|---|---|---|
| ggttgctccc | ggttgctaag | aagactatga | acaagtcaga | gaacctgctg | tttgctggtt | 60 |
| catcattagc | atcacaagtc | catgctgctg | ccgttaatgg | agataagggt | gctctacaga | 120 |
| ggctcatcgt | aggaaactct | gctcttaaag | acaaagaaga | tcagtttggg | agaacaccac | 180 |
| ttatgtattg | cgtgttggct | gacagattgg | attgtgcaga | tgctcttctg | aaggcaggag | 240 |
| cagatgtgaa | taaaactgac | catagccaga | gaacagccct | ccatcttgca | gcccagaagg | 300 |
| gaaattatcg | tttcatgaaa | ctcttactta | cacgcagagc | aaactggatg | caaaaggatc | 360 |
| tggaagagat | gactcctttg | cacttgacca | cccggcacag | gagccctaag | tgtttggcac | 420 |
| ttctgctgaa | gtttatggca | ccaggagaag | tggatacaca | ggataaaaac | aagcaaacag | 480 |
| ctctgcattg | gagtgcctac | tacaataacc | ctgagcatgt | gaagctgctc | atcaagcatg | 540 |
| attctaacat | tgggattcct | gatgttgaag | gcaagatccc | acttcactgg | gcagccaacc | 600 |
| ataaagatcc | aagtgctgtt | cacacagtga | gatgcattct | ggatgctgct | ccaacagagt | 660 |
| ctttactgaa | ctggcaagac | tacgagggtc | gaactcctct | tcactttgca | gttgctgatg | 720 |
| ggaatgtgac | cgtggttgat | gtcttgacct | catatgaaag | ctgcaatata | acgtcttatg | 780 |
| ataacttatt | tcgaacccca | ctgcactggg | cagctttatt | aggccatgca | cagattgtcc | 840 |
| atctcctttt | agaaagaaat | aagtctggaa | ctatcccatc | tgacagccaa | ggagccacac | 900 |
| ctttgcacta | tgctgctcag | agtaactttg | ctgaaacggt | taaagtgttt | ttaaaacatc | 960 |
| cttcagtgaa | agatgattca | gacctggaag | gagaacatc | ctttatgtgg | gcagctggca | 1020 |
| aaggcagtga | tgatgtcctt | agaactatgc | tgagcttaaa | atcggacata | gatattaaca | 1080 |
| tggctgacaa | atatggaggt | acagctttgc | atgctgctgc | tctttctggc | catgtcagca | 1140 |
| ccgtgaagtt | attactggaa | aataatgctc | aagtagatgc | tactgatgtt | atgaaaacata | 1200 |
| ctccacttt | ccgagcctgt | gagatgggac | acaaagatgt | gattcagaca | ctcattaaag | 1260 |
| gtggagcaag | ggtagatcta | gttgaccaag | atggacattc | tcttctacat | tgggcagcac | 1320 |
| tgggaggaaa | tgctgatgtt | tgccagatat | aatagaaaa | taagatcaat | ccaaatgtcc | 1380 |
| aggattatgc | aggaagaacc | cctttgcagt | gtgcagcata | tggaggctat | atcaactgca | 1440 |
| tggcagttct | catggaaaac | aatgcagacc | ctaacattca | agacaaagag | ggaagaacag | 1500 |
| ctttgcattg | gtcctgcaac | aatggatacc | ttgatgccat | taattactg | ctagactttg | 1560 |
| ctgctttccc | taatcagatg | gaaaacaatg | aagagagata | cacacccctt | gattatgctt | 1620 |
| tgcttggtga | cgccatgaa | gtgatccagt | tcatgttgga | gcacggtgcc | ctgtccatcg | 1680 |
| cagccataca | agacatcgcc | gccttcaaaa | tccaagctgt | ctacaaaggg | tacaaggtca | 1740 |
| gaaaagcctt | ccgagacagg | aaaaatctcc | tcatgaagca | tgaacagttg | agaaaagatg | 1800 |
| ctgctgccaa | aaagcgagag | gaagaaaaca | atgaaaaga | ggcagaacag | caaaaaggaa | 1860 |
| ggcggagccc | agattcctgc | agaccccagg | cccttccctg | tctgcctagc | acccaggatg | 1920 |
| tgcccagcag | gcagagccgg | gcccccagca | agcagcctcc | tgctggcaac | gtggcccaag | 1980 |
| gccctgagcc | aagagacagc | agaggatctc | caggagggtc | tctaggcgga | gccctccaga | 2040 |
| aggagcagca | tgtttcctca | gatttgcagg | gaacaaactc | cagaaggcca | aatgaaacag | 2100 |

```
ccagagaaca ttctaaaggc caatctgctt gtgtccactt cagacccaat gaaggcagtg    2160
atggaagcag gcatccagga gttccctctg ttgagaagtc cagaggtgag acagctggcg    2220
atgagcggtg tgcaaagggg aaaggtttcg tgaagcagcc ctcctgtatc agggtggctg    2280
ggcctgatga gaaggagag gactccaggc gggcaggtgc aagccttcca ccgcacgata    2340
gccactggaa gcccagcagg cggcatgaca cagaacccaa ggccaaatgt gccccccaga    2400
aaaggcgcac tcaagagctc agaggaggaa ggtgctctcc ggctggttct agccgccctg    2460
gcagtgcccg gggggaggcg gtccatgctg gcagaatcc tccccaccat cgtacaccaa    2520
gaaacaaagt gacacaagcc aagctcacag gagggctcta ttcacatttg ccacagagca    2580
cagaggagtt gaggtcagga gctaggaggc tggagacatc taccctgtcc gaggactttc    2640
aggtatctaa ggagactgat ccagcacctg gtcccctctc tgggcagagt gtgaatattg    2700
accttctccc cgtagagctc cgactgcaga taattcagag agaacgaagg aggaaggagc    2760
tgtttcgcaa aaagaacaag gcagcagcag tcatccagcg cgcctggcga agctaccagc    2820
tcaggaagca cctgtcccac cttcggcata tgaagcagct ggagctgga gatgtggaca    2880 gatggaggca agagtctaca gcattgctcc tccaggtttg gaggaaggaa ctggaactaa    2940 aattcccca aaccactgca gtaagcaagg cccccaagag tccatccaag ggcacctcag    3000
gcacaaagtc caccaagcac tcagtgctta agcaaatcta tggttgttct cacgaaggga    3060
aaatacatca tcctacaaga tctgtaaaag cctcttctgt gctgcgtctc aactcagtga    3120
gcaacctaca gtgtatacat ctccttgaga acagtggaag atcaaagaac ttttcttata    3180
acctgcaatc agctactcag ccaaaaaaca aaacaaaacc ttgactgcct atggaggaag    3240
actgtgttcg ggggagctgg catagctagt gcagagttca gattttctgc tgataatctt    3300
ttacaccttg ggaaaacttt aatatccgta cctgaaggct gattcaccta aaaatgtgtt    3360
aactgaaaga aaatgtcaga atgtttcctt tctgctctta cacagcattg ttttgtcaat    3420
caacacagcc tgcactgaaa ggacctgcat agactatgtc tgtgcaaagt gcctgagtgt    3480
ctgctttcac ctcagtctgt acagttggaa atgagaattc ataattaaca gcaaaatcta    3540
aggaaaacta aataaaa                                                   3558
```

<210> SEQ ID NO 28
<211> LENGTH: 602
<212> TYPE: PRT
<213> ORGANISM: Homo sapiens

<400> SEQUENCE: 28

```
Met Asn Lys Ser Glu Asn Leu Leu Phe Ala Gly Ser Ser Leu Ala Ser
1               5                   10                  15

Gln Val His Ala Ala Val Asn Gly Asp Lys Gly Ala Leu Gln Arg
            20                  25                  30

Leu Ile Val Gly Asn Ser Ala Leu Lys Asp Lys Glu Asp Gln Phe Gly
        35                  40                  45

Arg Thr Pro Leu Met Tyr Cys Val Leu Ala Asp Arg Leu Asp Cys Ala
    50                  55                  60

Asp Ala Leu Leu Lys Ala Gly Ala Asp Val Asn Lys Thr Asp His Ser
65                  70                  75                  80

Gln Arg Thr Ala Leu His Leu Ala Ala Gln Lys Gly Asn Tyr Arg Phe
                85                  90                  95

Met Lys Leu Leu Leu Thr Arg Arg Ala Asn Trp Met Gln Lys Asp Leu
            100                 105                 110
```

```
Glu Glu Met Thr Pro Leu His Leu Thr Thr Arg His Arg Ser Pro Lys
        115                 120                 125

Cys Leu Ala Leu Leu Lys Phe Met Ala Pro Gly Glu Val Asp Thr
    130                 135                 140

Gln Asp Lys Asn Lys Gln Thr Ala Leu His Trp Ser Ala Tyr Tyr Asn
145                 150                 155                 160

Asn Pro Glu His Val Lys Leu Leu Ile Lys His Asp Ser Asn Ile Gly
                165                 170                 175

Ile Pro Asp Val Glu Gly Lys Ile Pro Leu His Trp Ala Ala Asn His
            180                 185                 190

Lys Asp Pro Ser Ala Val His Thr Val Arg Cys Ile Leu Asp Ala Ala
                195                 200                 205

Pro Thr Glu Ser Leu Leu Asn Trp Gln Asp Tyr Glu Gly Arg Thr Pro
    210                 215                 220

Leu His Phe Ala Val Ala Asp Gly Asn Val Thr Val Val Asp Val Leu
225                 230                 235                 240

Thr Ser Tyr Glu Ser Cys Asn Ile Thr Ser Tyr Asp Asn Leu Phe Arg
            245                 250                 255

Thr Pro Leu His Trp Ala Ala Leu Leu Gly His Ala Gln Ile Val His
                260                 265                 270

Leu Leu Leu Glu Arg Asn Lys Ser Gly Thr Ile Pro Ser Asp Ser Gln
            275                 280                 285

Gly Ala Thr Pro Leu His Tyr Ala Ala Gln Ser Asn Phe Ala Glu Thr
            290                 295                 300

Val Lys Val Phe Leu Lys His Pro Ser Val Lys Asp Asp Ser Asp Leu
305                 310                 315                 320

Glu Gly Arg Thr Ser Phe Met Trp Ala Ala Gly Lys Gly Ser Asp Asp
            325                 330                 335

Val Leu Arg Thr Met Leu Ser Leu Lys Ser Asp Ile Asp Ile Asn Met
            340                 345                 350

Ala Asp Lys Tyr Gly Gly Thr Ala Leu His Ala Ala Ala Leu Ser Gly
            355                 360                 365

His Val Ser Thr Val Lys Leu Leu Glu Asn Asn Ala Gln Val Asp
            370                 375                 380

Ala Thr Asp Val Met Lys His Thr Pro Leu Phe Arg Ala Cys Glu Met
385                 390                 395                 400

Gly His Lys Asp Val Ile Gln Thr Leu Ile Lys Gly Gly Ala Arg Val
            405                 410                 415

Asp Leu Val Asp Gln Asp Gly His Ser Leu Leu His Trp Ala Ala Leu
            420                 425                 430

Gly Gly Asn Ala Asp Val Cys Gln Ile Leu Ile Glu Asn Lys Ile Asn
            435                 440                 445

Pro Asn Val Gln Asp Tyr Ala Gly Arg Thr Pro Leu Gln Cys Ala Ala
    450                 455                 460

Tyr Gly Gly Tyr Ile Asn Cys Met Ala Val Leu Met Glu Asn Asn Ala
465                 470                 475                 480

Asp Pro Asn Ile Gln Asp Lys Glu Gly Arg Thr Ala Leu His Trp Ser
                485                 490                 495

Cys Asn Asn Gly Tyr Leu Asp Ala Ile Lys Leu Leu Leu Asp Phe Ala
            500                 505                 510

Ala Phe Pro Asn Gln Met Glu Asn Asn Glu Glu Arg Tyr Thr Pro Leu
            515                 520                 525

Asp Tyr Ala Leu Leu Gly Glu Arg His Glu Val Ile Gln Phe Met Leu
```

```
                530             535             540
Glu His Gly Ala Leu Ser Ile Ala Ala Ile Gln Asp Ile Ala Ala Phe
545                 550                 555                 560

Lys Ile Gln Ala Val Tyr Lys Gly Tyr Lys Val Arg Lys Ala Phe Arg
                565                 570                 575

Asp Arg Lys Asn Leu Leu Met Lys His Glu Gln Leu Arg Lys Asp Ala
            580                 585                 590

Ala Ala Lys Lys Arg Glu Glu Glu Asn Lys
        595                 600

<210> SEQ ID NO 29
<211> LENGTH: 3558
<212> TYPE: DNA
<213> ORGANISM: Homo sapiens

<400> SEQUENCE: 29
ggttgctccc ggttgctaag aagactatga acaagtcaga gaacctgctg tttgctggtt    60
catcattagc atcacaagtc catgctgctg ccgttaatgg agataagggt gctctacaga   120
ggctcatcgt aggaaactct gctcttaaag acaaagaaga tcagtttggg agaacaccac   180
ttatgtattg cgtgttggct gacagattgg attgtgcaga tgctcttctg aaggcaggag   240
cagatgtgaa taaaactgac catagccaga gaacagccct ccatcttgca gcccagaagg   300
gaaattatcg tttcatgaaa ctcttactta cacgcagagc aaactggatg caaaaggatc   360
tggaagagat gactcctttg cacttgacca cccggcacag gagccctaag tgtttggcac   420
ttctgctgaa gtttatggca ccaggagaag tggatacaca ggataaaaac aagcaaacag   480
ctctgcattg gagtgcctac tacaataacc ctgagcatgt gaagctgctc atcaagcatg   540
attctaacat tgggattcct gatgttgaag gcaagatccc acttcactgg gcagccaacc   600
ataaagatcc aagtgctgtt cacacagtga gatgcattct ggatgctgct ccaacagagt   660
ctttactgaa ctggcaagac tacgagggtc gaactcctct tcactttgca gttgctgatg   720
ggaatgtgac cgtggttgat gtcttgacct catatgaaag ctgcaatata acgtcttatg   780
ataacttatt tcgaacccca ctgcactggg cagctttatt aggccatgca cagattgtcc   840
atctcctttt agaaagaaat aagtctggaa ctatcccatc tgacagccaa ggagccacac   900
ctttgcacta tgctgctcag agtaactttg ctgaaacggt taaagtgttt ttaaaacatc   960
cttcagtgaa agatgattca gacctggaag gagaacatc ctttatgtgg gcagctggca  1020
aaggcagtga tgatgtcctt agaactatgc tgagcttaaa atcggacata gatattaaca  1080
tggctgacaa atatggaggt acagctttgc atgctgctgc tctttctggc catgtcagca  1140
ccgtgaagtt attactggaa aataatgctc aagtagatgc tactgatgtt atgaaacata  1200
ctccactttt ctgagcctgt gagatgggac acaaagatgt gattcagaca ctcattaaag  1260
gtggagcaag ggtagatcta gttgaccaag atggacattc tcttctacat tgggcagcac  1320
tgggaggaaa tgctgatgtt tgccagatat aatagaaaa taagatcaat ccaaatgtcc  1380
aggattatgc aggaagaacc cctttgcagt gtgcagcata tggaggctat atcaactgca  1440
tggcagttct catggaaaac aatgcagacc ctaacattca agacaaagag ggaagaacag  1500
ctttgcattg gtcctgcaac aatggatacc ttgatgccat taattactg ctagactttg  1560 ctgctttccc taatcagatg gaaaacaatg aagagagata cacacccctt gattatgctt  1620
tgcttggtga gcgccatgaa gtgatccagt tcatgttgga gcacggtgcc ctgtccatcg  1680
cagccataca agacatcgcc gccttcaaaa tccaagctgt ctacaaaggg tacaaggtca  1740
```

```
gaaaagccttccgagacaggaaaaatctcctcatgaagcatgaacagttgagaaaagatg    1800
ctgctgccaaaaagcgagaggaagaaaacaaacgaaagaggcagaacagcaaaaaggaa    1860
ggcggagcccagattcctgcagaccccaggcccttccctgtctgcctagcacccaggatg    1920
tgcccagcaggcagagccggccccccagcaagcagcctcctgctggcaacgtggcccaag    1980
gccctgagccaagagacagcagaggatctccaggagggtctctaggcggagccctccaga    2040
aggagcagcatgtttcctcagatttgcaggaacaaactccagaaggccaaatgaaacag    2100
ccagagaacattctaaaggccaatctgcttgtgtccacttcagacccaatgaaggcagtg    2160
atggaagcaggcatccaggagttccctctgttgagaagtcagaggtgagacagctggcg    2220
atgagcggttgcaaaggggaaaggtttcgtgaagcagcctcctgtatcagggtggctg    2280
ggcctgatgaaaaggagagactccaggcgggcaggtgcaagccttccaccgcacgata    2340
gccactggaagcccagcaggcggcatgacacagaacccaaggccaaatgtgccccccaga    2400
aaaggcgcactcaagagctcagaggaggaaggtgctctccggctggttctagccgccctg    2460
gcagtgcccggggggaggcgtccatgctggcagaatcctccccaccatcgtacaccaa    2520
gaaacaaagtgacacaagccaagctcacaggagggctctattcacatttgccacagagca    2580
cagaggagttgaggtcaggagctaggaggctggagacatctaccctgtccgaggactttc    2640
aggtatctaaggagactgatccagcacctggtccctctctgggcagagtgtgaatattg    2700
accttctcccgtagagctccgactgcagataattcagagagaacgaaggaggaaggagc    2760
tgtttcgcaaaaagaacaaggcagcagcagtcatccagcgcgcctggcgaagctaccagc    2820
tcaggaagcacctgtcccaccttcggcatatgaagcagctggagctggagtgtggaca    2880
gatggaggcagagtctacagcattgctcctccaggtttgaggaaggaactggaactaa    2940
aattcccccaaaccactgcagtaagcaaggccccccaagagtccatccaagggcacctcag    3000
gcacaaagtccaccaagcactcagtgcttaagcaaatctatggttgttctcacgaaggga    3060
aaatacatcatcctacaagatctgtaaaagcctcttctgtgctgcgtctcaactcagtga    3120
gcaacctacagtgtatacatctccttgagaacagtggaagatcaaagaacttttcttata    3180
acctgcaatcagctactcagccaaaaaacaaaacaaaacccttgactgcctatggaggaag    3240
actgtgttcgggggagctggcatagctagtgcagagttcagatttctgctgataatctt    3300
ttacaccttgggaaaactttaatatccgtacctgaaggctgattcacctaaaaatgtgtt    3360
aactgaaagaaaatgtcagaatgtttccttctgctcttacacagcattgttttgtcaat    3420
caacacagcctgcactgaaaggacctgcatagactatgtctgtgcaaagtgcctgagtgt    3480
ctgctttcactcagtctgtacagttggaaatgagaattcataattaacagcaaatcta    3540
aggaaaactaaaataaaa                                              3558
```

<210> SEQ ID NO 30
<211> LENGTH: 395
<212> TYPE: PRT
<213> ORGANISM: Homo sapiens

<400> SEQUENCE: 30

```
Met Asn Lys Ser Glu Asn Leu Leu Phe Ala Gly Ser Ser Leu Ala Ser
1               5                   10                  15
Gln Val His Ala Ala Ala Val Asn Gly Asp Lys Gly Ala Leu Gln Arg
            20                  25                  30
Leu Ile Val Gly Asn Ser Ala Leu Lys Asp Lys Glu Asp Gln Phe Gly
        35                  40                  45
```

```
Arg Thr Pro Leu Met Tyr Cys Val Leu Ala Asp Arg Leu Asp Cys Ala
    50                  55                  60

Asp Ala Leu Leu Lys Ala Gly Ala Asp Val Asn Lys Thr Asp His Ser
65                  70                  75                  80

Gln Arg Thr Ala Leu His Leu Ala Ala Gln Lys Gly Asn Tyr Arg Phe
            85                  90                  95

Met Lys Leu Leu Leu Thr Arg Arg Ala Asn Trp Met Gln Lys Asp Leu
                100                 105                 110

Glu Glu Met Thr Pro Leu His Leu Thr Thr Arg His Arg Ser Pro Lys
            115                 120                 125

Cys Leu Ala Leu Leu Lys Phe Met Ala Pro Gly Glu Val Asp Thr
    130                 135                 140

Gln Asp Lys Asn Lys Gln Thr Ala Leu His Trp Ser Ala Tyr Tyr Asn
145                 150                 155                 160

Asn Pro Glu His Val Lys Leu Leu Ile Lys His Asp Ser Asn Ile Gly
                165                 170                 175

Ile Pro Asp Val Glu Gly Lys Ile Pro Leu His Trp Ala Ala Asn His
            180                 185                 190

Lys Asp Pro Ser Ala Val His Thr Val Arg Cys Ile Leu Asp Ala Ala
    195                 200                 205

Pro Thr Glu Ser Leu Leu Asn Trp Gln Asp Tyr Glu Gly Arg Thr Pro
    210                 215                 220

Leu His Phe Ala Val Ala Asp Gly Asn Val Thr Val Val Asp Val Leu
225                 230                 235                 240

Thr Ser Tyr Glu Ser Cys Asn Ile Thr Ser Tyr Asp Asn Leu Phe Arg
            245                 250                 255

Thr Pro Leu His Trp Ala Ala Leu Leu Gly His Ala Gln Ile Val His
                260                 265                 270

Leu Leu Leu Glu Arg Asn Lys Ser Gly Thr Ile Pro Ser Asp Ser Gln
    275                 280                 285

Gly Ala Thr Pro Leu His Tyr Ala Ala Gln Ser Asn Phe Ala Glu Thr
    290                 295                 300

Val Lys Val Phe Leu Lys His Pro Ser Val Lys Asp Ser Asp Leu
305                 310                 315                 320

Glu Gly Arg Thr Ser Phe Met Trp Ala Ala Gly Lys Gly Ser Asp Asp
            325                 330                 335

Val Leu Arg Thr Met Leu Ser Leu Lys Ser Asp Ile Asp Ile Asn Met
                340                 345                 350

Ala Asp Lys Tyr Gly Gly Thr Ala Leu His Ala Ala Ala Leu Ser Gly
            355                 360                 365

His Val Ser Thr Val Lys Leu Leu Leu Glu Asn Asn Ala Gln Val Asp
    370                 375                 380

Ala Thr Asp Val Met Lys His Thr Pro Leu Phe
385                 390                 395

<210> SEQ ID NO 31
<211> LENGTH: 3558
<212> TYPE: DNA
<213> ORGANISM: Homo sapiens

<400> SEQUENCE: 31
ggttgctccc ggttgctaag aagactatga acaagtcaga gaacctgctg tttgctggtt    60
catcattagc atcacaagtc catgctgctg ccgttaatgg agataagggt gctctacaga   120
```

```
ggctcatcgt aggaaactct gctcttaaag acaaagaaga tcagtttggg agaacaccac    180
ttatgtattg cgtgttggct gacagattgg attgtgcaga tgctcttctg aaggcaggag    240
cagatgtgaa taaaactgac catagccaga gaacagccct ccatcttgca gcccagaagg    300
gaaattatcg tttcatgaaa ctcttactta cacgcagagc aaactggatg caaaaggatc    360
tggaagagat gactcctttg cacttgacca cccggcacag gagccctaag tgtttggcac    420
ttctgctgaa gtttatggca ccaggagaag tggatacaca ggataaaaac aagcaaacag    480
ctctgcattg gagtgcctac tacaataacc ctgagcatgt gaagctgctc atcaagcatg    540
attctaacat tgggattcct gatgttgaag gcaagatccc acttcactgg gcagccaacc    600
ataaagatcc aagtgctgtt cacacagtga gatgcattct ggatgctgct ccaacagagt    660
ctttactgaa ctggcaagac tacgagggtc gaactcctct tcactttgca gttgctgatg    720
ggaatgtgac cgtggttgat gtcttgacct catatgaaag ctgcaatata cgtcttatg    780 ataacttatt tcgaacccca ctgcactggg cagctttatt aggccatgca cagattgtcc    840
atctcctttt agaaagaaat aagtctggaa ctatcccatc tgacagccaa ggagccacac    900 cttgcacta tgctgctcag agtaactttg ctgaaacggt taaagtgttt ttaaaacatc    960
cttcagtgaa agatgattca gacctggaag gaagaacatc ctttatgtgg gcagctggca   1020
aaggcagtga tgatgtcctt agaactatgc tgagcttaaa atcggacata gatattaaca   1080
tggctgacaa atatggaggt acagctttgc atgctgctgc tctttctggc catgtcagca   1140
ccgtgaagtt attactggaa aataatgctc aagtagatgc tactgatgtt atgaaacata   1200
ctccactttt ccgagcctgt gagatgggac acaaagatgt gattcagaca ctcattaaag   1260
gtggagcaag ggtagatcta gttgaccaag atggacattc tcttctacat tgggcagcac   1320
tgggaggaaa tgctgatgtt tgccagatat aatagaaaa taagatcaat ccaaatgtcc   1380
aggattatgc aggaagaacc cctttgcagt gtgcagcata tggaggctat atcaactgca   1440
tggcagttct catggaaaac aatgcagacc gtaacattca agacaaagag ggaagaacag   1500
ctttgcattg gtcctgcaac aatggatacc ttgatgccat taaattactg ctagactttg   1560
ctgctttccc taatcagatg gaaaacaatg aagagagata cacacccctt gattatgctt   1620
tgcttggtga cgccatgaa gtgatccagt tcatgttgga gcacggtgcc ctgtccatcg   1680
cagccataca agacatcgcc gccttcaaaa tccaagctgt ctacaaaggg tacaaggtca   1740
gaaaagcctt ccgagacagg aaaaatctcc tcatgaagca tgaacagttg agaaaagatg   1800
ctgctgccaa aaagcgagag gaagaaaaca acgaaaaga ggcagaacag caaaaaggaa   1860
ggcggagccc agattcctgc agaccccagg cccttccctg tctgcctagc acccaggatg   1920
tgcccagcag gcagagccgg gcccccagca agcagcctcc tgctggcaac gtggcccaag   1980
gccctgagcc aagagacagc agaggatctc caggagggtc tctaggcgga gccctccaga   2040
aggagcagca tgtttcctca gatttgcagg aacaaactc cagaaggcca atgaaacag   2100 ccagagaaca ttctaaaggc caatctgctt gtgtccactt cagacccaat gaaggcagtg   2160
atggaagcag gcatccagga gttccctctg ttgagaagtc cagaggtgag acagctggcg   2220
atgagcggtg tgcaaagggg aaaggtttcg tgaagcagcc ctcctgtatc agggtggctg   2280
ggcctgatga gaaggagag gactccaggc gggcaggtgc aagccttcca ccgcacgata   2340
gccactggaa gcccagcagg cggcatgaca cagaacccaa ggccaaatgt gccccccaga   2400
aaaggcgcac tcaagagctc agaggaggaa ggtgctctcc ggctggttct agccgccctg   2460
gcagtgcccg gggggaggcg gtccatgctg ggcagaatcc tccccaccat cgtacaccaa   2520
```

-continued

| | |
|---|---|
| gaaacaaagt gacacaagcc aagctcacag gagggctcta ttcacatttg ccacagagca | 2580 |
| cagaggagtt gaggtcagga gctaggaggc tggagacatc taccctgtcc gaggactttc | 2640 |
| aggtatctaa ggagactgat ccagcacctg gtcccctctc tgggcagagt gtgaatattg | 2700 |
| accttctccc cgtagagctc cgactgcaga taattcagag agaacgaagg aggaaggagc | 2760 |
| tgtttcgcaa aaagaacaag gcagcagcag tcatccagcg cgcctggcga agctaccagc | 2820 |
| tcaggaagca cctgtcccac cttcggcata tgaagcagct tggagctgga gatgtggaca | 2880 |
| gatggaggca agagtctaca gcattgctcc tccaggtttg gaggaaggaa ctggaactaa | 2940 |
| aattccccca aaccactgca gtaagcaagg cccccaagag tccatccaag ggcacctcag | 3000 |
| gcacaaagtc caccaagcac tcagtgctta agcaaatcta tggttgttct cacgaaggga | 3060 |
| aaatacatca tcctacaaga tctgtaaaag cctcttctgt gctgcgtctc aactcagtga | 3120 |
| gcaacctaca gtgtatacat ctccttgaga acagtggaag atcaaagaac ttttcttata | 3180 |
| acctgcaatc agctactcag ccaaaaaaca aaacaaaacc ttgactgcct atggaggaag | 3240 |
| actgtgttcg ggggagctgg catagctagt gcagagttca gattttctgc tgataatctt | 3300 |
| ttacaccttg ggaaaacttt aatatccgta cctgaaggct gattcaccta aaaatgtgtt | 3360 |
| aactgaaaga aaatgtcaga atgtttcctt tctgctctta cacagcattg ttttgtcaat | 3420 |
| caacacagcc tgcactgaaa ggacctgcat agactatgtc tgtgcaaagt gcctgagtgt | 3480 |
| ctgctttcac ctcagtctgt acagttggaa atgagaattc ataattaaca gcaaatctaa | 3540 |
| aggaaaacta aaataaaa | 3558 |

<210> SEQ ID NO 32
<211> LENGTH: 1065
<212> TYPE: PRT
<213> ORGANISM: Homo sapiens

<400> SEQUENCE: 32

Met Asn Lys Ser Glu Asn Leu Leu Phe Ala Gly Ser Ser Leu Ala Ser
1               5                   10                  15

Gln Val His Ala Ala Val Asn Gly Asp Lys Gly Ala Leu Gln Arg
            20                  25                  30

Leu Ile Val Gly Asn Ser Ala Leu Lys Asp Lys Glu Asp Gln Phe Gly
        35                  40                  45

Arg Thr Pro Leu Met Tyr Cys Val Leu Ala Asp Arg Leu Asp Cys Ala
    50                  55                  60

Asp Ala Leu Leu Lys Ala Gly Ala Asp Val Asn Lys Thr Asp His Ser
65                  70                  75                  80

Gln Arg Thr Ala Leu His Leu Ala Ala Gln Lys Gly Asn Tyr Arg Phe
                85                  90                  95

Met Lys Leu Leu Leu Thr Arg Arg Ala Asn Trp Met Gln Lys Asp Leu
            100                 105                 110

Glu Glu Met Thr Pro Leu His Leu Thr Thr Arg His Arg Ser Pro Lys
        115                 120                 125

Cys Leu Ala Leu Leu Lys Phe Met Ala Pro Gly Glu Val Asp Thr
    130                 135                 140

Gln Asp Lys Asn Lys Gln Thr Ala Leu His Trp Ser Ala Tyr Tyr Asn
145                 150                 155                 160

Asn Pro Glu His Val Lys Leu Leu Ile Lys His Asp Ser Asn Ile Gly
                165                 170                 175

Ile Pro Asp Val Glu Gly Lys Ile Pro Leu His Trp Ala Ala Asn His

-continued

```
                    180                 185                 190
Lys Asp Pro Ser Ala Val His Thr Val Arg Cys Ile Leu Asp Ala Ala
                195                 200                 205
Pro Thr Glu Ser Leu Leu Asn Trp Gln Asp Tyr Glu Gly Arg Thr Pro
210                 215                 220
Leu His Phe Ala Val Ala Asp Gly Asn Val Thr Val Asp Val Leu
225                 230                 235                 240
Thr Ser Tyr Glu Ser Cys Asn Ile Thr Ser Tyr Asp Asn Leu Phe Arg
                245                 250                 255
Thr Pro Leu His Trp Ala Ala Leu Leu Gly His Ala Gln Ile Val His
                260                 265                 270
Leu Leu Leu Glu Arg Asn Lys Ser Gly Thr Ile Pro Ser Asp Ser Gln
                275                 280                 285
Gly Ala Thr Pro Leu His Tyr Ala Ala Gln Ser Asn Phe Ala Glu Thr
                290                 295                 300
Val Lys Val Phe Leu Lys His Pro Ser Val Lys Asp Asp Ser Asp Leu
305                 310                 315                 320
Glu Gly Arg Thr Ser Phe Met Trp Ala Ala Gly Lys Gly Ser Asp Asp
                325                 330                 335
Val Leu Arg Thr Met Leu Ser Leu Lys Ser Asp Ile Asp Ile Asn Met
                340                 345                 350
Ala Asp Lys Tyr Gly Gly Thr Ala Leu His Ala Ala Ala Leu Ser Gly
                355                 360                 365
His Val Ser Thr Val Lys Leu Leu Leu Glu Asn Asn Ala Gln Val Asp
                370                 375                 380
Ala Thr Asp Val Met Lys His Thr Pro Leu Phe Arg Ala Cys Glu Met
385                 390                 395                 400
Gly His Lys Asp Val Ile Gln Thr Leu Ile Lys Gly Gly Ala Arg Val
                    405                 410                 415
Asp Leu Val Asp Gln Asp Gly His Ser Leu Leu His Trp Ala Ala Leu
                420                 425                 430
Gly Gly Asn Ala Asp Val Cys Gln Ile Leu Ile Glu Asn Lys Ile Asn
                435                 440                 445
Pro Asn Val Gln Asp Tyr Ala Gly Arg Thr Pro Leu Gln Cys Ala Ala
450                 455                 460
Tyr Gly Gly Tyr Ile Asn Cys Met Ala Val Leu Met Glu Asn Asn Ala
465                 470                 475                 480
Asp Arg Asn Ile Gln Asp Lys Glu Gly Arg Thr Ala Leu His Trp Ser
                485                 490                 495
Cys Asn Asn Gly Tyr Leu Asp Ala Ile Lys Leu Leu Leu Asp Phe Ala
                500                 505                 510
Ala Phe Pro Asn Gln Met Glu Asn Asn Glu Glu Arg Tyr Thr Pro Leu
                515                 520                 525
Asp Tyr Ala Leu Leu Gly Glu Arg His Glu Val Ile Gln Phe Met Leu
                530                 535                 540
Glu His Gly Ala Leu Ser Ile Ala Ala Ile Gln Asp Ile Ala Ala Phe
545                 550                 555                 560
Lys Ile Gln Ala Val Tyr Lys Gly Tyr Lys Val Arg Lys Ala Phe Arg
                565                 570                 575
Asp Arg Lys Asn Leu Leu Met Lys His Glu Gln Leu Arg Lys Asp Ala
                580                 585                 590
Ala Ala Lys Lys Arg Glu Glu Asn Lys Arg Lys Glu Ala Glu Gln
                595                 600                 605
```

```
Gln Lys Gly Arg Arg Ser Pro Asp Ser Cys Arg Pro Gln Ala Leu Pro
    610                 615                 620
Cys Leu Pro Ser Thr Gln Asp Val Pro Ser Arg Gln Ser Arg Ala Pro
625                 630                 635                 640
Ser Lys Gln Pro Pro Ala Gly Asn Val Ala Gln Gly Pro Glu Pro Arg
                645                 650                 655
Asp Ser Arg Gly Ser Pro Gly Gly Ser Leu Gly Gly Ala Leu Gln Lys
            660                 665                 670
Glu Gln His Val Ser Ser Asp Leu Gln Gly Thr Asn Ser Arg Arg Pro
        675                 680                 685
Asn Glu Thr Ala Arg Glu His Ser Lys Gly Gln Ser Ala Cys Val His
    690                 695                 700
Phe Arg Pro Asn Glu Gly Ser Asp Gly Ser Arg His Pro Gly Val Pro
705                 710                 715                 720
Ser Val Glu Lys Ser Arg Gly Glu Thr Ala Gly Asp Glu Arg Cys Ala
                725                 730                 735
Lys Gly Lys Gly Phe Val Lys Gln Pro Ser Cys Ile Arg Val Ala Gly
            740                 745                 750
Pro Asp Glu Lys Gly Glu Asp Ser Arg Arg Ala Gly Ala Ser Leu Pro
        755                 760                 765
Pro His Asp Ser His Trp Lys Pro Ser Arg Arg His Asp Thr Glu Pro
    770                 775                 780
Lys Ala Lys Cys Ala Pro Gln Lys Arg Arg Thr Gln Glu Leu Arg Gly
785                 790                 795                 800
Gly Arg Cys Ser Pro Ala Gly Ser Ser Arg Pro Gly Ser Ala Arg Gly
                805                 810                 815
Glu Ala Val His Ala Gly Gln Asn Pro Pro His His Arg Thr Pro Arg
            820                 825                 830
Asn Lys Val Thr Gln Ala Lys Leu Thr Gly Gly Leu Tyr Ser His Leu
        835                 840                 845
Pro Gln Ser Thr Glu Glu Leu Arg Ser Gly Ala Arg Arg Leu Glu Thr
    850                 855                 860
Ser Thr Leu Ser Glu Asp Phe Gln Val Ser Lys Glu Thr Asp Pro Ala
865                 870                 875                 880
Pro Gly Pro Leu Ser Gly Gln Ser Val Asn Ile Asp Leu Leu Pro Val
                885                 890                 895
Glu Leu Arg Leu Gln Ile Ile Gln Arg Glu Arg Arg Lys Glu Leu
            900                 905                 910
Phe Arg Lys Lys Asn Lys Ala Ala Ala Val Ile Gln Arg Ala Trp Arg
        915                 920                 925
Ser Tyr Gln Leu Arg Lys His Leu Ser His Leu Arg His Met Lys Gln
    930                 935                 940
Leu Gly Ala Gly Asp Val Asp Arg Trp Arg Gln Glu Ser Thr Ala Leu
945                 950                 955                 960
Leu Leu Gln Val Trp Arg Lys Glu Leu Glu Leu Lys Phe Pro Gln Thr
                965                 970                 975
Thr Ala Val Ser Lys Ala Pro Lys Ser Pro Ser Lys Gly Thr Ser Gly
            980                 985                 990
Thr Lys Ser Thr Lys His Ser Val  Leu Lys Gln Ile Tyr  Gly Cys Ser
        995                 1000                1005
His Glu  Gly Lys Ile His His  Pro Thr Arg Ser Val  Lys Ala Ser
    1010                1015                1020
```

-continued

| Ser | Val | Leu | Arg | Leu | Asn | Val | Ser | Asn | Leu | Gln | Cys | Ile | His |
| | 1025 | | | | 1030 | | | | 1035 | | | | |

| Leu | Leu | Glu | Asn | Ser | Gly | Arg | Ser | Lys | Asn | Phe | Ser | Tyr | Asn | Leu |
| | 1040 | | | | 1045 | | | | 1050 | | | | | |

| Gln | Ser | Ala | Thr | Gln | Pro | Lys | Asn | Lys | Thr | Lys | Pro |
| | 1055 | | | | 1060 | | | | 1065 | | |

<210> SEQ ID NO 33
<211> LENGTH: 3557
<212> TYPE: DNA
<213> ORGANISM: Homo sapiens

<400> SEQUENCE: 33

```
ggttgctccc ggttgctaag aagactatga acaagtcaga gaacctgctg tttgctggtt      60
catcattagc atcacaagtc catgctgctg ccgttaatgg agataagggt gctctacaga     120
ggctcatcgt aggaaactct gctcttaaag acaaagaaga tcagtttggg agaacaccac     180
ttatgtattg cgtgttggct gacagattgg attgtgcaga tgctcttctg aaggcaggag     240
cagatgtgaa taaaactgac catagccaga gaacagccct ccatcttgca gcccagaagg     300
gaaattatcg tttcatgaaa ctcttactta cacgcagagc aaactggatg caaaaggatc     360
tggaagagat gactcctttg cacttgacca cccggcacag gagccctaag tgtttggcac     420
ttctgctgaa gtttatggca ccaggagaag tggatacaca ggataaaaac aagcaaacag     480
ctctgcattg gagtgcctac tacaataacc ctgagcatgt gaagctgctc atcaagcatg     540
attctaacat tgggattcct gatgttgaag gcaagatccc acttcactgg gcagccaacc     600
ataaagatcc aagtgctgtt cacacagtga gatgcattct ggatgctgct ccaacagagt     660
cttactgaa ctggcaagac tacgagggtc gaactcctct tcactttgca gttgctgatg     720
ggaatgtgac cgtggttgat gtcttgacct catatgaaag ctgcaatata cgtcttatg      780
ataacttatt tcgaaccca ctgcactggg cagctttatt aggccatgca cagattgtcc     840
atctcctttt agaaagaaat aagtctggaa ctatcccatc tgacagccaa ggagccacac     900
cttttgcacta tgctgctcag agtaactttg ctgaaacggt taaagtgttt ttaaaacatc     960
cttcagtgaa agatgattca gacctggaag aagaacatc ctttatgtgg gcagctggca    1020
aaggcagtga tgatgtcctt agaactatgc tgagcttaaa atcggacata gatattaaca    1080
tggctgacaa atatggaggt acagctttgc atgctgctgc tctttctggc catgtcagca    1140
ccgtgaagtt attactggaa ataatgctc aagtagatgc tactgatgtt atgaaacata    1200
ctccactttt ccgagcctgt gagatgggac acaaagatgt gattcagaca ctcattaaag    1260
gtggagcaag ggtagatcta gttgaccaag atggacattc tcttctacat gggcagcac    1320
tgggaggaaa tgctgatgtt tgccagatat aatagaaaa taagatcaat ccaaatgtcc    1380
aggattatgc aggaagaacc cctttgcagt gtgcagcata tggaggctat atcaactgca    1440
tggcagttct catggaaaac aatgcagacc ctaacattca agacaaagag ggaagaacag    1500
ctttgcattg gtcctgcaac aatggatacc ttgatgccat taattactg ctagacttg     1560
ctgctttccc taatcagatg gaaaacaatg aagagagata cacacccctt gattatgctt    1620
tgcttggtga cgccatgaa gtgatccagt tcatgttgga gcacggtgcc ctgtccatcg    1680
cagccataca agacatcgcc gccttcaaaa tccaagctgt ctacaaaggg tacaaggtca    1740
gaaaagcctt ccgagacagg aaaaatctcc tcatgaagca tgaacagttg agaaaagatg    1800
ctgctgccaa aaagcgagag gaagaaaaca acgaaaaga ggcagaacag caaaaaggaa    1860
```

-continued

```
ggcggagccc agattcctgc agaccccagg cccttccctg tctgcctagc acccaggatg   1920
tgcccagcag gcagagccgg ccccccagca agcagcctcc tgctggcaac gtggcccaag   1980
gccctgagcc aagagacagc agaggatctc caggagggtc tctaggcgga gccctccaga   2040
aggagcagca tgtttcctca gatttgcagg gaacaaactc cagaaggcca aatgaaacag   2100
ccagagaaca ttctaaaggc caatctgctt gtgtccactt cagacccaat gaaggcagtg   2160
atggaagcag gcatccagga gttccctctg ttgagaagtc cagaggtgag acagctggcg   2220
atgagcggtg tgcaaagggg aaaggtttcg tgaagcagcc ctcctgtatc agggtggctg   2280
ggcctgatga aaaggagag gactccaggc gggcaggtgc aagccttcca ccgcacgata   2340
gccactggaa gcccagcagg cggcatgaca cagaacccaa ggccaaatgt gccccccaga   2400
aaaggcgcac tcaagagctc agaggaggaa ggtgctctcc ggctggttct agccgccctg   2460
gcagtgcccg gggggaggcg gtccatgctg ggcagaatcc tccccaccat cgtacaccaa   2520
gaaacaaagt gacacaagcc aagctcacag gagggctcta ttcacatttg ccacagagca   2580
cagaggagtt gaggtcagga gctaggaggc tggagacatc taccctgtcc gaggactttc   2640
aggtatctaa ggagactgat ccagcacctg gtcccctctc tgggcagagt gtgaatattg   2700
accttctccc cgtagagctc cgactgcaga taattcagag agaacgaagg aggaaggagc   2760
tgtttcgcaa aaagaacaag gcagcagcag tcatccagcg cgcctggcga agctaccagc   2820
tcaggaagca cctgtcccac cttcggcata tgaagcagct tggagctgga gatgtggaca   2880
gatggaggca agagtctaca gcattgctcc tccaggtttg gaggaaggaa ctgaactaaa   2940
attcccccaa accactgcag taagcaaggc ccccaagagt ccatccaagg gcacctcagg   3000
cacaaagtcc accaagcact cagtgcttaa gcaaatctat ggttgttctc acgaagggaa   3060
aatacatcat cctacaagat ctgtaaaagc ctcttctgtg ctgcgtctca actcagtgag   3120
caacctacag tgtatacatc tccttgagaa cagtggaaga tcaaagaact tttcttataa   3180
cctgcaatca gctactcagc caaaaaacaa aacaaaacct tgactgccta tggaggaaga   3240
ctgtgttcgg gggagctggc atagctagtg cagagttcag atttctgct gataatcttt   3300
tacaccttgg gaaaacttta atatccgtac ctgaaggctg attcacctaa aaatgtgtta   3360
actgaaagaa aatgtcagaa tgtttccttt ctgctcttac acagcattgt tttgtcaatc   3420
aacacagcct gcactgaaag gacctgcata gactatgtct gtgcaaagtg cctgagtgtc   3480
tgctttcacc tcagtctgta cagttggaaa tgagaattca taattaacag caaaatctaa   3540
ggaaaactaa aataaaa                                                 3557
```

<210> SEQ ID NO 34
<211> LENGTH: 970
<212> TYPE: PRT
<213> ORGANISM: Homo sapiens

<400> SEQUENCE: 34

```
Met Asn Lys Ser Glu Asn Leu Leu Phe Ala Gly Ser Ser Leu Ala Ser
1               5                   10                  15

Gln Val His Ala Ala Val Asn Gly Asp Lys Gly Ala Leu Gln Arg
            20                  25                  30

Leu Ile Val Gly Asn Ser Ala Leu Lys Asp Lys Glu Asp Gln Phe Gly
        35                  40                  45

Arg Thr Pro Leu Met Tyr Cys Val Leu Ala Asp Arg Leu Asp Cys Ala
    50                  55                  60

Asp Ala Leu Leu Lys Ala Gly Ala Asp Val Asn Lys Thr Asp His Ser
```

```
                65                  70                  75                  80
Gln Arg Thr Ala Leu His Leu Ala Ala Gln Lys Gly Asn Tyr Arg Phe
                    85                  90                  95
Met Lys Leu Leu Leu Thr Arg Arg Ala Asn Trp Met Gln Lys Asp Leu
                    100                 105                 110
Glu Glu Met Thr Pro Leu His Leu Thr Thr Arg His Arg Ser Pro Lys
                    115                 120                 125
Cys Leu Ala Leu Leu Lys Phe Met Ala Pro Gly Glu Val Asp Thr
        130                 135                 140
Gln Asp Lys Asn Lys Gln Thr Ala Leu His Trp Ser Ala Tyr Tyr Asn
145                 150                 155                 160
Asn Pro Glu His Val Lys Leu Leu Ile Lys His Asp Ser Asn Ile Gly
                    165                 170                 175
Ile Pro Asp Val Glu Gly Lys Ile Pro Leu His Trp Ala Ala Asn His
                    180                 185                 190
Lys Asp Pro Ser Ala Val His Thr Val Arg Cys Ile Leu Asp Ala Ala
                    195                 200                 205
Pro Thr Glu Ser Leu Leu Asn Trp Gln Asp Tyr Glu Gly Arg Thr Pro
        210                 215                 220
Leu His Phe Ala Val Ala Asp Gly Asn Val Thr Val Val Asp Val Leu
225                 230                 235                 240
Thr Ser Tyr Glu Ser Cys Asn Ile Thr Ser Tyr Asp Asn Leu Phe Arg
                    245                 250                 255
Thr Pro Leu His Trp Ala Ala Leu Leu Gly His Ala Gln Ile Val His
                    260                 265                 270
Leu Leu Leu Glu Arg Asn Lys Ser Gly Thr Ile Pro Ser Asp Ser Gln
                    275                 280                 285
Gly Ala Thr Pro Leu His Tyr Ala Ala Gln Ser Asn Phe Ala Glu Thr
        290                 295                 300
Val Lys Val Phe Leu Lys His Pro Ser Val Lys Asp Asp Ser Asp Leu
305                 310                 315                 320
Glu Gly Arg Thr Ser Phe Met Trp Ala Ala Gly Lys Gly Ser Asp Asp
                    325                 330                 335
Val Leu Arg Thr Met Leu Ser Leu Lys Ser Asp Ile Asp Ile Asn Met
                    340                 345                 350
Ala Asp Lys Tyr Gly Gly Thr Ala Leu His Ala Ala Ala Leu Ser Gly
        355                 360                 365
His Val Ser Thr Val Lys Leu Leu Leu Glu Asn Asn Ala Gln Val Asp
        370                 375                 380
Ala Thr Asp Val Met Lys His Thr Pro Leu Phe Arg Ala Cys Glu Met
385                 390                 395                 400
Gly His Lys Asp Val Ile Gln Thr Leu Ile Lys Gly Gly Ala Arg Val
                    405                 410                 415
Asp Leu Val Asp Gln Asp Gly His Ser Leu Leu His Trp Ala Ala Leu
                    420                 425                 430
Gly Gly Asn Ala Asp Val Cys Gln Ile Leu Ile Glu Asn Lys Ile Asn
                    435                 440                 445
Pro Asn Val Gln Asp Tyr Ala Gly Arg Thr Pro Leu Gln Cys Ala Ala
        450                 455                 460
Tyr Gly Gly Tyr Ile Asn Cys Met Ala Val Leu Met Glu Asn Asn Ala
465                 470                 475                 480
Asp Pro Asn Ile Gln Asp Lys Glu Gly Arg Thr Ala Leu His Trp Ser
                    485                 490                 495
```

```
Cys Asn Asn Gly Tyr Leu Asp Ala Ile Lys Leu Leu Asp Phe Ala
            500                 505                 510

Ala Phe Pro Asn Gln Met Glu Asn Asn Glu Glu Arg Tyr Thr Pro Leu
            515                 520                 525

Asp Tyr Ala Leu Leu Gly Glu Arg His Glu Val Ile Gln Phe Met Leu
            530                 535                 540

Glu His Gly Ala Leu Ser Ile Ala Ala Ile Gln Asp Ile Ala Ala Phe
545                 550                 555                 560

Lys Ile Gln Ala Val Tyr Lys Gly Tyr Lys Val Arg Lys Ala Phe Arg
            565                 570                 575

Asp Arg Lys Asn Leu Leu Met Lys His Glu Gln Leu Arg Lys Asp Ala
            580                 585                 590

Ala Ala Lys Arg Glu Glu Asn Lys Arg Lys Glu Ala Glu Gln
            595                 600                 605

Gln Lys Gly Arg Arg Ser Pro Asp Ser Cys Arg Pro Gln Ala Leu Pro
            610                 615                 620

Cys Leu Pro Ser Thr Gln Asp Val Pro Ser Arg Gln Ser Arg Ala Pro
625                 630                 635                 640

Ser Lys Gln Pro Pro Ala Gly Asn Val Ala Gln Gly Pro Glu Pro Arg
            645                 650                 655

Asp Ser Arg Gly Ser Pro Gly Gly Ser Leu Gly Ala Leu Gln Lys
            660                 665                 670

Glu Gln His Val Ser Ser Asp Leu Gln Gly Thr Asn Ser Arg Arg Pro
            675                 680                 685

Asn Glu Thr Ala Arg Glu His Ser Lys Gly Gln Ser Ala Cys Val His
            690                 695                 700

Phe Arg Pro Asn Glu Gly Ser Asp Gly Ser Arg His Pro Gly Val Pro
705                 710                 715                 720

Ser Val Glu Lys Ser Arg Gly Glu Thr Ala Gly Asp Glu Arg Cys Ala
            725                 730                 735

Lys Gly Lys Gly Phe Val Lys Gln Pro Ser Cys Ile Arg Val Ala Gly
            740                 745                 750

Pro Asp Glu Lys Gly Glu Asp Ser Arg Arg Ala Gly Ala Ser Leu Pro
            755                 760                 765

Pro His Asp Ser His Trp Lys Pro Ser Arg Arg His Asp Thr Glu Pro
            770                 775                 780

Lys Ala Lys Cys Ala Pro Gln Lys Arg Thr Gln Glu Leu Arg Gly
785                 790                 795                 800

Gly Arg Cys Ser Pro Ala Gly Ser Ser Arg Pro Gly Ser Ala Arg Gly
            805                 810                 815

Glu Ala Val His Ala Gly Gln Asn Pro Pro His Arg Thr Pro Arg
            820                 825                 830

Asn Lys Val Thr Gln Ala Lys Leu Thr Gly Gly Leu Tyr Ser His Leu
            835                 840                 845

Pro Gln Ser Thr Glu Glu Leu Arg Ser Gly Ala Arg Arg Leu Glu Thr
850                 855                 860

Ser Thr Leu Ser Glu Asp Phe Gln Val Ser Lys Glu Thr Asp Pro Ala
865                 870                 875                 880

Pro Gly Pro Leu Ser Gly Gln Ser Val Asn Ile Asp Leu Leu Pro Val
            885                 890                 895

Glu Leu Arg Leu Gln Ile Ile Gln Arg Glu Arg Arg Lys Glu Leu
            900                 905                 910
```

```
Phe Arg Lys Lys Asn Lys Ala Ala Val Ile Gln Arg Ala Trp Arg
        915                 920                 925

Ser Tyr Gln Leu Arg Lys His Leu Ser His Leu Arg His Met Lys Gln
    930                 935                 940

Leu Gly Ala Gly Asp Val Asp Arg Trp Arg Gln Glu Ser Thr Ala Leu
945                 950                 955                 960

Leu Leu Gln Val Trp Arg Lys Glu Leu Glu
            965                 970

<210> SEQ ID NO 35
<211> LENGTH: 3558
<212> TYPE: DNA
<213> ORGANISM: Homo sapiens

<400> SEQUENCE: 35
ggttgctccc ggttgctaag aagactatga acaagtcaga gaacctgctg tttgctggtt      60
catcattagc atcacaagtc catgctgctg ccgttaatgg agataagggt gctctacaga     120
ggctcatcgt aggaaactct gctcttaaag acaagaaga tcagtttggg agaacaccac      180
ttatgtattg cgtgttggct gacagattgg attgtgcaga tgctcttctg aaggcaggag     240
cagatgtgaa taaaactgac catagccaga gaacagccct ccatcttgca gcccagaagg     300
gaaattatcg tttcatgaaa ctcttactta cacgcagagc aaactggatg caaaaggatc     360
tggaagagat gactcctttg cacttgacca cccggcacag gagccctaag tgtttggcac     420
ttctgctgaa gtttatggca ccaggagaag tggatacaca ggataaaaac aagcaaacag     480
ctctgcattg gagtgcctac tacaataacc ctgagcatgt gaagctgctc atcaagcatg     540
attctaacat tgggattcct gatgttgaag gcaagatccc acttcactgg gcagccaacc     600
ataaagatcc aagtgctgtt cacacagtga gatgcattct ggatgctgct ccaacagagt     660
ctttactgaa ctggcaagac tacgagggtc gaactcctct tcactttgca gttgctgatg     720
ggaatgtgac cgtggttgat gtcttgacct catatgaaag ctgcaatata cgtcttatg     780 ataacttatt tcgaaccccca ctgcactggg cagctttatt aggccatgca cagattgtcc     840
atctcctttt agaaagaaat aagtctggaa ctatcccatc tgacagccaa ggagccacac     900
ctttgcacta tgctgctcag agtaactttg ctgaaacggt taaagtgttt ttaaaacatc     960
cttcagtgaa agatgattca gacctggaag gaagaacatc ctttatgtgg gcagctggca    1020
aaggcagtga tgatgtcctt agaactatgc tgagcttaaa atcggacata gatattaaca    1080
tggctgacaa atatggaggt acagcttgc atgctgctgc tctttctggc catgtcagca    1140
ccgtgaagtt attactggaa aataatgctc aagtagatgc tactgatgtt atgaaacata    1200
ctccactttt ccgagcctgt gagatgggac acaaagatgt gattcagaca ctcattaaag    1260
gtggagcaag ggtagatcta gttgaccaag atggacattc tcttctacat tgggcagcac    1320
tgggaggaaa tgctgatgtt tgccagatat aatagaaaa taagatcaat ccaaatgtcc    1380
aggattatgc aggaagaacc ctttgcagt gtgcagcata tggaggctat atcaactgca    1440
tggcagttct catggaaaac aatgcagacc ctaacattca agacaaagag ggaagaacag    1500
ctttgcattg gtcctgcaac aatggatacc ttgatgccat taaattactg ctagactttg    1560
ctgctttccc taatcagatg gaaaacaatg aagagagata cacacccctt gattatgctt    1620
tgcttggtga gcgccatgaa gtgatccagt tcatgttgga gcacggtgcc ctgtccatcg    1680
cagccataca agacatcgcc gccttcaaaa tccaagctgt ctacaaaggg tacaaggtca    1740
gaaaagcctt ccgagacagg aaaaatctcc tcatgaagca tgaacagttg agaaaagatg    1800
```

-continued

```
ctgctgccaa aaagcgagag gaagaaaaca aacgaaaaga ggcagaacag caaaaaggaa      1860
ggcggagccc agattcctgc agaccccagg cccttccctg tctgcctagc acccaggatg      1920
tgcccagcag gcagagccgg gcccccagca agcagcctcc tgctggcaac gtggcccaag      1980
gccctgagcc aagagacagc agaggatctc caggagggtc tctaggcgga gccctccaga      2040
aggagcagca tgtttcctca gatttgcagg gaacaaactc cagaaggcca atgaaacag       2100 ccagagaaca ttctaaaggc caatctgctt gtgtccactt cagacccaat gaaggcagtg      2160
atggaagcag gcatccagga gttccctctg ttgagaagtc cagaggtgag acagctggcg      2220
atgagcggtg tgcaaagggg aaaggtttcg tgaagcagcc ctcctgtatc agggtggctg      2280
ggcctgatga aaaggagag gactccaggc gggcaggtgc aagccttcca ccgcacgata       2340
gccactggaa gcccagcagg cggcatgaca cagaacccaa ggccaaatgt gcccccccaga     2400 aaaggcgcac tcaagagctc agaggaggaa ggtgctctcc ggctggttct agccgccctg      2460
gcagtgcccg gggggaggcg gtccatgctg ggcagaatcc tccccaccat cgtacaccaa      2520
gaaacaaagt gacacaagcc aagctcacag gagggctcta ttcacatttg ccacagagca      2580
cagaggagtt gaggtcagga gctaggaggc tggagacatc taccctgtcc gaggactttc      2640
aggtatctaa ggagactgat ccagcacctg gtccctctc tggcagagt gtgaatattg        2700 accttctccc cgtagagctc cgactgcaga taattcagag agaatgaagg aggaaggagc      2760
tgtttcgcaa aaagaacaag gcagcagcag tcatccagcg cgcctggcga agctaccagc     2820
tcaggaagca cctgtcccac cttcggcata tgaagcagct tggagctgga gatgtggaca     2880
gatggaggca agagtctaca gcattgctcc tccaggtttg gaggaaggaa ctggaactaa     2940
aattccccca aaccactgca gtaagcaagg cccccaagag tccatccaag ggcacctcag     3000
gcacaaagtc caccaagcac tcagtgctta agcaaatcta tggttgttct cacgaaggga     3060
aaatacatca tcctacaaga tctgtaaaag cctcttctgt gctgcgtctc aactcagtga     3120
gcaacctaca gtgtatacat ctccttgaga acagtggaag atcaaagaac ttttcttata     3180
acctgcaatc agctactcag ccaaaaaaca aaacaaaacc ttgactgcct atggaggaag     3240
actgtgttcg ggggagctgg catagctagt gcagagttca gattttctgc tgataatctt     3300
ttacaccttg ggaaaacttt aatatccgta cctgaaggct gattcaccta aaaatgtgtt     3360
aactgaaaga aaatgtcaga atgtttcctt tctgctctta cacagcattg ttttgtcaat     3420
caacacagcc tgcactgaaa ggacctgcat agactatgtc tgtgcaaagt gcctgagtgt     3480
ctgctttcac ctcagtctgt acagttggaa atgagaattc ataattaaca gcaaaatcta     3540
aggaaaacta aaataaaa                                                    3558
```

<210> SEQ ID NO 36
<211> LENGTH: 906
<212> TYPE: PRT
<213> ORGANISM: Homo sapiens

<400> SEQUENCE: 36

```
Met Asn Lys Ser Glu Asn Leu Leu Phe Ala Gly Ser Ser Leu Ala Ser
1               5                   10                  15

Gln Val His Ala Ala Ala Val Asn Gly Asp Lys Gly Ala Leu Gln Arg
            20                  25                  30

Leu Ile Val Gly Asn Ser Ala Leu Lys Asp Lys Glu Asp Gln Phe Gly
        35                  40                  45

Arg Thr Pro Leu Met Tyr Cys Val Leu Ala Asp Arg Leu Asp Cys Ala
```

-continued

```
            50                  55                  60
Asp Ala Leu Leu Lys Ala Gly Ala Asp Val Asn Lys Thr Asp His Ser
65                  70                  75                  80
Gln Arg Thr Ala Leu His Leu Ala Ala Gln Lys Gly Asn Tyr Arg Phe
                85                  90                  95
Met Lys Leu Leu Leu Thr Arg Arg Ala Asn Trp Met Gln Lys Asp Leu
            100                 105                 110
Glu Glu Met Thr Pro Leu His Leu Thr Thr Arg His Arg Ser Pro Lys
            115                 120                 125
Cys Leu Ala Leu Leu Lys Phe Met Ala Pro Gly Glu Val Asp Thr
130                 135                 140
Gln Asp Lys Asn Lys Gln Thr Ala Leu His Trp Ser Ala Tyr Tyr Asn
145                 150                 155                 160
Asn Pro Glu His Val Lys Leu Leu Ile Lys His Asp Ser Asn Ile Gly
                165                 170                 175
Ile Pro Asp Val Glu Gly Lys Ile Pro Leu His Trp Ala Ala Asn His
            180                 185                 190
Lys Asp Pro Ser Ala Val His Thr Val Arg Cys Ile Leu Asp Ala Ala
                195                 200                 205
Pro Thr Glu Ser Leu Leu Asn Trp Gln Asp Tyr Glu Gly Arg Thr Pro
            210                 215                 220
Leu His Phe Ala Val Ala Asp Gly Asn Val Thr Val Val Asp Val Leu
225                 230                 235                 240
Thr Ser Tyr Glu Ser Cys Asn Ile Thr Ser Tyr Asp Asn Leu Phe Arg
                245                 250                 255
Thr Pro Leu His Trp Ala Ala Leu Leu Gly His Ala Gln Ile Val His
            260                 265                 270
Leu Leu Leu Glu Arg Asn Lys Ser Gly Thr Ile Pro Ser Asp Ser Gln
            275                 280                 285
Gly Ala Thr Pro Leu His Tyr Ala Ala Gln Ser Asn Phe Ala Glu Thr
290                 295                 300
Val Lys Val Phe Leu Lys His Pro Ser Val Lys Asp Asp Ser Asp Leu
305                 310                 315                 320
Glu Gly Arg Thr Ser Phe Met Trp Ala Ala Gly Lys Gly Ser Asp Asp
                325                 330                 335
Val Leu Arg Thr Met Leu Ser Leu Lys Ser Asp Ile Asp Ile Asn Met
            340                 345                 350
Ala Asp Lys Tyr Gly Gly Thr Ala Leu His Ala Ala Leu Ser Gly
                355                 360                 365
His Val Ser Thr Val Lys Leu Leu Leu Glu Asn Asn Ala Gln Val Asp
            370                 375                 380
Ala Thr Asp Val Met Lys His Thr Pro Leu Phe Arg Ala Cys Glu Met
385                 390                 395                 400
Gly His Lys Asp Val Ile Gln Thr Leu Ile Lys Gly Gly Ala Arg Val
                405                 410                 415
Asp Leu Val Asp Gln Asp Gly His Ser Leu Leu His Trp Ala Ala Leu
            420                 425                 430
Gly Gly Asn Ala Asp Val Cys Gln Ile Leu Ile Glu Asn Lys Ile Asn
            435                 440                 445
Pro Asn Val Gln Asp Tyr Ala Gly Arg Thr Pro Leu Gln Cys Ala Ala
            450                 455                 460
Tyr Gly Gly Tyr Ile Asn Cys Met Ala Val Leu Met Glu Asn Asn Ala
465                 470                 475                 480
```

```
Asp Pro Asn Ile Gln Asp Lys Glu Gly Arg Thr Ala Leu His Trp Ser
            485                 490                 495

Cys Asn Asn Gly Tyr Leu Asp Ala Ile Lys Leu Leu Leu Asp Phe Ala
        500                 505                 510

Ala Phe Pro Asn Gln Met Glu Asn Asn Glu Glu Arg Tyr Thr Pro Leu
    515                 520                 525

Asp Tyr Ala Leu Leu Gly Glu Arg His Glu Val Ile Gln Phe Met Leu
530                 535                 540

Glu His Gly Ala Leu Ser Ile Ala Ala Ile Gln Asp Ile Ala Ala Phe
545                 550                 555                 560

Lys Ile Gln Ala Val Tyr Lys Gly Tyr Lys Val Arg Lys Ala Phe Arg
                565                 570                 575

Asp Arg Lys Asn Leu Leu Met Lys His Glu Gln Leu Arg Lys Asp Ala
            580                 585                 590

Ala Ala Lys Lys Arg Glu Glu Asn Lys Arg Lys Glu Ala Glu Gln
        595                 600                 605

Gln Lys Gly Arg Arg Ser Pro Asp Ser Cys Arg Pro Gln Ala Leu Pro
    610                 615                 620

Cys Leu Pro Ser Thr Gln Asp Val Pro Ser Arg Gln Ser Arg Ala Pro
625                 630                 635                 640

Ser Lys Gln Pro Pro Ala Gly Asn Val Ala Gln Gly Pro Glu Pro Arg
                645                 650                 655

Asp Ser Arg Gly Ser Pro Gly Gly Ser Leu Gly Gly Ala Leu Gln Lys
            660                 665                 670

Glu Gln His Val Ser Ser Asp Leu Gln Gly Thr Asn Ser Arg Arg Pro
    675                 680                 685

Asn Glu Thr Ala Arg Glu His Ser Lys Gly Gln Ser Ala Cys Val His
    690                 695                 700

Phe Arg Pro Asn Glu Gly Ser Asp Gly Ser Arg His Pro Gly Val Pro
705                 710                 715                 720

Ser Val Glu Lys Ser Arg Gly Glu Thr Ala Gly Asp Glu Arg Cys Ala
                725                 730                 735

Lys Gly Lys Gly Phe Val Lys Gln Pro Ser Cys Ile Arg Val Ala Gly
            740                 745                 750

Pro Asp Glu Lys Gly Glu Asp Ser Arg Arg Ala Gly Ala Ser Leu Pro
    755                 760                 765

Pro His Asp Ser His Trp Lys Pro Ser Arg Arg His Asp Thr Glu Pro
    770                 775                 780

Lys Ala Lys Cys Ala Pro Gln Lys Arg Arg Thr Gln Glu Leu Arg Gly
785                 790                 795                 800

Gly Arg Cys Ser Pro Ala Gly Ser Ser Arg Pro Gly Ser Ala Arg Gly
                805                 810                 815

Glu Ala Val His Ala Gly Gln Asn Pro Pro His His Arg Thr Pro Arg
            820                 825                 830

Asn Lys Val Thr Gln Ala Lys Leu Thr Gly Gly Leu Tyr Ser His Leu
    835                 840                 845

Pro Gln Ser Thr Glu Glu Leu Arg Ser Gly Ala Arg Arg Leu Glu Thr
    850                 855                 860

Ser Thr Leu Ser Glu Asp Phe Gln Val Ser Lys Glu Thr Asp Pro Ala
865                 870                 875                 880

Pro Gly Pro Leu Ser Gly Gln Ser Val Asn Ile Asp Leu Leu Pro Val
                885                 890                 895
```

Glu Leu Arg Leu Gln Ile Ile Gln Arg Glu
         900                 905

<210> SEQ ID NO 37
<211> LENGTH: 3558
<212> TYPE: DNA
<213> ORGANISM: Homo sapiens

<400> SEQUENCE: 37

| | | | | | |
|---|---|---|---|---|---|
| ggttgctccc | ggttgctaag | aagactatga | acaagtcaga | gaacctgctg | tttgctggtt | 60 |
| catcattagc | atcacaagtc | catgctgctg | ccgttaatgg | agataagggt | gctctacaga | 120 |
| ggctcatcgt | aggaaactct | gctcttaaag | acaaagaaga | tcagtttggg | agaacaccac | 180 |
| ttatgtattg | cgtgttggct | gacagattgg | attgtgcaga | tgctcttctg | aaggcaggag | 240 |
| cagatgtgaa | taaaactgac | catagccaga | gaacagccct | ccatcttgca | gcccagaagg | 300 |
| gaaattatcg | tttcatgaaa | ctcttactta | cacgcagagc | aaactggatg | caaaaggatc | 360 |
| tggaagagat | gactcctttg | cacttgacca | cccggcacag | gagccctaag | tgtttggcac | 420 |
| ttctgctgaa | gttatggca | ccaggagaag | tggatacaca | ggataaaaac | aagcaaacag | 480 |
| ctctgcattg | gagtgcctac | tacaataacc | ctgagcatgt | gaagctgctc | atcaagcatg | 540 |
| attctaacat | tgggattcct | gatgttgaag | gcaagatccc | acttcactgg | gcagccaacc | 600 |
| ataaagatcc | aagtgctgtt | cacacagtga | gatgcattct | ggatgctgct | ccaacagagt | 660 |
| ctttactgaa | ctggcaagac | tacgagggtc | gaactcctct | tcactttgca | gttgctgatg | 720 |
| ggaatgtgac | cgtggttgat | gtcttgacct | catatgaaag | ctgcaatata | acgtcttatg | 780 |
| ataacttatt | tcgaaccccca | ctgcactggg | cagctttatt | aggccatgca | cagattgtcc | 840 |
| atctccttt | agaaagaaat | aagtctggaa | ctatcccatc | tgcagccaa | ggagccacac | 900 |
| ctttgcacta | tgctgctcag | gtaactttg | ctgaaacggt | taaagtgttt | ttaaaacatc | 960 |
| cttcagtgaa | agatgattca | gacctggaag | gaagaacatc | ctttatgtgg | gcagctggca | 1020 |
| aaggcagtga | tgatgtcctt | agaactatgc | tgagcttaaa | atcggacata | gatattaaca | 1080 |
| tggctgacaa | atatgaggt | acagctttgc | atgctgctgc | tcttctggc | catgtcagca | 1140 |
| ccgtgaagtt | attactggaa | aataatgctc | aagtagatgc | tactgatgtt | atgaaacata | 1200 |
| ctccactttt | ccgagcctgt | gagatgggac | acaaagatgt | gattcagaca | ctcattaaag | 1260 |
| gtggagcaag | ggtagatcta | gttgaccaag | atggacattc | tcttctacat | tgggcagcac | 1320 |
| tgggaggaaa | tgctgatgtt | tgccagatat | taatagaaaa | taagatcaat | ccaaatgtcc | 1380 |
| aggattatgc | aggaagaacc | cctttgcagt | gtgcagcata | tggaggctat | atcaactgca | 1440 |
| tggcagttct | catggaaaac | aatgcagacc | ctaacattca | agacaaagag | ggaagaacag | 1500 |
| ctttgcattg | gtcctgcaac | aatggatacc | ttgatgccat | taaattactg | ctagactttg | 1560 |
| ctgctttccc | taatcagatg | gaaaacaatg | aagagagata | cacaccccctt | gattatgctt | 1620 |
| tgcttggtga | gcgccatgaa | gtgatccagt | tcatgttgga | gcacggtgcc | ctgtccatcg | 1680 |
| cagcccataca | agacatcgcc | gccttcaaaa | tccaagctgt | ctacaaaggg | tacaaggtca | 1740 |
| gaaaagcctt | ccgagacagg | aaaaatctcc | tcatgaagca | tgaacagttg | agaaaagatg | 1800 |
| ctgctgccaa | aaagcgagag | gaagaaaaca | acgaaaaga | ggcagaacag | caaaaaggaa | 1860 |
| ggcggagccc | agattcctgc | agaccccagg | cccttccctg | tctgcctagc | acccaggatg | 1920 |
| tgccagcag | gcagagccgg | gcccccagca | agcagcctcc | tgctggcaac | gtggcccaag | 1980 |
| gccctgagcc | aagagacagc | agaggatctc | caggagggtc | tctaggcgga | gccctccaga | 2040 |

-continued

```
aggagcagca tgtttcctca gatttgcagg gaacaaactc cagaaggcca aatgaaacag    2100
ccagagaaca ttctaaaggc caatctgctt gtgtccactt cagacccaat gaaggcagtg    2160
atggaagcag gcatccagga gttccctctg ttgagaagtc cagaggtgag acagctggcg    2220
atgagcggtg tgcaaagggg aaaggtttcg tgaagcagcc ctcctgtatc agggtggctg    2280
ggcctgatga gaaggagag gactccaggc gggcaggtgc aagccttcca ccgcacgata    2340
gccactggaa gcccagcagg cggcatgaca cagaacccaa ggccaaatgt gcccccaga    2400 aaaggcgcac tcaagagctc agaggaggaa ggtgctctcc ggctggttct agccgccctg    2460
gcagtgcccg gggggaggcg gtccatgctg gcagaatcc tccccaccat cgtacaccaa    2520
gaaacaaagt gacacaagcc aagctcacag gagggctcta ttcacatttg ccacagagca    2580
cagaggagtt gaggtcagga gctaggaggc tggagacatc taccctgtcc gaggactttc    2640
aggtatctaa ggagactgat ccagcacctg gtccctctc tgggcagagt gtgaatattg    2700
accttctccc cgtagagctc cgactgcaga taattcagag agaatgaagg aggaaggagc    2760
tgtttcgcaa aagaacaag gcagcagcag tcatccagcg cgcctggcga agctaccagc    2820
tcaggaagca cctgtcccac cttcggcata tgaagcagct tggagctgga gatgtggaca    2880
gatggaggca agagtctaca gcattgctcc tccaggtttg gaggaaggaa ctggaactaa    2940
aattccccca aaccactgca gtaagcaagg cccccaagag tccatccaag ggcacctcag    3000
gcacaaagtc caccaagcac tcagtgctta agcaaatcta tggttgttct cacgaaggga    3060
aaatacatca tcctacaaga tctgtaaaag cctcttctgt gctgcgtctc aactcagtga    3120
gcaacctaca gtgtatacat ctccttgaga acagtggaag atcaaagaac ttttcttata    3180
acctgcaatc agctactcag ccaaaaaaca aaacaaaacc ttgactgcct atggaggaag    3240
actgtgttcg ggggagctgg catagctagt gcagagttca gattttctgc tgataatctt    3300
ttacaccttg ggaaaacttt aatatccgta cctgaaggct gattcaccta aaaatgtgtt    3360
aactgaaaga aaatgtcaga atgtttcctt tctgctctta cacagcattg ttttgtcaat    3420
caacacagcc tgcactgaaa ggacctgcat agactatgtc tgtgcaaagt gcctgagtgt    3480
ctgctttcac ctcagtctgt acagttggaa atgagaattc ataattaaca gcaaaatcta    3540
aggaaaacta aaataaaa                                                  3558
```

<210> SEQ ID NO 38
<211> LENGTH: 906
<212> TYPE: PRT
<213> ORGANISM: Homo sapiens

<400> SEQUENCE: 38

```
Met Asn Lys Ser Glu Asn Leu Leu Phe Ala Gly Ser Ser Leu Ala Ser
1               5                   10                  15

Gln Val His Ala Ala Val Asn Gly Asp Lys Gly Ala Leu Gln Arg
            20                  25                  30

Leu Ile Val Gly Asn Ser Ala Leu Lys Asp Lys Glu Asp Gln Phe Gly
        35                  40                  45

Arg Thr Pro Leu Met Tyr Cys Val Leu Ala Asp Arg Leu Asp Cys Ala
    50                  55                  60

Asp Ala Leu Leu Lys Ala Gly Ala Asp Val Asn Lys Thr Asp His Ser
65                  70                  75                  80

Gln Arg Thr Ala Leu His Leu Ala Ala Gln Lys Gly Asn Tyr Arg Phe
                85                  90                  95

Met Lys Leu Leu Leu Thr Arg Arg Ala Asn Trp Met Gln Lys Asp Leu
```

```
                    100                 105                 110
Glu Glu Met Thr Pro Leu His Leu Thr Thr Arg His Arg Ser Pro Lys
            115                 120                 125
Cys Leu Ala Leu Leu Leu Lys Phe Met Ala Pro Gly Glu Val Asp Thr
        130                 135                 140
Gln Asp Lys Asn Lys Gln Thr Ala Leu His Trp Ser Ala Tyr Tyr Asn
145                 150                 155                 160
Asn Pro Glu His Val Lys Leu Leu Ile Lys His Asp Ser Asn Ile Gly
                165                 170                 175
Ile Pro Asp Val Glu Gly Lys Ile Pro Leu His Trp Ala Ala Asn His
            180                 185                 190
Lys Asp Pro Ser Ala Val His Thr Val Arg Cys Ile Leu Asp Ala Ala
        195                 200                 205
Pro Thr Glu Ser Leu Leu Asn Trp Gln Asp Tyr Glu Gly Arg Thr Pro
    210                 215                 220
Leu His Phe Ala Val Ala Asp Gly Asn Val Thr Val Val Asp Val Leu
225                 230                 235                 240
Thr Ser Tyr Glu Ser Cys Asn Ile Thr Ser Tyr Asp Asn Leu Phe Arg
                245                 250                 255
Thr Pro Leu His Trp Ala Ala Leu Leu Gly His Ala Gln Ile Val His
            260                 265                 270
Leu Leu Leu Glu Arg Asn Lys Ser Gly Thr Ile Pro Ser Asp Ser Gln
        275                 280                 285
Gly Ala Thr Pro Leu His Tyr Ala Ala Gln Ser Asn Phe Ala Glu Thr
    290                 295                 300
Val Lys Val Phe Leu Lys His Pro Ser Val Lys Asp Asp Ser Asp Leu
305                 310                 315                 320
Glu Gly Arg Thr Ser Phe Met Trp Ala Ala Gly Lys Gly Ser Asp Asp
                325                 330                 335
Val Leu Arg Thr Met Leu Ser Leu Lys Ser Asp Ile Asp Ile Asn Met
            340                 345                 350
Ala Asp Lys Tyr Gly Gly Thr Ala Leu His Ala Ala Ala Leu Ser Gly
        355                 360                 365
His Val Ser Thr Val Lys Leu Leu Leu Glu Asn Asn Ala Gln Val Asp
    370                 375                 380
Ala Thr Asp Val Met Lys His Thr Pro Leu Phe Arg Ala Cys Glu Met
385                 390                 395                 400
Gly His Lys Asp Val Ile Gln Thr Leu Ile Lys Gly Gly Ala Arg Val
                405                 410                 415
Asp Leu Val Asp Gln Asp Gly His Ser Leu Leu His Trp Ala Ala Leu
            420                 425                 430
Gly Gly Asn Ala Asp Val Cys Gln Ile Leu Ile Glu Asn Lys Ile Asn
        435                 440                 445
Pro Asn Val Gln Asp Tyr Ala Gly Arg Thr Pro Leu Gln Cys Ala Ala
    450                 455                 460
Tyr Gly Gly Tyr Ile Asn Cys Met Ala Val Leu Met Glu Asn Asn Ala
465                 470                 475                 480
Asp Pro Asn Ile Gln Asp Lys Glu Gly Arg Thr Ala Leu His Trp Ser
                485                 490                 495
Cys Asn Asn Gly Tyr Leu Asp Ala Ile Lys Leu Leu Leu Asp Phe Ala
            500                 505                 510
Ala Phe Pro Asn Gln Met Glu Asn Asn Glu Glu Arg Tyr Thr Pro Leu
        515                 520                 525
```

```
Asp Tyr Ala Leu Leu Gly Glu Arg His Glu Val Ile Gln Phe Met Leu
    530                 535                 540

Glu His Gly Ala Leu Ser Ile Ala Ala Ile Gln Asp Ile Ala Ala Phe
545                 550                 555                 560

Lys Ile Gln Ala Val Tyr Lys Gly Tyr Lys Val Arg Lys Ala Phe Arg
                565                 570                 575

Asp Arg Lys Asn Leu Leu Met Lys His Glu Gln Leu Arg Lys Asp Ala
            580                 585                 590

Ala Ala Lys Lys Arg Glu Glu Asn Lys Arg Lys Glu Ala Glu Gln
        595                 600                 605

Gln Lys Gly Arg Arg Ser Pro Asp Ser Cys Arg Pro Gln Ala Leu Pro
    610                 615                 620

Cys Leu Pro Ser Thr Gln Asp Val Pro Ser Arg Ser Arg Ala Pro
625                 630                 635                 640

Ser Lys Gln Pro Pro Ala Gly Asn Val Ala Gln Gly Pro Glu Pro Arg
                645                 650                 655

Asp Ser Arg Gly Ser Pro Gly Gly Ser Leu Gly Gly Ala Leu Gln Lys
            660                 665                 670

Glu Gln His Val Ser Ser Asp Leu Gln Gly Thr Asn Ser Arg Arg Pro
        675                 680                 685

Asn Glu Thr Ala Arg Glu His Ser Lys Gly Gln Ser Ala Cys Val His
    690                 695                 700

Phe Arg Pro Asn Glu Gly Ser Asp Gly Ser Arg His Pro Gly Val Pro
705                 710                 715                 720

Ser Val Glu Lys Ser Arg Gly Glu Thr Ala Gly Asp Glu Arg Cys Ala
                725                 730                 735

Lys Gly Lys Gly Phe Val Lys Gln Pro Ser Cys Ile Arg Val Ala Gly
            740                 745                 750

Pro Asp Glu Lys Gly Glu Asp Ser Arg Arg Ala Gly Ala Ser Leu Pro
        755                 760                 765

Pro His Asp Ser His Trp Lys Pro Ser Arg Arg His Asp Thr Glu Pro
    770                 775                 780

Lys Ala Lys Cys Ala Pro Gln Lys Arg Arg Thr Gln Glu Leu Arg Gly
785                 790                 795                 800

Gly Arg Cys Ser Pro Ala Gly Ser Ser Arg Pro Gly Ser Ala Arg Gly
                805                 810                 815

Glu Ala Val His Ala Gly Gln Asn Pro Pro His His Arg Thr Pro Arg
            820                 825                 830

Asn Lys Val Thr Gln Ala Lys Leu Thr Gly Gly Leu Tyr Ser His Leu
        835                 840                 845

Pro Gln Ser Thr Glu Glu Leu Arg Ser Gly Ala Arg Arg Leu Glu Thr
    850                 855                 860

Ser Thr Leu Ser Glu Asp Phe Gln Val Ser Lys Glu Thr Asp Pro Ala
865                 870                 875                 880

Pro Gly Pro Leu Ser Gly Gln Ser Val Asn Ile Asp Leu Leu Pro Val
                885                 890                 895

Glu Leu Arg Leu Gln Ile Ile Gln Arg Glu
            900                 905
```

<210> SEQ ID NO 39
<211> LENGTH: 3559
<212> TYPE: DNA
<213> ORGANISM: Homo sapiens

<400> SEQUENCE: 39

```
ggttgctccc ggttgctaag aagactatga acaagtcaga gaacctgctg tttgctggtt      60
catcattagc atcacaagtc catgctgctg ccgttaatgg agataagggt gctctacaga     120
ggctcatcgt aggaaactct gctcttaaag acaaagaaga tcagtttggg agaacaccac     180
ttatgtattg cgtgttggct gacagattgg attgtgcaga tgctcttctg aaggcaggag     240
cagatgtgaa taaaactgac catagccaga gaacagccct ccatcttgca gcccagaagg     300
gaaattatcg tttcatgaaa ctcttactta cacgcagagc aaactggatg caaaaggatc     360
tggaagagat gactcctttg cacttgacca cccggcacag gagccctaag tgtttggcac     420
ttctgctgaa gtttatggca ccaggagaag tggatacaca ggataaaaac aagcaaacag     480
ctctgcattg gagtgcctac tacaataacc ctgagcatgt gaagctgctc atcaagcatg     540
attctaacat tgggattcct gatgttgaag gcaagatccc acttcactgg gcagccaacc     600
ataaagatcc aagtgctgtt cacacagtga gatgcattct ggatgctgct ccaacagagt     660
ctttactgaa ctggcaagac tacgagggtc gaactcctct tcactttgca gttgctgatg     720
ggaatgtgac cgtggttgat gtcttgacct catatgaaag ctgcaatata cgtcttatg     780
ataacttatt tcgaacccca ctgcactggg cagctttatt aggccatgca cagattgtcc     840
atctcctttt agaagaaat aagtctggaa ctatcccatc tgcacagcca ggagccacac     900
ctttgcacta tgctgctcag agtaactttg ctgaaacggt taaagtgttt ttaaaacatc     960
cttcagtgaa agatgattca gacctggaag gaagaacatc ctttatgtgg gcagctggca    1020
aaggcagtga tgatgtcctt agaactatgc tgagcttaaa atcggacata gatattaaca    1080
tggctgacaa atatggaggt acagctttgc atgctgctgc tctttctggc catgtcagca    1140
ccgtgaagtt attactggaa aataatgctc aagtagatgc tactgatgtt atgaaacata    1200
ctccactttt ccgagcctgt gagatgggac acaaagatgt gattcagaca ctcattaaag    1260
gtggagcaag ggtagatcta gttgaccaag atggacattc tcttctacat tgggcagcac    1320
tgggaggaaa tgctgatgtt tgccagatat aatagaaaa taagatcaat ccaaatgtcc    1380
aggattatgc aggaagaacc cctttgcagt gtgcagcata tggaggctat atcaactgca    1440
tggcagttct catggaaaac aatgcagacc ctaacattca agacaaagag gaagaacag    1500
ctttgcattg gtcctgcaac aatggatacc ttgatgccat taaattactg ctagactttg    1560
ctgctttccc taatcagatg gaaaacaatg aagagagata cacacccctt gattatgctt    1620
tgcttggtga gcgccatgaa gtgatccagt tcatgttgga gcacggtgcc ctgtccatcg    1680
cagccataca agacatcgcc gccttcaaaa tccaagctgt ctacaaaggg tacaaggtca    1740
gaaaagcctt ccgagacagg aaaaatctcc tcatgaagca tgaacagttg agaaaagatg    1800
ctgctgccaa aaagcgagag gaagaaaaca acgaaaaga ggcagaacag caaaaggaa    1860
ggcggagccc agattcctgc agaccccagg cccttccctg tctgcctagc acccaggatg    1920
tgcccagcag gcagagccgg gcccccagca agcagcctcc tgctggcaac gtggcccaag    1980
gccctgagcc aagagacagc agaggatctc caggagggtc tctaggcgga gcctccagaa    2040
aggagcagca tgtttcctca gatttgcagg aacaaactc cagaaggcca aatgaaacag    2100
ccagagaaca ttctaaaggc caatctgctt gtgtccactt cagacccaat gaaggcagtg    2160
atggaagcag gcatccagga gttccctctg ttgagaagtc cagaggtgag acagctggcg    2220
atgagcggtg tgcaaagggg aaaggtttcg tgaagcagcc ctcctgtatc agggtggctg    2280
ggcctgatga gaaaggagag gactccaggc gggcaggtgc aagccttcca ccgcacgata    2340
```

-continued

```
gccactggaa gcccagcagg cggcatgaca cagaacccaa ggccaaatgt gccccccaga      2400
aaaggcgcac tcaagagctc agaggaggaa ggtgctctcc ggctggttct agccgccctg      2460
gcagtgcccg gggggaggcg gtccatgctg ggcagaatcc tccccaccat cgtacaccaa      2520
gaaacaaagt gacacaagcc aagctcacag gagggctcta ttcacatttg ccacagagca      2580
cagaggagtt gaggtcagga gctaggaggc tggagacatc taccctgtcc gaggactttc      2640
aggtatctaa ggagactgat ccagcacctg gtcccctctc tgggcagagt gtgaatattg      2700
accttctccc cgtagagctc cgactgcaga taattcagag agaacgaagg aggaaggagc      2760
tgtttcgcaa aaaagaacaa ggcagcagca gtcatccagc gcgcctggcg aagctaccag      2820
ctcaggaagc acctgtccca ccttcggcat atgaagcagc ttggagctgg agatgtggac      2880
agatggaggc aagagtctac agcattgctc ctccaggttt ggaggaagga actggaacta      2940
aaattccccc aaaccactgc agtaagcaag gcccccaaga gtccatccaa gggcacctca      3000
ggcacaaagt ccaccaagca ctcagtgctt aagcaaatct atggttgttc tcacgaaggg      3060
aaaatacatc atcctacaag atctgtaaaa gcctcttctg tgctgcgtct caactcagtg      3120
agcaacctac agtgtataca tctccttgag aacagtggaa gatcaaagaa ctttctcttat     3180 aacctgcaat cagctactca gccaaaaaac aaaacaaaac cttgactgcc tatgcaggaa      3240
gactgtgttc gggggagctg gcatagctag tgcagagttc agattttctg ctgataatct      3300
tttacaccct tgggaaaactt taatatccgt acctgaaggc tgattcacct aaaaatgtgt     3360
taactgaaag aaaaatgtcag aatgtttcct ttctgctctt acacagcatt gttttgtcaa     3420
tcaacacagc ctgcactgaa aggacctgca tagactatgt ctgtgcaaag tgcctgagtg      3480
tctgctttca cctcagtctg tacagttgga aatgagaatt cataattaac agcaaaatct      3540
aaggaaaact aaaataaaa                                                   3559
```

<210> SEQ ID NO 40
<211> LENGTH: 1001
<212> TYPE: PRT
<213> ORGANISM: Homo sapiens

<400> SEQUENCE: 40

```
Met Asn Lys Ser Glu Asn Leu Leu Phe Ala Gly Ser Ser Leu Ala Ser
1               5                   10                  15

Gln Val His Ala Ala Val Asn Gly Asp Lys Gly Ala Leu Gln Arg
            20                  25                  30

Leu Ile Val Gly Asn Ser Ala Leu Lys Asp Lys Glu Asp Gln Phe Gly
        35                  40                  45

Arg Thr Pro Leu Met Tyr Cys Val Leu Ala Asp Arg Leu Asp Cys Ala
    50                  55                  60

Asp Ala Leu Leu Lys Ala Gly Ala Asp Val Asn Lys Thr Asp His Ser
65                  70                  75                  80

Gln Arg Thr Ala Leu His Leu Ala Ala Gln Lys Gly Asn Tyr Arg Phe
                85                  90                  95

Met Lys Leu Leu Leu Thr Arg Arg Ala Asn Trp Met Gln Lys Asp Leu
            100                 105                 110

Glu Glu Met Thr Pro Leu His Leu Thr Thr Arg His Arg Ser Pro Lys
        115                 120                 125

Cys Leu Ala Leu Leu Leu Lys Phe Met Ala Pro Gly Glu Val Asp Thr
    130                 135                 140

Gln Asp Lys Asn Lys Gln Thr Ala Leu His Trp Ser Ala Tyr Tyr Asn
```

-continued

```
        145                 150                 155                 160
Asn Pro Glu His Val Lys Leu Leu Ile Lys His Asp Ser Asn Ile Gly
                    165                 170                 175
Ile Pro Asp Val Glu Gly Lys Ile Pro Leu His Trp Ala Ala Asn His
                180                 185                 190
Lys Asp Pro Ser Ala Val His Thr Val Arg Cys Ile Leu Asp Ala Ala
                195                 200                 205
Pro Thr Glu Ser Leu Leu Asn Trp Gln Asp Tyr Glu Gly Arg Thr Pro
            210                 215                 220
Leu His Phe Ala Val Ala Asp Gly Asn Val Thr Val Val Asp Val Leu
225                 230                 235                 240
Thr Ser Tyr Glu Ser Cys Asn Ile Thr Ser Tyr Asp Asn Leu Phe Arg
                245                 250                 255
Thr Pro Leu His Trp Ala Ala Leu Leu Gly His Ala Gln Ile Val His
                260                 265                 270
Leu Leu Leu Glu Arg Asn Lys Ser Gly Thr Ile Pro Ser Asp Ser Gln
            275                 280                 285
Gly Ala Thr Pro Leu His Tyr Ala Ala Gln Ser Asn Phe Ala Glu Thr
        290                 295                 300
Val Lys Val Phe Leu Lys His Pro Ser Val Lys Asp Ser Asp Leu
305                 310                 315                 320
Glu Gly Arg Thr Ser Phe Met Trp Ala Ala Gly Lys Gly Ser Asp Asp
                325                 330                 335
Val Leu Arg Thr Met Leu Ser Leu Lys Ser Asp Ile Asp Ile Asn Met
                340                 345                 350
Ala Asp Lys Tyr Gly Gly Thr Ala Leu His Ala Ala Leu Ser Gly
                355                 360                 365
His Val Ser Thr Val Lys Leu Leu Leu Glu Asn Asn Ala Gln Val Asp
            370                 375                 380
Ala Thr Asp Val Met Lys His Thr Pro Leu Phe Arg Ala Cys Glu Met
385                 390                 395                 400
Gly His Lys Asp Val Ile Gln Thr Leu Ile Lys Gly Gly Ala Arg Val
                405                 410                 415
Asp Leu Val Asp Gln Asp Gly His Ser Leu Leu His Trp Ala Ala Leu
                420                 425                 430
Gly Gly Asn Ala Asp Val Cys Gln Ile Leu Ile Glu Asn Lys Ile Asn
                435                 440                 445
Pro Asn Val Gln Asp Tyr Ala Gly Arg Thr Pro Leu Gln Cys Ala Ala
            450                 455                 460
Tyr Gly Gly Tyr Ile Asn Cys Met Ala Val Leu Met Glu Asn Asn Ala
465                 470                 475                 480
Asp Pro Asn Ile Gln Asp Lys Glu Gly Arg Thr Ala Leu His Trp Ser
                485                 490                 495
Cys Asn Asn Gly Tyr Leu Asp Ala Ile Lys Leu Leu Leu Asp Phe Ala
            500                 505                 510
Ala Phe Pro Asn Gln Met Glu Asn Asn Glu Glu Arg Tyr Thr Pro Leu
        515                 520                 525
Asp Tyr Ala Leu Leu Gly Glu Arg His Glu Val Ile Gln Phe Met Leu
    530                 535                 540
Glu His Gly Ala Leu Ser Ile Ala Ala Ile Gln Asp Ile Ala Ala Phe
545                 550                 555                 560
Lys Ile Gln Ala Val Tyr Lys Gly Tyr Lys Val Arg Lys Ala Phe Arg
                565                 570                 575
```

```
Asp Arg Lys Asn Leu Leu Met Lys His Glu Gln Leu Arg Lys Asp Ala
            580                 585                 590

Ala Ala Lys Lys Arg Glu Glu Glu Asn Lys Arg Lys Glu Ala Glu Gln
        595                 600                 605

Gln Lys Gly Arg Arg Ser Pro Asp Ser Cys Arg Pro Gln Ala Leu Pro
        610                 615                 620

Cys Leu Pro Ser Thr Gln Asp Val Pro Ser Arg Gln Ser Arg Ala Pro
625                 630                 635                 640

Ser Lys Gln Pro Pro Ala Gly Asn Val Ala Gln Gly Pro Glu Pro Arg
                645                 650                 655

Asp Ser Arg Gly Ser Pro Gly Gly Ser Leu Gly Gly Ala Leu Gln Lys
                660                 665                 670

Glu Gln His Val Ser Ser Asp Leu Gln Gly Thr Asn Ser Arg Arg Pro
            675                 680                 685

Asn Glu Thr Ala Arg Glu His Ser Lys Gly Gln Ser Ala Cys Val His
        690                 695                 700

Phe Arg Pro Asn Glu Gly Ser Asp Gly Ser Arg His Pro Gly Val Pro
705                 710                 715                 720

Ser Val Glu Lys Ser Arg Gly Glu Thr Ala Gly Asp Glu Arg Cys Ala
                725                 730                 735

Lys Gly Lys Gly Phe Val Lys Gln Pro Ser Cys Ile Arg Val Ala Gly
            740                 745                 750

Pro Asp Glu Lys Gly Glu Asp Ser Arg Arg Ala Gly Ala Ser Leu Pro
        755                 760                 765

Pro His Asp Ser His Trp Lys Pro Ser Arg Arg His Asp Thr Glu Pro
        770                 775                 780

Lys Ala Lys Cys Ala Pro Gln Lys Arg Arg Thr Gln Glu Leu Arg Gly
785                 790                 795                 800

Gly Arg Cys Ser Pro Ala Gly Ser Ser Arg Pro Gly Ser Ala Arg Gly
                805                 810                 815

Glu Ala Val His Ala Gly Gln Asn Pro Pro His Arg Thr Pro Arg
            820                 825                 830

Asn Lys Val Thr Gln Ala Lys Leu Thr Gly Gly Leu Tyr Ser His Leu
        835                 840                 845

Pro Gln Ser Thr Glu Glu Leu Arg Ser Gly Ala Arg Arg Leu Glu Thr
        850                 855                 860

Ser Thr Leu Ser Glu Asp Phe Gln Val Ser Lys Glu Thr Asp Pro Ala
865                 870                 875                 880

Pro Gly Pro Leu Ser Gly Gln Ser Val Asn Ile Asp Leu Leu Pro Val
                885                 890                 895

Glu Leu Arg Leu Gln Ile Ile Gln Arg Glu Arg Arg Arg Lys Glu Leu
            900                 905                 910

Phe Arg Lys Lys Glu Gln Gly Ser Ser His Pro Ala Arg Leu Ala
        915                 920                 925

Lys Leu Pro Ala Gln Glu Ala Pro Val Pro Ser Ala Tyr Glu Ala
        930                 935                 940

Ala Trp Ser Trp Arg Cys Gly Gln Met Glu Ala Arg Val Tyr Ser Ile
945                 950                 955                 960

Ala Pro Pro Gly Leu Glu Glu Gly Thr Gly Thr Lys Ile Pro Pro Asn
                965                 970                 975

His Cys Ser Lys Gln Gly Pro Gln Glu Ser Ile Gln Gly His Leu Arg
                980                 985                 990
```

```
His Lys Val His Gln Ala Leu Ser  Ala
        995             1000

<210> SEQ ID NO 41
<211> LENGTH: 3558
<212> TYPE: DNA
<213> ORGANISM: Homo sapiens

<400> SEQUENCE: 41
ggttgctccc ggttgctaag aagactatga acaagtcaga gaacctgctg tttgctggtt      60
catcattagc atcacaagtc catgctgctg ccgttaatgg agataagggt gctctacaga     120
ggctcatcgt aggaaactct gctcttaaag acaaagaaga tcagtttggg agaacaccac     180
ttatgtattg cgtgttggct gacagattgg attgtgcaga tgctcttctg aaggcaggag     240
cagatgtgaa taaaactgac catagccaga gaacagccct ccatcttgca gcccagaagg     300
gaaattatcg tttcatgaaa ctcttactta cacgcagagc aaactggatg caaaaggatc     360
tggaagagat gactcctttg cacttgacca cccggcacag gagccctaag tgtttggcac     420
ttctgctgaa gttatggca ccaggagaag tggatacaca ggataaaaac aagcaaacag     480
ctctgcattg gagtgcctac tacaataacc ctgagcatgt gaagctgctc atcaagcatg     540
attctaacat tgggattcct gatgttgaag gcaagatccc acttcactgg gcagccaacc     600
ataaagatcc aagtgctgtt cacacagtga gatgcattct ggatgctgct caacagagt      660 ctttactgaa ctggcaagac tacgagggtc gaactcctct tcactttgca gttgctgatg     720
ggaatgtgac cgtggttgat gtcttgacct catatgaaag ctgcaatata cgtcttatg      780 ataacttatt tcgaaccccca ctgcactggg cagctttatt aggccatgca cagattgtcc     840
atctcctttt agaaagaaat aagtctggaa ctatcccatc tgcagccaa ggagccacac     900 ctttgcacta tgctgctcag agtaactttg ctgaaacggt taaagtgttt ttaaaacatc     960
cttcagtgaa agatgattca gacctggaag gaagaacatc ctttatgtgg gcagctggca    1020
aaggcagtga tgatgtcctt agaactatgc tgagcttaaa atcggacata gatattaaca    1080
tggctgacaa atatggaggt acagctttgc atgctgctgc tctttctggc catgtcagca    1140
ccgtgaagtt attactggaa aataatgctc aagtagatgc tactgatgtt atgaaacata    1200
ctccactttt ccgagcctgt gagatgggac acaaagatgt gattcagaca ctcattaaag    1260
gtggagcaag ggtagatcta gttgaccaag atggacattc tcttctacat tgggcagcac    1320
tgggaggaaa tgctgatgtt tgccagatat aatagaaaa taagatcaat ccaaatgtcc    1380
aggattatgc aggaagaacc cctttgcagt gtgcagcata tggaggctat atcaactgca    1440
tggcagttct catggaaaac aatgcagacc ctaacattca agacaaagag ggaagaacag    1500
cttcgcattg gtcctgcaac aatggatacc ttgatgccat taaattactg ctagactttg    1560
ctgctttccc taatcagatg gaaaacaatg aagagagata cacacccctt gattatgctt    1620
tgcttggtga gcgccatgaa gtgatccagt tcatgttgga gcacggtgcc ctgtccatcg    1680
cagccataca agacatcgcc gccttcaaaa tccaagctgt ctacaaaggg tacaaggtca    1740
gaaaagcctt ccgagacagg aaaaatctcc tcatgaagca tgaacagttg agaaaagatg    1800
ctgctgccaa aaagcgagag gaagaaaaca acgaaaaga ggcagaacag caaaaggaa    1860 ggcggagccc agattcctgc agaccccagg cccttccctg tctgcctagc acccaggatg    1920
tgcccagcag gcagagccgg gcccccagca agcagcctcc tgctggcaac gtggcccaag    1980
gccctgagcc aagagacagc agaggatctc caggagggtc tctaggcgga gccctccaga    2040
```

-continued

```
aggagcagca tgtttcctca gatttgcagg gaacaaactc cagaaggcca aatgaaacag    2100
ccagagaaca ttctaaaggc caatctgctt gtgtccactt cagacccaat gaaggcagtg    2160
atggaagcag gcatccagga gttccctctg ttgagaagtc cagaggtgag acagctggcg    2220
atgagcggtg tgcaaagggg aaaggtttcg tgaagcagcc ctcctgtatc agggtggctg    2280
ggcctgatga gaaggagag gactccaggc gggcaggtgc aagccttcca ccgcacgata    2340
gccactggaa gcccagcagg cggcatgaca cagaacccaa ggccaaatgt gccccccaga    2400
aaaggcgcac tcaagagctc agaggaggaa ggtgctctcc ggctggttct agccgccctg    2460
gcagtgcccg gggggaggcg gtccatgctg gcagaatcc tccccaccat cgtacaccaa    2520
gaaacaaagt gacacaagcc aagctcacag gagggctcta ttcacatttg ccacagagca    2580
cagaggagtt gaggtcagga gctaggaggc tggagacatc taccctgtcc gaggactttc    2640
aggtatctaa ggagactgat ccagcacctg gtccctctc tgggcagagt gtgaatattg    2700
accttctccc cgtagagctc cgactgcaga taattcagag agaacgaagg aggaaggagc    2760
tgtttcgcaa aaagaacaag gcagcagcag tcatccagcg cgcctggcga agctaccagc    2820
tcaggaagca cctgtcccac cttcggcata tgaagcagct tggagctgga gatgtggaca    2880
gatggaggca agagtctaca gcattgctcc tccaggtttg gaggaaggaa ctggaactaa    2940
aattccccca aaccactgca gtaagcaagg ccccaagag tccatccaag ggcacctcag    3000
gcacaaagtc caccaagcac tcagtgctta agcaaatcta tggttgttct cacgaaggga    3060
aaatacatca tcctacaaga tctgtaaaag cctcttctgt gctgcgtctc aactcagtga    3120
gcaacctaca gtgtatacat ctccttgaga acagtggaag atcaaagaac ttttcttata    3180
acctgcaatc agctactcag ccaaaaaaca aaacaaaacc ttgactgcct atggaggaag    3240
actgtgttcg ggggagctgg catagctagt gcagagttca gattttctgc tgataatctt    3300
ttacaccttg ggaaaacttt aatatccgta cctgaaggct gattcaccta aaaatgtgtt    3360
aactgaaaga aaatgtcaga atgtttcctt tctgctctta cacagcattg ttttgtcaat    3420
caacacagcc tgcactgaaa ggacctgcat agactatgtc tgtgcaaagt gcctgagtgt    3480
ctgctttcac ctcagtctgt acagttggaa atgagaattc ataattaaca gcaaaatcta    3540
aggaaaacta aaataaaa                                                  3558
```

<210> SEQ ID NO 42
<211> LENGTH: 1065
<212> TYPE: PRT
<213> ORGANISM: Homo sapiens

<400> SEQUENCE: 42

```
Met Asn Lys Ser Glu Asn Leu Leu Phe Ala Gly Ser Ser Leu Ala Ser
1               5                   10                  15

Gln Val His Ala Ala Val Asn Gly Asp Lys Gly Ala Leu Gln Arg
            20                  25                  30

Leu Ile Val Gly Asn Ser Ala Leu Lys Asp Lys Glu Asp Gln Phe Gly
        35                  40                  45

Arg Thr Pro Leu Met Tyr Cys Val Leu Ala Asp Arg Leu Asp Cys Ala
    50                  55                  60

Asp Ala Leu Leu Lys Ala Gly Ala Asp Val Asn Lys Thr Asp His Ser
65                  70                  75                  80

Gln Arg Thr Ala Leu His Leu Ala Ala Gln Lys Gly Asn Tyr Arg Phe
                85                  90                  95

Met Lys Leu Leu Leu Thr Arg Arg Ala Asn Trp Met Gln Lys Asp Leu
```

-continued

```
                100                 105                 110
Glu Glu Met Thr Pro Leu His Leu Thr Thr Arg His Arg Ser Pro Lys
        115                 120                 125

Cys Leu Ala Leu Leu Leu Lys Phe Met Ala Pro Gly Glu Val Asp Thr
        130                 135                 140

Gln Asp Lys Asn Lys Gln Thr Ala Leu His Trp Ser Ala Tyr Tyr Asn
145                 150                 155                 160

Asn Pro Glu His Val Lys Leu Leu Ile Lys His Asp Ser Asn Ile Gly
                165                 170                 175

Ile Pro Asp Val Glu Gly Lys Ile Pro Leu His Trp Ala Ala Asn His
            180                 185                 190

Lys Asp Pro Ser Ala Val His Thr Val Arg Cys Ile Leu Asp Ala Ala
                195                 200                 205

Pro Thr Glu Ser Leu Leu Asn Trp Gln Asp Tyr Glu Gly Arg Thr Pro
        210                 215                 220

Leu His Phe Ala Val Ala Asp Gly Asn Val Thr Val Val Asp Val Leu
225                 230                 235                 240

Thr Ser Tyr Glu Ser Cys Asn Ile Thr Ser Tyr Asp Asn Leu Phe Arg
                245                 250                 255

Thr Pro Leu His Trp Ala Ala Leu Leu Gly His Ala Gln Ile Val His
            260                 265                 270

Leu Leu Leu Glu Arg Asn Lys Ser Gly Thr Ile Pro Ser Asp Ser Gln
        275                 280                 285

Gly Ala Thr Pro Leu His Tyr Ala Ala Gln Ser Asn Phe Ala Glu Thr
        290                 295                 300

Val Lys Val Phe Leu Lys His Pro Ser Val Lys Asp Asp Ser Asp Leu
305                 310                 315                 320

Glu Gly Arg Thr Ser Phe Met Trp Ala Ala Gly Lys Gly Ser Asp Asp
                325                 330                 335

Val Leu Arg Thr Met Leu Ser Leu Lys Ser Asp Ile Asp Ile Asn Met
            340                 345                 350

Ala Asp Lys Tyr Gly Gly Thr Ala Leu His Ala Ala Leu Ser Gly
        355                 360                 365

His Val Ser Thr Val Lys Leu Leu Leu Glu Asn Asn Ala Gln Val Asp
        370                 375                 380

Ala Thr Asp Val Met Lys His Thr Pro Leu Phe Arg Ala Cys Glu Met
385                 390                 395                 400

Gly His Lys Asp Val Ile Gln Thr Leu Ile Lys Gly Gly Ala Arg Val
                405                 410                 415

Asp Leu Val Asp Gln Asp Gly His Ser Leu Leu His Trp Ala Ala Leu
            420                 425                 430

Gly Gly Asn Ala Asp Val Cys Gln Ile Leu Ile Glu Asn Lys Ile Asn
        435                 440                 445

Pro Asn Val Gln Asp Tyr Ala Gly Arg Thr Pro Leu Gln Cys Ala Ala
        450                 455                 460

Tyr Gly Gly Tyr Ile Asn Cys Met Ala Val Leu Met Glu Asn Asn Ala
465                 470                 475                 480

Asp Pro Asn Ile Gln Asp Lys Glu Gly Arg Thr Ala Ser His Trp Ser
                485                 490                 495

Cys Asn Asn Gly Tyr Leu Asp Ala Ile Lys Leu Leu Leu Asp Phe Ala
            500                 505                 510

Ala Phe Pro Asn Gln Met Glu Asn Asn Glu Glu Arg Tyr Thr Pro Leu
        515                 520                 525
```

```
Asp Tyr Ala Leu Leu Gly Glu Arg His Glu Val Ile Gln Phe Met Leu
    530                 535                 540

Glu His Gly Ala Leu Ser Ile Ala Ala Ile Gln Asp Ile Ala Ala Phe
545                 550                 555                 560

Lys Ile Gln Ala Val Tyr Lys Gly Tyr Lys Val Arg Lys Ala Phe Arg
                565                 570                 575

Asp Arg Lys Asn Leu Leu Met Lys His Glu Gln Leu Arg Lys Asp Ala
            580                 585                 590

Ala Ala Lys Lys Arg Glu Glu Asn Lys Arg Lys Glu Ala Glu Gln
        595                 600                 605

Gln Lys Gly Arg Arg Ser Pro Asp Ser Cys Arg Pro Gln Ala Leu Pro
    610                 615                 620

Cys Leu Pro Ser Thr Gln Asp Val Pro Ser Gln Ser Arg Ala Pro
625                 630                 635                 640

Ser Lys Gln Pro Pro Ala Gly Asn Val Ala Gln Gly Pro Glu Pro Arg
                645                 650                 655

Asp Ser Arg Gly Ser Pro Gly Gly Ser Leu Gly Gly Ala Leu Gln Lys
            660                 665                 670

Glu Gln His Val Ser Ser Asp Leu Gln Gly Thr Asn Ser Arg Arg Pro
        675                 680                 685

Asn Glu Thr Ala Arg Glu His Ser Lys Gly Gln Ser Ala Cys Val His
690                 695                 700

Phe Arg Pro Asn Glu Gly Ser Asp Gly Ser Arg His Pro Gly Val Pro
705                 710                 715                 720

Ser Val Glu Lys Ser Arg Gly Glu Thr Ala Gly Asp Glu Arg Cys Ala
                725                 730                 735

Lys Gly Lys Gly Phe Val Lys Gln Pro Ser Cys Ile Arg Val Ala Gly
            740                 745                 750

Pro Asp Glu Lys Gly Glu Asp Ser Arg Arg Ala Gly Ala Ser Leu Pro
        755                 760                 765

Pro His Asp Ser His Trp Lys Pro Ser Arg Arg His Asp Thr Glu Pro
770                 775                 780

Lys Ala Lys Cys Ala Pro Gln Lys Arg Arg Thr Gln Glu Leu Arg Gly
785                 790                 795                 800

Gly Arg Cys Ser Pro Ala Gly Ser Ser Arg Pro Gly Ser Ala Arg Gly
                805                 810                 815

Glu Ala Val His Ala Gly Gln Asn Pro Pro His His Arg Thr Pro Arg
            820                 825                 830

Asn Lys Val Thr Gln Ala Lys Leu Thr Gly Gly Leu Tyr Ser His Leu
        835                 840                 845

Pro Gln Ser Thr Glu Glu Leu Arg Ser Gly Ala Arg Arg Leu Glu Thr
850                 855                 860

Ser Thr Leu Ser Glu Asp Phe Gln Val Ser Lys Glu Thr Asp Pro Ala
865                 870                 875                 880

Pro Gly Pro Leu Ser Gly Gln Ser Val Asn Ile Asp Leu Leu Pro Val
                885                 890                 895

Glu Leu Arg Leu Gln Ile Ile Gln Arg Glu Arg Arg Lys Glu Leu
            900                 905                 910

Phe Arg Lys Lys Asn Lys Ala Ala Ala Val Ile Gln Arg Ala Trp Arg
        915                 920                 925

Ser Tyr Gln Leu Arg Lys His Leu Ser His Leu Arg His Met Lys Gln
930                 935                 940
```

-continued

```
Leu Gly Ala Gly Asp Val Asp Arg Trp Arg Gln Glu Ser Thr Ala Leu
945                 950                 955                 960

Leu Leu Gln Val Trp Arg Lys Glu Leu Glu Leu Lys Phe Pro Gln Thr
                965                 970                 975

Thr Ala Val Ser Lys Ala Pro Lys Ser Pro Ser Lys Gly Thr Ser Gly
            980                 985                 990

Thr Lys Ser Thr Lys His Ser Val Leu Lys Gln Ile Tyr Gly Cys Ser
        995                 1000                1005

His Glu Gly Lys Ile His His Pro Thr Arg Ser Val Lys Ala Ser
    1010                1015                1020

Ser Val Leu Arg Leu Asn Ser Val Ser Asn Leu Gln Cys Ile His
    1025                1030                1035

Leu Leu Glu Asn Ser Gly Arg Ser Lys Asn Phe Ser Tyr Asn Leu
    1040                1045                1050

Gln Ser Ala Thr Gln Pro Lys Asn Lys Thr Lys Pro
    1055                1060                1065

<210> SEQ ID NO 43
<211> LENGTH: 19
<212> TYPE: DNA
<213> ORGANISM: Artificial Sequence
<220> FEATURE:
<223> OTHER INFORMATION: Synthetic

<400> SEQUENCE: 43
gtcggacatg caaatcagg                                                  19

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
aagccttcag gattgctgtg                                                 20

<210> SEQ ID NO 45
<211> LENGTH: 18
<212> TYPE: DNA
<213> ORGANISM: Artificial Sequence
<220> FEATURE:
<223> OTHER INFORMATION: Synthetic

<400> SEQUENCE: 45
acatggcctg ccagtgac                                                   18

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
acgtgtagga aggcggtctc                                                 20

<210> SEQ ID NO 47
<211> LENGTH: 19
<212> TYPE: DNA
<213> ORGANISM: Artificial Sequence
<220> FEATURE:
<223> OTHER INFORMATION: Synthetic
```

<400> SEQUENCE: 47
gaggcctcca tgtgctttc                                            19

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
tgaccctcat tgagaactgc                                           20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
ttgtgctctg tctgggagtc                                           20

<210> SEQ ID NO 50
<211> LENGTH: 18
<212> TYPE: DNA
<213> ORGANISM: Artificial Sequence
<220> FEATURE:
<223> OTHER INFORMATION: Synthetic

<400> SEQUENCE: 50
ctcccccagg gacttctg                                             18

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
ttctgacagt ggtcgacgtg                                           20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
cactgttgat ttcccctctc                                           20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
ttcctggttg gatcgttctg                                           20

<210> SEQ ID NO 54

```
<211> LENGTH: 19
<212> TYPE: DNA
<213> ORGANISM: Artificial Sequence
<220> FEATURE:
<223> OTHER INFORMATION: Synthetic

<400> SEQUENCE: 54
aggcctgtgg agacctgac                                                      19

<210> SEQ ID NO 55
<211> LENGTH: 19
<212> TYPE: DNA
<213> ORGANISM: Artificial Sequence
<220> FEATURE:
<223> OTHER INFORMATION: Synthetic

<400> SEQUENCE: 55
catgttggga gctttgtgg                                                      19

<210> SEQ ID NO 56
<211> LENGTH: 19
<212> TYPE: DNA
<213> ORGANISM: Artificial Sequence
<220> FEATURE:
<223> OTHER INFORMATION: Synthetic

<400> SEQUENCE: 56
atctgagcac cgttggttg                                                      19

<210> SEQ ID NO 57
<211> LENGTH: 18
<212> TYPE: DNA
<213> ORGANISM: Artificial Sequence
<220> FEATURE:
<223> OTHER INFORMATION: Synthetic

<400> SEQUENCE: 57
ggtttccaca gggaggtg                                                       18

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
accatcccct atgcaaacac                                                     20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gaccagagct gaaatctctt                                                     20

<210> SEQ ID NO 60
<211> LENGTH: 19
<212> TYPE: DNA
<213> ORGANISM: Artificial Sequence
<220> FEATURE:
<223> OTHER INFORMATION: Synthetic

<400> SEQUENCE: 60
```
cacagtggct ttcctgctg                                                    19

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
tgtggtgggt tgatctgttt                                                   20

<210> SEQ ID NO 62
<211> LENGTH: 18
<212> TYPE: DNA
<213> ORGANISM: Artificial Sequence
<220> FEATURE:
<223> OTHER INFORMATION: Synthetic

<400> SEQUENCE: 62
ccctggtgtc tgctcctg                                                     18

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
agcaatagcc ccttgtggag                                                   20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
tctctcccac tcctctgagc                                                   20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
tggcagtggt gtctctaagc                                                   20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
ttggcaacag tggagatacg                                                   20

<210> SEQ ID NO 67
<211> LENGTH: 20
<212> TYPE: DNA

```
<213> ORGANISM: Artificial Sequence
<220> FEATURE:
<223> OTHER INFORMATION: Synthetic

<400> SEQUENCE: 67
tcttgctgag cacctgtgac                                                    20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
cactcgctgc gtgtattagt                                                    20

<210> SEQ ID NO 69
<211> LENGTH: 18
<212> TYPE: DNA
<213> ORGANISM: Artificial Sequence
<220> FEATURE:
<223> OTHER INFORMATION: Synthetic

<400> SEQUENCE: 69
ccttgttggc ctctcgtg                                                      18

<210> SEQ ID NO 70
<211> LENGTH: 19
<212> TYPE: DNA
<213> ORGANISM: Artificial Sequence
<220> FEATURE:
<223> OTHER INFORMATION: Synthetic

<400> SEQUENCE: 70
ggaaccaccc atgaccttg                                                     19

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
cagggaatac ttggaggaag                                                    20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
gcagagaggt tgctggtgag                                                    20

<210> SEQ ID NO 73
<211> LENGTH: 18
<212> TYPE: DNA
<213> ORGANISM: Artificial Sequence
<220> FEATURE:
<223> OTHER INFORMATION: Synthetic

<400> SEQUENCE: 73
aggctctggc caacactg                                                      18
```

```
<210> SEQ ID NO 74
<211> LENGTH: 22
<212> TYPE: DNA
<213> ORGANISM: Artificial Sequence
<220> FEATURE:
<223> OTHER INFORMATION: Synthetic

<400> SEQUENCE: 74
catccatctg ttaactggaa gc                                              22

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
cctggaccca caagtctgag                                                 20

<210> SEQ ID NO 76
<211> LENGTH: 23
<212> TYPE: DNA
<213> ORGANISM: Artificial Sequence
<220> FEATURE:
<223> OTHER INFORMATION: Synthetic

<400> SEQUENCE: 76
gacgagcagt taaaccacca tag                                             23

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
gctaaaggtg gggaacactc                                                 20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
gtgccttcaa ggtttcactg                                                 20

<210> SEQ ID NO 79
<211> LENGTH: 18
<212> TYPE: DNA
<213> ORGANISM: Artificial Sequence
<220> FEATURE:
<223> OTHER INFORMATION: Synthetic

<400> SEQUENCE: 79
catcagatgc ggggtctc                                                   18

<210> SEQ ID NO 80
<211> LENGTH: 20
<212> TYPE: DNA
<213> ORGANISM: Artificial Sequence
<220> FEATURE:
```

<223> OTHER INFORMATION: Synthetic

<400> SEQUENCE: 80
cctgacatgc acaaatgacc                                                    20

<210> SEQ ID NO 81
<211> LENGTH: 2392
<212> TYPE: DNA
<213> ORGANISM: Homo sapiens

<400> SEQUENCE: 81

| | | | | | |
|---|---|---|---|---|---|
| cgcctccagg | cccctccccg | cgtcgcgacg | cacgctgccc | cggaaggccg | cggcgctgta | 60 |
| gtgcggcgcc | ccaggttctt | tagtggaaga | acgcgaagcg | aggatgagtg | atccgtggag | 120 |
| gcagtaacag | gcgcggcgag | ggagaagtga | ttcccgaaga | atcaaggctg | gccggaccc | 180 |
| ggtggcctgg | caacagggta | ataagagaaa | tgaagccaac | aggtacagac | ccaaggatct | 240 |
| tatctatagc | tgctgaagtt | gcaaaaagcc | ctgagcagaa | tgtccctgtt | atactgttga | 300 |
| agttaaaaga | ataataaac | atcacacctt | taggaagctc | agagttgaag | aaaatcaaac | 360 |
| aagatatata | ttgttatgat | ctcattcaat | attgcctctt | ggtcctcagt | caagattatt | 420 |
| ctcgaatcca | gggtggttgg | actacaattt | cccagcttac | acagatatta | agccattgct | 480 |
| gtgtgggctt | ggagccagga | gaagatgcag | aggaatttta | caatgaatta | cttccatcag | 540 |
| ctgcagaaaa | ttttctagtt | ttggggagac | aattacaaac | atgttttatc | aatgcagcta | 600 |
| aggctgaaga | aaaagatgaa | ttactacact | ttttccaaat | tgtgactgat | tctctcttct | 660 |
| ggcttttggg | aggccatgtt | gaacttattc | agaatgtact | acaaagtgat | catttcttac | 720 |
| atttactgca | agctgacaat | gtccaaatag | gatctgcagt | catgatgatg | ctacagaata | 780 |
| tattacagat | caacagtggt | gatttactca | gaataggaag | aaaagccctg | tattcaattt | 840 |
| tagatgaagt | tattttcaag | cttttttcaa | ctcctagtcc | agttataaga | agtactgcta | 900 |
| caaaactcct | actgttgatg | gctgaatccc | atcaggaaat | tttgatttta | ctgagacaaa | 960 |
| gtacctgcta | caaggactc | agacgtctac | taagtaaaca | ggaaactggg | actgaattca | 1020 |
| gtcaagaact | tagacagctt | gttggccttt | taagcccaat | ggtctatcag | gaagtagaag | 1080 |
| agcagaaact | acatcaagca | gcatgcttga | ttcaagccta | ttggaagggt | tttcagacaa | 1140 |
| gaaagagatt | aaagaagctt | ccatctgctg | tgattgcttt | gcagaggagt | ttcagatcca | 1200 |
| aacgatcaaa | gatgttgctg | gagataaata | ggcagaagga | agaagaggac | ctcaaattac | 1260 |
| aattgcaact | tcaaagacag | agagccatga | gactttcccg | agaattgcag | ctgagtatgc | 1320 |
| tcgaaatagt | tcatccaggt | caggtggaga | acactatcg | ggaaatggaa | gagaaatcag | 1380 |
| cactgaatat | ccagaaacat | ggagagggt | acagggaaag | gaaaaatttt | caccaacaga | 1440 |
| ggcagtctct | catagagtat | aaagcagctg | tcacacttca | aagagcagcg | cttaaattcc | 1500 |
| tagcgaagtg | ccgtaagaaa | aagaaactat | ttgctccttg | gcgaggactc | caagaactca | 1560 |
| ctgatgcacg | ccgagttgaa | ctgaagaaac | gagtggatga | ctatgtcaga | agacatttgg | 1620 |
| gctctccaat | gtcagatgtg | gtcagtaggg | agctccatgc | ccaagctcaa | gaacgactgc | 1680 |
| aacactactt | tatgggcagg | gccctagaag | agcgagccca | gcagcacaga | gaagctctga | 1740 |
| tagcacagat | cagcaccaac | gttgaacagc | taatgaaggc | accaagtctg | aaggaggcag | 1800 |
| aagggaaaga | acctgagctc | ttcctaagta | gatccaggcc | tgtggcagcc | aaggccaagc | 1860 |
| aggcccatct | cacaacccctg | aagcacatac | aagcaccctg | gtggaagaag | cttgagaagg | 1920 |
| aatctggaga | tgagattgat | gttccaaagg | atgagcttag | tatagaatta | gaaaatttat | 1980 |

-continued

```
tcattggtgg aaccaaacca ccttagtgag taaccctaag aattgacaca aatctcatat      2040
tttaggagat tatattggtt ctgcctctgg catgctggta gactagggcc atcctaactt      2100
attattttcc agaggttctc ctccagacaa gacctgcagt aagcaaagag ttatattcta      2160
cctctctctc aattttcttt ttcttttctc tgtatcctca tccttagcca cacacagatt      2220
tgtgtggctt ttattgtaga actaaactta gcatagtgtt ctgttgttta catgaagtgt      2280
gttttctttt ggtttcttct gttttccaac taaatatttt tttctaaata aatattttca      2340
acaattgatt tgaaaaaaaa aaaaaaaaaa aaaaaaaaaa aaaaaaaaaa aa              2392
```

<210> SEQ ID NO 82
<211> LENGTH: 598
<212> TYPE: PRT
<213> ORGANISM: Homo sapiens

<400> SEQUENCE: 82

```
Met Lys Pro Thr Gly Thr Asp Pro Arg Ile Leu Ser Ile Ala Ala Glu
1               5                   10                  15

Val Ala Lys Ser Pro Glu Gln Asn Val Pro Val Ile Leu Leu Lys Leu
            20                  25                  30

Lys Glu Ile Ile Asn Ile Thr Pro Leu Gly Ser Ser Glu Leu Lys Lys
        35                  40                  45

Ile Lys Gln Asp Ile Tyr Cys Tyr Asp Leu Ile Gln Tyr Cys Leu Leu
    50                  55                  60

Val Leu Ser Gln Asp Tyr Ser Arg Ile Gln Gly Gly Trp Thr Thr Ile
65                  70                  75                  80

Ser Gln Leu Thr Gln Ile Leu Ser His Cys Cys Val Gly Leu Glu Pro
                85                  90                  95

Gly Glu Asp Ala Glu Glu Phe Tyr Asn Glu Leu Leu Pro Ser Ala Ala
            100                 105                 110

Glu Asn Phe Leu Val Leu Gly Arg Gln Leu Gln Thr Cys Phe Ile Asn
        115                 120                 125

Ala Ala Lys Ala Glu Glu Lys Asp Glu Leu Leu His Phe Phe Gln Ile
    130                 135                 140

Val Thr Asp Ser Leu Phe Trp Leu Gly Gly His Val Glu Leu Ile
145                 150                 155                 160

Gln Asn Val Leu Gln Ser Asp His Phe Leu His Leu Gln Ala Asp
                165                 170                 175

Asn Val Gln Ile Gly Ser Ala Val Met Met Met Leu Gln Asn Ile Leu
            180                 185                 190

Gln Ile Asn Ser Gly Asp Leu Leu Arg Ile Gly Arg Lys Ala Leu Tyr
        195                 200                 205

Ser Ile Leu Asp Glu Val Ile Phe Lys Leu Phe Ser Thr Pro Ser Pro
    210                 215                 220

Val Ile Arg Ser Thr Ala Thr Lys Leu Leu Leu Met Ala Glu Ser
225                 230                 235                 240

His Gln Glu Ile Leu Ile Leu Arg Gln Ser Thr Cys Tyr Lys Gly
                245                 250                 255

Leu Arg Arg Leu Leu Ser Lys Gln Glu Thr Gly Thr Glu Phe Ser Gln
            260                 265                 270

Glu Leu Arg Gln Leu Val Gly Leu Leu Ser Pro Met Val Tyr Gln Glu
        275                 280                 285

Val Glu Glu Gln Lys Leu His Gln Ala Ala Cys Leu Ile Gln Ala Tyr
    290                 295                 300
```

```
Trp Lys Gly Phe Gln Thr Arg Lys Arg Leu Lys Lys Leu Pro Ser Ala
305                 310                 315                 320
Val Ile Ala Leu Gln Arg Ser Phe Arg Ser Lys Arg Ser Lys Met Leu
            325                 330                 335
Leu Glu Ile Asn Arg Gln Lys Glu Glu Asp Leu Lys Leu Gln Leu
        340                 345                 350
Gln Leu Gln Arg Gln Arg Ala Met Arg Leu Ser Arg Glu Leu Gln Leu
            355                 360                 365
Ser Met Leu Glu Ile Val His Pro Gly Gln Val Glu Lys His Tyr Arg
    370                 375                 380
Glu Met Glu Glu Lys Ser Ala Leu Asn Ile Gln Lys His Trp Arg Gly
385                 390                 395                 400
Tyr Arg Glu Arg Lys Asn Phe His Gln Gln Arg Gln Ser Leu Ile Glu
            405                 410                 415
Tyr Lys Ala Ala Val Thr Leu Gln Arg Ala Ala Leu Lys Phe Leu Ala
            420                 425                 430
Lys Cys Arg Lys Lys Lys Lys Leu Phe Ala Pro Trp Arg Gly Leu Gln
            435                 440                 445
Glu Leu Thr Asp Ala Arg Arg Val Glu Leu Lys Lys Arg Val Asp Asp
    450                 455                 460
Tyr Val Arg Arg His Leu Gly Ser Pro Met Ser Asp Val Val Ser Arg
465                 470                 475                 480
Glu Leu His Ala Gln Ala Gln Glu Arg Leu Gln His Tyr Phe Met Gly
            485                 490                 495
Arg Ala Leu Glu Glu Arg Ala Gln Gln His Arg Glu Ala Leu Ile Ala
            500                 505                 510
Gln Ile Ser Thr Asn Val Glu Gln Leu Met Lys Ala Pro Ser Leu Lys
    515                 520                 525
Glu Ala Glu Gly Lys Glu Pro Glu Leu Phe Leu Ser Arg Ser Arg Pro
    530                 535                 540
Val Ala Ala Lys Ala Lys Gln Ala His Leu Thr Thr Leu Lys His Ile
545                 550                 555                 560
Gln Ala Pro Trp Trp Lys Lys Leu Gly Glu Glu Ser Gly Asp Glu Ile
            565                 570                 575
Asp Val Pro Lys Asp Glu Leu Ser Ile Glu Leu Glu Asn Leu Phe Ile
            580                 585                 590
Gly Gly Thr Lys Pro Pro
        595

<210> SEQ ID NO 83
<211> LENGTH: 2390
<212> TYPE: DNA
<213> ORGANISM: Homo sapiens

<400> SEQUENCE: 83
cgcctccagg ccccttcccg cgtcgcgacg cacgctgccc cggaaggccg cggcgctgta    60
gtgcggcgcc ccaggttctt tagtggaaga acgcgaagcg aggatgagtg atccgtggag   120
gcagtaacag gcgcggcgag ggagaagtga ttcccgaaga atcaaggctg gccggacccc   180
ggtggcctgg caacagggta ataagagaaa tgaagccaac aggtacagac ccaaggatct   240
tatctatagc tgctgaagtt gcaaaaagcc ctgagcagaa tgtccctgtt atactgttga   300
agttaaaaga aataataaac atcacacctt taggaagctc agagttgaag aaaatcaaac   360
aagatatata ttgttatgat ctcattcaat attgcctctt ggtcctcagt caagattatt   420
```

```
ctcgaatcca gggtggttgg actacaattt cccagcttac acagatatta agccattgct     480
gtgtgggctt ggagccagga aagatgcag aggaatttta caatgaatta cttccatcag     540
ctgcagaaaa ttttctagtt ttggggagac aattacaaac atgttttatc aatgcagcta    600
aggctgaaga aaaagatgaa ttactacact ttccaaattg tgactgattc tctcttctgg    660
cttttgggag gccatgttga acttattcag aatgtactac aaagtgatca tttcttacat    720
ttactgcaag ctgacaatgt ccaaatagga tctgcagtca tgatgatgct acagaatata    780
ttacagatca acagtggtga tttactcaga ataggaagaa aagccctgta ttcaatttta    840
gatgaagtta tttttcaagct tttttcaact cctagtccag ttataagaag tactgctaca    900
aaactcctac tgttgatggc tgaatcccat caggaaattt tgattttact gagacaaagt    960
acctgctaca aaggactcag acgtctacta agtaaacagg aaactgggac tgaattcagt   1020
caagaactta gacagcttgt tggccttta gcccaatgg tctatcagga agtagaagag      1080
cagaaactac atcaagcagc atgcttgatt caagcctatt ggaagggttt tcagacaaga   1140
aagagattaa agaagcttcc atctgctgtg attgctttgc agaggagttt cagatccaaa    1200
cgatcaaaga tgttgctgga gataaatagg cagaaggaag aagaggacct caaattacaa    1260
ttgcaacttc aaagacagag agccatgaga cttttcccgag aattgcagct gagtatgctc    1320
gaaatagttc atccaggtca ggtggagaaa cactatcggg aaatggaaga gaaatcagca    1380
ctgaatatcc agaaacattg gagagggtac agggaaagga aaattttca ccaacagagg     1440 cagtctctca tagagtataa agcagctgtc acacttcaaa gagcagcgct taaattccta    1500
gcgaagtgcc gtaagaaaaa gaaactattt gctccttggc gaggactcca agaactcact    1560
gatgcacgcc gagttgaact gaagaaacga gtggatgact atgtcagaag acatttgggc   1620
tctccaatgt cagatgtggt cagtagggag ctccatgccc aagctcaaga acgactgcaa    1680
cactacttta tgggcagggc cctagaagag cgagcccagc agcacagaga agctctgata    1740
gcacagatca gcaccaacgt tgaacagcta atgaaggcac caagtctgaa ggaggcagaa    1800
gggaaagaac ctgagctctt cctaagtaga tccaggcctg tggcagccaa ggccaagcag    1860
gcccatctca aaccctgaa gcacatacaa gcaccctggt ggaagaagct tggagaagaa    1920
tctggagatg agattgatgt tccaaaggat gagcttagta tagaattaga aaatttattc    1980
attggtggaa ccaaaccacc ttagtgagta accctaagaa ttgacacaaa tctcatattt    2040
taggagatta tattggttct gcctctggca tgctggtaga ctagggccat cctaacttat    2100
tattttccag aggttctcct ccagacaaga cctgcagtaa gcaaagagtt atattctacc    2160
tctctctcaa ttttctttt cttttctctg tatcctcatc cttagccaca cacagatttg     2220
tgtggctttt attgtagaac taaacttagc atagtgttct gttgtttaca tgaagtgtgt    2280
ttttctttgg tttcttctgt tttccaacta aatatttttt tctaaataaa tattttcaac    2340
aattgatttg aaaaaaaaaa aaaaaaaaaa aaaaaaaaa aaaaaaaaa                 2390

<210> SEQ ID NO 84
<211> LENGTH: 2388
<212> TYPE: DNA
<213> ORGANISM: Homo sapiens

<400> SEQUENCE: 84
cgcctccagg cccctcccg cgtcgcgacg cacgctgccc cggaaggccg cggcgctgta     60
gtgcggcgcc ccaggttctt tagtggaaga acgcgaagcg aggatgagtg atccgtggag    120
```

```
gcagtaacag gcgcggcgag ggagaagtga ttcccgaaga atcaaggctg ggccggaccc     180
ggtggcctgg caacagggta ataagagaaa tgaagccaac aggtacagac ccaaggatct     240
tatctatagc tgctgaagtt gcaaaaagcc ctgagcagaa tgtccctgtt atactgttga     300
agttaaaaga aataataaac atcacacctt taggaagctc agagttgaag aaaatcaaac     360
aagatatata ttgttatgat ctcattcaat attgcctctt ggtcctcagt caagattatt     420
ctcgaatcca gggtggttgg actacaattt cccagcttac acagatatta agccattgct     480
gtgtgggctt ggagccagga gaagatgcag aggaatttta caatgaatta cttccatcag     540
ctgcagaaaa ttttctagtt tggggagaca aattacaaac atgttttatc aatgcagcta     600
aggctgaaga aaaagatgaa ttactacact ttttccaaat tgtgactgat tcttctggct     660
tttgggaggc catgttgaac ttattcagaa tgtactacaa agtgatcatt tcttacattt     720
actgcaagct gacaatgtcc aaataggatc tgcagtcatg atgatgctac agaatatatt     780
acagatcaac agtggtgatt tactcagaat aggaagaaaa gccctgtatt caattttaga     840
tgaagttatt ttcaagcttt tttcaactcc tagtccagtt ataagaagta ctgctacaaa     900
actcctactg ttgatggctg aatcccatca ggaaattttg attttactga gacaaagtac     960
ctgctacaaa ggactcagac gtctactaag taaacaggaa actgggactg aattcagtca    1020
agaacttaga cagcttgttg gccttttaag cccaatggtc tatcaggaag tagaagagca    1080
gaaactacat caagcagcat gcttgattca agcctattgg aagggttttc agacaagaaa    1140
gagattaaag aagcttccat ctgctgtgat tgctttgcag aggagtttca gatccaaacg    1200
atcaaagatg ttgctggaga taaataggca gaaggaagaa gaggacctca aattacaatt    1260
gcaacttcaa agacagagag ccatgagact tcccgagaaa ttgcagctga gtatgctcga    1320
aatagttcat ccaggtcagg tggagaaaca ctatcgggaa atggaagaga atcagcact    1380
gaatatccag aaacattgga gagggtacag ggaaaggaaa aattttcacc aacagaggca    1440
gtctctcata gagtataaag cagctgtcac acttcaaaga gcagcgctta aattcctagc    1500
gaagtgccgt aagaaaaaga aactatttgc tccttggcga ggactccaag aactcactga    1560
tgcacgccga gttgaactga agaaacgagt ggatgactat gtcagaagac atttgggctc    1620
tccaatgtca gatgtggtca gtagggagct ccatgcccaa gctcaagaac gactgcaaca    1680
ctactttatg ggcagggccc tagaagagcg agcccagcag cacagagaag ctctgatagc    1740
acagatcagc accaacgttg aacagctaat gaaggcacca agtctgaagg aggcagaagg    1800
gaaagaacct gagctcttcc taagtagatc caggcctgtg gcagccaagg ccaagcaggc    1860
ccatctcaca accctgaagc acatacaagc accctggtgg aagaagcttg gagaagaatc    1920
tggagatgag attgatgttc caaaggatga gcttagtata gaattagaaa atttattcat    1980
tggtggaacc aaaccacctt agtgagtaac cctaagaatt gacacaaatc tcatatttta    2040
ggagattata ttggttctgc ctctggcatg ctggtagact agggccatcc taacttatta    2100
ttttccagag gttctcctcc agacaagacc tgcagtaagc aaagagttat attctacctc    2160
tctctcaatt ttcttttct tttctctgta tcctcatcct tagccacaca cagatttgtg    2220
tggcttttat tgtagaacta aacttagcat agtgttctgt tgtttacatg aagtgtgttt    2280
ttctttggtt tcttctgttt tccaactaaa tattttttc taaataaata ttttcaacaa    2340
ttgatttgaa aaaaaaaaaa aaaaaaaaaa aaaaaaaaaa aaaaaaa                  2388

<210> SEQ ID NO 85
<211> LENGTH: 2384
```

<212> TYPE: DNA
<213> ORGANISM: Homo sapiens

<400> SEQUENCE: 85

```
cgcctccagg ccccttcccg cgtcgcgacg cacgctgccc cggaaggccg cggcgctgta      60
gtgcggcgcc ccaggttctt tagtggaaga acgcgaagcg aggatgagtg atccgtggag     120
gcagtaacag gcgcggcgag ggagaagtga ttcccgaaga atcaaggctg gccggaccc      180
ggtggcctgg caacagggta ataagagaaa tgaagccaac aggtacagac ccaaggatct     240
tatctatagc tgctgaagtt gcaaaaagcc ctgagcagaa tgtccctgtt atactgttga     300
agttaaaaga aataataaac atcacacctt taggaagctc agagttgaag aaaatcaaac     360
aagatatata ttgttatgat ctcattcaat attgcctctt ggtcctcagt caagattatt     420
ctcgaatcca gggtggttgg actacaattt cccagcttac acagatatta agccattgct     480
gtgtgggctt ggagccagga gaagatgcag aggaatttta caatgaatta cttccatcag     540
ctgcagaaaa ttttctagtt ttggggagac aattacaaac atgttttatc aatgcagcta     600
aggctgaaga aaaagatgaa ttactacact ttttccaaat tgtgactgat tcttctggct     660
tttgggaggc catgttgaac ttattcagaa tgtactacaa agtgatcatt tcttacattt     720
actgcaagct gacaatgtcc aaataggatc tgcagtcatg atgatgctac agaatatatt     780
acagatcaac agtggtgatt tactcagaat aggaagaaaa gccctgtatt caatttagaa     840
tgaagttatt ttcaagcttt tttcaactcc tagtccagtt ataagaagta ctgctacaaa     900
actcctactg ttgatggctg aatcccatca ggaaattttg attttactga acaaagtac     960
ctgctacaaa ggactcagac gtctactaag taaacaggaa actgggactg aattcagtca    1020
agaacttagc ttgttggcct tttaagccca atggtctatc aggaagtaga agagcagaaa    1080
ctacatcaag cagcatgctt gattcaagcc tattggaagg ttttcagac aagaaagaga    1140
ttaaagaagc ttccatctgc tgtgattgct ttgcagagga gtttcagatc caaacgatca    1200
aagatgttgc tggagataaa taggcagaag gaagaagagg acctcaaatt acaattgcaa    1260
cttcaaagac agagagccat gagactttcc cgagaattgc agctgagtat gctcgaaata    1320
gttcatccag gtcaggtgga gaaacactat cgggaaatgg aagagaaatc agcactgaat    1380
atccagaaac attggagagg gtacagggaa aggaaaaatt ttcaccaaca gaggcagtct    1440
ctcatagagt ataaagcagc tgtcacactt caaagagcag cgcttaaatt cctagcgaag    1500
tgccgtaaga aaaagaaact atttgctcct tggcgaggac tccaagaact cactgatgca    1560
cgccgagttg aactgaagaa acgagtggat gactatgtca aagacatttt gggctctcca    1620
atgtcagatg tggtcagtag ggagctccat gcccaagctc aagaacgact gcaacactac    1680
tttatgggca gggccctaga agagcgagcc cagcagcaca gagaagctct gatagcacag    1740
atcagcacca acgttgaaca gctaatgaag gcaccaagtc tgaaggaggc agaagggaaa    1800
gaacctgagc tcttcctaag tagatccagg cctgtggcag ccaaggccaa gcaggcccat    1860
ctcacaaccc tgaagcacat acaagcaccc tggtggaaga agcttggaga agaatctgga    1920
gatgagattg atgttccaaa ggatgagctt agtatagaat tagaaaattt attcattggt    1980
ggaaccaaac cacctagtg agtaacccta agaattgaca caaatctcat attttaggag    2040
attatattgg ttctgcctct ggcatgctgg tagactaggg ccatcctaac ttattatttt    2100
ccagaggttc tcctcagac aagacctgca gtaagcaaag agttatattc tacctctctc    2160
tcaatttttct ttttctttc tctgtatcct catccttagc cacacacaga tttgtgtggc    2220
```

-continued

| | | |
|---|---|---|
| ttttattgta gaactaaact tagcatagtg ttctgttgtt tacatgaagt gtgtttttct | 2280 | |
| ttggtttctt ctgttttcca actaaatatt tttttctaaa taaatatttt caacaattga | 2340 | |
| tttgaaaaaa aaaaaaaaaa aaaaaaaaaa aaaaaaaaaa aaaa | 2384 | |

<210> SEQ ID NO 86
<211> LENGTH: 2388
<212> TYPE: DNA
<213> ORGANISM: Homo sapiens

<400> SEQUENCE: 86

| | | |
|---|---|---|
| cgcctccagg cccccttcccg cgtcgcgacg cacgctgccc cggaaggccg cggcgctgta | 60 | |
| gtgcggcgcc ccaggttctt tagtggaaga acgcgaagcg aggatgagtg atccgtggag | 120 | |
| gcagtaacag gcgcggcgag ggagaagtga ttcccgaaga atcaaggctg ggccggaccc | 180 | |
| ggtggcctgg caacagggta ataagagaaa tgaagccaac aggtacagac ccaaggatct | 240 | |
| tatctatagc tgctgaagtt gcaaaaagcc ctgagcagaa tgtccctgtt atactgttga | 300 | |
| agttaaaaga aataataaac atcacacctt taggaagctc agagttgaag aaaatcaaac | 360 | |
| aagatatata ttgttatgat ctcattcaat attgcctctt ggtcctcagt caagattatt | 420 | |
| ctcgaatcca gggtggttgg actacaattt cccagcttac acagatatta agccattgct | 480 | |
| gtgtgggctt ggagccagga gaagatgcag aggaattta caatgaatta cttccatcag | 540 | |
| ctgcagaaaa ttttctagtt ttggggagac aattacaaac atgttttatc aatgcagcta | 600 | |
| aggctgaaga aaaagatgaa ttactacact ttttccaaat tgtgactgat tctctcttct | 660 | |
| ggcttttggg aggccatgtt gaacttattc agaatgtact acaaagtgat catttcttac | 720 | |
| atttactgca agctgacaat gtccaaatag gatctgcagt catgatgatg ctacagaata | 780 | |
| tattacagat caacagtggt gatttactca gaataggaag aaaagccctg tattcaattt | 840 | |
| tagatgaagt tattttcaag ctttttttcaa ctcctagtcc agttataaga agtactgcta | 900 | |
| caaaactcct actgttgatg gctgaatccc atcaggaaat tttgatttta ctgagacaaa | 960 | |
| gtacctgcta caaggactc agacgtctac taagtaaaca ggaaactggg actgaattca | 1020 | |
| gtcaagaact tagcttgttg gccttttaag cccaatggtc tatcaggaag tagaagagca | 1080 | |
| gaaactacat caagcagcat gcttgattca agcctattgg aagggttttc agacaagaaa | 1140 | |
| gagattaaag aagcttccat ctgctgtgat tgctttgcag aggagtttca gatccaaacg | 1200 | |
| atcaaagatg ttgctggaga taaataggca gaaggaagaa gaggacctca aattacaatt | 1260 | |
| gcaacttcaa agatagagag ccatgagact ttcccgagaa ttgcagctga gtatgctcga | 1320 | |
| aatagttcat ccaggtcagg tgagaaaaca ctatcgggaa atggaagaga atcagcact | 1380 | |
| gaatatccag aaacattgga gagggtacag ggaaaggaaa aatttcacc aacagaggca | 1440 | |
| gtctctcata gagtataaag cagctgtcac acttcaaaga gcagcgctta aattcctagc | 1500 | |
| gaagtgccgt aagaaaaaga aactatttgc tccttggcga ggactccaag aactcactga | 1560 | |
| tgcacgccga gttgaactga agaaacgagt ggatgactat gtcagaagac atttgggctc | 1620 | |
| tccaatgtca gatgtggtca gtagggagct ccatgcccaa gctcaagaac gactgcaaca | 1680 | |
| ctactttatg ggcagggccc tagaagagcg agcccagcag cacagagaag ctctgatagc | 1740 | |
| acagatcagc accaacgttg aacagctaat gaaggcacca gtctgaagg aggcagaagg | 1800 | |
| gaaagaacct gagctcttcc taagtagatc caggcctgtg gcagccaagg ccaagcaggc | 1860 | |
| ccatctcaca accctgaagc acatacaagc accctggtgg aagaagcttg gagaagaatc | 1920 | |
| tggagatgag attgatgttc caaaggatga gcttagtata gaattagaaa atttattcat | 1980 | |

```
tggtggaacc aaaccacctt agtgagtaac cctaagaatt gacacaaatc tcatatttta    2040
ggagattata ttggttctgc ctctggcatg ctggtagact agggccatcc taacttatta    2100
ttttccagag gttctcctcc agacaagacc tgcagtaagc aaagagttat attctacctc    2160
tctctcaatt ttcttttttct tttctctgta tcctcatcct tagccacaca cagatttgtg    2220
tggcttttat tgtagaacta aacttagcat agtgttctgt tgtttacatg aagtgtgttt    2280
ttctttggtt tcttctgttt tccaactaaa tattttttc taaataaata ttttcaacaa    2340
ttgatttgaa aaaaaaaaaa aaaaaaaaaa aaaaaaaaaa aaaaaaaa                  2388

<210> SEQ ID NO 87
<211> LENGTH: 2392
<212> TYPE: DNA
<213> ORGANISM: Homo sapiens

<400> SEQUENCE: 87
cgcctccagg cccctttccccg cgtcgcgacg cacgctgccc cggaaggccg cggcgctgta      60
gtgcggcgcc ccaggttctt tagtggaaga acgcgaagcg aggatgagtg atccgtggag     120
gcagtaacag gcgcggcgag ggagaagtga ttcccgaaga atcaaggctg ggccggaccc     180
ggtggcctgg caacagggta ataagagaaa tgaagccaac aggtacagac ccaaggatct     240
tatctatagc tgctgaagtt gcaaaaagcc ctgagcagaa tgtccctgtt atactgttga     300
agttaaaaga ataataaac atcacacctt taggaagctc agagttgaag aaaatcaaac     360
aagatatata ttgttatgat ctcattcaat attgcctctt ggtcctcagt caagattatt     420
ctcgaatcca gggtggttgg actacaattt cccagcttac acagatatta agccattgct     480
gtgtgggctt ggagccagga gaagatgcag aggaatttta caatgaatta cttccatcag     540
ctgcagaaaa ttttctagtt ttggggagac aattacaaac atgttttatc aatgcagcta     600
aggctgaaga aaaagatgaa ttactacact ttttccaaat tgtgactgat tctctcttct     660
ggcttttggg aggccatgtt gaacttattc agaatgtact acaaagtgat catttcttac     720
atttactgca agctgacaat gtccaaatag gatctgcagt catgatgatg ctacagaata     780
tattacagat caacagtggt gatttactca gaataggaag aaaagccctg tattcaattt     840
tagatgaagt tattttcaag cttttttcaa ctcctagtcc agttataaga agtactgcta     900
caaaactcct actgttgatg gctgaatccc atcaggaaat tttgatttta ctgagacaaa     960
gtacctgcta caaaggactc agacgtctac taagtaaaca ggaaactggg actgaattca    1020
gtcaagaact tagacagctt gttggccttt taagcccaat ggtctatcag gaagtagaag    1080
agcagaaact acatcaagca gcatgcttga ttcaagccta ttggaagggt tttcagacaa    1140
gaaagagatt aaagaagctt ccatctgctg tgattgcttt gcagaggagt ttcagatcca    1200
aatgatcaaa gatgttgctg gagataaata ggcagaagga agaagaggac ctcaaattac    1260
aattgcaact tcaaagacag agagccatga gactttcccg agaattgcag ctgagtatgc    1320
tcgaaatagt tcatccaggt caggtggaga acactatcg ggaaatggaa gagaaatcag    1380
cactgaatat ccagaaacat tggagagggt acagggaaag gaaaaatttt caccaacaga    1440
ggcagtctct catagagtat aaagcagctg tcacacttca aagagcagcg cttaaattcc    1500
tagcgaagtg ccgtaagaaa aagaaactat ttgctccttg gcgaggactc caagaactca    1560
ctgatgcacg ccgagttgaa ctgaagaaac gagtggatga ctatgtcaga agacatttgg    1620
gctctccaat gtcagatgtg gtcagtaggg agctccatgc ccaagctcaa gaacgactgc    1680
```

-continued

```
aacactactt tatgggcagg gccctagaag agcgagccca gcagcacaga gaagctctga    1740
tagcacagat cagcaccaac gttgaacagc taatgaaggc accaagtctg aaggaggcag    1800
aagggaaaga acctgagctc ttcctaagta gatccaggcc tgtggcagcc aaggccaagc    1860
aggcccatct cacaaccctg aagcacatac aagcaccctg gtggaagaag cttggagaag    1920
aatctggaga tgagattgat gttccaaagg atgagcttag tatagaatta gaaaatttat    1980
tcattggtgg aaccaaacca ccttagtgag taaccctaag aattgacaca aatctcatat    2040
tttaggagat tatattggtt ctgcctctgg catgctggta gactagggcc atcctaactt    2100
attattttcc agaggttctc ctccagacaa gacctgcagt aagcaaagag ttatattcta    2160
cctctctctc aattttcttt ttcttttctc tgtatcctca tccttagcca cacacagatt    2220
tgtgtggctt ttattgtaga actaaactta gcatagtgtt ctgttgttta catgaagtgt    2280
gttttctttt ggtttcttct gttttccaac taaatatttt tttctaaata aatattttca    2340
acaattgatt tgaaaaaaaa aaaaaaaaa aaaaaaaaa aaaaaaaaaa aa              2392
```

<210> SEQ ID NO 88
<211> LENGTH: 2394
<212> TYPE: DNA
<213> ORGANISM: Homo sapiens

<400> SEQUENCE: 88

```
cgcctccagg ccccttcccg cgtcgcgacg cacgctgccc cggaaggccg cggcgctgta     60
gtgcggcgcc ccaggttctt tagtggaaga acgcgaagcg aggatgagtg atccgtggag    120
gcagtaacag gcgcggcgag ggagaagtga ttcccgaaga atcaaggctg gccggaccc    180 ggtggcctgg caacaggggta ataagagaaa tgaagccaac aggtacagac ccaaggatct    240
tatctatagc tgctgaagtt gcaaaaagcc ctgagcagaa tgtccctgtt atactgttga    300
agttaaaaga ataataaac atcacacctt taggaagctc agagttgaag aaaatcaaac    360
aagatatata ttgttatgat ctcattcaat attgcctctt ggtcctcagt caagattatt    420
ctcgaatcca gggtggttgg actacaattt cccagcttac acagatatta agccattgct    480
gtgtgggctt ggagccagga gaagatgcag aggaatttta caatgaatta cttccatcag    540
ctgcagaaaa ttttctagtt ttggggagac aattacaaac atgttttatc aatgcagcta    600
aggctgaaga aaaagatgaa ttactacact ttttccaaat tgtgactgat tctctcttct    660
ggcttttggg aggccatgtt gaacttattc agaatgtact acaaagtgat catttcttac    720
atttactgca agctgacaat gtccaaatag gatctgcagt catgatgatg ctacagaata    780
tattacagat caacagtggt gatttactca gaataggaag aaaagccctg tattcaattt    840
tagatgaagt tattttcaag cttttttcaa ctcctagtcc agttataaga agtactgcta    900
caaaactcct actgttgatg gctgaatccc atcaggaaat tttgatttta ctgagacaaa    960
gtacctgcta caaaggactc agacgtctac taagtaaaca ggaaactggg actgaattca   1020
gtcaagaact tagacagctt gttggccttt taagcccaat ggtctatcag gaagtagaag   1080
agcagaaact acatcaagca gcatgcttga ttcaagccta ttggaagggt tttcagacaa   1140
gaaagagatt aaagaagctt ccatctgctg tgattgcttt gcagaggagt ttcagatcca   1200
aacgatcaaa gatgttgctg gagataaata ggcagaagga agaagaggac ctcaaattac   1260
aattgcaact tcaaagacag agagagccat gagactttcc cgagaattgc agctgagtat   1320
gctcgaaata gttcatccag gtcaggtgga gaaacactat cggaaatgg aagagaaatc   1380 agcactgaat atccagaaac attggagagg gtacagggaa aggaaaaatt tcaccaaca   1440
```

-continued

```
gaggcagtct ctcatagagt ataaagcagc tgtcacactt caaagagcag cgcttaaatt    1500
cctagcgaag tgccgtaaga aaagaaact atttgctcct tggcgaggac tccaagaact    1560
cactgatgca cgccgagttg aactgaagaa acgagtggat gactatgtca gaagacattt    1620
gggctctcca atgtcagatg tggtcagtag ggagctccat gcccaagctc aagaacgact    1680
gcaacactac tttatgggca gggccctaga gagcgagcc cagcagcaca gagaagctct    1740
gatagcacag atcagcacca acgttgaaca gctaatgaag gcaccaagtc tgaaggaggc    1800
agaagggaaa gaacctgagc tcttcctaag tagatccagg cctgtggcag ccaaggccaa    1860
gcaggcccat ctcacaaccc tgaagcacat acaagcaccc tggtggaaga agcttggaga    1920
agaatctgga gatgagattg atgttccaaa ggatgagctt agtatagaat tagaaaattt    1980
attcattggt ggaaccaaac caccttagtg agtaacccta agaattgaca caaatctcat    2040
attttaggag attatattgg ttctgcctct ggcatgctgg tagactaggg ccatcctaac    2100
ttattatttt ccagaggttc tcctccagac aagacctgca gtaagcaaag agttatattc    2160
tacctctctc tcaattttct ttttctttc tctgtatcct catccttagc cacacacaga    2220
tttgtgtggc ttttattgta gaactaaact tagcatagtg ttctgttgtt tacatgaagt    2280 gtgttttct ttggtttctt ctgttttcca actaaatatt tttttctaaa taaatatttt    2340
caacaattga tttgaaaaaa aaaaaaaaaa aaaaaaaaaa aaaaaaaaaa aaaa    2394

<210> SEQ ID NO 89
<211> LENGTH: 2392
<212> TYPE: DNA
<213> ORGANISM: Homo sapiens

<400> SEQUENCE: 89
cgcctccagg cccttcccg cgtcgcgacg cacgctgccc cggaaggccg cggcgctgta      60
gtgcggcgcc ccaggttctt tagtggaaga acgcgaagcg aggatgagtg atccgtggag    120
gcagtaacag gcgcggcgag ggagaagtga ttcccgaaga atcaaggctg gccggaccc     180 ggtggcctgg caacagggta ataagagaaa tgaagccaac aggtacagac ccaaggatct    240
tatctatagc tgctgaagtt gcaaaaagcc ctgagcagaa tgtccctgtt atactgttga    300
agttaaaaga ataataaac atcacacctt taggaagctc agagttgaag aaaatcaaac    360
aagatatata ttgttatgat ctcattcaat attgcctctt ggtcctcagt caagattatt    420
ctcgaatcca gggtggttgg actacaattt cccagcttac acagatatta agccattgct    480
gtgtgggctt ggagccagga aagatgcag aggaattta caatgaatta cttccatcag    540
ctgcagaaaa ttttctagtt ttggggagac aattacaaac atgttttatc aatgcagcta    600
aggctgaaga aaaagatgaa ttactacact ttttccaaat tgtgactgat tctctcttct    660
ggcttttggg aggccatgtt gaacttattc agaatgtact acaaagtgat catttcttac    720
atttactgca agctgacaat gtccaaatag gatctgcagt catgatgatg ctacagaata    780
tattacagat caacagtggt gatttactca gaataggaag aaaagccctg tattcaattt    840
tagatgaagt tatttttcaag cttttttcaa ctcctagtcc agtataaga agtactgcta    900 caaaactcct actgttgatg gctgaatccc atcaggaaat tttgatttta ctgagacaaa    960
gtacctgcta caaaggactc agacgtctac taagtaaaca ggaaactggg actgaattca   1020
gtcaagaact tagacagctt gttggccttt taagcccaat ggtctatcag gaagtagaag   1080 agcagaaaact acatcaagca gcatgcttga ttcaagccta ttggaagggt tttcagacaa   1140
```

-continued

| | |
|---|---|
| gaaagagatt aaagaagctt ccatctgctg tgattgcttt gcagaggagt ttcagatcca | 1200 |
| aacgatcaaa gatgttgctg gagataaata ggcagaagga agaagaggac ctcaaattac | 1260 |
| aattgcaact tcaaagacag agagccatga gactttcccg agaattgcag ctgagtatgc | 1320 |
| tcgaaatagt tcatccaggt caggtggaga acactatcg ggaaatggaa gagaaatcag | 1380 |
| cactgaatat ccagaaacat tggagagggt acagggaaag gaaaaatttt caccaacaga | 1440 |
| ggcagtctct catagagtat aaagcagctg tcacacttca aagagcagcg cttaaattcc | 1500 |
| tagcgaagtg ccgtaagaaa aagaaactat ttgctccttg gcgaggactc caagaactca | 1560 |
| ctgatgcacg ccgagttgaa ctgaagaaat gagtggatga ctatgtcaga agacatttgg | 1620 |
| gctctccaat gtcagatgtg gtcagtaggg agctccatgc ccaagctcaa gaacgactgc | 1680 |
| aacactactt tatgggcagg gccctagaag agcgagccca gcagcacaga gaagctctga | 1740 |
| tagcacagat cagcaccaac gttgaacagc taatgaaggc accaagtctg aaggaggcag | 1800 |
| aagggaaaga acctgagctc ttcctaagta gatccaggcc tgtggcagcc aaggccaagc | 1860 |
| aggcccatct cacaaccctg aagcacatac aagcaccctg gtggaagaag cttggagaag | 1920 |
| aatctggaga tgagattgat gttccaaagg atgagcttag tatagaatta gaaaatttat | 1980 |
| tcattggtgg aaccaaacca ccttagtgag taaccctaag aattgacaca atctcatat | 2040 |
| tttaggagat tatattggtt ctgcctctgg catgctggta gactagggcc atcctaactt | 2100 |
| attattttcc agaggttctc ctccagacaa gacctgcagt aagcaaagag ttatattcta | 2160 |
| cctctctctc aattttcttt ttcttttctc tgtatcctca tccttagcca cacacagatt | 2220 |
| tgtgtggctt ttattgtaga actaaactta gcatagtgtt ctgttgttta catgaagtgt | 2280 |
| gttttctttt ggtttcttct gttttccaac taaatatttt tttctaaata aatattttca | 2340 |
| acaattgatt tgaaaaaaaa aaaaaaaaaa aaaaaaaaaa aaaaaaaaa aa | 2392 |

<210> SEQ ID NO 90
<211> LENGTH: 2390
<212> TYPE: DNA
<213> ORGANISM: Homo sapiens

<400> SEQUENCE: 90

| | |
|---|---|
| cgcctccagg ccccttcccg cgtcgcgacg cacgctgccc cggaaggccg cggcgctgta | 60 |
| gtgcggcgcc ccaggttctt tagtggaaga acgcgaagcg aggatgagtg atccgtggag | 120 |
| gcagtaacag gcgcggcgag ggagaagtga ttcccgaaga atcaaggctg gccggacccc | 180 |
| ggtggcctgg caacagggta ataagagaaa tgaagccaac aggtacagac ccaaggatct | 240 |
| tatctatagc tgctgaagtt gcaaaaagcc ctgagcagaa tgtccctgtt atactgttga | 300 |
| agttaaaaga aataataaac atcacacctt taggaagctc agagttgaag aaaatcaaac | 360 |
| aagatatata ttgttatgat ctcattcaat attgcctctt ggtcctcagt caagattatt | 420 |
| ctcgaatcca gggtggttgg actacaattt cccagcttac acagatatta agccattgct | 480 |
| gtgtgggctt ggagccagga gaagatgcag aggaaatttta caatgaatta cttccatcag | 540 |
| ctgcagaaaa tttctagtt ttggggagac aattacaaac atgttttatc aatgcagcta | 600 |
| aggctgaaga aaaagatgaa ttactacact tttttccaaat tgtgactgat tctctcttct | 660 |
| ggcttttggg aggccatgtt gaacttattc agaatgtact acaaagtgat catttccttac | 720 |
| atttactgca agctgacaat gtccaaatag gatctgcagt catgatgatg ctacagaata | 780 |
| tattacagat caacagtggt gatttactca gaataggaag aaaagccctg tattcaatt | 840 |
| tagatgaagt tattttcaag cttttttcaa ctcctagtcc agttataaga agtactgcta | 900 |

-continued

```
caaaactcct actgttgatg gctgaatccc atcaggaaat tttgatttta ctgagacaaa      960
gtacctgcta caaaggactc agacgtctac taagtaaaca ggaaactggg actgaattca     1020
gtcaagaact tagacagctt gttggccttt taagcccaat ggtctatcag gaagtagaag     1080
agcagaaact acatcaagca gcatgcttga ttcaagccta ttggaagggt tttcagacaa     1140
gaaagagatt aaagaagctt ccatctgctg tgattgcttt gcagaggagt ttcagatcca     1200
aacgatcaaa gatgttgctg gagataaata ggcagaagga agaagaggac ctcaaattac     1260
aattgcaact tcaaagacag agagccatga gactttcccg agaattgcag ctgagtatgc     1320
tcgaaatagt tcatccaggt caggtggaga acactatcg ggaaatggaa gagaaatcag      1380
cactgaatat ccagaaacat tggagagggt acagggaaag gaaaaatttt caccaacaga    1440
ggcagtctct catagagtat aaagcagctg tcacacttca aagagcagcg cttaaattcc     1500
tagcgaagtg ccgtaagaaa agaaactat ttgctccttg gcgaggactc caagaactca      1560
ctgatgcacg ccgagttgaa ctgaagaaac gagtggatga ctatgtcaga agacatttgg    1620
gctctccaat gtcagatgtg gtcagtaggg agctccatgc ccaagctcaa gaacgactgc    1680
aacactactt tatgggcagg gccctagaag agcgagccca gcagcagaga agctctgata    1740
gcacagatca gcaccaacgt tgaacagcta atgaaggcac caagtctgaa ggaggcagaa    1800
gggaaagaac ctgagctctt cctaagtaga tccaggcctg tggcagccaa ggccaagcag    1860
gcccatctca caaccctgaa gcacatacaa gcaccctggt ggaagaagct tggagaagaa    1920
tctggagatg agattgatgt tccaaaggat gagcttagta tagaattaga aaatttattc    1980
attggtggaa ccaaaccacc ttagtgagta accctaagaa ttgacacaaa tctcatattt    2040
taggagatta tattggttct gcctctggca tgctggtaga ctagggccat cctaacttat    2100
tattttccag aggttctcct ccagacaaga cctgcagtaa gcaaagagtt atattctacc    2160
tctctctcaa ttttcttttt cttttctctg tatcctcatc cttagccaca cacagatttg    2220
tgtggctttt attgtagaac taaacttagc atagtgttct gttgtttaca tgaagtgtgt    2280
ttttctttgg tttcttctgt tttccaacta aatattttt tctaaataaa tattttcaac     2340
aattgatttg aaaaaaaaaa aaaaaaaaaa aaaaaaaaaa aaaaaaaaa                 2390
```

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
cactgacagc accacgaatg      20

<210> SEQ ID NO 92
<211> LENGTH: 19
<212> TYPE: DNA
<213> ORGANISM: Artificial Sequence
<220> FEATURE:
<223> OTHER INFORMATION: Synthetic

<400> SEQUENCE: 92
gaggcaggga aaggatgtg      19

<210> SEQ ID NO 93
<211> LENGTH: 18
<212> TYPE: DNA

```
<213> ORGANISM: Artificial Sequence
<220> FEATURE:
<223> OTHER INFORMATION: Synthetic

<400> SEQUENCE: 93
tctcgggcag aattcgag                                                  18

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
agggacactg gtggagactg                                                20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
aggaggggag agaaggacac                                                20

<210> SEQ ID NO 96
<211> LENGTH: 19
<212> TYPE: DNA
<213> ORGANISM: Artificial Sequence
<220> FEATURE:
<223> OTHER INFORMATION: Synthetic

<400> SEQUENCE: 96
catgaggcca tctgtcacc                                                 19

<210> SEQ ID NO 97
<211> LENGTH: 18
<212> TYPE: DNA
<213> ORGANISM: Artificial Sequence
<220> FEATURE:
<223> OTHER INFORMATION: Synthetic

<400> SEQUENCE: 97
aggatacccg tggggaag                                                  18

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
caagcccact ttcaatccac                                                20

<210> SEQ ID NO 99
<211> LENGTH: 18
<212> TYPE: DNA
<213> ORGANISM: Artificial Sequence
<220> FEATURE:
<223> OTHER INFORMATION: Synthetic

<400> SEQUENCE: 99
ccagctgaat gcccactg                                                  18
```

<210> SEQ ID NO 100
<211> LENGTH: 19
<212> TYPE: DNA
<213> ORGANISM: Artificial Sequence
<220> FEATURE:
<223> OTHER INFORMATION: Synthetic

<400> SEQUENCE: 100
cagtggtccg agtcacagg                                                  19

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
gaggaactcg ctcctaaatg c                                               21

<210> SEQ ID NO 102
<211> LENGTH: 18
<212> TYPE: DNA
<213> ORGANISM: Artificial Sequence
<220> FEATURE:
<223> OTHER INFORMATION: Synthetic

<400> SEQUENCE: 102
accgggcttg tgctgtag                                                   18

<210> SEQ ID NO 103
<211> LENGTH: 22
<212> TYPE: DNA
<213> ORGANISM: Artificial Sequence
<220> FEATURE:
<223> OTHER INFORMATION: Synthetic

<400> SEQUENCE: 103
tgcccactac atttatcctc ac                                              22

<210> SEQ ID NO 104
<211> LENGTH: 24
<212> TYPE: DNA
<213> ORGANISM: Artificial Sequence
<220> FEATURE:
<223> OTHER INFORMATION: Synthetic

<400> SEQUENCE: 104
gcaaacatat ttgtgaactt ttgc                                            24

<210> SEQ ID NO 105
<211> LENGTH: 23
<212> TYPE: DNA
<213> ORGANISM: Artificial Sequence
<220> FEATURE:
<223> OTHER INFORMATION: Synthetic

<400> SEQUENCE: 105
cgacgattat cttacaaatg tgg                                             23

<210> SEQ ID NO 106
<211> LENGTH: 20
<212> TYPE: DNA
<213> ORGANISM: Artificial Sequence
<220> FEATURE:

-continued

<223> OTHER INFORMATION: Synthetic

<400> SEQUENCE: 106
ggggacagag ggttttcttg                                               20

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
gacaggcaca gtgcaaaaac                                               20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
gggttcacaa ggtccaacag                                               20

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
aggtcagaac ctcagcgaag                                               20

<210> SEQ ID NO 110
<211> LENGTH: 21
<212> TYPE: DNA
<213> ORGANISM: Artificial Sequence
<220> FEATURE:
<223> OTHER INFORMATION: Synthetic

<400> SEQUENCE: 110
gcactggtca ccgtatgatt c                                             21

<210> SEQ ID NO 111
<211> LENGTH: 18
<212> TYPE: DNA
<213> ORGANISM: Artificial Sequence
<220> FEATURE:
<223> OTHER INFORMATION: Synthetic

<400> SEQUENCE: 111
acgctggaag cgtgactc                                                 18

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
cgagggagcc cacactctac                                               20

<210> SEQ ID NO 113
<211> LENGTH: 598
<212> TYPE: PRT
<213> ORGANISM: Mus musculus

<400> SEQUENCE: 113

```
Met Lys Pro Pro Gly Thr Asp Pro Gly Ile Leu Ser Leu Ala Ala Glu
1               5                   10                  15

Val Ala Arg Ser Pro Glu Gln Asn Val Pro Val Ile Leu Leu Lys Val
            20                  25                  30

Lys Glu Ile Ile Asn Asn Thr Pro Leu Gly Ser Ser Glu Leu Lys Lys
        35                  40                  45

Val Lys Gln Asp Ile Tyr Cys Tyr Asp Leu Ile Gln Tyr Cys Leu Leu
    50                  55                  60

Val Leu Ser Gln Asp Ser Ser Arg Ile Gln Gly Trp Ser Thr Ile
65                  70                  75                  80

Ser Gln Leu Thr Gln Ile Leu Ser His Cys Cys Val Gly Leu Glu Pro
                85                  90                  95

Gly Glu Asp Gly Glu Glu Phe Tyr Lys Glu Leu Leu Pro Ser Ala Ala
            100                 105                 110

Glu Asn Phe Leu Ile Leu Gly Arg Arg Leu Gln Thr Cys Phe Ile Asn
        115                 120                 125

Ala Thr Lys Gly Glu Glu Gln Asp Lys Leu Leu His Phe Phe Gln Ile
    130                 135                 140

Val Thr Asp Ser Leu Phe Trp Leu Leu Gly Gly His Val Gln Leu Ile
145                 150                 155                 160

Gln Asn Val Leu Gln Ser Asp His Phe Leu His Leu Leu Gln Thr Asp
                165                 170                 175

Asn Val Gln Ile Gly Ala Ser Val Met Thr Leu Leu Gln Asn Ile Leu
            180                 185                 190

Gln Ile Asn Ser Gly Asn Leu Leu Lys Ile Glu Gly Lys Ala Leu His
        195                 200                 205

Ser Ile Leu Asp Glu Ile Leu Phe Lys Leu Leu Ser Thr Pro Ser Pro
    210                 215                 220

Val Ile Arg Ser Thr Ala Thr Lys Leu Leu Leu Val Leu Ala Glu Ser
225                 230                 235                 240

His Gln Glu Ile Leu Ile Leu Leu Arg Leu Ser Ala Cys Tyr Lys Gly
                245                 250                 255

Leu Arg Ser Leu Leu Asn Lys Gln Glu Thr Leu Thr Glu Phe Ser Arg
            260                 265                 270

Glu Leu Arg Gln Leu Val Asp Leu Leu Thr Pro Lys Ile His Gln Glu
        275                 280                 285

Val Glu Glu Gln Lys Leu His Lys Ala Ala Cys Leu Ile Gln Ala Tyr
    290                 295                 300

Trp Lys Gly Phe Gln Thr Arg Lys Arg Leu Lys Lys Leu Pro Ser Ala
305                 310                 315                 320

Val Ile Ala Leu Gln Arg Ser Phe Arg Ser Lys Arg Thr Lys Met Met
                325                 330                 335

Leu Glu Leu Asn Arg Gln Lys Glu Glu Asp Leu Arg Leu Lys Trp
            340                 345                 350

Gln Leu Gln Arg Gln Arg Ala Met Arg Leu Ser Arg Glu Ser Arg Leu
        355                 360                 365

Asn Met Leu Glu Ile Ile His Pro Gly Gln Val Glu Lys Tyr Asn Arg
    370                 375                 380
```

```
Glu Met Glu Glu Lys Ser Ala Leu Thr Ile Gln Lys His Trp Arg Gly
385                 390                 395                 400

Tyr Arg Glu Arg Lys Asn Phe Arg Gln Gln Arg Pro Ser Leu Thr Glu
            405                 410                 415

Tyr Lys Ala Ala Val Thr Leu Gln Arg Ala Val Leu Lys Phe Leu Ala
        420                 425                 430

Lys Cys Arg Lys Lys Lys Leu Phe Ala Ser Trp His Gly Leu Gln
        435                 440                 445

Glu Leu Thr Asp Ala Arg Arg Val Glu Leu Lys Gln Gln Val Asp Asp
    450                 455                 460

Tyr Val Lys Arg His Pro Cys Ser Gln Met Ser Glu Ala Ala Ser Arg
465                 470                 475                 480

Glu Leu His Ala Gln Ala Gln Glu Arg Leu Gln His Tyr Phe Met Gly
                485                 490                 495

Arg Ala Ile Glu Glu Arg Ala Gln Gln His Arg Glu Ala Leu Met Ala
                500                 505                 510

Gln Ile Ser Thr Asn Ile Glu Gln Leu Met Lys Ala Pro Ser Leu Lys
            515                 520                 525

Glu Ala Glu Gly Lys Glu Pro Glu Gln Phe Leu Ser Arg Ser Arg Pro
530                 535                 540

Val Ala Ala Lys Ala Lys Gln Ala His Leu Thr Thr Leu Lys His Ile
545                 550                 555                 560

Gln Ala Pro Trp Trp Lys Lys Leu Gly Glu Glu Pro Gly Asp Glu Val
                565                 570                 575

Asp Val Pro Lys Asp Glu Leu Ser Ile Asp Leu Gly Met Leu Phe Ile
            580                 585                 590

Gly Gly Thr Lys Pro Pro
            595

<210> SEQ ID NO 114
<211> LENGTH: 598
<212> TYPE: PRT
<213> ORGANISM: Rattus norvegicus

<400> SEQUENCE: 114

Met Lys Pro Ala Gly Thr Asp Pro Arg Ile Leu Ser Leu Ala Ala Glu
1               5                   10                  15

Val Ala Lys Ser Pro Glu Gln Asn Val Pro Val Ile Leu Leu Lys Leu
            20                  25                  30

Lys Glu Ile Ile Asn Asn Thr Pro Leu Gly Ser Ser Glu Leu Lys Lys
        35                  40                  45

Val Lys Gln Asp Ile Tyr Cys Tyr Asp Leu Ile Gln Tyr Cys Leu Leu
    50                  55                  60

Val Leu Ser Gln Asp Ser Ser Arg Ile Gln Gly Gly Trp Ser Thr Ile
65                  70                  75                  80

Ser Gln Leu Thr Gln Ile Leu Ser His Cys Cys Val Gly Leu Glu Pro
                85                  90                  95

Gly Glu Asp Gly Glu Glu Phe Tyr Lys Glu Leu Leu Pro Ser Ala Ala
            100                 105                 110

Glu Asn Phe Leu Val Leu Gly Arg Arg Leu Gln Thr Cys Phe Ile Asn
        115                 120                 125

Ala Thr Lys Gly Glu Glu Gln Asp Lys Leu Leu His Phe Gln Ile
    130                 135                 140

Val Thr Asp Ser Leu Phe Trp Leu Leu Gly Gly His Ile Gln Leu Ile
145                 150                 155                 160
```

```
Gln Asn Val Leu Gln Ser Asp His Phe Leu His Leu Gln Thr Asp
            165                 170                 175
Asn Val Gln Ile Gly Ala Thr Val Met Thr Leu Leu Gln Asn Ile Leu
            180                 185                 190
Gln Ile Asn Ser Gly Asn Leu Leu Lys Ile Glu Gly Lys Ala Leu His
            195                 200                 205
Ser Ile Leu Asp Glu Ile Leu Phe Lys Leu Leu Ser Thr Pro Ser Pro
    210                 215                 220
Val Ile Arg Ser Thr Ala Thr Lys Leu Leu Val Leu Ala Glu Ser
225                 230                 235                 240
His Gln Glu Ile Leu Ile Leu Arg Leu Ser Ala Cys Tyr Lys Gly
                245                 250                 255
Leu Arg Ser Leu Leu Asn Lys Gln Glu Thr Leu Thr Glu Phe Ser Arg
            260                 265                 270
Glu Leu Arg Gln Leu Val Asp Leu Leu Thr Pro Lys Ile Gln Gln Glu
            275                 280                 285
Val Glu Glu Gln Lys Leu His Lys Ala Ala Cys Leu Ile Gln Ala Tyr
290                 295                 300
Trp Lys Gly Phe Gln Thr Arg Lys Arg Leu Lys Lys Leu Pro Ser Ala
305                 310                 315                 320
Val Ile Ala Leu Gln Arg Ser Phe Arg Ala Lys Arg Thr Lys Met Leu
                325                 330                 335
Leu Glu Leu Asn Arg Gln Lys Glu Glu Glu Asp Leu Arg Leu Arg Leu
            340                 345                 350
Gln Leu Gln Lys Gln Arg Ala Met Arg Leu Ser Arg Glu Ser Arg Leu
            355                 360                 365
Ser Met Leu Glu Ile Ile His Pro Gly Gln Val Glu Lys Tyr Asn Arg
    370                 375                 380
Glu Ile Glu Glu Lys Ser Ala Leu Thr Ile Gln Lys His Trp Arg Gly
385                 390                 395                 400
Tyr Arg Glu Arg Lys Asn Phe Arg Gln Gln Arg Pro Ser Leu Thr Glu
                405                 410                 415
Tyr Lys Ala Ala Val Thr Leu Gln Arg Ala Val Leu Lys Phe Leu Ala
            420                 425                 430
Lys Cys Arg Lys Lys Lys Leu Phe Ala Ser Trp His Gly Leu Gln
            435                 440                 445
Glu Leu Thr Asp Ala Arg Arg Val Glu Leu Lys Gln Gln Val Asp Asp
    450                 455                 460
Tyr Val Lys Arg His Pro Gly Ser Gln Met Ser Asp Val Ala Ser Arg
465                 470                 475                 480
Glu Leu His Ala Gln Ala Glu Arg Leu Gln His Tyr Phe Met Gly
                485                 490                 495
Arg Ala Ile Glu Glu Arg Ala Gln Gln His Arg Glu Ala Leu Met Ala
            500                 505                 510
Gln Ile Ser Thr Asn Ile Glu Gln Leu Met Lys Ala Pro Ser Leu Lys
            515                 520                 525
Glu Ala Glu Gly Lys Glu Pro Glu Gln Phe Leu Ser Arg Ser Arg Pro
    530                 535                 540
Val Ala Ala Lys Ala Lys Gln Ala His Leu Thr Thr Leu Lys His Ile
545                 550                 555                 560
Gln Ala Pro Trp Trp Lys Lys Leu Gly Glu Glu Pro Gly Asp Glu Met
                565                 570                 575
```

-continued

Asp Val Pro Lys Asp Glu Leu Ser Ile Asp Leu Gly Thr Leu Phe Ile
            580                 585                 590

Gly Gly Thr Lys Pro Pro
        595

<210> SEQ ID NO 115
<211> LENGTH: 598
<212> TYPE: PRT
<213> ORGANISM: Homo sapiens

<400> SEQUENCE: 115

Met Lys Pro Thr Gly Thr Asp Pro Arg Ile Leu Ser Ile Ala Ala Glu
1               5                   10                  15

Val Ala Lys Ser Pro Glu Gln Asn Val Pro Val Ile Leu Leu Lys Leu
            20                  25                  30

Lys Glu Ile Ile Asn Ile Thr Pro Leu Gly Ser Ser Glu Leu Lys Lys
        35                  40                  45

Ile Lys Gln Asp Ile Tyr Cys Tyr Asp Leu Ile Gln Tyr Cys Leu Leu
    50                  55                  60

Val Leu Ser Gln Asp Tyr Ser Arg Ile Gln Gly Gly Trp Thr Thr Ile
65                  70                  75                  80

Ser Gln Leu Thr Gln Ile Leu Ser His Cys Cys Val Gly Leu Glu Pro
                85                  90                  95

Gly Glu Asp Ala Glu Glu Phe Tyr Asn Glu Leu Leu Pro Ser Ala Ala
            100                 105                 110

Glu Asn Phe Leu Val Leu Gly Arg Gln Leu Gln Thr Cys Phe Ile Asn
        115                 120                 125

Ala Ala Lys Ala Glu Glu Lys Asp Glu Leu Leu His Phe Phe Gln Ile
    130                 135                 140

Val Thr Asp Ser Leu Phe Trp Leu Leu Gly Gly His Val Glu Leu Ile
145                 150                 155                 160

Gln Asn Val Leu Gln Ser Asp His Phe His Leu Leu Gln Ala Asp
                165                 170                 175

Asn Val Gln Ile Gly Ser Ala Val Met Met Met Leu Gln Asn Ile Leu
            180                 185                 190

Gln Ile Asn Ser Gly Asp Leu Leu Arg Ile Gly Arg Lys Ala Leu Tyr
        195                 200                 205

Ser Ile Leu Asp Glu Val Ile Phe Lys Leu Phe Ser Thr Pro Ser Pro
    210                 215                 220

Val Ile Arg Ser Thr Ala Thr Lys Leu Leu Leu Met Ala Glu Ser
225                 230                 235                 240

His Gln Glu Ile Leu Ile Leu Arg Gln Ser Thr Cys Tyr Lys Gly
                245                 250                 255

Leu Arg Arg Leu Leu Ser Lys Gln Glu Thr Gly Thr Glu Phe Ser Gln
            260                 265                 270

Glu Leu Arg Gln Leu Val Gly Leu Ser Pro Met Val Tyr Gln Glu
        275                 280                 285

Val Glu Glu Gln Lys Leu His Gln Ala Ala Cys Leu Ile Gln Ala Tyr
    290                 295                 300

Trp Lys Gly Phe Gln Thr Arg Lys Arg Leu Lys Lys Leu Pro Ser Ala
305                 310                 315                 320

Val Ile Ala Leu Gln Arg Ser Phe Arg Ser Lys Arg Ser Lys Met Leu
                325                 330                 335

Leu Glu Ile Asn Arg Gln Lys Glu Glu Asp Leu Lys Leu Gln Leu
            340                 345                 350

Gln Leu Gln Arg Gln Arg Ala Met Arg Leu Ser Arg Glu Leu Gln Leu
            355                 360                 365

Ser Met Leu Glu Ile Val His Pro Gly Gln Val Glu Lys His Tyr Arg
        370                 375                 380

Glu Met Glu Glu Lys Ser Ala Leu Ile Ile Gln Lys His Trp Arg Gly
385                 390                 395                 400

Tyr Arg Glu Arg Lys Asn Phe His Gln Arg Gln Ser Leu Ile Glu
            405                 410                 415

Tyr Lys Ala Ala Val Thr Leu Gln Arg Ala Ala Leu Lys Phe Leu Ala
            420                 425                 430

Lys Cys Arg Lys Lys Lys Leu Phe Ala Pro Trp Arg Gly Leu Gln
            435                 440                 445

Glu Leu Thr Asp Ala Arg Val Glu Leu Lys Lys Arg Val Asp Asp
        450                 455                 460

Tyr Val Arg Arg His Leu Gly Ser Pro Met Ser Asp Val Val Ser Arg
465                 470                 475                 480

Glu Leu His Ala Gln Ala Gln Glu Arg Leu Gln His Tyr Phe Met Gly
            485                 490                 495

Arg Ala Leu Glu Glu Arg Ala Gln Gln His Arg Glu Ala Leu Ile Ala
            500                 505                 510

Gln Ile Ser Thr Asn Val Glu Gln Leu Met Lys Ala Pro Ser Leu Lys
            515                 520                 525

Glu Ala Glu Gly Lys Glu Pro Glu Leu Phe Leu Ser Arg Ser Arg Pro
        530                 535                 540

Val Ala Ala Lys Ala Lys Gln Ala His Leu Thr Thr Leu Lys His Ile
545                 550                 555                 560

Gln Ala Pro Trp Trp Lys Lys Leu Gly Glu Glu Ser Gly Asp Glu Ile
            565                 570                 575

Asp Val Pro Lys Asp Glu Leu Ser Ile Glu Leu Glu Asn Leu Phe Ile
        580                 585                 590

Gly Gly Thr Lys Pro Pro
        595

<210> SEQ ID NO 116
<211> LENGTH: 595
<212> TYPE: PRT
<213> ORGANISM: Danio rerio

<400> SEQUENCE: 116

Met Gly Pro Ser Gly Asp Glu Ile Tyr Pro Glu Leu Lys Asp Leu Val
1               5                   10                  15

Glu Asp Thr Arg Glu Ile Ser Glu Asp Lys Phe Asn Asp Val Leu Ser
            20                  25                  30

Lys Leu Lys Glu Leu Leu Asp Leu Lys Ser Leu Gly Asp Gln Arg Asp
        35                  40                  45

Leu Glu Val Cys Arg Leu Arg Leu Tyr Thr His Gly Val Leu Gln Tyr
    50                  55                  60

Cys Ser Ser Ser Leu Arg Phe Arg Pro Ala Arg Ile Gln Gly Gly Tyr
65                  70                  75                  80

Ala Ala Leu Thr Gln Ile Ala Asp Leu Ser Thr Cys Cys Val Gly
            85                  90                  95

Leu Ala Ala Phe Arg Asp Ile Glu Val Phe Ser His Glu Phe Leu Pro
            100                 105                 110

Ser Val Val Glu Ser Leu Leu Phe Leu Ala Glu Arg Leu Met Asn Arg

```
            115                 120                 125
Ala Leu Arg Asp Lys Ala Pro Ser Glu Met Ile Arg Leu Phe Arg Lys
        130                 135                 140
Val Phe Asp Ser Ile Gly Trp Leu Leu Arg Ala His Arg His Leu Ile
145                 150                 155                 160
His His Val Leu Arg Cys Lys His Tyr Glu Ser Val Gln Ile Cys Glu
                165                 170                 175
Asp Asp Asp Val Ser Ile Val Thr Val Thr Leu Trp Asn Asp Ile Phe
            180                 185                 190
Arg Thr Asn Ser Ala Val Leu Ala Glu Met Gly Asn Arg Ala Leu Thr
        195                 200                 205
Asp Ile Met Asp Asp Ile Val Tyr Lys Met Ser Ser Ser Asn Pro
    210                 215                 220
Val Ile Gly Arg Ala Ala Val Lys Thr Leu Val Leu Ile Leu Asp His
225                 230                 235                 240
Ser Ser Ser Thr Gln Gln Leu Ile Gln Arg Arg Tyr Arg Gly Leu Ser
                245                 250                 255
Asp Leu Ala Glu Lys Asp Trp Arg Gly Lys Gly Phe Asp Ser Ala Leu
            260                 265                 270
Asp Gln Leu Ile Asp His Leu Gln Leu Asp Val Pro Trp Lys Glu Pro
        275                 280                 285
Lys Glu Ser Ser Glu Glu Cys Val Arg Ala Ala Cys Val Ile Gln Ala
    290                 295                 300
Ala Trp Arg Ala His Leu Thr Arg Arg Leu Lys Lys Leu Pro Arg
305                 310                 315                 320
Ala Val Ser Thr Leu Gln Arg Ser Phe Arg Glu Lys Arg Arg Gln Gln
                325                 330                 335
Gln Glu His Thr Glu Arg Arg Ala Glu Glu Leu Arg His Gln
            340                 345                 350
Val Cys Leu Arg Arg Gln Arg Ala Met Arg Leu Phe Arg Gln His Gln
        355                 360                 365
Leu His Leu Met Glu Ile Leu Pro Ala Gly Gln Val Gln Arg Tyr Leu
    370                 375                 380
Gly Glu Leu Glu Asn Lys Ala Ala Leu Val Ile Gln Arg Val Trp Arg
385                 390                 395                 400
Gly His Arg Glu Arg His Phe Gln Gln His Lys His Ile Leu Arg
                405                 410                 415
Arg His Arg Ala Ala Val Thr Leu Gln Arg Ala Val Leu Leu Phe Leu
            420                 425                 430
Lys Arg Arg Lys Ala Gln Arg Asn Ile Leu Thr Pro Leu Lys Ala Pro
        435                 440                 445
Lys Gly Leu Thr Asp Ser Arg Arg Thr Glu Leu Arg Lys Gln Ile Gln
    450                 455                 460
Glu His Ile Ser Leu His Pro Ser Ser Val Gln Ser Ala Glu Gly Ser
465                 470                 475                 480
Ala Glu Leu His Gln Arg Ala Gln Ser Leu Leu His Arg His Leu Val
                485                 490                 495
Asn Arg Ala Ser Asp Arg Ala Gln Glu Gln His Arg Gln Ala Leu Leu
            500                 505                 510
Ala Gln Ile Asn Thr Asp Ile Glu Leu Leu Leu Asn Ala Pro Ser Leu
        515                 520                 525
Arg Asp Val Arg Glu Glu Asp Val Asn Leu Phe Leu Ser Arg Ser Cys
    530                 535                 540
```

```
Pro Val Ala Thr Arg Ala Arg Gln Ser His Asn Ala Leu Leu Gln Ser
545                 550                 555                 560

Met Arg Leu Pro Trp Trp Arg Thr Leu Gly Asp Asp Leu Ser Asn Pro
                565                 570                 575

Glu Glu Pro Arg Lys Asp Tyr Asp Ile Asp Ile Glu Ser Leu Tyr Leu
            580                 585                 590

Gly Gly Ser
        595

<210> SEQ ID NO 117
<211> LENGTH: 580
<212> TYPE: PRT
<213> ORGANISM: Ciona intestinalis

<400> SEQUENCE: 117

Met Asp Asp Thr Glu Asp Ser Ile Glu Val Leu Lys Ile Ala Glu Leu
1               5                   10                  15

Val Ala Glu Ala Asn Asn Ala Ala Ile Pro Gly Leu Leu Leu Gln Leu
                20                  25                  30

Lys Pro Leu Leu Asp Lys Ala Ser Val Thr Ser Gln Glu Val Arg Val
            35                  40                  45

Ile Arg Arg Ser Ile Trp Lys Tyr Asp Leu Leu Ser Trp Cys Ala Ile
50                  55                  60

Ala Leu Gln Tyr Glu Tyr Thr Arg Val Lys Gly Gly Leu Glu Ser Ala
65                  70                  75                  80

Val Arg Ile Ser His Ile Leu Cys Asp Cys Cys His Ile Asp Val Asn
                85                  90                  95

Glu Ser Gln Glu Phe Ser Gln Thr Thr Leu Pro Ser Ala Val His Ser
            100                 105                 110

Phe Leu Lys Ile Ile Arg Gln Phe Gln Gln Arg Ile Glu Glu Lys Leu
        115                 120                 125

Lys Pro Pro Ile Leu Gln Thr Val Thr Asp Ala Glu Leu Cys Asp Glu
130                 135                 140

Met Leu Thr Leu Leu Thr Ser Leu Ile Thr Ser His Pro His Leu Cys
145                 150                 155                 160

Lys Pro Leu Leu Ser Cys Gly Asp Leu Leu Arg Ile Ile Met Glu Asp
                165                 170                 175

Asn His Gly His Leu Ile Ser Leu Arg Ala Ile Ser Ile Ile Asp Arg
            180                 185                 190

Ala Ile Arg Val Asn Arg Tyr Cys Val Ser Gln Val Asp Arg Pro Thr
        195                 200                 205

Ile Gln Ser Leu Leu Asp Glu Leu Val Tyr Lys Leu Thr Thr Ser Ser
210                 215                 220

Asp Glu Asp Leu Ala Lys Ser Ser Ser Arg Leu Ile Val Ser Leu Ser
225                 230                 235                 240

Asp Ala His Pro Pro Leu Val Pro Leu Met Val Thr Arg Phe Lys Gly
                245                 250                 255

Leu Lys Ala Ile Leu Arg Arg Trp Asp Gly Gln Gly Phe Asp Arg Glu
            260                 265                 270

Leu Ser Lys Leu Val Ala Val Leu Glu Ala Gly Thr Val Glu Asn Ala
        275                 280                 285

Lys Leu Tyr Arg Lys Arg Asn Ala Val Ala Val Ile Trp Ala Tyr Tyr
        290                 295                 300

Gln Gly Trp Lys Ala Arg Thr Arg Val Ala Lys Leu Lys Gln Ala Ile
```

-continued

```
305                 310                 315                 320
Pro Lys Leu Gln Gly Ser Phe Arg Arg Arg Glu Glu Arg Val Gly
                325                 330                 335
Glu Glu Glu Met Glu Arg Thr Gly Arg Leu Gln Val Ser Gln Gln Lys
            340                 345                 350
Leu Glu Asn Arg Arg Ser Leu Arg Lys Met Arg Glu Lys Gln Leu Val
            355                 360                 365
Ala Met Glu Ile Val Pro Ala Gly Arg Ile Ser Asp His Ile Gln Asp
        370                 375                 380
Glu Glu Ser Ser Ala Ala Val Arg Ile Gln Ala His Trp Arg Ala His
385                 390                 395                 400
Lys Gln Arg Lys Val Phe Ser Ala Lys Arg Lys Val His Arg Glu Asn
                405                 410                 415
Ser Ala Ala Val Val Ile Gln Lys Gln Val Lys Lys Phe Leu Arg Lys
                420                 425                 430
Lys Thr Asn Pro Glu Val Leu Val Ala Gly Ser Leu Asn Gln Tyr Met
            435                 440                 445
Val Asp Asn Asp Gln Arg Glu Lys Ile Met Glu Lys Ile Lys Asn Trp
    450                 455                 460
Gln Thr Val Asn Lys Arg Ser Gly Val Pro Ile Asp Glu Ala Thr Lys
465                 470                 475                 480
Ile His Glu Arg Ala Gln Gln Met Ile Leu Leu His His Arg Arg Lys
                485                 490                 495
Leu Ala Thr Lys Asn Glu Glu Glu Gln Leu Arg Met Met Met Ile Arg
            500                 505                 510
Ile Lys Met Asp Glu Asp Val Leu Ser Asp Leu Pro Pro Leu Asn Glu
            515                 520                 525
Ala Thr Glu Glu Ser Val Asp Leu Leu Ala Cys Lys Ser Ser Ile Val
            530                 535                 540
Gln Ala Ala Ala Glu Ile Glu His His Lys Gln Leu Arg Val Asn Arg
545                 550                 555                 560
Glu Pro Trp Trp Lys Arg Leu Asn Asp Asp Asn Thr Asp Asp Val Asp
                565                 570                 575
Cys Trp Ala Lys
            580
```

What is claimed is:

1. A method for detection of a variant NPHP5 nucleic acid in a subject, comprising:
   a) providing a biological sample from a subject, wherein said biological sample comprises a NPHP5 nucleic acid; and
   b) detecting a variant NPHP5 nucleic acid in said biological sample, wherein said variant NPHP5 nucleic acid is selected from the group consisting of SEQ ID NOs:83-90.

2. The method of claim 1, wherein said detecting said variant NPHP5 nucleic acid in said biological sample is indicative of Senior-Loken syndrome in said subject.

3. The method of claim 1, wherein said biological sample is selected from the group consisting of a blood sample, a tissue sample, a urine sample, and an amniotic fluid sample.

4. The method of claim 1, wherein said subject is selected from the group consisting of an embryo, a fetus, a newborn animal, and a young animal.

5. The method of claim 4, wherein said animal is a human.

6. The method of claim 1, wherein said detecting a variant NPHP5 nucleic acid comprises performing a nucleic acid hybridization assay.

* * * * *

UNITED STATES PATENT AND TRADEMARK OFFICE
CERTIFICATE OF CORRECTION

PATENT NO. : 7,517,648 B2
APPLICATION NO. : 11/061626
DATED : April 14, 2009
INVENTOR(S) : Hildebrandt et al.

It is certified that error appears in the above-identified patent and that said Letters Patent is hereby corrected as shown below:

In the Specifications:

At column 1, line 9, please insert the section heading and paragraph:

--STATEMENT REGARDING FEDERALLY SPONSORED RESEARCH OR DEVELOPMENT
 This invention was made with government support under DK069274 awarded by the National Institutes of Health. The government has certain rights in the invention.--

Signed and Sealed this
Eighteenth Day of June, 2013

Teresa Stanek Rea
*Acting Director of the United States Patent and Trademark Office*